(12) United States Patent
Senger et al.

(10) Patent No.: US 9,388,437 B2
(45) Date of Patent: Jul. 12, 2016

(54) ACYLTRANSFERASES AND USES THEREOF IN FATTY ACID PRODUCTION

(75) Inventors: Toralf Senger, Heidelberg (DE); Laurent Marty, Heidelberg (DE); Sten Stymne, Landskrona (SE); Jenny Lindberg Yilmaz, Bfaerred (SE); Johnathan A. Napier, Preston (GB); Olga Sayanova, Redbourne (GB); Richard Haslam, Buckinghamshire (GB); Ruiz Lopez Noemi, Harpenden (GB)

(73) Assignee: BASF Plant Science Company GmbH, Ludwigshafen (DE)

( * ) Notice: Subject to any disclaimer, the term of this patent is extended or adjusted under 35 U.S.C. 154(b) by 392 days.

(21) Appl. No.: 13/806,269

(22) PCT Filed: Jun. 21, 2011

(86) PCT No.: PCT/EP2011/060315
§ 371 (c)(1),
(2), (4) Date: Dec. 21, 2012

(87) PCT Pub. No.: WO2011/161093
PCT Pub. Date: Dec. 29, 2011

(65) Prior Publication Data
US 2013/0097733 A1    Apr. 18, 2013

Related U.S. Application Data

(60) Provisional application No. 61/358,431, filed on Jun. 25, 2010.

(30) Foreign Application Priority Data

Jun. 25, 2010   (EP) .................................... 10167342

(51) Int. Cl.
| | |
|---|---|
| *C12P 7/64* | (2006.01) |
| *A23D 9/02* | (2006.01) |
| *C11C 1/04* | (2006.01) |
| *C12N 9/10* | (2006.01) |
| *C12N 15/82* | (2006.01) |

(52) U.S. Cl.
CPC ................ *C12P 7/6427* (2013.01); *A23D 9/02* (2013.01); *C11C 1/045* (2013.01); *C12N 9/1029* (2013.01); *C12N 15/8247* (2013.01); *A23V 2002/00* (2013.01); *A23V 2250/187* (2013.01); *A23V 2250/1862* (2013.01); *A23V 2250/1868* (2013.01); *A23V 2250/1882* (2013.01); *Y02P 20/52* (2015.11)

(58) Field of Classification Search
None
See application file for complete search history.

(56) References Cited

U.S. PATENT DOCUMENTS

2012/0060242 A1    3/2012    Senger et al.

FOREIGN PATENT DOCUMENTS

| | | |
|---|---|---|
| WO | WO-93/10241 A1 | 5/1993 |
| WO | WO-94/13814 A1 | 6/1994 |
| WO | WO-95/27791 A1 | 10/1995 |
| WO | WO-96/24674 A1 | 8/1996 |
| WO | WO-98/27203 A1 | 6/1998 |
| WO | WO-98/55625 A1 | 12/1998 |
| WO | WO-98/55631 A1 | 12/1998 |
| WO | WO-98/55632 A1 | 12/1998 |
| WO | WO-0018889 A2 | 4/2000 |
| WO | WO-00/42195 A2 | 7/2000 |
| WO | WO-2007/106905 A2 | 9/2007 |
| WO | WO-2009/085169 A2 | 7/2009 |
| WO | WO-2009/143398 A1 | 11/2009 |
| WO | WO-2009/143401 A2 | 11/2009 |

OTHER PUBLICATIONS

Jako et al. Seed-Specific Over-Expression of an Arabidopsis cDNA Encoding a Diacylglycerol Acyltransferase Enhances Seed Oil Content and Seed Weight. Plant Physiology. 126:861-874, Jun. 2001.*
Friedberg (Automated protein function prediction—the genomic challenge. Brief. Bioinformatics. 7: 225-242, 2006).*
Fourgoux-Nicol et al (1999, Plant Molecular Biology 40: 857-872).*
Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
Shih et al (Multiple lysophosphatidic acid acyltransferases in Neisseria meningitidis. Mol Microbiol. 32(5): 942-52, Jun. 1999).*
International Search Report for PCT/EP2011/060315, mailed Oct. 17, 2011.
Vazhappilly, R., et al., "Heterotrophic Production Potential of Omega-3 Polyunsaturated Fatty Acids by Microalgae and Algae-Like Microorganisms", Botanica Marina, vol. 41, (1998), pp. 553-558.
Totani, N., et al., "The Filamentous Fungus *Mortierella alpina*, High in Arachidonic Acid", Lipids, vol. 22, No. 12, (1987), pp. 1060-1062.
Akimoto, M., et al., "Carbon Dioxide Fixation and Polyunsaturated Fatty Acid Production by the Red Alga *Porphyridium cruentum*, Applied Biochemistry and Biotechnology", vol. 73, (1998), pp. 269-278.
Abbadi, A., et al., "Transgenic Oilseeds as Sustainable Source of Nutritionally Relevant C20 and C22 Polyunsaturated Fatty Acids?", Eur. J. Lipid Sci., Technol., vol. 103, (2001), pp. 106-113.

(Continued)

*Primary Examiner* — Medina A Ibrahim
*Assistant Examiner* — Wayne Zhong
(74) *Attorney, Agent, or Firm* — Drinker Biddle & Reath LLP

(57) ABSTRACT

The present invention relates to the recombinant manufacture of polyunsaturated fatty acids. Specifically, it relates to acyltransferase polypeptides, polynucleotides encoding said acyltransferases as well as vectors, host cells, non-human transgenic organisms containing said polynucletides. Moreover, the present invention contemplates methods for the manufacture of polyunsaturated fatty acids as well as oils obtained by such methods.

24 Claims, 12 Drawing Sheets

(56) References Cited

OTHER PUBLICATIONS

Figure 1:
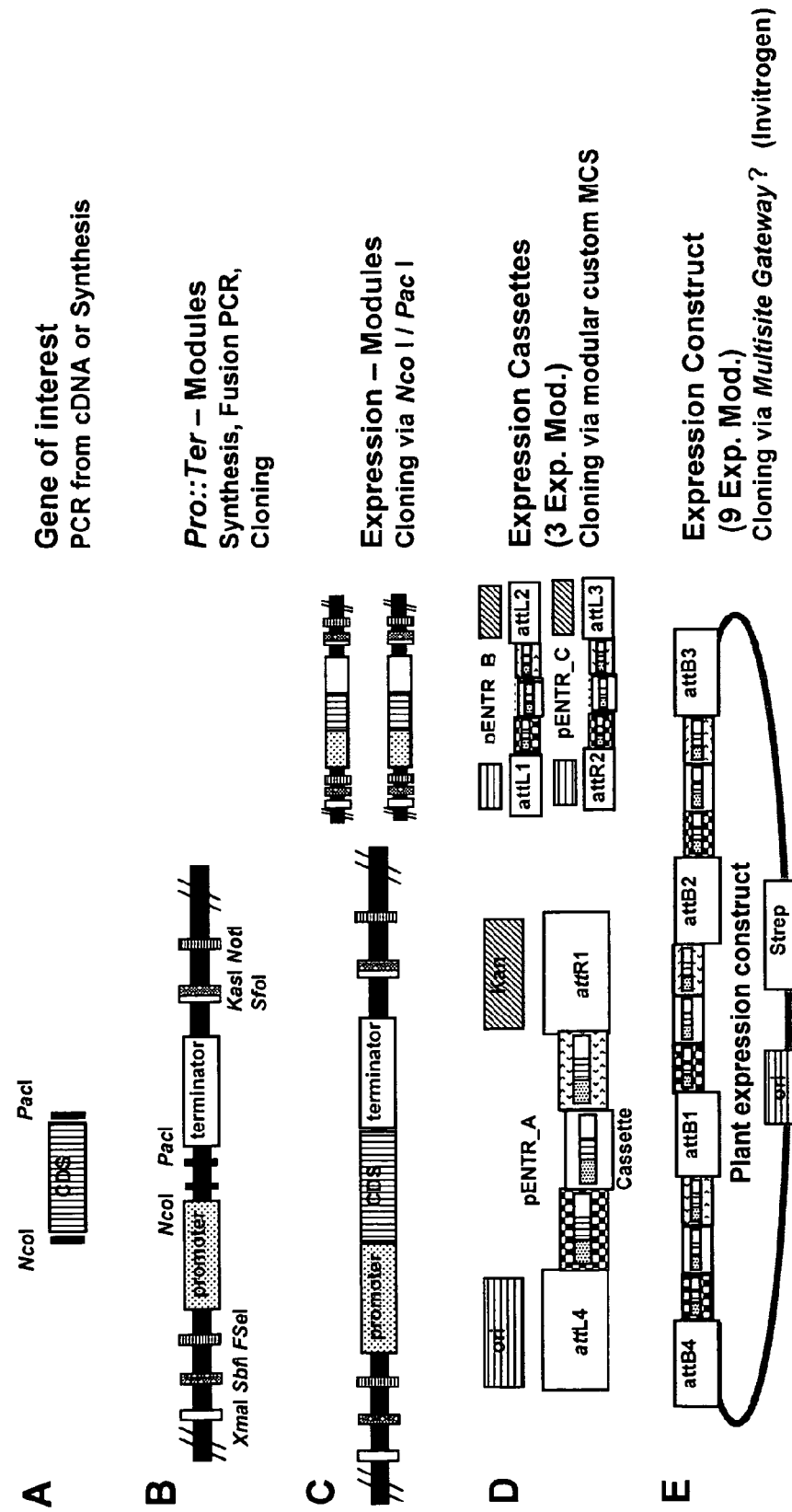

Zank, T.K., et al., "Cloning and Functional Expression of the First Plant Fatty Acid Elongase Specific for Δ6-Polyunsaturated Fatty Acids", Biochemical Society Transactions, vol. 28, (2000), pp. 654-658.

Slabas, A. R., et al., "Acyltransferases and their Role in the Biosynthesis of Lipids-Opportunities for New Oils, Journal of Plant Physiology", vol. 158, (2001), pp. 505-513.

Frentzen, M., "Acyltransferases from Basic Science to Modified Seed Oils", Fett/Lipid, vol. 100, No. 4-5, (1998), pp. 161-166.

Cases, S., et al., "Identification of a Gene Encoding an Acyl CoA:Diacylglycerol Acyltransferase, a Key Enzyme in Triacylglycerol Synthesis", Proc. Natl. Acad. Sci. USA, vol. 95, (1998), pp. 13018-13023.

Akermoun, M., et al., "Complex Lipid Biosynthesis: Phospholipid Synthesis", Biochemical Society Transactions, vol. 28, (2000), pp. 713-715.

Fraser, T., et al., "Partial Purification and Photoaffinity Labelling of Sunflower Acyl-CoA:Lysophophatidylcholine Acyltransferase", Biochemical Society Transactions, vol. 28, (2000), pp. 715-718.

Stymne, S., et al., "Evidence for the Reversibility of the Acyl-CoA:Lysophophatidylcholine Acyltransferase in Microsomal Preparations from Developing Safflower (*Carthamus tinctorius L.*) Cotyledons and Rat Liver", Biochem. J., vol. 223, (1984), pp. 305-314.

Yamashita, A., et al., "ATP-Independent Fatty Acyl-Coenzyme A Synthesis from Phospholipid", The Journal of Biological Chemistry, vol. 276, No. 29, (2001), pp. 26745-26752.

Zhang, C., et al., "A Thraustochytrid Diacyglycerol Acyltransferase 2 with Broad Substrate Specificity Strongly Increases Oleic Acid Content in Engineered Arabidopsis thaliana Seeds", Journal of Experimental Botany, 2013, vol. 64, No. 11, pp. 3189-3200.

International Preliminary Report on Patentability for PCT/EP2011/060315 dated Dec. 28, 2012.

\* cited by examiner

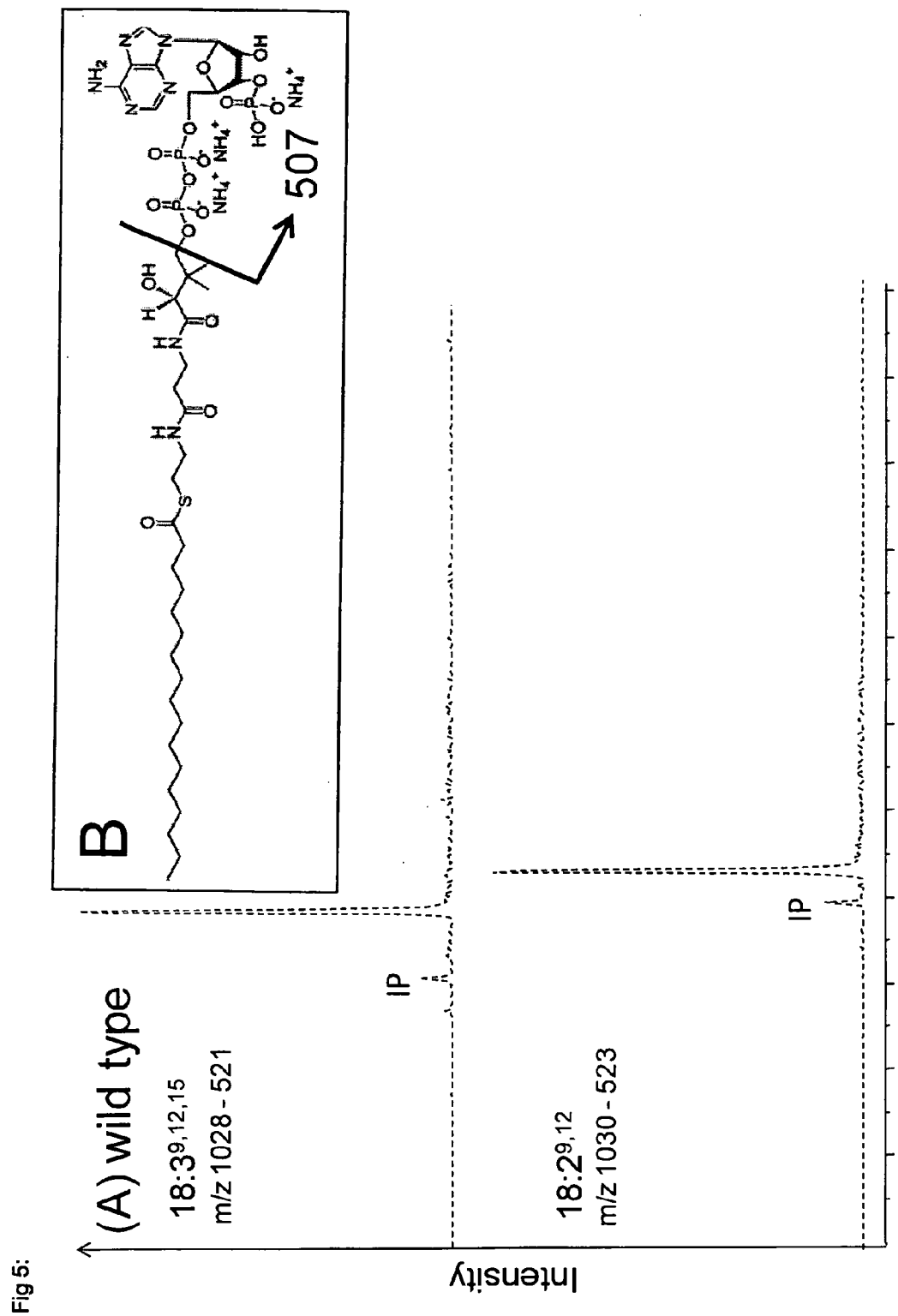

SEQUENCE LISTING

<160> NUMBER OF SEQ ID NOS: 114

<210> SEQ ID NO 1
<211> LENGTH: 1485
<212> TYPE: DNA
<213> ORGANISM: Nannochloropsis oculata

<400> SEQUENCE: 1

| | | | | | |
|---|---|---|---|---|---|
| atggacaagg | cactggcacc | gttgggggag | accctgggct | ttgagatcgg | catgctcaag | 60 |
| tatgttctgg | ccatgttcct | cgcctacccg | ctatcgggca | tccttaatat | cttgcccact | 120 |
| gccaatgcca | agcatgcttt | ctccttattg | gtgggcttgt | ggtacgcgca | ggagattttt | 180 |
| ggcaaccagt | gggtgcattc | gttcctctcc | tcggccgtgt | cctacctcat | cgtctgcctc | 240 |
| ggcccccgga | agcacatagc | caccctggtc | ttcctcttca | ccatgacgta | catgagcgtc | 300 |
| agtcacctgt | accgcctcta | cgtggactac | ttgggatggt | cgctggactt | cacaggaccc | 360 |
| cagatgatcc | tgaccatcaa | gctctcgtcg | ttcgcctaca | atgtgtatga | cggcgtggtg | 420 |
| gatctcgacg | ccatctccaa | gccccaggag | aacaagctca | agatccgtgt | cttcaaggag | 480 |
| aggctccgct | acgccatcac | atccattcct | tccccttgg | ccttcttcgg | ctacgtctac | 540 |
| tccttctcca | ccttcctggc | aggtccggcg | ttcgagtact | cagactatgc | atccgtcatt | 600 |
| gacggctcgg | ccttctccaa | gaagggaggg | aaggagggag | ggaaggaggg | aggagcaccc | 660 |
| tcctcgttgc | tggctgcgtt | gtggcgcctt | ctccagggtg | tcctgtgcct | ggctctccac | 720 |
| ctcgtcggct | ctgccaagtt | cagcctcagc | gacgtcctct | ccgacgaagt | cctggccatg | 780 |
| cccttcttcg | agcgctggct | cttcactctc | atcgccctct | tcttctgccg | aatgaagtac | 840 |
| tacttcgctt | ggaaggtggc | ggaaggctcc | tgcgtcgtgg | ccggcttcgg | tttcgaaggc | 900 |
| tatgcggagg | acgggtcggt | gaaggggtgg | aacggcatct | ctaatatgga | tatattaggt | 960 |
| ttcgaggcgg | ccaccaatac | cgccgaggcc | tccaaggcct | ggaacaaggg | cacccaaaag | 1020 |
| tggttgcagc | gatacgtcta | ttttcgcaac | agcgagtccc | tccttatcac | gtacttcgtc | 1080 |
| tccgccttct | ggcatggctt | ctacccgggc | tactacctct | tcttcttctc | catcgcgctg | 1140 |
| gtgcagacgg | tgcagagggc | gtggcagaag | aaggtgtctc | cttacttcac | ctccaccatt | 1200 |
| cccgccctct | accacctcct | ctgcatcctc | gttttctccg | cctacatcaa | ttacttctcg | 1260 |
| atcgtctttc | aggtcctggc | ctgggaccgg | gcgatggcgg | tgtggaagag | cgcgcattac | 1320 |
| tggggtcatg | tcgccaccgc | gggcgccttt | gttctcacct | ccgtgctgcc | ctctcccaag | 1380 |
| aaggaggcgg | ggaagaaggt | tttagaggaa | agaaagaagg | ctttgaggga | aggaaggaga | 1440 |
| tttagaggga | aggaagaagg | tttagaggga | aggaagaaag | tttag | 1485 |

<210> SEQ ID NO 2
<211> LENGTH: 494
<212> TYPE: PRT
<213> ORGANISM: Nannochloropsis oculata

<400> SEQUENCE: 2

Met Asp Lys Ala Leu Ala Pro Leu Gly Glu Thr Leu Gly Phe Glu Ile
1               5                   10                  15

Gly Met Leu Lys Tyr Val Leu Ala Met Phe Leu Ala Tyr Pro Leu Ser
            20                  25                  30

Gly Ile Leu Asn Ile Leu Pro Thr Ala Asn Ala Lys His Ala Phe Ser
        35                  40                  45

Leu Leu Val Gly Leu Trp Tyr Ala Gln Glu Ile Phe Gly Asn Gln Trp
    50                  55                  60

```
Val His Ser Phe Leu Ser Ser Ala Val Ser Tyr Leu Ile Val Cys Leu
 65                  70                  75                  80

Gly Pro Arg Lys His Ile Ala Thr Leu Val Phe Leu Phe Thr Met Thr
                 85                  90                  95

Tyr Met Ser Val Ser His Leu Tyr Arg Leu Tyr Val Asp Tyr Leu Gly
            100                 105                 110

Trp Ser Leu Asp Phe Thr Gly Pro Gln Met Ile Leu Thr Ile Lys Leu
        115                 120                 125

Ser Ser Phe Ala Tyr Asn Val Tyr Asp Gly Val Val Asp Leu Asp Ala
    130                 135                 140

Ile Ser Lys Pro Gln Glu Asn Lys Leu Lys Ile Arg Val Phe Lys Glu
145                 150                 155                 160

Arg Leu Arg Tyr Ala Ile Thr Ser Ile Pro Ser Pro Leu Ala Phe Phe
                165                 170                 175

Gly Tyr Val Tyr Ser Phe Ser Thr Phe Leu Ala Gly Pro Ala Phe Glu
            180                 185                 190

Tyr Ser Asp Tyr Ala Ser Val Ile Asp Gly Ser Ala Phe Ser Lys Lys
        195                 200                 205

Gly Gly Lys Glu Gly Gly Lys Glu Gly Gly Ala Pro Ser Ser Leu Leu
210                 215                 220

Ala Ala Leu Trp Arg Leu Leu Gln Gly Val Leu Cys Leu Ala Leu His
225                 230                 235                 240

Leu Val Gly Ser Ala Lys Phe Ser Leu Ser Asp Val Leu Ser Asp Glu
                245                 250                 255

Val Leu Ala Met Pro Phe Phe Glu Arg Trp Leu Phe Thr Leu Ile Ala
            260                 265                 270

Leu Phe Phe Cys Arg Met Lys Tyr Tyr Phe Ala Trp Lys Val Ala Glu
        275                 280                 285

Gly Ser Cys Val Val Ala Gly Phe Gly Phe Glu Gly Tyr Ala Glu Asp
290                 295                 300

Gly Ser Val Lys Gly Trp Asn Gly Ile Ser Asn Met Asp Ile Leu Gly
305                 310                 315                 320

Phe Glu Ala Ala Thr Asn Thr Ala Glu Ala Ser Lys Ala Trp Asn Lys
                325                 330                 335

Gly Thr Gln Lys Trp Leu Gln Arg Tyr Val Tyr Phe Arg Asn Ser Glu
            340                 345                 350

Ser Leu Leu Ile Thr Tyr Phe Val Ser Ala Phe Trp His Gly Phe Tyr
        355                 360                 365

Pro Gly Tyr Tyr Leu Phe Phe Phe Ser Ile Ala Leu Val Gln Thr Val
        370                 375                 380

Gln Arg Ala Trp Gln Lys Lys Val Ser Pro Tyr Phe Thr Ser Thr Ile
385                 390                 395                 400

Pro Ala Leu Tyr His Leu Leu Cys Ile Leu Val Phe Ser Ala Tyr Ile
                405                 410                 415

Asn Tyr Phe Ser Ile Val Phe Gln Val Leu Ala Trp Asp Arg Ala Met
            420                 425                 430

Ala Val Trp Lys Ser Ala His Tyr Trp Gly His Val Ala Thr Ala Gly
        435                 440                 445

Ala Phe Val Leu Thr Ser Val Leu Pro Ser Pro Lys Lys Glu Ala Gly
        450                 455                 460

Lys Lys Val Leu Glu Glu Arg Lys Lys Ala Leu Arg Glu Gly Arg Arg
465                 470                 475                 480
```

Phe Arg Gly Lys Glu Glu Gly Leu Glu Gly Arg Lys Lys Val
                485                 490

<210> SEQ ID NO 3
<211> LENGTH: 1908
<212> TYPE: DNA
<213> ORGANISM: Nannochloropsis oculata

<400> SEQUENCE: 3

```
attttcagca aagtaatcaa gataataaac aaaaacaatc ctataaagga aaaacaacag      60
gagcccatga cgttccacga gaagcacctc gatgcattgg tgtccttctt cgggagctgg     120
gtgccgctag cagacaagac ggtctacttg accgtgcctg gtatgdacaa ggcactggca     180
ccgttggggg agaccctggg cttgagatc ggcatgctca agtatgttct ggccatgttc      240
ctcgcctacc cgctatcggg catccttaat atcttgccca ctgccaatgc caagcatgct     300
ttctccttat tggtgggctt gtggtacgcg caggagattt ttggcaacca gtgggtgcat     360
tcgttcctct cctcggccgt gtcctacctc atcgtctgcc tcggcccccg aagcacata      420
gccaccctgg tcttcctctt caccatgacg tacatgagcg tcagtcacct gtaccgcctc     480
tacgtggact acttgggatg gtcgctggac ttcacaggac cccagatgat cctgaccatc     540
aagctctcgt cgttcgccta caatgtgtat gacggcgtgg tggatctcga cgccatctcc     600
aagccccagg agaacaagct caagatccgt gtcttcaagg agaggctccg ctacgccatc     660
acatccattc cttccccctt ggccttcttc ggctacgtct actccttctc caccttcctg     720
gcaggtccgg cgttcgagta ctcagactat gcatccgtca ttgacggctc ggccttctcc     780
aagaagggag ggaaggaggg agggaaggag ggaggagcac cctcctcgtt gctggctgcg     840
ttgtggcgcc ttctccaggg tgtcctgtgc ctggctctcc acctcgtcgg ctctgccaag     900
ttcagcctca gcgacgtcct ctccgacgaa gtcctggcca tgcccttctt cgagcgctgg     960
ctcttcactc tcatcgccct cttcttctgc cgaatgaagt actacttcgc ttggaaggtg    1020
gcggaaggct cctgcgtcgt ggccggcttc ggtttcgaag gctatgcgga ggacgggtcg    1080
gtgaagggt ggaacggcat ctctaatatg gatatattag gtttcgaggc ggccaccaat    1140
accgccgagg cctccaaggc ctggaacaag gcacccaaa agtggttgca gcgatacgtc    1200
tattttcgca acagcgagtc cctccttatc acgtacttcg tctccgcctt ctggcatggc    1260
ttctacccgg gctactacct cttcttcttc tccatcgcgc tggtgcagac ggtgcagagg    1320
gcgtggcaga agaaggtgtc tccttacttc acctccacca ttcccgccct ctaccacctc    1380
ctctgcatcc tcgttttctc cgcctacatc aattacttct cgatcgtctt tcaggtcctg    1440
gcctgggacc gggcgatggc ggtgtggaag agcgcgcatt actggggtca tgtcgccacc    1500
gcgggcgcct ttgttctcac ctccgtgctg ccctctccca agaaggaggc ggggaagaag    1560
gttttagagg aaagaaagaa ggctttgagg gaaggaagga gatttagagg gaaggaagaa    1620
ggtttagagg gaaggaagaa agtttagagg gaaggaagaa ggtttagagg gaagggagga    1680
ggttttatag agggaaggga ggaggtttta tagagggaag gaagaaggct ttgagggaag    1740
gaaggaggtt tagattcctc gcataaggca ttggaattta aatagtggtg ggcctgtctg    1800
gctttccgtg aaggagagca accataatgt gtgaccaacg ctttggcacc gcaaccacca    1860
taataacagc actaacaaaa agaagaacaa caataagaag gaggagat                 1908
```

<210> SEQ ID NO 4
<211> LENGTH: 1776
<212> TYPE: DNA

<213> ORGANISM: Nannochloropsis oculata

<400> SEQUENCE: 4

| | | | | | |
|---|---|---|---|---|---|
| atgaccacga | ctgtcatctc | tagctcgatg | gggcccatcc | tggcctatta | tacgtgtgcc | 60 |
| acaatcacca | tctacgtagt | gctcggccgc | ttttccagtc | caaacccgcg | cttgagatgg | 120 |
| ctgaagctca | aagacctgga | gaacattgag | actgcgaacc | cggccgcgca | cccttcagag | 180 |
| tctgattcta | tgcctcttaa | ttctggcaat | ctatcgtctt | ccaagcccat | tgccgcagct | 240 |
| gagatgcttc | aaactccctc | ggcatcgtcg | tcctcgccct | cggcatcccc | agagcgcaaa | 300 |
| gctcctatga | tgcggaagct | ttcctttctc | gccacgactg | gagtcatcga | aaatccctt | 360 |
| atgaacaata | cttgggatat | ctccaggttg | gaacgcgtta | aatgtgcgat | attcggtcca | 420 |
| atgctcatcc | cccccgtct | gctcctgctc | tttgtgtcac | ttcttggtgc | ctacgggttc | 480 |
| ggcaagctct | ctaccattgg | cgcagaacta | gagcgcccct | gcctcgatg | gcgcatcgac | 540 |
| ctgcagcacc | ccatgaagtt | ttttgcccgc | gggattatgt | ttgcattggg | ctaccattgg | 600 |
| atctccatca | aggaaagca | agcaagcccg | caacacgctc | ctatcgttgt | ctccaatcat | 660 |
| tgctccttct | gtgaagccat | ctatctgcct | gggcgcctct | tgtccatggc | tgtttcccgc | 720 |
| cgggagaatg | ccgctatccc | ttttttttgga | gggctgatgc | aacaagtcca | atgcatcttc | 780 |
| gtctcgcgca | ccgacaaaga | ctcccggacc | actgtcgcca | acgagatctt | gagacgctcc | 840 |
| aaaatagaaa | gggggcagtg | gcaccgtcaa | ctcctcgtct | tcccagaagg | gaccaccacg | 900 |
| aacgggagtg | ccgtgatcag | cttcaaagtc | ggctccttg | ccggtggggt | aagcgtgcag | 960 |
| ccagtcgctg | tatcctaccc | ttccaaccaa | atctgcgatc | catcatgggt | cagtggtggg | 1020 |
| ccgcatcccg | gcgagattct | gtttaaattg | ctgtgtcagc | catggaacag | tatgaatgtt | 1080 |
| actttcctgc | ctgtgtataa | tcccgacgcc | gctgaaattg | atgatcccgt | gctgtttagc | 1140 |
| acaaatgtca | ggcggttgat | agccgcagag | ttgggcgtgc | ctgccagtga | tcacacattc | 1200 |
| gatgacgttt | tgttgttaat | ggaggcaaag | aagctagggt | accagggggg | tcttcgtgat | 1260 |
| tgcatctctg | agctgaaaaa | tatgcgaaag | attctagaaa | ttgacctggc | aaaagcgaaa | 1320 |
| gaatatttgc | atgaatttc | tcagcttgac | acaaacagga | aggggctgtt | atcatacccc | 1380 |
| caattcatta | agccttcgg | ctcgcaggat | tcagacgcac | ttcggagtct | attttgtgtg | 1440 |
| ttagacgtgc | aagatcgggg | agtgatcaat | ttggtggagt | acaccacagg | ttagcactg | 1500 |
| ttgaatgagc | aaggcaccga | tggttttgat | ggggccatgc | gcttgatttt | caaagttcaa | 1560 |
| gattcgagtg | gggagggggcg | gctgtcgaag | gaagacacgg | caaaggtgct | gcggcggctg | 1620 |
| tggcctgacg | tgacgacgga | gctgttcgac | tcgacgtttg | ctgcggcgga | cacagataat | 1680 |
| aacgggacgt | tgagcgctga | tgagtttctg | gcgttggcga | ggtcaaatca | acacttgtgc | 1740 |
| ccgtcgctca | agagctcgtt | gtgcgggagg | ctttga | | | 1776 |

<210> SEQ ID NO 5
<211> LENGTH: 591
<212> TYPE: PRT
<213> ORGANISM: Nannochloropsis oculata

<400> SEQUENCE: 5

Met Thr Thr Thr Val Ile Ser Ser Ser Met Gly Pro Ile Leu Ala Tyr
1               5                   10                  15

Tyr Thr Cys Ala Thr Ile Thr Ile Tyr Val Val Leu Gly Arg Phe Ser
            20                  25                  30

Ser Pro Asn Pro Arg Leu Arg Trp Leu Lys Leu Lys Asp Leu Glu Asn

```
            35                  40                  45
Ile Glu Thr Ala Asn Pro Ala His Pro Ser Glu Ser Asp Ser Met
 50                  55                  60

Pro Leu Asn Ser Gly Asn Leu Ser Ser Lys Pro Ile Ala Ala Ala
 65                  70                  75                  80

Glu Met Leu Gln Thr Pro Ser Ala Ser Ser Ser Pro Ser Ala Ser
                 85                  90                  95

Pro Glu Arg Lys Ala Pro Met Met Arg Lys Leu Ser Phe Leu Ala Thr
                100                 105                 110

Thr Gly Val Ile Glu Asn Pro Phe Met Asn Asn Thr Trp Asp Ile Ser
                115                 120                 125

Arg Leu Glu Arg Val Lys Cys Ala Ile Phe Gly Pro Met Leu Ile Pro
                130                 135                 140

Pro Arg Leu Leu Leu Leu Phe Val Ser Leu Leu Gly Ala Tyr Gly Phe
145                 150                 155                 160

Gly Lys Leu Ser Thr Ile Gly Ala Glu Leu Glu Arg Pro Leu Pro Arg
                165                 170                 175

Trp Arg Ile Asp Leu Gln His Pro Met Lys Phe Phe Ala Arg Gly Ile
                180                 185                 190

Met Phe Ala Leu Gly Tyr His Trp Ile Ser Ile Lys Gly Lys Gln Ala
                195                 200                 205

Ser Pro Gln His Ala Pro Ile Val Val Ser Asn His Cys Ser Phe Cys
210                 215                 220

Glu Ala Ile Tyr Leu Pro Gly Arg Leu Leu Ser Met Ala Val Ser Arg
225                 230                 235                 240

Arg Glu Asn Ala Ala Ile Pro Phe Phe Gly Gly Leu Met Gln Gln Val
                245                 250                 255

Gln Cys Ile Phe Val Ser Arg Thr Asp Lys Asp Ser Arg Thr Thr Val
                260                 265                 270

Ala Asn Glu Ile Leu Arg Arg Ser Lys Ile Glu Arg Gly Gln Trp His
                275                 280                 285

Arg Gln Leu Leu Val Phe Pro Glu Gly Thr Thr Thr Asn Gly Ser Ala
290                 295                 300

Val Ile Ser Phe Lys Val Gly Ser Phe Ala Gly Gly Val Ser Val Gln
305                 310                 315                 320

Pro Val Ala Val Ser Tyr Pro Ser Asn Gln Ile Cys Asp Pro Ser Trp
                325                 330                 335

Val Ser Gly Gly Pro His Pro Gly Glu Ile Leu Phe Lys Leu Leu Cys
                340                 345                 350

Gln Pro Trp Asn Ser Met Asn Val Thr Phe Leu Pro Val Tyr Asn Pro
                355                 360                 365

Asp Ala Glu Ile Asp Asp Pro Val Leu Phe Ser Thr Asn Val Arg
                370                 375                 380

Arg Leu Ile Ala Ala Glu Leu Gly Val Pro Ala Ser Asp His Thr Phe
385                 390                 395                 400

Asp Asp Val Leu Leu Leu Met Glu Ala Lys Lys Leu Gly Tyr Gln Gly
                405                 410                 415

Gly Leu Arg Asp Cys Ile Ser Glu Leu Lys Asn Met Arg Lys Ile Leu
                420                 425                 430

Glu Ile Asp Leu Ala Lys Ala Lys Glu Tyr Leu His Glu Phe Ser Gln
                435                 440                 445

Leu Asp Thr Asn Arg Lys Gly Leu Leu Ser Tyr Pro Gln Phe Ile Lys
                450                 455                 460
```

```
Ala Phe Gly Ser Gln Asp Ser Asp Ala Leu Arg Ser Leu Phe Cys Val
465                 470                 475                 480

Leu Asp Val Gln Asp Arg Gly Val Ile Asn Leu Val Glu Tyr Thr Thr
            485                 490                 495

Gly Leu Ala Leu Leu Asn Glu Gln Gly Thr Asp Gly Phe Asp Gly Ala
                500                 505                 510

Met Arg Leu Ile Phe Lys Val Gln Asp Ser Ser Gly Glu Gly Arg Leu
            515                 520                 525

Ser Lys Glu Asp Thr Ala Lys Val Leu Arg Arg Leu Trp Pro Asp Val
530                 535                 540

Thr Thr Glu Leu Phe Asp Ser Thr Phe Ala Ala Ala Asp Thr Asp Asn
545                 550                 555                 560

Asn Gly Thr Leu Ser Ala Asp Glu Phe Leu Ala Leu Ala Arg Ser Asn
                565                 570                 575

Gln His Leu Cys Pro Ser Leu Lys Ser Ser Leu Cys Gly Arg Leu
                580                 585                 590

<210> SEQ ID NO 6
<211> LENGTH: 2247
<212> TYPE: DNA
<213> ORGANISM: Nannochloropsis oculata

<400> SEQUENCE: 6
aaaaagtttg agattttcag caaagtaatc aagataataa acaaaaacaa tcctataaag      60
gaaaaacaac agggactatt tcgcctcgct cctcacgcct gcccaattag gggaccaacg     120
atcacaacta tgaccacgac tgtcatctct agctcgatgg ggcccatcct ggcctattat     180
acgtgtgcca caatcaccat ctacgtagtg ctcggccgct tttccagtcc aaacccgcgc     240
ttgagatggc tgaagctcaa agacctggag aacattgaga ctgcgaaccc ggccgcgcac     300
ccttcagagt ctgattctat gcctcttaat tctggcaatc tatcgtcttc caagcccatt     360
gccgcagctg agatgcttca aactccctcg gcatcgtcgt cctcgccctc ggcatcccca     420
gagcgcaaag ctcctatgat gcggaagctt cctttctcg ccacgactgg agtcatcgaa     480
aatccctta tgaacaatac ttgggatatc tccaggttgg aacgcgttaa atgtgcgata     540
ttcggtccaa tgctcatccc ccccgtctg ctcctgctct tgtgtcact tcttggtgcc     600
tacgggttcg gcaagctctc taccattggc gcagaactag agcgccctt gcctcgatgg     660
cgcatcgacc tgcagcaccc catgaagttt tttgcccgcg ggattatgtt tgcattgggc     720
taccattgga tctccatcaa aggaaagcaa gcaagcccgc aacacgctcc tatcgttgtc     780
tccaatcatt gctccttctg tgaagccatc tatctgcctg ggcgcctctt gtccatggct     840
gtttcccgcc gggagaatgc cgctatccct tttttggag ggctgatgca acaagtccaa     900
tgcatcttcg tctcgcgcac cgacaaagac tcccggacca ctgtcgccaa cgagatcttg     960
agacgctcca aaatagaaag ggggcagtgg caccgtcaac tcctcgtctt cccagaaggg    1020
accaccacga acgggagtgc cgtgatcagc ttcaaagtcg gctccttttgc cggtggggta    1080
agcgtgcagc cagtcgctgt atcctaccct tccaaccaaa tctgcgatcc atcatgggtc    1140
agtggtgggc cgcatcccgg cgagattctg tttaaattgc tgtgtcagcc atggaacagt    1200
atgaatgtta ctttcctgcc tgtgtataat cccgacgccg ctgaaattga tgatcccgtg    1260
ctgtttagca caaatgtcag gcggttgata gccgcagagt gggcgtgcc tgccagtgat    1320
cacacattcg atgacgtttt gttgttaatg gaggcaaaga agctagggta ccaggggggt    1380
```

```
cttcgtgatt gcatctctga gctgaaaaat atgcgaaaga ttctagaaat tgacctggca      1440
aaagcgaaag aatatttgca tgaatttttct cagcttgaca caaacaggaa ggggctgtta     1500
tcataccccc aattcattaa agccttcggc tcgcaggatt cagacgcact tcggagtcta      1560 tttttgtgtgt tagacgtgca agatcgggga gtgatcaatt tggtggagta caccacaggg    1620
ttagcactgt tgaatgagca aggcaccgat ggttttgatg gggccatgcg cttgattttc      1680
aaagttcaag attcgagtgg ggaggggcgg ctgtcgaagg aagacacggc aaaggtgctg     1740
cggcggctgt ggcctgacgt gacgacggag ctgttcgact cgacgtttgc tgcggcggac     1800
acagataata acgggacgtt gagcgctgat gagtttctgg cgttggcgag gtcaaatcaa     1860
cacttgtgcc cgtcgctcaa gagctcgttg tgcgggaggc tttgagtaaa tgttttatgc     1920
tgcatgtttt ataagaagca tgtatgtgaa aatgtaaata gattagacct ggtgtagatt     1980
ggctaggagt ttaataggca aggcttcatg tcgaaaaaaa atgtgccgcg attaaagtga     2040
ggaaaacaca ctcattttctt tacacaattt ggaacacttt gttcctctat ttcgcataaa    2100
acagcgacca gcaattcaac cgcacgagcg tctcatagca ccaaaccttc ctgttcatcc     2160
ctccaacctt cctcctcccc ccttcgcccct tctgtctctc cactttcatt ccctcccaac    2220
catttactca tgcaatcctc tcggcct                                         2247
```

<210> SEQ ID NO 7
<211> LENGTH: 1134
<212> TYPE: DNA
<213> ORGANISM: Thraustochytrium aureum

<400> SEQUENCE: 7

```
atggagggca tcgagtcgat agtggacgac gacttttgga agtgcttcca gagccggaaa     60
ccgcgaccct ggaactggaa tgcctacttg tggccgctgt gggctgcggg tgtctttatc    120
cggtactttg tccttttccc gatccggctt gcgattttg cgatgggctg gattctgttc     180
ggaatcggga tgttggtcac gcaaacctgc tttccgcacg ggccgcgtcg cacctcgctt    240
gagcacggac tgatctcgat gatgtgcggc gtgttctgta tcacctgggg gcggtcatc     300 cggtaccacg ggtcgccggt caagccgcga gagggcgagt gccagcccgt gtacgttgcc    360
aaccacactt cgatgatcga cgtcatcatc ttgcagcaga tgcgctgctt ttcgctcgtg    420
ggccagcgcc acaaaggcat cgtgcggttt ttgcaagagg tcgtgctggg ctgtttgcag    480
tgcgtctggt tcgaccgcgg cgagatcaag acagggcag ccgtggcgcg caagctcaac     540
gagcatgcga acgacccgac tcgcaacccg ctgctcgtgt ttccggaggg aacgtgcgtg    600
aacaatgagt acgtgatcca gttcaagaag gcatctttg agatcggcgc ccccgtggtc    660
ccagtcgcca tcaagtacaa caaaatgttc gtggaccccgt tctggaactc gcgcgcgcag   720
tcgttcccga tgcacctcgt agagctcatg acctcgtggt gcctcatttg cgaggtttgg    780
tacctcaagc cgctcgagcg catggagcgc gagtcgtcca ccgatttgc agcacgcgtg     840 aagaaggcga ttgcggacca ggccggcctt aagaacgtca actgggacgg ctacatgaag    900
tattggaagc catcggagcg ttacttgcgc gcgcgccagg cgatcttcgc caaaactctc    960
cgcaaaatcc actcgcgctc tttggagcag gacaaggctg accggcaggc cattctgcac    1020
gacctggacg gcgcgttccc ggattctggg acacaccgcg gcgagcgcga gtcgccaaga   1080
gagccgggtc tgcggcgccg ccaggcggcc tccgcgccgg agaagccctt atag          1134
```

<210> SEQ ID NO 8
<211> LENGTH: 377

<212> TYPE: PRT
<213> ORGANISM: Thraustochytrium aureum

<400> SEQUENCE: 8

Met Glu Gly Ile Glu Ser Ile Val Asp Asp Asp Phe Trp Lys Cys Phe
1               5                   10                  15

Gln Ser Arg Lys Pro Arg Pro Trp Asn Trp Asn Ala Tyr Leu Trp Pro
            20                  25                  30

Leu Trp Ala Ala Gly Val Phe Ile Arg Tyr Phe Val Leu Phe Pro Ile
        35                  40                  45

Arg Leu Ala Ile Phe Ala Met Gly Trp Ile Leu Phe Gly Ile Gly Met
    50                  55                  60

Leu Val Thr Gln Thr Cys Phe Pro His Gly Pro Arg Arg Thr Ser Leu
65                  70                  75                  80

Glu His Gly Leu Ile Ser Met Met Cys Gly Val Phe Cys Ile Thr Trp
                85                  90                  95

Gly Ala Val Ile Arg Tyr His Gly Ser Pro Val Lys Pro Arg Glu Gly
            100                 105                 110

Glu Cys Gln Pro Val Tyr Val Ala Asn His Thr Ser Met Ile Asp Val
        115                 120                 125

Ile Ile Leu Gln Gln Met Arg Cys Phe Ser Leu Val Gly Gln Arg His
    130                 135                 140

Lys Gly Ile Val Arg Phe Leu Gln Glu Val Val Leu Gly Cys Leu Gln
145                 150                 155                 160

Cys Val Trp Phe Asp Arg Gly Glu Ile Lys Asp Arg Ala Ala Val Ala
                165                 170                 175

Arg Lys Leu Asn Glu His Ala Asn Asp Pro Thr Arg Asn Pro Leu Leu
            180                 185                 190

Val Phe Pro Glu Gly Thr Cys Val Asn Asn Glu Tyr Val Ile Gln Phe
        195                 200                 205

Lys Lys Gly Ile Phe Glu Ile Gly Ala Pro Val Val Pro Val Ala Ile
    210                 215                 220

Lys Tyr Asn Lys Met Phe Val Asp Pro Phe Trp Asn Ser Arg Ala Gln
225                 230                 235                 240

Ser Phe Pro Met His Leu Val Glu Leu Met Thr Ser Trp Cys Leu Ile
                245                 250                 255

Cys Glu Val Trp Tyr Leu Lys Pro Leu Glu Arg Met Glu Arg Glu Ser
            260                 265                 270

Ser Thr Asp Phe Ala Ala Arg Val Lys Lys Ala Ile Ala Asp Gln Ala
        275                 280                 285

Gly Leu Lys Asn Val Asn Trp Asp Gly Tyr Met Lys Tyr Trp Lys Pro
    290                 295                 300

Ser Glu Arg Tyr Leu Arg Ala Arg Gln Ala Ile Phe Ala Lys Thr Leu
305                 310                 315                 320

Arg Lys Ile His Ser Arg Ser Leu Glu Gln Asp Lys Ala Asp Arg Gln
                325                 330                 335

Ala Ile Leu His Asp Leu Asp Gly Ala Phe Pro Asp Ser Gly Thr His
            340                 345                 350

Arg Gly Glu Arg Glu Ser Pro Arg Glu Pro Gly Leu Arg Arg Arg Gln
        355                 360                 365

Ala Ala Ser Ala Pro Gly Glu Ala Leu
    370                 375

<210> SEQ ID NO 9

<211> LENGTH: 1288
<212> TYPE: DNA
<213> ORGANISM: Thraustochytrium aureum

<400> SEQUENCE: 9

```
atggagggca tcgagtcgat agtggacgac gacttttgga agtgcttcca gagccggaaa      60
ccgcgaccct ggaactggaa tgcctacttg tggccgctgt gggctgcggg tgtctttatc     120
cggtactttg tccttttccc gatccggctt gcgattttg cgatgggctg gattctgttc      180
ggaatcggga tgttggtcac gcaaacctgc tttccgcacg gccgcgtcg cacctcgctt      240
gagcacggac tgatctcgat gatgtgcggc gtgttctgta tcacctgggg ggcggtcatc     300
cggtaccacg ggtcgccggt caagccgcga gagggcgagt gccagcccgt gtacgttgcc    360
aaccacactt cgatgatcga cgtcatcatc ttgcagcaga tgcgctgctt ttcgctcgtg    420
ggccagcgcc acaaaggcat cgtgcggttt ttgcaagagg tcgtgctggg ctgtttgcag    480
tgcgtctggt tcgaccgcgg cgagatcaag gacagggcag ccgtggcgcg caagctcaac    540
gagcatgcga acgacccgac tcgcaacccg ctgctcgtgt tccggaggg aacgtgcgtg    600
aacaatgagt acgtgatcca gttcaagaag ggcatctttg agatcggcgc ccccgtggtc    660
ccagtcgcca tcaagtacaa caaaatgttc gtggacccgt ctggaactc gcgcgcgcag     720
tcgttcccga tgcacctcgt agagctcatg acctcgtggt gcctcatttg cgaggtttgg   780
tacctcaagc cgctcgagcg catggagcgc gagtcgtcca ccgattttgc agcacgcgtg    840
aagaaggcga ttgcggacca ggccggcctt aagaacgtca actgggacgg ctacatgaag    900
tattggaagc atcggagcg ttacttgcgc gcgcgccagg cgatcttcgc caaaactctc    960
cgcaaaatcc actcgcgctc tttggagcag acaaggctg accggcaggc cattctgcac    1020
gacctggacg gcgcgttccc ggattctggg acacaccgcg gcgagcgcga gtcgccaaga    1080
gagccgggtc tgcggcgccg ccaggcggcc tccgcgccgg agaagccctt atagcggcgt   1140
ttgccttgca cgctgatcaa cgtggggcat gtgggtgctc tgtggccaag agcaggccgt    1200
gcgctcggca ctgcagcgct acgctcagac ttttcgcggt ggggcatgca tgcatccaaa    1260
catttcttc cttcttccaa aaaaaaaa                                        1288
```

<210> SEQ ID NO 10
<211> LENGTH: 1284
<212> TYPE: DNA
<213> ORGANISM: Nannochloropsis oculata

<400> SEQUENCE: 10

```
atgaagacgc ccacgagcct ggcgtgcgga gcctgcacgg cagccgtgtt aatgtgtttc     60
acaacaacag cagatgccct tgccagcaca tcacaaccgg gcagcgttgg cgtggctgtc   120
gcgcggcggc caccaggctt ccactcgata gggcgatcat cagccacgac taggagaata   180
agcaggggag ggatagagga tctcggaacc catcacacgt ggggcggcag gatgtcgcag   240
cagcaccagc agcaccagca gcaccagcag caccgtcggc gtaggaggac acccactatg   300
ctagtggaga cagacgtgaa ggtaaaagag gaagcgggga ttggccacgg atcaggaagc   360
aacgaaagtg gcaacaggag cggcaagagc gggtctgcgg cggcagacgc ctcagaaggt   420
acaggcccac cgccagtgcc cgtggatacc ttccggcaca agagcttggc ggaggtcccg   480
acggactatg gacccctacct gaccattaaa gggttcaaga tcaatgcctt tggcttctat    540
ttctgcttcg tggccctatt ctgggcgatc ccctgggggtg tcttcctcat cctgtacaag    600
gcgagtttgg agttcatgga caagatcgat cctcgccggt acaacgtgga ccgctccagt   660
```

```
tccctatggg gctggctgac cagtatcagt actgactcct tacccgacat tacgggcatg    720
gagaacattc ccaagggacc ggcggtcttc gtcgccaacc acgcctcctg gatggacgtg    780
ccctacactg cccaactgcc catccgcgcc aagtacctag cgaaagctga cctggccaag    840
atcccaatcc tgggcaacgc catgagcatg gctcagcacg tcctcctcga tcgagacgac    900
aagcgcagtc aaatggaagc cctgcgctct gctctcctga tcctcaagac aggcaccccc    960
atcttcgtct ccccgaggg cacccgtggg cctcaaggcc gaatgcagac ctttaagatg   1020
ggtgcattca aggtggcgac caaggcgggc gtgcctatag tgcctgtatc tatcgcgggg   1080
acgcatgtca tgatgcccaa ggaggtgatc atgcctcaat gtgctggccg gggaatcacc   1140
gccattcatg tccaccctcc catctccatc aagggccgca cggaccagga gctgtcggat   1200
ctggcgtttg atactattaa caatgcattg tcagatgagc agcgggctat gcctagcagg   1260
aagaaggacg attcgagagc ttaa                                          1284

<210> SEQ ID NO 11
<211> LENGTH: 427
<212> TYPE: PRT
<213> ORGANISM: Nannochloropsis oculata

<400> SEQUENCE: 11

Met Lys Thr Pro Thr Ser Leu Ala Cys Gly Ala Cys Thr Ala Ala Val
1               5                  10                  15

Leu Met Cys Phe Thr Thr Thr Ala Asp Ala Leu Ala Ser Thr Ser Gln
            20                  25                  30

Pro Gly Ser Val Gly Val Ala Ala Arg Arg Pro Gly Phe His
        35                  40                  45

Ser Ile Gly Arg Ser Ser Ala Thr Thr Arg Arg Ile Ser Arg Gly Gly
    50                  55                  60

Ile Glu Asp Leu Gly Thr His His Thr Trp Gly Gly Arg Met Ser Gln
65                  70                  75                  80

Gln His Gln Gln His Gln Gln His Gln Gln His Arg Arg Arg Arg Arg
                85                  90                  95

Thr Pro Thr Met Leu Val Glu Thr Asp Val Lys Val Lys Glu Glu Ala
            100                 105                 110

Gly Ile Gly His Gly Ser Gly Ser Asn Glu Ser Gly Asn Arg Ser Gly
        115                 120                 125

Lys Ser Gly Ser Ala Ala Ala Asp Ala Ser Glu Gly Thr Gly Pro Pro
    130                 135                 140

Pro Val Pro Val Asp Thr Phe Arg His Lys Ser Leu Ala Glu Val Pro
145                 150                 155                 160

Thr Asp Tyr Gly Pro Tyr Leu Thr Ile Lys Gly Phe Lys Ile Asn Ala
                165                 170                 175

Phe Gly Phe Tyr Phe Cys Phe Val Ala Leu Phe Trp Ala Ile Pro Trp
            180                 185                 190

Gly Val Phe Leu Ile Leu Tyr Lys Ala Ser Leu Glu Phe Met Asp Lys
        195                 200                 205

Ile Asp Pro Arg Arg Tyr Asn Val Asp Arg Ser Ser Leu Trp Gly
    210                 215                 220

Trp Leu Thr Ser Ile Ser Thr Asp Ser Leu Pro Asp Ile Thr Gly Met
225                 230                 235                 240

Glu Asn Ile Pro Lys Gly Pro Ala Val Phe Val Ala Asn His Ala Ser
                245                 250                 255
```

```
Trp Met Asp Val Pro Tyr Thr Ala Gln Leu Pro Ile Arg Ala Lys Tyr
            260                 265                 270

Leu Ala Lys Ala Asp Leu Ala Lys Ile Pro Ile Leu Gly Asn Ala Met
        275                 280                 285

Ser Met Ala Gln His Val Leu Leu Asp Arg Asp Asp Lys Arg Ser Gln
    290                 295                 300

Met Glu Ala Leu Arg Ser Ala Leu Leu Ile Leu Lys Thr Gly Thr Pro
305                 310                 315                 320

Ile Phe Val Phe Pro Glu Gly Thr Arg Gly Pro Gln Gly Arg Met Gln
                325                 330                 335

Thr Phe Lys Met Gly Ala Phe Lys Val Ala Thr Lys Ala Gly Val Pro
            340                 345                 350

Ile Val Pro Val Ser Ile Ala Gly Thr His Val Met Met Pro Lys Glu
        355                 360                 365

Val Ile Met Pro Gln Cys Ala Gly Arg Gly Ile Thr Ala Ile His Val
    370                 375                 380

His Pro Pro Ile Ser Ile Lys Gly Arg Thr Asp Gln Glu Leu Ser Asp
385                 390                 395                 400

Leu Ala Phe Asp Thr Ile Asn Asn Ala Leu Ser Asp Glu Gln Arg Ala
                405                 410                 415

Met Pro Ser Arg Lys Lys Asp Asp Ser Arg Ala
            420                 425
```

<210> SEQ ID NO 12
<211> LENGTH: 1826
<212> TYPE: DNA
<213> ORGANISM: Nannochloropsis oculata

<400> SEQUENCE: 12

```
aagataataa caaaaacaat cctctaaaag gaaaacaaca ggtgtacaat tccaggacag      60
acgacaagtg attcatgaag acgcccacga gcctggcgtg cggagcctgc acggcagccg     120
tgttaatgtg tttcacaaca acagcagatg cccttgccag cacatcacaa ccgggcagcg     180
ttggcgtggc tgtcgcgcgg cggccaccag gcttccactc gatagggcga tcatcagcca     240
cgactaggag aataagcagg ggagggatag aggatctcgg aacccatcac acgtggggcg     300
gcaggatgtc gcagcagcac cagcagcacc agcagcacca gcagcaccgt cggcgtagga     360
ggacacccac tatgctagtg gagacagacg tgaaggtaaa agaggaagcg gggattggcc     420
acggatcagg aagcaacgaa agtggcaaca ggagcggcaa gagcgggtct gcggcggcag     480
acgcctcaga aggtacaggc ccaccgccag tgcccgtgga taccttccgg cacaagagct     540
tggcggaggt cccgacggac tatggaccct acctgaccat taagggttc aagatcaatg      600
cctttggctt ctatttctgc ttcgtggccc tattctgggc gatcccctgg ggtgtcttcc     660
tcatcctgta caaggcgagt ttggagttca tggacaagat cgatcctcgc ggtacaacg      720
tggaccgctc cagttccta tggggctggc tgaccagtat cagtactgac tccttacccg      780
acattacggg catggagaac attcccaagg gaccggcggt cttcgtcgcc aaccacgcct     840
cctggatgga cgtgccctac actgcccaac tgcccatccg cgccaagtac ctagcgaaag     900
ctgacctggc caagatccca atcctgggca acgccgtgag catggctcag cacgtcctcc     960
tcgatcgaga cgacaagcgc agtcaaatgg aagccctgcg ctctgctctc ctgatcctca    1020
agacaggcac ccccatcttc gtcttccccg agggcacccg tgggcctcaa ggccgaatgc    1080
agacctttaa gatgggtgca ttcaaggtgg cgaccaaggc gggcgtgcct atagtgcctg    1140
```

```
tatctatcgc ggggacgcat gtcatgatgc ccaaggaggt gatcatgcct caatgtgctg    1200
gccggggaat caccgccatt catgtccacc ctcccatctc catcaagggc cgcacggacc    1260
aggagctgtc ggatctggcg tttgatacta ttaacaatgc attgtcagat gagcagcggg    1320
ctatgcctag caggaagaag gacgattcga gagcttaaga agaaggaaaa gagaagatgt    1380
gaaggaatga ggtgaaggca tgtcaacaat aggagataga gatcatgaag agatgagagc    1440
gagggaatca aaacccgttc agtaagccct gtgtagatca tatgcaggaa aagtgagcaa    1500
caggagcggc aggagaagca gttgggcgca tcgagaaaga caattaccaa gcaggaggca    1560
ataaaaggca attatcgaat agatttggag cgggggggtca gcgcacagcc gaacaagatg    1620
ccgtgtgctt agcagcagca gaatccgacc atagcgtaaa cctcacgaat gtttgtggtg    1680
agaagatggc aaatcaaatt cttcatcgtt tgtttgcaat tggtgatgca tgagattcct    1740
atagaccaga gagactggga agcttcacct ggagtaacag aaagaaagac taacagacga    1800
caacaaaaaa aaaaaaaaaa aaaaaa                                         1826

<210> SEQ ID NO 13
<211> LENGTH: 1395
<212> TYPE: DNA
<213> ORGANISM: Nannochloropsis oculata

<400> SEQUENCE: 13
atggtcagga ggaagatgga cgtggacagc tcggccgccg gcgaagcggc gtcagctacg      60
agcaacggcg ccaacgtccc gtcgtccacc tcctctacag cctccgcttc ttcctcctcc     120
aaaggcaccc tacccgcacg tgtccaggcc ctgcaaacga aggccgccac attgcctcag     180 ccttttatcga atgtggcaaa acgcgccttg tactacgagg cggaaatgct ctggcaatca     240
atcaaggatg agctgcccgc cgagcacccg gaccaggcct cttttacttgc ggcaatcgac     300 cagttcgaga ccaaccttct acgcatcagt cccgctcagc tcgccaccac ctctttacga     360
cggatcctac aacaactcga catgctcctg cgaatcatta cttgctccct ctacctctgc     420
cttctagggg tcatcacatt tttgcccatg atcactctcg ttcccatcct cgaccgcctc     480
ctcgtaatcc tgggctggcc ccgtcgtttc ctcatctacg aactggccaa aaaggcatct     540
gcacgtggat ttctctacct ggccggtgtt ttctacacgg aagaagggaa gcaagccaat     600
gggtatgaaa ccccccttgt cctcctcttt caacacggct cgaaccttga tggcttcttg     660
atcttggatt ccttttcctca attctttaaa tcaatcggga agacgacat cttttctcatg     720 ccttacgtag ggtggatggc atatgtgtac ggcattctac ctatcgaccg caagcatcgt     780
aacgaagcaa tcaaacagct aggacgagcc accgcgtct gtacctctgg tgtggccgtc     840
gctctttccc ccgaggggac acgtagcaag accggacaat tgatgcgatt caagaaaggg     900 ccgtttttact tacaagccga gacatcggct actgtcaccc ctcttgtcat cgttggaaat     960
tacgagttgt ggcctccaaa ctatttcttt acctgtcctg gcaggtggt gatgaggtat    1020 ctccccccca ttgaccattc ctccctccct ccctcggttg gtcggaacaa agacgagttc    1080
agtcgatatg tgcgcaagca gatgtttgag gccattgatg atatcatggc tggttccgag    1140
gagggaggga aggaggtagg ggagaagagg aaaaaatatg cgccgggggg gaaattgacc    1200
tggtggttgc ggggagtgaa tttggcatgc atgtgcctgt tttggttgat ggtaaaggcg    1260
gcgtggatgg tggtaacggg ggtgagtgac gcgtatgggt tcagtagggg ggcgttggcg    1320 ggggattcg ttgcatacac ggtgagtgtg actgctggcc tgtatatatt gtactgcaag    1380
gcgccggcgt cgtga                                                   1395
```

<210> SEQ ID NO 14
<211> LENGTH: 464
<212> TYPE: PRT
<213> ORGANISM: Nannochloropsis oculata

<400> SEQUENCE: 14

```
Met Val Arg Arg Lys Met Asp Val Asp Ser Ser Ala Ala Gly Glu Ala
1               5                   10                  15

Ala Ser Ala Thr Ser Asn Gly Ala Asn Val Pro Ser Thr Ser Ser
            20                  25                  30

Thr Ala Ser Ala Ser Ser Ser Lys Gly Thr Leu Pro Ala Arg Val
            35                  40                  45

Gln Ala Leu Gln Thr Lys Ala Ala Thr Leu Pro Gln Pro Leu Ser Asn
    50                  55                  60

Val Ala Lys Arg Ala Leu Tyr Tyr Glu Ala Glu Met Leu Trp Gln Ser
65                  70                  75                  80

Ile Lys Asp Glu Leu Pro Ala Glu His Pro Asp Gln Ala Ser Leu Leu
                85                  90                  95

Ala Ala Ile Asp Gln Phe Glu Thr Asn Leu Leu Arg Ile Ser Pro Ala
            100                 105                 110

Gln Leu Ala Thr Thr Ser Leu Arg Arg Ile Leu Gln Gln Leu Asp Met
        115                 120                 125

Leu Leu Arg Ile Ile Thr Cys Ser Leu Tyr Leu Cys Leu Leu Gly Val
    130                 135                 140

Ile Thr Phe Leu Pro Met Ile Thr Leu Val Pro Ile Leu Asp Arg Leu
145                 150                 155                 160

Leu Val Ile Leu Gly Trp Pro Arg Arg Phe Leu Ile Tyr Glu Leu Ala
                165                 170                 175

Lys Lys Ala Ser Ala Arg Gly Phe Leu Tyr Leu Ala Gly Val Phe Tyr
            180                 185                 190

Thr Glu Glu Gly Lys Gln Ala Asn Gly Tyr Glu Thr Pro Leu Val Leu
        195                 200                 205

Leu Phe Gln His Gly Ser Asn Leu Asp Gly Phe Leu Ile Leu Asp Ser
    210                 215                 220

Phe Pro Gln Phe Phe Lys Ser Ile Gly Lys Asp Asp Ile Phe Leu Met
225                 230                 235                 240

Pro Tyr Val Gly Trp Met Ala Tyr Val Tyr Gly Ile Leu Pro Ile Asp
                245                 250                 255

Arg Lys His Arg Asn Glu Ala Ile Lys Gln Leu Gly Arg Ala Thr Arg
            260                 265                 270

Val Cys Thr Ser Gly Val Ala Val Ala Leu Ser Pro Glu Gly Thr Arg
        275                 280                 285

Ser Lys Thr Gly Gln Leu Met Arg Phe Lys Lys Gly Pro Phe Tyr Leu
    290                 295                 300

Gln Ala Glu Thr Ser Ala Thr Val Thr Pro Leu Val Ile Val Gly Asn
305                 310                 315                 320

Tyr Glu Leu Trp Pro Pro Asn Tyr Phe Phe Thr Cys Pro Gly Gln Val
                325                 330                 335

Val Met Arg Tyr Leu Pro Pro Ile Asp His Ser Ser Leu Pro Pro Ser
            340                 345                 350

Val Gly Arg Asn Lys Asp Glu Phe Ser Arg Tyr Val Arg Lys Gln Met
        355                 360                 365

Phe Glu Ala Ile Asp Asp Ile Met Ala Gly Ser Glu Glu Gly Gly Lys
```

```
                370              375              380
Glu Val Gly Glu Lys Arg Lys Tyr Ala Pro Gly Gly Lys Leu Thr
385              390              395              400

Trp Trp Leu Arg Gly Val Asn Leu Ala Cys Met Cys Leu Phe Trp Leu
             405              410              415

Met Val Lys Ala Ala Trp Met Val Val Thr Gly Val Ser Asp Ala Tyr
                 420              425              430

Gly Phe Ser Arg Gly Ala Leu Ala Gly Gly Phe Val Ala Tyr Thr Val
             435              440              445

Ser Val Thr Ala Gly Leu Tyr Ile Leu Tyr Cys Lys Ala Pro Ala Ser
                 450              455              460

<210> SEQ ID NO 15
<211> LENGTH: 1771
<212> TYPE: DNA
<213> ORGANISM: Nannochloropsis oculata

<400> SEQUENCE: 15
```

| | | | | | |
|---|---|---|---|---|---|
| atttttcagc | aaagtaatca | agataataaa | caaaaacaat | cctataaagg | aaaaacaaca | 60 |
| ggacaaatca | atggtcagga | ggaagatgga | cgtggacagc | tcggccgccg | gcgaagcggc | 120 |
| gtcagctacg | agcaacggcg | ccaacgtccc | gtcgtccacc | tcctctacag | cctccgcttc | 180 |
| ttcctcctcc | aaaggcaccc | tacccgcacg | tgtccaggcc | ctgcaaacga | aggccgccac | 240 |
| attgcctcag | cctttatcga | atgtggcaaa | acgcgccttg | tactacgagg | cggaaatgct | 300 |
| ctggcaatca | atcaaggatg | agctgcccgc | cgagcacccg | gaccaggcct | ctttacttgc | 360 |
| ggcaatcgac | cagttcgaga | ccaaccttct | acgcatcagt | cccgctcagc | tcgccaccac | 420 |
| ctctttacga | cggatcctac | aacaactcga | catgctcctg | cgaatcatta | cttgctccct | 480 |
| ctacctctgc | cttctagggg | tcatcacatt | tttgcccatg | atcactctcg | ttcccatcct | 540 |
| cgaccgcctc | ctcgtaatcc | tgggctggcc | ccgtcgtttc | ctcatctacg | aactggccaa | 600 |
| aaaggcatct | gcacgtggat | ttctctacct | ggccggtgtt | ttctacacgg | aagaagggaa | 660 |
| gcaagccaat | gggtatgaaa | ccccccttgt | cctcctcttt | caacacggct | cgaaccttga | 720 |
| tggcttcttg | atcttggatt | cctttcctca | attcttaaa | tcaatcggga | aagacgacat | 780 |
| cttttctcatg | ccttacgtag | ggtggatggc | atatgtgtac | ggcattctac | ctatcgaccg | 840 |
| caagcatcgt | aacgaagcaa | tcaaacagct | aggacgagcc | acccgcgtct | gtacctctgg | 900 |
| tgtggccgtc | gctctttccc | ccgaggggac | acgtagcaag | accggacaat | tgatgcgatt | 960 |
| caagaaaggg | ccgtttttact | tacaagccga | gacatcggct | actgtcaccc | ctcttgtcat | 1020 |
| cgttggaaat | tacgagttgt | ggcctccaaa | ctatttcttt | acctgtcctg | ggcaggtggt | 1080 |
| gatgaggtat | ctccccccca | ttgaccattc | ctccctccct | ccctcggttg | gtcggaacaa | 1140 |
| agacgagttc | agtcgatatg | tgcgcaagca | gatgtttgag | gccattgatg | atatcatggc | 1200 |
| tggttccgag | gagggaggga | aggaggtagg | ggagaagagg | aaaaaatatg | cgccgggggg | 1260 |
| gaaattgacc | tggtggttgc | ggggagtgaa | tttggcatgc | atgtgcctgt | tttggttgat | 1320 |
| ggtaaaggcg | gcgtggatgg | tggtaacggg | ggtgagtgac | gcgtatgggt | tcagtagggg | 1380 |
| ggcgttggcg | gggggattcg | ttgcatacac | ggtgagtgtg | actgctggcc | tgtatatatt | 1440 |
| gtactgcaag | gcgccggcgt | cgtgagaggg | gggaagggag | gggggaagga | gagatagaag | 1500 |
| acgaggtaga | ggtagatgtg | agtgtgagat | agcgcgagta | ttatcttgaa | gaaaagagat | 1560 |
| gaattgtagt | agaagagtcg | ggtatttag | cagggagaga | atattgtatg | gagggtaaac | 1620 | gtgtgggaaa gaggagggag ggacctgaga tggataatga agaatactga gagagagcgc     1680 gtgacacgtt cattgcttcc tcggattagt tgcctgtgca taagttaaag ataatagaga     1740 ggaatggcgc tcgcatgctc ctctttacac t                                    1771

<210> SEQ ID NO 16
<211> LENGTH: 1026
<212> TYPE: DNA
<213> ORGANISM: Nannochloropsis oculata

<400> SEQUENCE: 16
atggcaccct ccccaccggc cccgccacct gcacccgaga accctacaa cctattgcca       60 cccaagcgcc ccaatccgca gtactggcgg tatgcaagcc ttgccgcctt ccttctcact     120
tgcttcctgg cccctccag taactcgtgg gccaccaccc tccgccgcgc ctgctgggcg     180
gcgtactgga cgacctacct ggacacaagc tataaggacg gctcacgggc ctggccctgg     240
tttcagcgat tgcgaatctg gcgtatgtat tgcggctatt tgcagggcaa agtcatttgc     300
acggtgccct tggacccggc gcagcaattt atcttcgcgg cccatcccca cggcattggt     360
acctggaacc atttcctgac catgactgac ggctgtcgat ttctctcctc ctcctacccc     420
cgcccgcggc tcgacctggg tgcgacagta cttttcttca tccccttctt aaaggaaatt     480
ctgctttggc taggctgtgt ggatgctgga gcggccacgg ctcatgcggt tttggcgcgg     540
ggctactcct ccctcattta catcggtgga gaaaaagagc agatttggac acggcgaggc     600
aaagacatcg tggtggtacg tccccgcaag ggttttttgca agctggccct ccagcataac     660
tgccccatct accggtcta cgcatttggg gaaaacgatc tgtatcgcac gttcaaccac     720
ctcaaggact ccagctgtg ggtggctagc gccttcaagc tcgcttttcc tccttgttgg     780
ggcgtcctct tcctcccctt cctcccccctc ccgtctcta tcacggtggt gatgggcgag     840
cccttgctac ccagagcaca aaaggaagt gcgagaagga gtggtggagg aaaagggtg     900 gagccgacga gggaggaggt ggaggagctg cacttccgat acgtggaggc cttgcagaag     960
ttgtttgacg cacacaaagt caggcaggga gggaggagcg aagaggccac cttagtggtc    1020
aaatga                                                              1026

<210> SEQ ID NO 17
<211> LENGTH: 341
<212> TYPE: PRT
<213> ORGANISM: Nannochloropsis oculata

<400> SEQUENCE: 17

Met Ala Pro Ser Pro Ala Pro Pro Ala Pro Glu Asn Pro Tyr
1               5                   10                  15

Asn Leu Leu Pro Pro Lys Arg Pro Asn Pro Gln Tyr Trp Arg Tyr Ala
                20                  25                  30

Ser Leu Ala Ala Phe Leu Leu Thr Cys Phe Leu Ala Pro Ser Ser Asn
            35                  40                  45

Ser Trp Ala Thr Thr Leu Arg Arg Ala Cys Trp Ala Ala Tyr Trp Thr
        50                  55                  60

Thr Tyr Leu Asp Thr Ser Tyr Lys Asp Gly Ser Arg Ala Trp Pro Trp
65                  70                  75                  80

Phe Gln Arg Leu Arg Ile Trp Arg Met Tyr Cys Gly Tyr Leu Gln Gly
                85                  90                  95

Lys Val Ile Cys Thr Val Pro Leu Asp Pro Ala Gln Gln Phe Ile Phe
            100                 105                 110

```
Ala Ala His Pro His Gly Ile Gly Thr Trp Asn His Phe Leu Thr Met
        115                 120                 125

Thr Asp Gly Cys Arg Phe Leu Ser Ser Tyr Pro Arg Pro Arg Leu
    130                 135                 140

Asp Leu Gly Ala Thr Val Leu Phe Phe Ile Pro Phe Leu Lys Glu Ile
145                 150                 155                 160

Leu Leu Trp Leu Gly Cys Val Asp Ala Gly Ala Thr Ala His Ala
                165                 170                 175

Val Leu Ala Arg Gly Tyr Ser Ser Leu Ile Tyr Ile Gly Gly Lys
            180                 185                 190

Glu Gln Ile Trp Thr Arg Arg Gly Lys Asp Ile Val Val Arg Pro
        195                 200                 205

Arg Lys Gly Phe Cys Lys Leu Ala Leu Gln His Asn Cys Pro Ile Val
    210                 215                 220

Pro Val Tyr Ala Phe Gly Glu Asn Asp Leu Tyr Arg Thr Phe Asn His
225                 230                 235                 240

Leu Lys Asp Phe Gln Leu Trp Val Ala Ser Ala Phe Lys Leu Ala Phe
                245                 250                 255

Pro Pro Cys Trp Gly Val Leu Phe Leu Pro Phe Leu Pro Leu Pro Val
                260                 265                 270

Ser Ile Thr Val Val Met Gly Glu Pro Leu Leu Pro Arg Ala Gln Lys
            275                 280                 285

Gly Ser Ala Arg Arg Ser Gly Gly Lys Gly Val Glu Pro Thr Arg
        290                 295                 300

Glu Glu Val Glu Glu Leu His Phe Arg Tyr Val Glu Ala Leu Gln Lys
305                 310                 315                 320

Leu Phe Asp Ala His Lys Val Arg Gln Gly Gly Arg Ser Glu Ala
                325                 330                 335

Thr Leu Val Val Lys
            340

<210> SEQ ID NO 18
<211> LENGTH: 1100
<212> TYPE: DNA
<213> ORGANISM: Nannochloropsis oculata

<400> SEQUENCE: 18
attttcagca aagtaatcaa gataataaac aaaaacaatc ctataaagga aaaacaacag      60
aacgatggca ccctccccac cggccccgcc acctgcaccc gagaacccct acaacctatt     120
gccacccaag cgcccaatc cgcagtactg gcggtatgca agccttgccg ccttccttct      180
cacttgcttc ctggcccctt ccagtaactc gtgggccacc accctccgcc gcgcctgctg     240
ggcggcgtac tggacgacct acctggacac aagctataag gacggctcac gggcctggcc     300
ctggtttcag cgattgcgaa tctggcgtat gtattgcggc tatttgcagg gcaaagtcat     360
ttgcacggtg cccttggacc cggcgcagca atttatcttc gcggcccatc ccacggcat      420 tggtacctgg aaccatttcc tgaccatgac tgacggctgt cgatttctct cctcctccta     480
cccccgcccg cggctcgacc tgggtgcgac agtacttttc ttcatcccct tcttaaagga     540
aattctgctt tggctaggct gtgtggatgc tggagcggcc acggctcatg cggttttggc     600
gcggggctac tcctcccctca tttacatcgg tggagaaaaa gagcagattt ggacacggcg     660
aggcaaagac atcgtggtgg tacgtccccg caagggtttt tgcaagctgg ccctccagca     720
taactgcccc atcgtaccgg tctacgcatt tggggaaaac gatctgtatc gcacgttcaa     780
```

```
ccacctcaag gacttccagc tgtgggtggc tagcgccttc aagctcgctt ttcctccttg      840
ttggggcgtc ctcttcctcc ccttcctccc cctccccgtc tctatcacgg tggtgatggg      900
cgagcccttg ctacccagag cacaaaaagg aagtgcgaga aggagtggtg gaggaaaagg      960
ggtggagccg acgagggagg aggtggagga gctgcacttc cgatacgtgg aggccttgca     1020
gaagttgttt gacgcacaca aagtcaggca gggagggagg agcgaagagg ccaccttagt     1080
ggtcaaatga ggaaacaccc                                                 1100

<210> SEQ ID NO 19
<211> LENGTH: 1206
<212> TYPE: DNA
<213> ORGANISM: Nannochloropsis oculata

<400> SEQUENCE: 19
atgggtctat ttggcagcgg gatcaaggaa aagacggagg ctgagaccgc gcaggtggag       60
cagcaagagc aggcgaagct gaagcaaaaa ccttctctac tgcgggagcg caagggaggt      120
aatataacca aggagcccca gacgccctcg agtaatctga ggcctgcccg ttccccgacc      180
gaggtggact ggagctcctt ccctgagggc agctacacgc gcttcgggca tggcggggac      240
tggtggacgc taatcaaggg gacgattgcc attttgttca cgtggggggac ctggctggct      300 ggcggcttgt ctccttttg gatgacttgg ttgtatacgc acggatacaa gaggacattc      360
tattcgatca taggcccttt gctttacccg ctttttcttgc ccgtgccagc ttggcctgga      420
tttgtccgat tcattttaaa catggctgga tattttgagg gcggtgcggc gatgtacgtc      480
gaaaactctt tcaaaggccg caatgtgaat ggtcctatca tgttggccat gccccccat      540 ggcatcatgc ctcactcttt ccttctcaac ggtgccgggc ggatccacgc gcagaaaccg      600
gaggtattcc tccctccaca ctatcaagat atgtctctta atcgacggg cgtggcggag      660 ccgttgttgt ttcggattcc gtttatttcg gcatttcttt attttttttgg gtgtgcggag      720 cctgcgtcga aggagatgat gcacgacatc ttggggaggc aggtgccgtt tgggatcctg      780
gtgggtggct ccgaggaaat cctcctcatg gagtaccaga aggaaaacat ctacatcctc      840
gaacgtaaag gttttattaa atacgcccctt cagcatggcc acaccatcgc cattggctac      900
ctcttcggcg agtccaacct ctaccacacc atcacctggg gacgcaagac ccgcctcgcc      960
ctcttcaaaa aattcaagat tccgttattt tggcttggg gacgttggtt ctttccctta     1020
ctccctgagc gagcagcgcc tttgaatgct gtcgttggca accctattga tttgcccagg     1080
atagccaacc caagccaggc ggacattgac aaataccatg cgatgtacat tgagaaattg     1140
acagatttgt ttgaacggaa taaggcggcc tttgggtatt cagatcggac gttgaatttc     1200
ttttag                                                               1206

<210> SEQ ID NO 20
<211> LENGTH: 401
<212> TYPE: PRT
<213> ORGANISM: Nannochloropsis oculata

<400> SEQUENCE: 20

Met Gly Leu Phe Gly Ser Gly Ile Lys Glu Lys Thr Glu Ala Glu Thr
1               5                   10                  15

Ala Gln Val Glu Gln Gln Glu Gln Ala Lys Leu Lys Gln Lys Pro Ser
                20                  25                  30

Leu Leu Arg Glu Arg Lys Gly Gly Asn Ile Thr Lys Glu Pro Gln Thr
            35                  40                  45
```

```
Pro Ser Ser Asn Leu Arg Pro Ala Arg Ser Pro Thr Glu Val Asp Trp
    50                  55                  60

Ser Ser Phe Pro Glu Gly Ser Tyr Thr Arg Phe Gly His Gly Gly Asp
65                  70                  75                  80

Trp Trp Thr Leu Ile Lys Gly Thr Ile Ala Ile Leu Phe Thr Trp Gly
                85                  90                  95

Thr Trp Leu Ala Gly Gly Leu Ser Pro Phe Trp Met Thr Trp Leu Tyr
            100                 105                 110

Thr His Gly Tyr Lys Arg Thr Phe Tyr Ser Ile Ile Gly Pro Leu Leu
            115                 120                 125

Tyr Pro Leu Phe Leu Pro Val Pro Ala Trp Pro Gly Phe Val Arg Phe
130                 135                 140

Ile Leu Asn Met Ala Gly Tyr Phe Glu Gly Gly Ala Ala Met Tyr Val
145                 150                 155                 160

Glu Asn Ser Phe Lys Gly Arg Asn Val Asn Gly Pro Ile Met Leu Ala
                165                 170                 175

Met His Pro His Gly Ile Met Pro His Ser Phe Leu Leu Asn Gly Ala
            180                 185                 190

Gly Arg Ile His Ala Gln Lys Pro Glu Val Phe Leu Pro Pro His Tyr
            195                 200                 205

Gln Asp Met Ser Leu Lys Ser Thr Gly Val Ala Glu Pro Leu Leu Phe
210                 215                 220

Arg Ile Pro Phe Ile Ser Ala Phe Leu Tyr Phe Gly Cys Ala Glu
225                 230                 235                 240

Pro Ala Ser Lys Glu Met Met His Asp Ile Leu Gly Arg Gln Val Pro
                245                 250                 255

Phe Gly Ile Leu Val Gly Gly Ser Glu Glu Ile Leu Leu Met Glu Tyr
            260                 265                 270

Gln Lys Glu Asn Ile Tyr Ile Leu Glu Arg Lys Gly Phe Ile Lys Tyr
            275                 280                 285

Ala Leu Gln His Gly Tyr Thr Ile Ala Ile Gly Tyr Leu Phe Gly Glu
            290                 295                 300

Ser Asn Leu Tyr His Thr Ile Thr Trp Gly Arg Lys Thr Arg Leu Ala
305                 310                 315                 320

Leu Phe Lys Lys Phe Lys Ile Pro Leu Phe Leu Ala Trp Gly Arg Trp
                325                 330                 335

Phe Phe Pro Leu Leu Pro Glu Arg Ala Ala Pro Leu Asn Ala Val Val
            340                 345                 350

Gly Asn Pro Ile Asp Leu Pro Arg Ile Ala Asn Pro Ser Gln Ala Asp
            355                 360                 365

Ile Asp Lys Tyr His Ala Met Tyr Ile Glu Lys Leu Thr Asp Leu Phe
370                 375                 380

Glu Arg Asn Lys Ala Ala Phe Gly Tyr Ser Asp Arg Thr Leu Asn Phe
385                 390                 395                 400

Phe
```

<210> SEQ ID NO 21
<211> LENGTH: 1772
<212> TYPE: DNA
<213> ORGANISM: Nannochloropsis oculata

<400> SEQUENCE: 21
attttcagca aagtaatcaa gataataaac aaaacaatc ctataaagga aaaacaacag        60
acatcaacac aggtacttgc agccaccact gcagcaatta tagcaccatc acgaccacta       120

-continued

```
tgggtctatt tggcagcggg atcaaggaaa agacggaggc tgagaccgcg caggtggagc      180
agcaagagca ggcgaagctg aagcaaaaac cttctctact gcgggagcgc aagggaggta      240
atataaccaa ggagccccag acgccctcga gtaatctgag gcctgcccgt tccccgaccg      300
aggtggactg gagctccttc cctgagggca gctacacgcg cttcgggcat ggcggggact      360
ggtggacgct aatcaagggg acgattgcca ttttgttcac gtgggggacc tggctggctg      420
gcggcttgtc tccctttggg atgacttggt tgtatacgca cggatacaag aggacattct      480
attcgatcat aggcccttg ctttacccgc ttttcttgcc cgtgccagct tggcctggat       540
ttgtccgatt cattttaaac atggctggat attttgaggg cggtgcggcg atgtacgtcg      600
aaaactcttt caaaggccgc aatgtgaatg gtcctatcat gttggccatg caccccatg      660 gcatcatgcc tcactctttc cttctcaacg gtgccgggcg gatccacgcg cagaaaccgg      720
aggtattcct ccctccacac tatcaagata tgtctcttaa atcgacgggc gtggcggagc      780
cgttgttgtt tcggattccg tttatttcgg catttcttta ttttttgggg tgtgcggagc      840
ctgcgtcgaa ggagatgatg cacgacatct ggggaggca ggtgccgttt gggatcctgg       900
tgggtggctc cgaggaaatc ctcctcatgg agtaccagaa ggaaaacatc tacatcctcg      960
aacgtaaagg ttttattaaa tacgcccttc agcatggcta caccatcgcc attggctacc     1020
tcttcggcga gtccaacctc taccacacca tcacctgggg acgcaagacc cgcctcgccc     1080
tcttcaaaaa attcaagatt ccgttatttt tggcttgggg acgttggttc tttcccttac     1140
tccctgagcg agcagcgcct ttgaatgctg tcgttggcaa ccctattgat ttgcccagga     1200
tagccaaccc aagccaggcg gacattgaca aataccatgc gatgtacatt gagaaattga     1260
cagatttgtt tgaacggaat aaggcggcct ttgggtattc agatcggacg ttgaatttct     1320
tttaggtggg tgggaggaaa ggagggtaag agggagggtg ggaaggtgtg tgtaggggg t    1380 gagtgttcag gcattgttgt tcaggcatgg aaagagactg acccaaccaa ctgaaaagga     1440
gatagacaag caagcacacc atggggtcaa tgatcgtgat tagagagaag atgggcaaga     1500
gggagggact gatccggtgt aaatatagac acatgactga atgaagaagc aaggagagaa     1560
tggagaggaa tcagcagcag cagcagcagc agcagcagag aacaatagct cttaaggcag     1620
cagctacaac aatcaaaaca cgaacaagag cgaaaagtcc aaacgctaag attcgacacg     1680
gagaacaaga acgaagaacg gtgatatcaa cagggaataa ttgtacgaac gaagcatgag     1740
tctagtgaaa acaacaaaaa aaaacaaaaa aa                                   1772
```

<210> SEQ ID NO 22
<211> LENGTH: 1173
<212> TYPE: DNA
<213> ORGANISM: Nannochloropsis oculata

<400> SEQUENCE: 22

```
atgttgagta tccccgagtc gtcctcgccc ctctcggacc ggactctggt gaagaatgga       60
ggcaaggaga ccgagctttc cacgccggtc accgctccca cttcggaccg ctcgcgtacc      120
tacagtgatg gctattcgac ccccaagtcc tacacattgg aggtcgatcc caaatttat       180 aagcgggtat gcgatgctga tgacgtgtgg acacgcacac agggtgcatt tgctcttctc      240
atgctctggg gcgtctggct tgccgggtcc ttttctgtgt tttggtggcc ctatttagta      300
gtgaaggggt attatactgc tgccctagct atggcagtga tcatggcata tccgtatgtg      360
gtcaaggtca agcaaagccc ggcatttatt cgcttcatct tgagcggcgc gggatggttt      420
```

```
aagggcggga cgtgtttgta tttggaggag tcgatgaagc agatcgacac cagcgagtct    480
gtcctcctct gtcagcatcc gcatggtctc ttcacctatg gcttcatcca aaacgggtct    540
gctgcccgca tcgatgcccg caaacccgag gtttatgtgc ctgccgcatt tcgtcacatg    600
aaacccaacg ccaaggcctt cgtggaacct ttgctattca aaatcccgct tatccgtcac    660
tttatcaccg ccttcggcaa cgccgccccg gcgaccaaaa aagagatgca ccgtctcatg    720
tccactaaaa ttcccctggg gctgttaccg ggtgggtcgg aagagatcat cttaagccac    780
catggccatg agcgggtgta catcctcaaa cggaaaggct tcctcaagta cgcattacaa    840
catggctaca cgatttgcat tggttacaca ttcggggagt ccgactcgta ccgcaccttg    900
gactggggcg tgaagtttcg tacgtggtac ctgaagacct tccgcgttcc actctttgcg    960
tgctggggga cgtggtggtg ccccctcttg ccacggggga aggtggcgct tgagacagtc   1020
gttgggaacc catttcggtt gcccaagatt gtagatccga gccaggagga tattgataag   1080
tggcatgcgg tgtatgtgca aaaacttgta gatttgtttg atcggaacaa ggccaagttc   1140
gggtatgggg acagggagct ggatttcttt tag                                 1173
```

<210> SEQ ID NO 23
<211> LENGTH: 390
<212> TYPE: PRT
<213> ORGANISM: Nannochloropsis oculata

<400> SEQUENCE: 23

```
Met Leu Ser Ile Pro Glu Ser Ser Pro Leu Ser Asp Arg Thr Leu
1               5                   10                  15

Val Lys Asn Gly Gly Lys Glu Thr Glu Leu Ser Thr Pro Val Thr Ala
            20                  25                  30

Pro Thr Ser Asp Arg Ser Arg Thr Tyr Ser Asp Gly Tyr Ser Thr Pro
        35                  40                  45

Lys Ser Tyr Thr Leu Glu Val Asp Pro Lys Phe Tyr Lys Arg Val Cys
    50                  55                  60

Asp Ala Asp Asp Val Trp Thr Arg Thr Gln Gly Ala Phe Ala Leu Leu
65                  70                  75                  80

Met Leu Trp Gly Val Trp Leu Ala Gly Ser Phe Ser Val Phe Trp Trp
                85                  90                  95

Pro Tyr Leu Val Val Lys Gly Tyr Tyr Thr Ala Ala Leu Ala Met Ala
            100                 105                 110

Val Ile Met Ala Tyr Pro Tyr Val Lys Val Lys Gln Ser Pro Ala
        115                 120                 125

Phe Ile Arg Phe Ile Leu Ser Gly Ala Gly Trp Phe Lys Gly Gly Thr
130                 135                 140

Cys Leu Tyr Leu Glu Glu Ser Met Lys Gln Ile Asp Thr Ser Glu Ser
145                 150                 155                 160

Val Leu Leu Cys Gln His Pro His Gly Leu Phe Thr Tyr Gly Phe Ile
                165                 170                 175

Gln Asn Gly Ser Ala Ala Arg Ile Asp Ala Arg Lys Pro Glu Val Tyr
            180                 185                 190

Val Pro Ala Ala Phe Arg His Met Lys Pro Asn Ala Lys Ala Phe Val
        195                 200                 205

Glu Pro Leu Leu Phe Lys Ile Pro Leu Ile Arg His Phe Ile Thr Ala
    210                 215                 220

Phe Gly Asn Ala Ala Pro Ala Thr Lys Lys Glu Met His Arg Leu Met
225                 230                 235                 240
```

```
Ser Thr Lys Ile Pro Leu Gly Leu Leu Pro Gly Gly Ser Glu Glu Ile
            245                 250                 255

Ile Leu Ser His His Gly His Glu Arg Val Tyr Ile Leu Lys Arg Lys
            260                 265                 270

Gly Phe Leu Lys Tyr Ala Leu Gln His Gly Tyr Thr Ile Cys Ile Gly
            275                 280                 285

Tyr Thr Phe Gly Glu Ser Asp Ser Tyr Arg Thr Leu Asp Trp Gly Val
            290                 295                 300

Lys Phe Arg Thr Trp Tyr Leu Lys Thr Phe Arg Val Pro Leu Phe Ala
305                 310                 315                 320

Cys Trp Gly Thr Trp Trp Cys Pro Leu Leu Pro Arg Gly Lys Val Ala
                325                 330                 335

Leu Glu Thr Val Val Gly Asn Pro Phe Arg Leu Pro Lys Ile Val Asp
            340                 345                 350

Pro Ser Gln Glu Asp Ile Asp Lys Trp His Ala Val Tyr Val Gln Lys
            355                 360                 365

Leu Val Asp Leu Phe Asp Arg Asn Lys Ala Lys Phe Gly Tyr Gly Asp
            370                 375                 380

Arg Glu Leu Asp Phe Phe
385                 390

<210> SEQ ID NO 24
<211> LENGTH: 1239
<212> TYPE: DNA
<213> ORGANISM: Nannochloropsis oculata

<400> SEQUENCE: 24
attttcagca aagtaatcaa gataataaac aaaaacaatc ctataaaagg aaaaacaaca     60
ggtagaatgt tgagtatccc cgagtcgtcc tcgcccctct cggaccggac tctggtgaag    120
aatggaggca aggagaccga gctttccacg ccggtcaccg ctcccacttc ggaccgctcg    180
cgtacctaca gtgatggcta ttcgaccccc aagtcctaca cattggaggt cgatcccaaa    240
ttttataagc gggtatgcga tgctgatgac gtgtggacac gcacacaggg tgcatttgct    300
cttctcatgc tctgggggcgt ctggcttgcc gggtcctttt ctgtgttttg gtggccctat    360
ttagtagtga agggtatta tactgctgcc ctagctatgg cagtgatcat ggcatatccg    420
tatgtggtca aggtcaagca aagcccggca tttattcgct tcatcttgag cggcgcggga    480
tggtttaagg gcgggacgtg tttgtatttg gaggagtcga tgaagcagat cgacaccagc    540
gagtctgtcc tcctctgtca gcatccgcat ggtctcttca cctatggctt catccaaaac    600
gggtctgctg cccgcatcga tgcccgcaaa cccgaggttt atgtgcctgc cgcatttcgt    660
cacatgaaac ccaacgccaa ggccttcgtg aacctttgc tattcaaaat cccgcttatc    720
cgtcacttta tcaccgcctt cggcaacgcc gccccggcga ccaaaaaaga gatgcaccgt    780
ctcatgtcca ctaaaattcc cctggggctg ttaccgggtg gtcggaaga gatcatctta    840 agccaccatg gccatgagcg ggtgtacatc ctcaaacgga aaggcttcct caagtacgca    900
ttacaacatg gctacacgat ttgcattggt tacacattcg gggagtccga ctcgtaccgc    960
accttggact ggggcgtgaa gtttcgtacg tggtacctga agaccttccg cgttccactc   1020
tttgcgtgct gggggacgtg gtggtgcccc ctcttgccac ggggggaaggt ggcgcttgag   1080 acagtcgttg gaacccatt tcggttgccc aagattgtag atccgagcca ggaggatatt   1140
gataagtggc atgcggtgta tgtgcaaaaa cttgtagatt tgtttgatcg gaacaaggcc   1200
aagttcgggt atggggacag ggagctggat ttcttttag                          1239
```

<210> SEQ ID NO 25
<211> LENGTH: 1089
<212> TYPE: DNA
<213> ORGANISM: Nannochloropsis oculata

<400> SEQUENCE: 25

```
atgacgccgc aagccgatat caccagcaag acgacatcca accccaagac ggctgcatcc      60
tcccctcca agacctcgcc cccgccgtt caatacaaag cagggaatgg caaggtgatc       120
acggtggcca tggccgagca agacgacggg aacatgggca ttttccgcga gtgttgtgcg     180
atggtgacaa tggggataat catgtcgtgg tactacatcg tcgtcgttct ctccctcctg     240
tgcttggtgg ggatctcctt cttccctgcc tggcgggcgg tggcggcgac ggttttgta     300
ctcatgtgga gtgcggcgct tttgccgctc gactaccagg ggtgggacgc tttctgcaac    360
tcatgtatct tcaggctgtg gcgggactac ttccactacg aatacgtcct ggaagaaatg   420
atcgacccca acaagcgcta cctcttcgct gagatgcccc acggaatctt ccctggggga  480
gaggtgattt ccatttctat caccaagcag cttttccccg ggagccgcgt cggctccatt  540
ggtgcgagtg tcatcttcct ccttccgggc tccggcact tcttcgcctg gatcgggtgt   600
cggcccgcga gcccggagaa tatcaaaaag atttttgatg atgggcagga ttgtgccgtg  660
acggtgggag gggtcgccga gatgtttctg gttggaggag agaaggagcg gctctaccta  720
aaaaagcaca agggtttcgt tcgagaggcc atgaagaacg gcgcggacct ggtccctgtc  780
ttctgcttcg gcaacagcaa gttgttcaat gtggtggggg agagcagtcg ggtgtccatg  840
ggcctgatga agcgtctctc gaggaggctc aaagccagcg tcctcatttt ctacggccgt  900
ctcttcctac ccattccgat ccgccacccg ctcttgttcg tggtgggaaa gccctgccg   960
gtcgtgcaga tgcagagcc gaccaaggag gagatcgcgg cgacgcacgc actcttttgc  1020
gagaaggtgg aggagcttta ctacaaattc aggccggaat gggagacgcg cccgttgtcc  1080
attgagtaa                                                        1089
```

<210> SEQ ID NO 26
<211> LENGTH: 362
<212> TYPE: PRT
<213> ORGANISM: Nannochloropsis oculata

<400> SEQUENCE: 26

```
Met Thr Pro Gln Ala Asp Ile Thr Ser Lys Thr Thr Ser Asn Pro Lys
1               5                   10                  15

Thr Ala Ala Ser Ser Pro Ser Lys Thr Ser Pro Ala Val Gln Tyr
            20                  25                  30

Lys Ala Gly Asn Gly Lys Val Ile Thr Val Ala Met Ala Glu Gln Asp
        35                  40                  45

Asp Gly Asn Met Gly Ile Phe Arg Glu Cys Cys Ala Met Val Thr Met
    50                  55                  60

Gly Ile Ile Met Ser Trp Tyr Tyr Ile Val Val Leu Ser Leu Leu
65                  70                  75                  80

Cys Leu Val Gly Ile Ser Phe Phe Pro Ala Trp Arg Ala Val Ala Ala
                85                  90                  95

Thr Val Phe Val Leu Met Trp Ser Ala Ala Leu Leu Pro Leu Asp Tyr
            100                 105                 110

Gln Gly Trp Asp Ala Phe Cys Asn Ser Cys Ile Phe Arg Leu Trp Arg
        115                 120                 125
```

Asp Tyr Phe His Tyr Glu Tyr Val Leu Glu Glu Met Ile Asp Pro Asn
    130                 135                 140

Lys Arg Tyr Leu Phe Ala Glu Met Pro His Gly Ile Phe Pro Trp Gly
145                 150                 155                 160

Glu Val Ile Ser Ile Ser Ile Thr Lys Gln Leu Phe Pro Gly Ser Arg
                165                 170                 175

Val Gly Ser Ile Gly Ala Ser Val Ile Phe Leu Leu Pro Gly Leu Arg
                180                 185                 190

His Phe Phe Ala Trp Ile Gly Cys Arg Pro Ala Ser Pro Glu Asn Ile
            195                 200                 205

Lys Lys Ile Phe Asp Asp Gly Gln Asp Cys Ala Val Thr Val Gly Gly
210                 215                 220

Val Ala Glu Met Phe Leu Val Gly Gly Glu Lys Glu Arg Leu Tyr Leu
225                 230                 235                 240

Lys Lys His Lys Gly Phe Val Arg Glu Ala Met Lys Asn Gly Ala Asp
                245                 250                 255

Leu Val Pro Val Phe Cys Phe Gly Asn Ser Lys Leu Phe Asn Val Val
                260                 265                 270

Gly Glu Ser Ser Arg Val Ser Met Gly Leu Met Lys Arg Leu Ser Arg
            275                 280                 285

Arg Leu Lys Ala Ser Val Leu Ile Phe Tyr Gly Arg Leu Phe Leu Pro
290                 295                 300

Ile Pro Ile Arg His Pro Leu Leu Phe Val Val Gly Lys Pro Leu Pro
305                 310                 315                 320

Val Val Gln Asn Ala Glu Pro Thr Lys Glu Glu Ile Ala Ala Thr His
                325                 330                 335

Ala Leu Phe Cys Glu Lys Val Glu Glu Leu Tyr Tyr Lys Phe Arg Pro
                340                 345                 350

Glu Trp Glu Thr Arg Pro Leu Ser Ile Glu
            355                 360

<210> SEQ ID NO 27
<211> LENGTH: 1609
<212> TYPE: DNA
<213> ORGANISM: Nannochloropsis oculata

<400> SEQUENCE: 27
attttcagca aagtaatcaa gataataaac aaaaacaatc ctataaagga aaaacaacag     60
agagacaagt aggccaccag cattggtttc caccatgacg ccgcaagccg atatcaccag    120
caagacgaca tccaaccccca agacggctgc atcctccccc tccaagacct cgccccccgc    180
cgttcaatac aaagcaggga atggcaaggt gatcacggtg ccatggccga gcaagacga    240 cgggaacatg gcattttcc gcgagtgttg tgcgatggtg acaatgggga taatcatgtc    300
gtggtactac atcgtcgtcg ttctctccct cctgtgcttg gtgggatct ccttcttccc    360 tgcctggcgg gcgtggcgg cgacggtttt tgtactcatg tggagtgcgg cgcttttgcc    420
gctcgactac caggggtggg acgctttctg caactcatgt atcttcaggc tgtggcggga    480
ctacttccac tacgaatacg tcctggaaga aatgatcgac cccaacaagc gctacctctt    540
cgctgagatg ccccacggaa tcttcccctg gggagaggtg atttccattt ctatcaccaa    600
gcagcttttc cccgggagcc gcgtcggctc cattggtgcg agtgtcatct tcctccttcc    660
gggcctccgg cacttcttcg cctggatcgg tgtcggccc gcgagcccgg agaatatcaa    720
aaagattttt gatgatgggc aggattgtgc cgtgacggtg gaggggtcg ccgagatgtt    780

```
tctggttgga ggagagaagg agcggctcta cctaaaaaag cacaagggtt tcgttcgaga      840
ggccatgaag aacggcgcgg acctggtccc tgtcttctgc ttcggcaaca gcaagttgtt      900
caatgtggtg ggggagagca gtcgggtgtc catgggcctg atgaagcgtc tctcgaggag      960
gctcaaagcc agcgtcctca ttttctacgg ccgtctcttc ctacccattc cgatccgcca     1020
cccgctcttg ttcgtggtgg gaaagcccct gccggtcgtg cagaatgcag agccgaccaa     1080
ggaggagatc gcggcgacgc acgcactctt ttgcgagaag gtggaggagc tttactacaa     1140
attcaggccg gaatgggaga cgcgcccgtt gtccattgag taaaatacgt ggacggagaa     1200
agcgaggggc gtgtgtttga gtatctgatt gtgattgtga ttgtctgtgt ctgcacgtgt     1260
gtgtgtacga ttacttctgg tgcttgtgcg gttttgaaag taactgtaaa ggtcagaaga     1320
gattagaaga cgagacttgg atacgatgaa gggtgaagaa gaaatttaaa acaattttga     1380
gattttattc atgtctgagg aataaatgta gatgttagaa aatttgaggt agttctcggt     1440
acttgtcccc tatcatccgt gtttagtaac gaggtacatc cgtgcgacgg tcggtggaa     1500 gtagccagcg tcatcagaga gaggtctcac acacgatcgt gtgtccttgc acatgtcttt     1560
tccatttaac acgaattact ttttttttaaa aaaataataa aaaaaaata                1609
```

<210> SEQ ID NO 28
<211> LENGTH: 1464
<212> TYPE: DNA
<213> ORGANISM: Nannochloropsis oculata

<400> SEQUENCE: 28

```
atggcttacc tcttccgtcg tcgaagcaaa ggcgagggca acagcactag cagcagctgc       60
tcttctctgt cggaagataa taagggcacg tccatccact cttccgaaat cgagccgcgc      120
gctcccgcca cgtccaaagc cacgacaagc agcataaagg agattgggaa gccctcattg      180
cccaccgccg cacatttatc accacccagc ataagcaagg cagatagaaa tttcgccatt      240
gccgcagtag cagcaggagc actggagggg gctgcagcag gcgccgtgac agcaccaccc      300
accgaccaat ctccgaagaa gcagtacggg cagggtggta ctggggagcg agggaaggag      360
gcagaaggtg gacgagaacg aagtggaagc gtcggcaacc ttttactgtc atcaattaat      420 tcgtttttcaa gctgcacgtc cctatccttt ttggccggcg aggacgagac cccgtctcct      480
cccgagacag ggcctgctgg gattgatttc tcgacaccgg ctcatccgac catgcaactt      540
gtggacttca tcatcacttt tctcttggtg cattatattc aagtcttcta ctccctagtc      600
ctcctcttca tctacctcgt caagcacggt cacagatggc cgtacctcct cgctgccatc      660 tacgccccctt cgtacttcat tcctttacag cgattgggcg gatggccgtt caaaggattc      720
atgcgtcggc ccttttggcg gtgtgtccaa aggaccttag ctctccaggt ggaaagagag      780
gtcgagctgc gtccagacga acagtacatt tttggttggc accccacgg gatcttgctc      840 ttgtcccggt ttgcaatcta tgggggtctg tgggaaaagc ttttttccggg tattcatttc      900 aagacgctag cggcaagtcc tctgttttgg attccaccta ttcgcgaagt gtcgatcttg      960
ctgggtgggg tggatgcagg cagggcatca gcagcacggg cactcacaga cggctactcc     1020
gtctctcttt atccgggggg aagcaaggaa atctacacca ctgatcccta cactcctgaa     1080
acgaccctgg tcctgaaaat ccgcaaaggc ttcattcgca tggccctccg ctatggctgt     1140
ccactcgtgc ctgtgtacac gtttggagaa aaatacgcct accatcggct agggccggcc     1200
acgggctttg cgcgctggct gttggcagtg ctgaaagtcc ctttcttgat cttttgggga     1260
cgatggggca cattcatgcc gctcaaggag acgcaggtgt cagtggtggt gggcaagcca     1320
```

```
ctgcgcgtgc ccaaaatcga tggagatcct gcccctgagg tggtggagga atggttgcac   1380
agatactgcg acgaagtcca ggcgttgttc cagcgacaca agaacaaata cgcaaagcct   1440
gaggagttca ttgcgatcgc ctaa                                          1464
```

<210> SEQ ID NO 29
<211> LENGTH: 487
<212> TYPE: PRT
<213> ORGANISM: Nannochloropsis oculata

<400> SEQUENCE: 29

```
Met Ala Tyr Leu Phe Arg Arg Arg Ser Lys Gly Glu Gly Asn Ser Thr
1               5                   10                  15

Ser Ser Ser Cys Ser Ser Leu Ser Glu Asp Asn Lys Gly Thr Ser Ile
            20                  25                  30

His Ser Ser Glu Ile Glu Pro Arg Ala Pro Ala Thr Ser Lys Ala Thr
        35                  40                  45

Thr Ser Ser Ile Lys Glu Ile Gly Lys Pro Ser Leu Pro Thr Ala Ala
    50                  55                  60

His Leu Ser Pro Pro Ser Ile Ser Lys Ala Asp Arg Asn Phe Ala Ile
65                  70                  75                  80

Ala Ala Val Ala Ala Gly Ala Leu Glu Gly Ala Ala Ala Gly Ala Val
                85                  90                  95

Thr Ala Pro Pro Thr Asp Gln Ser Pro Lys Lys Gln Tyr Gly Gln Gly
            100                 105                 110

Gly Thr Gly Glu Arg Gly Lys Glu Ala Glu Gly Gly Arg Glu Arg Ser
        115                 120                 125

Gly Ser Val Gly Asn Leu Leu Leu Ser Ser Ile Asn Ser Phe Ser Ser
    130                 135                 140

Cys Thr Ser Leu Ser Phe Leu Ala Gly Glu Asp Glu Thr Pro Ser Pro
145                 150                 155                 160

Pro Glu Thr Gly Pro Ala Gly Ile Asp Phe Ser Thr Pro Ala His Pro
                165                 170                 175

Thr Met Gln Leu Val Asp Phe Ile Ile Thr Phe Leu Leu Val His Tyr
            180                 185                 190

Ile Gln Val Phe Tyr Ser Leu Val Leu Leu Phe Ile Tyr Leu Val Lys
        195                 200                 205

His Gly His Arg Trp Pro Tyr Leu Leu Ala Ala Ile Tyr Ala Pro Ser
    210                 215                 220

Tyr Phe Ile Pro Leu Gln Arg Leu Gly Gly Trp Pro Phe Lys Gly Phe
225                 230                 235                 240

Met Arg Arg Pro Phe Trp Arg Cys Val Gln Arg Thr Leu Ala Leu Gln
                245                 250                 255

Val Glu Arg Glu Val Glu Leu Arg Pro Asp Glu Gln Tyr Ile Phe Gly
            260                 265                 270

Trp His Pro His Gly Ile Leu Leu Leu Ser Arg Phe Ala Ile Tyr Gly
        275                 280                 285

Gly Leu Trp Glu Lys Leu Phe Pro Gly Ile His Phe Lys Thr Leu Ala
    290                 295                 300

Ala Ser Pro Leu Phe Trp Ile Pro Ile Arg Glu Val Ser Ile Leu
305                 310                 315                 320

Leu Gly Gly Val Asp Ala Gly Arg Ala Ser Ala Arg Ala Leu Thr
                325                 330                 335

Asp Gly Tyr Ser Val Ser Leu Tyr Pro Gly Gly Ser Lys Glu Ile Tyr
```

```
                    340              345              350
Thr Thr Asp Pro Tyr Thr Pro Glu Thr Thr Leu Val Leu Lys Ile Arg
            355                  360              365
Lys Gly Phe Ile Arg Met Ala Leu Arg Tyr Gly Cys Pro Leu Val Pro
        370              375              380
Val Tyr Thr Phe Gly Glu Lys Tyr Ala Tyr His Arg Leu Gly Pro Ala
385              390              395              400
Thr Gly Phe Ala Arg Trp Leu Leu Ala Val Leu Lys Val Pro Phe Leu
                405              410              415
Ile Phe Trp Gly Arg Trp Gly Thr Phe Met Pro Leu Lys Glu Thr Gln
            420              425              430
Val Ser Val Val Gly Lys Pro Leu Arg Val Pro Lys Ile Asp Gly
        435              440              445
Asp Pro Ala Pro Glu Val Val Glu Glu Trp Leu His Arg Tyr Cys Asp
    450              455              460
Glu Val Gln Ala Leu Phe Gln Arg His Lys Asn Lys Tyr Ala Lys Pro
465              470              475              480
Glu Glu Phe Ile Ala Ile Ala
                485
```

<210> SEQ ID NO 30
<211> LENGTH: 1682
<212> TYPE: DNA
<213> ORGANISM: Nannochloropsis oculata

<400> SEQUENCE: 30

```
attttcagca aaagtaatca agataataaa caaaaacaat cctataaagg aaaaacaaca      60
gggcacccag ggtgacgccg gcgaccccaa cactatggct tacctcttcc gtcgtcgaag     120
caaaggcgag ggcaacagca ctagcagcag ctgctcttct ctgtcggaag ataataaggg     180
cacgtccatc cactcttccg aaatcgagcc gcgcgctccc gccacgtcca agccacgac      240
aagcagcata aaggagattg ggaagccctc attgcccacc gccgcacatt tatcaccacc     300
cagcataagc aaggcagata gaaatttcgc cattgccgca gtagcagcag gagcactgga     360
gggggctgca gcaggcgccg tgacagcacc acccaccgac caatctccga agaagcagta     420
cgggcagggt ggtactgggg agcgagggaa ggaggcagaa ggtggacgag aacgaagtgg     480
aagcgtcggc aaccttttac tgtcatcaat taattcgttt tcaagctgca cgtccctatc     540
cttttggcc ggcgaggacg agacccegtc tcctcccgag acagggcctg ctgggattga     600
tttctcgaca ccggctcatc cgaccatgca acttgtggac ttcatcatca cttttctctt     660
ggtgcattat attcaagtct tctactccct agtcctcctc ttcatctacc tcgtcaagca     720
cggtcacaga tggccgtacc tcctcgctgc catctacgcc ccttcgtact tcattccttt     780
acagcgattg ggcggatggc cgttcaaagg attcatgcgt cggccctttt ggcggtgtgt     840
ccaaaggacc ttagctctcc agttggaaag agaggtcgag ctgcgtccag acgaacagta     900
cattttggt tggcaccccc acgggatctt gctcttgtcc cggtttgcaa tctatgggg       960
tctgtgggaa aagcttttc cgggtattca tttcaagacg ctagcggcaa gtcctctgtt     1020
ttggattcca cctattcgcg aagtgtcgat cttgctgggt gggtggatg caggcagggc    1080
atcagcagca cgggcactca cagacggcta ctccgtctct ctttatccgg ggggaagcaa     1140
ggaaatctac accactgatc cctacactcc tgaaacgacc ctggtcctga aaatccgcaa    1200
aggcttcatt cgcatggccc tccgctatgg ctgtccactc gtgcctgtgt acacgtttgg     1260
```

| | |
|---|---|
| agaaaaatac gcctaccatc ggctagggcc ggccacgggc tttgcgcgct ggctgttggc | 1320 |
| agtgctgaaa gtccctttct tgatcttttg gggacgatgg ggcacattca tgccgctcaa | 1380 |
| ggagacgcag gtgtcagtgg tggtgggcaa gccactgcgc gtgcccaaaa tcgatggaga | 1440 |
| tcctgcccct gaggtggtgg aggaatggtt gcacagatac tgcgacgaag tccaggcgtt | 1500 |
| gttccagcga cacaagaaca aatacgcaaa gcctgaggag ttcattgcga tcgcctaaaa | 1560 |
| gggaaaaaaa gtaaaaccct tccctccctt ccttccttct tttattacac atgcccctgc | 1620 |
| accaaccacg cgacatgagg ggacggaagg agctggatgc ggtgtggttt gtctgttcag | 1680 |
| ga | 1682 |

<210> SEQ ID NO 31
<211> LENGTH: 1539
<212> TYPE: DNA
<213> ORGANISM: Nannochloropsis oculata

<400> SEQUENCE: 31

| | |
|---|---|
| atgcctttttg gacgggctgc atcagcctgg atttcggcct cagcattgtt gccagccttg | 60 |
| gcggacccaa ctttcctttg cggcaccgcc atcgtgggcc tcgtcgttat gtactacatt | 120 |
| gtcagcggcc aaaggtgtgc acgagctttg cgtccttccc caggggtgat tcgaaggaaa | 180 |
| atgagttttt gttcggcggc ctgtgcggat ggtcccatgc ctgagcacgc caagatgaac | 240 |
| cctgtcgatc ctattatcaa tgccgtggtg cttttcgagg gggaggcgcc cacgcgtgcg | 300 |
| gcggtggaat cggccatctt gccgctcttt gaattcgaac ggtttcgctc ccggaaggtt | 360 |
| aagattggtg atgattggta ttgggaagtg ctgccttcct tgacgctag acgcatgtg | 420 |
| attgaagact ctttcaaggg tgccagcatc gatgacttgt tcttcgcct ggaggtgtgg | 480 |
| tcccagaaac ccctgcatgt accggtgac gggcccgcct tgaatttgc tttgcttcgg | 540 |
| aatcaggata gaagggggcc ctctgctgtg atttgtcgta tcaaccatgc gattggtgat | 600 |
| ggtgtctctc tggccaagtt gatccccac gtgttcaagg acattgacgg ccagtcactg | 660 |
| ccgatcgggg agaagtttcg ccggcgggaa gcagggttca gccgactttt ccgcaccct | 720 |
| tttaccttgc tggcttcgct tttcaaggta ttgggtacgc ctactacggc gtttgatact | 780 |
| gacgtggggt tgacgattcc ggataaaaag aatattacct ttacggggcg tcggtgcatt | 840 |
| gtgcgtatcc ccaccgtgaa gctttcgttc atcaagagca ttaaaaatgc ggcgaatgtg | 900 |
| actgtgaacg atgtggtgat gagcgcggtt gctggggccg tgcatcgatt tcgttgcgcg | 960 |
| caaaaagatc ctgcaatgct cgacccttta tcccattgta aagtccgtac acgcgctttg | 1020 |
| atgcctgtgg cttttgccccg ggaggaggga gatcctgtca aggctttgcg aaacaagtgg | 1080 |
| agttttgctt ccgtggcgat gcccgtgggg gtcaagggga gtttggaacg cttgcatgca | 1140 |
| gcgaatgcca cgatgactgc gttgaaaaac agtccgatag tgatcgtgca gaatatggtg | 1200 |
| gaggctaacc taggggcacg cttgccgtgg acagtggcaa aacaaaccgc gtttgactcg | 1260 |
| tttgtgaggc acacgtttgt gtttagcaat gtaccgggtc cgaacatgcc tataacattt | 1320 |
| gccggtcggg aagtgtcggg actgtatatg gcgtttgcga atttgattcc tcaggtgggc | 1380 |
| gctctgtcct tgaacggcaa gatcttcacc tgtctggtgc tggacgacga ggtcacgccg | 1440 |
| ggggcacgtg aactaggaga gcatttttatt gacgagttga tggacttggc tcgaaggacg | 1500 |
| gggctggaaa atgtaaagaa ggaggatatt ttcgggtga | 1539 |

<210> SEQ ID NO 32
<211> LENGTH: 512

<212> TYPE: PRT
<213> ORGANISM: Nannochloropsis oculata

<400> SEQUENCE: 32

Met Pro Phe Gly Arg Ala Ala Ser Ala Trp Ile Ser Ala Ser Ala Leu
1               5                   10                  15

Leu Pro Ala Leu Ala Asp Pro Thr Phe Leu Cys Gly Thr Ala Ile Val
            20                  25                  30

Gly Leu Val Val Met Tyr Tyr Ile Val Ser Gly Gln Arg Cys Ala Arg
        35                  40                  45

Ala Leu Arg Pro Ser Pro Gly Val Ile Arg Arg Lys Met Ser Phe Cys
    50                  55                  60

Ser Ala Ala Cys Ala Asp Gly Pro Met Pro Glu His Ala Lys Met Asn
65                  70                  75                  80

Pro Val Asp Pro Ile Ile Asn Ala Val Val Leu Phe Glu Gly Glu Ala
                85                  90                  95

Pro Thr Arg Ala Ala Val Glu Ser Ala Ile Leu Pro Leu Phe Glu Phe
            100                 105                 110

Glu Arg Phe Arg Ser Arg Lys Val Lys Ile Gly Asp Asp Trp Tyr Trp
        115                 120                 125

Glu Val Leu Pro Ser Phe Asp Ala Arg Thr His Val Ile Glu Asp Ser
    130                 135                 140

Phe Lys Gly Ala Ser Ile Asp Asp Leu Phe Leu Arg Leu Glu Val Trp
145                 150                 155                 160

Ser Gln Lys Pro Leu His Val Pro Val Asp Gly Pro Ala Phe Glu Phe
                165                 170                 175

Ala Leu Leu Arg Asn Gln Asp Lys Lys Gly Pro Ser Ala Val Ile Cys
            180                 185                 190

Arg Ile Asn His Ala Ile Gly Asp Gly Val Ser Leu Ala Lys Leu Ile
        195                 200                 205

Pro His Val Phe Lys Asp Ile Asp Gly Gln Ser Leu Pro Ile Gly Glu
    210                 215                 220

Lys Phe Arg Arg Glu Ala Gly Phe Lys Pro Thr Phe Arg Thr Pro
225                 230                 235                 240

Phe Thr Leu Leu Ala Ser Leu Phe Lys Val Leu Gly Thr Pro Thr Thr
                245                 250                 255

Ala Phe Asp Thr Asp Val Gly Leu Thr Ile Pro Asp Lys Lys Asn Ile
            260                 265                 270

Thr Phe Thr Gly Arg Arg Cys Ile Val Arg Ile Pro Thr Val Lys Leu
        275                 280                 285

Ser Phe Ile Lys Ser Ile Lys Asn Ala Ala Asn Val Thr Val Asn Asp
    290                 295                 300

Val Val Met Ser Ala Val Ala Gly Ala Val His Arg Phe Arg Cys Ala
305                 310                 315                 320

Gln Lys Asp Pro Ala Met Leu Asp Pro Leu Ser His Cys Lys Val Arg
                325                 330                 335

Thr Arg Ala Leu Met Pro Val Ala Leu Pro Arg Glu Glu Gly Asp Pro
            340                 345                 350

Val Lys Ala Leu Arg Asn Lys Trp Ser Phe Ala Ser Val Ala Met Pro
        355                 360                 365

Val Gly Val Lys Gly Ser Leu Glu Arg Leu His Ala Ala Asn Ala Thr
    370                 375                 380

Met Thr Ala Leu Lys Asn Ser Pro Ile Val Ile Val Gln Asn Met Val
385                 390                 395                 400

```
Glu Ala Asn Leu Gly Ala Arg Leu Pro Trp Thr Val Ala Lys Gln Thr
                405                 410                 415

Ala Phe Asp Ser Phe Val Arg His Thr Phe Val Phe Ser Asn Val Pro
            420                 425                 430

Gly Pro Asn Met Pro Ile Thr Phe Ala Gly Arg Glu Val Ser Gly Leu
        435                 440                 445

Tyr Met Ala Phe Ala Asn Leu Ile Pro Gln Val Gly Ala Leu Ser Leu
    450                 455                 460

Asn Gly Lys Ile Phe Thr Cys Leu Val Leu Asp Asp Glu Val Thr Pro
465                 470                 475                 480

Gly Ala Arg Glu Leu Gly Glu His Phe Ile Asp Glu Leu Met Asp Leu
                485                 490                 495

Ala Arg Arg Thr Gly Leu Glu Asn Val Lys Lys Glu Asp Ile Phe Gly
            500                 505                 510

<210> SEQ ID NO 33
<211> LENGTH: 1904
<212> TYPE: DNA
<213> ORGANISM: Nannochloropsis oculata

<400> SEQUENCE: 33
attttcagca aagtaatcaa gataataaac aaaacaatc ctataaagga aaaacaacag     60
ccacacagac gccccagctt caactctcca cacgcgattt gccagtgagg gtcgtgcacc   120
ctccgcaacc acgagccttt tccacagtag tcatcctgcc catcacgctt aaaatcatgc   180
cttttggacg ggctgcatca gcctggattt cggcctcagc attgttgcca gccttggcgg   240
acccaacttt cctttgcggc accgccatcg tgggcctcgt cgttatgtac tacattgtca   300
gcggccaaag tgtgcacga gctttgcgtc cttccccagg ggtgattcga aggaaaatga   360 gttttttgttc ggcggcctgt gcggatggtc ccatgcctga gcacgccaag atgaaccctg   420
tcgatcctat tatcaatgcc gtggtgcttt tcgagggga ggcgcccacg cgtgcggcgg   480
tggaatcggc catcttgccg ctctttgaat cgaacggtt tcgctcccgg aaggttaaga   540
ttggtgatga ttggtattgg gaagtgctgc cttcctttga cgctaggacg catgtgattg   600
aagactcttt caagggtgcc agcatcgatg acttgtttct tcgcctggag gtgtggtccc   660
agaaacccct gcatgtaccg gtggacgggc ccgcctttga atttgctttg cttcggaatc   720
aggataagaa gggccctct gctgtgattt gtcgtatcaa ccatgcgatt ggtgatggtg   780
tctctctggc caagttgatc ccccacgtgt tcaaggacat tgacggccag tcactgccga   840 tcgggagaa gtttcgccgg cgggaagcag ggttcaagcc gactttccgc acccctttta   900
ccttgctggc ttcgctttc aaggtattgg gtacgcctac tacggcgttt gatactgacg   960
tggggttgac gattccggat aaaaagaata ttaccttac ggggcgtcgg tgcattgtgc  1020
gtatccccac cgtgaagctt tcgttcatca agagcattaa aaatgcggcg aatgtgactg  1080
tgaacgatgt ggtgatgagc gcggttgctg gggccgtgca tcgatttcgt tgcgcgcaaa  1140
aagatcctgc aatgctcgac ccttttatccc attgtaaagt ccgtacacgc gctttgatgc  1200
ctgtggcttt gccccgggag gagggagatc ctgtcaaggc tttgcgaaac aagtggagtt  1260
ttgcttccgt ggcgatgccc gtgggggtca aggggagttt ggaacgcttg catgcagcga  1320
atgccacgat gactgcgttg aaaaacagtc cgatagtgat cgtgcagaat atggtggagg  1380
ctaacctagg ggcacgcttg ccgtggacag tgcaaaaaca aaccgcgttt gactcgtttg  1440
tgaggcacac gttgtgtttt agcaatgtac cgggtccgaa catgcctata acatttgccg  1500
```

```
gtcgggaagt gtcgggactg tatatggcgt ttgcgaattt gattcctcag gtgggcgctc    1560
tgtccttgaa cggcaagatc ttcacctgtc tggtgctgga cgacgaggtc acgccggggg    1620
cacgtgaact aggagagcat tttattgacg agttgatgga cttggctcga aggacggggc    1680
tggaaaatgt aaagaaggag gatattttcg ggtgagaagc ctagaggaga gagggataga    1740
aggagggaag gatggagatg gttttttgtac atgcgcgtgt cggtggctgc cgcggctgtc   1800
attggtgagg cgatcggtag ggtaaataga atgaactcat aagagaatga agagtgagaa    1860
agaagagcat ccgtaagcgg gaaacaaaaa aaaaaaaaaa aaaa                     1904
```

<210> SEQ ID NO 34
<211> LENGTH: 1083
<212> TYPE: DNA
<213> ORGANISM: Nannochloropsis oculata

<400> SEQUENCE: 34

```
atggccaagg ctaacttccc gcccgcggcg cgctatgtta atatgacgca ggtctatgcg      60
acaggcgctc acaatatgcc ggacgaggac cgcgtcaagg tcatgaacgg gctgtccaag     120
cccgtgacga aggccaaggc aggtgatttg gggtttgggg atgttgagtc catgacggcc     180
tgggaagagt ttgtggcggc tatgttcttg ttgatcattg tgggaagcat gctttggatt     240
ccgattgcgg tggtcggttt tgtcctgtgt gtccgcagcg cggtggcgtg ggtggtgatg     300
ctcatcgtgt tcttcgccct gagcctgcac ccagtcccgc gcattcatga tatggttcat     360
tcgcctttga atcactttat attcaagtac ttcagtctta aaatggcgag tgatgcacca     420
ctggatagtg ctgggcgcta tatctttgtt gctccgccgc atgggtgct gccgatgggg      480 aatcttatga cggtgcacgc gatgaaggct tgtggtggat tggagttccg tgggctgacg     540
acagatgtcg cgctcaggct gccttttattt cgacattact taggcgccat ggtactatt     600 gccgcgactg ggcacgtggc gaagcagtac ctcgacgaag ggtggtcaat aggcatatct     660
tcgggcggag tcgcggaaat tttcgaggta aataataagg atgaagtggt gttgatgaag     720
gagaggaagg gctttgtgaa gctcgcccctt cgcacgggaa ctccgctggt ggcttgttat    780
atatttggga ataccaagct gttgtcggcg tggtatgatg atggaggtgt gttgcagggt     840
ctttcacgtt atttgaaatg tggtgtgttg ccactttggg gtcggtttgg attgccgctt     900
atgcaccgcc atccggtgct gggcgcgatg caaagccga ttgtggtccc caaggtggag      960
ggggagccta cgcaggagat gatagatgat taccataatc tcttctgtca gacgctggtc    1020
gatctctttg ataggtacaa gggcttatat ggctggccgg acaagaagct gcttataaag    1080
tga                                                                  1083
```

<210> SEQ ID NO 35
<211> LENGTH: 360
<212> TYPE: PRT
<213> ORGANISM: Nannochloropsis oculata

<400> SEQUENCE: 35

```
Met Ala Lys Ala Asn Phe Pro Pro Ala Ala Arg Tyr Val Asn Met Thr
1               5                   10                  15

Gln Val Tyr Ala Thr Gly Ala His Asn Met Pro Asp Glu Asp Arg Val
            20                  25                  30

Lys Val Met Asn Gly Leu Ser Lys Pro Val Thr Glu Ala Lys Ala Gly
        35                  40                  45

Asp Leu Gly Phe Gly Asp Val Glu Ser Met Thr Ala Trp Glu Glu Phe
```

```
                  50                  55                  60
Val Ala Ala Met Phe Leu Leu Ile Ile Val Gly Ser Met Leu Trp Ile
 65                  70                  75                  80

Pro Ile Ala Val Val Gly Phe Val Leu Cys Val Arg Ser Ala Val Ala
                     85                  90                  95

Trp Val Val Met Leu Ile Val Phe Phe Ala Leu Ser Leu His Pro Val
                    100                 105                 110

Pro Arg Ile His Asp Met Val His Ser Pro Leu Asn His Phe Ile Phe
                115                 120                 125

Lys Tyr Phe Ser Leu Lys Met Ala Ser Asp Ala Pro Leu Asp Ser Ala
                130                 135                 140

Gly Arg Tyr Ile Phe Val Ala Pro Pro His Gly Val Leu Pro Met Gly
145                 150                 155                 160

Asn Leu Met Thr Val His Ala Met Lys Ala Cys Gly Gly Leu Glu Phe
                    165                 170                 175

Arg Gly Leu Thr Thr Asp Val Ala Leu Arg Leu Pro Leu Phe Arg His
                180                 185                 190

Tyr Leu Gly Ala Ile Gly Thr Ile Ala Ala Thr Gly His Val Ala Lys
                195                 200                 205

Gln Tyr Leu Asp Glu Gly Trp Ser Ile Gly Ile Ser Ser Gly Gly Val
210                 215                 220

Ala Glu Ile Phe Glu Val Asn Asn Lys Asp Glu Val Val Leu Met Lys
225                 230                 235                 240

Glu Arg Lys Gly Phe Val Lys Leu Ala Leu Arg Thr Gly Thr Pro Leu
                    245                 250                 255

Val Ala Cys Tyr Ile Phe Gly Asn Thr Lys Leu Leu Ser Ala Trp Tyr
                260                 265                 270

Asp Asp Gly Gly Val Leu Gln Gly Leu Ser Arg Tyr Leu Lys Cys Gly
                275                 280                 285

Val Leu Pro Leu Trp Gly Arg Phe Gly Leu Pro Leu Met His Arg His
290                 295                 300

Pro Val Leu Gly Ala Met Ala Lys Pro Ile Val Val Pro Lys Val Glu
305                 310                 315                 320

Gly Glu Pro Thr Gln Glu Met Ile Asp Asp Tyr His Asn Leu Phe Cys
                    325                 330                 335

Gln Thr Leu Val Asp Leu Phe Arg Tyr Lys Gly Leu Tyr Gly Trp
                340                 345                 350

Pro Asp Lys Lys Leu Leu Ile Lys
                355                 360

<210> SEQ ID NO 36
<211> LENGTH: 1362
<212> TYPE: DNA
<213> ORGANISM: Nannochloropsis oculata

<400> SEQUENCE: 36
attttcagca aagtaatcaa gataataaac aaaaacaatc ctataaagga aaacaacag       60 gaggcatcac aagcaatatg gccaaggcta acttcccgcc cgcggcgcgc tatgttaata      120
tgacgcaggt ctatgcgaca ggcgctcaca atatgccgga cgaggaccgc gtcaaggtca      180
tgaacgggct gtccaagccc gtgacggagg ccaaggcagg tgatttgggg tttggggatg      240
ttgagtccat gacggcctgg gaagagtttg tggcggctat gttcttgttg atcattgtgg      300
gaagcatgct ttggattccg attgcggtgg tcggttttgt cctgtgtgtc cgcagcgcgg      360
```

```
tggcgtgggt ggtgatgctc atcgtgttct tcgccctgag cctgcaccca gtcccgcgca      420
ttcatgatat ggttcattcg cctttgaatc actttatatt caagtacttc agtcttaaaa      480
tggcgagtga tgcaccactg gatagtgctg ggcgctatat ctttgttgct ccgccgcatg      540
gggtgctgcc gatggggaat cttatgacgg tgcacgcgat gaaggcttgt ggtggattgg      600
agttccgtgg gctgacgaca gatgtcgcgc tcaggctgcc tttatttcga cattacttag      660
gcgccattgg tactattgcc gcgactgggc acgtggcgaa gcagtacctc gacgaagggt      720
ggtcaatagg catatcttcg ggcggagtcg cggaaatttt cgaggtaaat aataaggatg      780
aagtggtgtt gatgaaggag aggaagggct tgtgaagct cgcccttcgc acggaactc        840 cgctggtggc ttgttatata tttgggaata ccaagctgtt gtcggcgtgg tatgatgatg      900
gaggtgtgtt gcagggtctt tcacgttatt tgaaatgtgg tgtgttgcca ctttggggtc      960
ggtttggatt gccgcttatg caccgccatc cggtgctggg cgcgatggca aagccgattg     1020
tggtccccaa ggtggagggg gagcctacgc aggagatgat agatgattac cataatctct     1080
tctgtcagac gctggtcgat ctctttgata ggtacaaggg cttatatggc tggccggaca     1140
agaagctgct tataaagtga gtggggtaga gtagattgcg tgacggggg gagaggggga      1200 tgaatgcaat tgtagaagga attctaggga tttttgcgta ggcgttttgt atctagtcgt     1260
gtagggatag gggcatttgt tcaggaggtg aaagttttgt cggtgtatcc aaagaccaaa     1320
tgcagcacaa caaatcaaag aaagcatgaa aacacaatcc aa                        1362

<210> SEQ ID NO 37
<211> LENGTH: 1695
<212> TYPE: DNA
<213> ORGANISM: Nannochloropsis oculata

<400> SEQUENCE: 37
atgttgttgc agggattaag ctggtctttt ttgaccttgt cgattgtggt agaaatcttg        60
tttgtgatct cgacgtttgc tgtggggttt gagttgtttg ttggagcggc ggtggtggcg      120
ggcggcttct ttttggtctc ggaagtgttg atgattgtga gtttgcattt ttatatgcct      180
acgacgacca cgactgtgac aacgaccggg ttggcggtga tggaggagaa ggtgaggag       240 gtggaggaga tgatggtggg gaaggaggga gtggggaag aggacgagga gatggtggag       300
gaaaaggtgg acgtgacgac agcggcgacg acgaacgcac tcttaagaac cgaaaagcag      360
cggctgctct tggcgaaaga gagtgctacg accactacta ctaccgcgac tgtgaccacg      420
gggcagacca gcaagacgtc tacttcattt atgcctgtcc gggtcgacga ggcttccctt      480
gagcaattcc gccggctcac cgttataacc gttctgagta atatgcaata cctgcccttc      540
ctccttccca tcctcccttt tgtcctctca ggtcttcctc tccctgtggc atcttttcac      600
tggttcggcg cttttttgttg tctgacctca gcggtcgttt taaacgccta tgtcaaaacc      660
acgttggcca aagctgggaa tcgtatttcc tccttccagc gctccctcct taatgtcctc      720
cccacgctca tttatgccgc gccgggtctt atttgctttt ttgcgtggag tcaacaccaa      780
ggtgggaggg aggacgggaa ggagcgcgcg gtgactgcgt tcccggcttg ggcggcgctc      840
acggccatgc attacctgta cctctttctc acgtttcgcg gaaatccgga agtaacggga      900
gagaggtact taggcgaaaa gctagagctg tggaaaggcg gttggtcatt gtactatttt      960
ttagaaggga tagatcaata ttttcaggcg aagttggtct tcatggaccc gaaactggat     1020
ctgaagggga aaccgcatgt gtttgcgttt cacccacacg gagtccagcc gtttacgacg     1080
ttttggattc agctttcgcg ggcctggagg gagggagtgg ggaagggaca gagattctgt     1140
```

-continued

```
gtgatgactg cgagtgttat gcattatgtg ccgttaatgc gcgatatatt acagtggctc    1200
ggggggcggg aagtgagcag ggaagccatt tcgtacgcac tggaccgtaa acagtcagta    1260
ttgttggttc caggcggaca acaagagatg atggagtccc aatctcagat gggcgagatt    1320
cggatcatta cgaagcacgt cggcttcatt agattagcac tccagacagg cgcgccgctc    1380
gtgcctgtgc tctcatttgg cgaagttgaa gtgatggatt ttgtccggta cccgcgtcta    1440
cagcgtttct ttatctcgcg catcggtatt ccggttccct tcttcccata tggattgttt    1500
ggatttccca tcccaaggcc cgtgcccgtg acggtcgtgt ttggccgtcc gattgcagtg    1560
gagaaagtgg agcaaccgac gcaggaagag gtgcgtaaat tgtcgaaaaa gtactttgaa    1620
agtatccagg aggtgtttga taaaaataag gcgaaggccc tggggcatgg aaatcataaa    1680
ttggtcctgt tgtga                                                    1695

<210> SEQ ID NO 38
<211> LENGTH: 564
<212> TYPE: PRT
<213> ORGANISM: Nannochloropsis oculata

<400> SEQUENCE: 38

Met Leu Leu Gln Gly Leu Ser Trp Ser Phe Leu Thr Leu Ser Ile Val
1               5                   10                  15

Val Glu Ile Leu Phe Val Ile Ser Thr Phe Ala Val Gly Phe Glu Leu
                20                  25                  30

Phe Val Gly Ala Ala Val Val Ala Gly Gly Phe Phe Leu Val Ser Glu
            35                  40                  45

Val Leu Met Ile Val Ser Leu His Phe Tyr Met Pro Thr Thr Thr Thr
        50                  55                  60

Thr Val Thr Thr Thr Gly Leu Ala Val Met Glu Glu Lys Val Glu Glu
65                  70                  75                  80

Val Glu Glu Met Met Val Gly Lys Glu Gly Val Gly Glu Glu Asp Glu
                85                  90                  95

Glu Met Val Glu Glu Lys Val Asp Val Thr Thr Ala Ala Thr Thr Asn
                100                 105                 110

Ala Leu Leu Arg Thr Glu Lys Gln Arg Leu Leu Ala Lys Glu Ser
            115                 120                 125

Ala Thr Thr Thr Thr Thr Thr Ala Thr Val Thr Thr Gly Gln Thr Ser
        130                 135                 140

Lys Thr Ser Thr Ser Phe Met Pro Val Arg Val Asp Glu Ala Ser Leu
145                 150                 155                 160

Glu Gln Phe Arg Arg Leu Thr Val Ile Thr Val Leu Ser Asn Met Gln
                165                 170                 175

Tyr Leu Pro Phe Leu Leu Pro Ile Leu Pro Phe Val Leu Ser Gly Leu
                180                 185                 190

Pro Leu Pro Val Ala Ser Phe His Trp Phe Gly Ala Phe Cys Cys Leu
            195                 200                 205

Thr Ser Ala Val Val Leu Asn Ala Tyr Val Lys Thr Thr Leu Ala Lys
        210                 215                 220

Ala Gly Asn Arg Ile Ser Ser Phe Gln Arg Ser Leu Leu Asn Val Leu
225                 230                 235                 240

Pro Thr Leu Ile Tyr Ala Ala Pro Gly Leu Ile Cys Phe Phe Ala Trp
                245                 250                 255

Ser Gln His Gln Gly Gly Arg Glu Asp Gly Lys Glu Arg Ala Val Thr
                260                 265                 270
```

```
Ala Phe Pro Ala Trp Ala Ala Leu Thr Ala Met His Tyr Leu Tyr Leu
        275                 280                 285

Phe Leu Thr Phe Arg Gly Asn Pro Glu Val Thr Gly Glu Arg Tyr Leu
290                 295                 300

Gly Glu Lys Leu Glu Leu Trp Lys Gly Gly Trp Ser Leu Tyr Tyr Phe
305                 310                 315                 320

Leu Glu Gly Ile Asp Gln Tyr Phe Gln Ala Lys Leu Val Phe Met Asp
                325                 330                 335

Pro Lys Leu Asp Leu Lys Gly Lys Pro His Val Phe Ala Phe His Pro
            340                 345                 350

His Gly Val Gln Pro Phe Thr Thr Phe Trp Ile Gln Leu Ser Arg Ala
        355                 360                 365

Trp Arg Glu Gly Val Gly Lys Gly Gln Arg Phe Cys Val Met Thr Ala
370                 375                 380

Ser Val Met His Tyr Val Pro Leu Met Arg Asp Ile Leu Gln Trp Leu
385                 390                 395                 400

Gly Gly Arg Glu Val Ser Arg Glu Ala Ile Ser Tyr Ala Leu Asp Arg
                405                 410                 415

Lys Gln Ser Val Leu Leu Val Pro Gly Gly Gln Gln Glu Met Met Glu
            420                 425                 430

Ser Gln Ser Gln Met Gly Glu Ile Arg Ile Ile Thr Lys His Val Gly
        435                 440                 445

Phe Ile Arg Leu Ala Leu Gln Thr Gly Ala Pro Leu Val Pro Val Leu
    450                 455                 460

Ser Phe Gly Glu Val Glu Val Met Asp Phe Val Arg Tyr Pro Arg Leu
465                 470                 475                 480

Gln Arg Phe Phe Ile Ser Arg Ile Gly Ile Pro Val Pro Phe Phe Pro
                485                 490                 495

Tyr Gly Leu Phe Gly Phe Pro Ile Pro Arg Pro Val Pro Val Thr Val
            500                 505                 510

Val Phe Gly Arg Pro Ile Ala Val Glu Lys Val Glu Gln Pro Thr Gln
        515                 520                 525

Glu Glu Val Arg Lys Leu Ser Lys Lys Tyr Phe Glu Ser Ile Gln Glu
530                 535                 540

Val Phe Asp Lys Asn Lys Ala Lys Ala Leu Gly His Gly Asn His Lys
545                 550                 555                 560

Leu Val Leu Leu

<210> SEQ ID NO 39
<211> LENGTH: 2074
<212> TYPE: DNA
<213> ORGANISM: Nannochloropsis oculata

<400> SEQUENCE: 39
aagggaggga gggaagagcg caccagaagg ccgtacgaaa gcaatggcgt ttttggcagc      60 cattttggg aggagccaag tttatgttgt tgcagggatt aagctggtct ttttttgacct    120 tgtcgattgt ggtagaaatc ttgtttgtga tctcgacgtt tgctgtgggg tttgagttgt    180
ttgttggagc ggcggtggtg gcgggcggct tcttttttggt ctcggaagtg ttgatgattg    240
tgagtttgca ttttttatatg cctacgacga ccacgactgt gacaacgacc gggttggcgg    300
tgatggagga gaaggtggag gaggtggagg agatgatggt ggggaaggag ggagtggggg    360
aagaggacga ggagatggtg gaggaaaagg tggacgtgac gacagcggcg acgacgaacg    420
```

```
cactcttaag aaccgaaaag cagcggctgc tcttggcgaa agagagtgct acgaccacta      480
ctactaccgc gactgtgacc acggggcaga ccagcaagac gtctacttca tttatgcctg      540
tccgggtcga cgaggcttcc cttgagcaat ccgccggct caccgttata accgttctga       600
gtaatatgca atacctgccc ttcctccttc ccatcctccc ttttgtcctc tcaggtcttc      660
ctctccctgt ggcatctttt cactggttcg gcgcttttg ttgtctgacc tcagcggtcg       720
ttttaaacgc ctatgtcaaa accacgttgg ccaaagctgg gaatcgtatt tcctccttcc      780
agcgctccct ccttaatgtc ctccccacgc tcatttatgc cgcgccgggt cttatttgct      840
tttttgcgtg gagtcaacac caaggtggga gggaggacgg gaaggagcgc gcggtgactg      900
cgttcccggc ttgggcggcg ctcacggcca tgcattacct gtacctcttt ctcacgtttc      960
gcggaaatcc ggaagtaacg ggagagaggt acttaggcga aaagctagag ctgtggaaag     1020
gcggttggtc attgtactat ttttagaag ggatagatca atattttcag gcgaagttgg     1080
tcttcatgga cccgaaactg gatctgaagg gaaaccgca tgtgtttgcg tttcacccac     1140
acggagtcca gccgtttacg acgttttgga ttcagctttc gcgggcctgg agggagggag     1200
tggggaaggg acagagattc tgtgtgatga ctgcgagtgt tatgcattat gtgccgttaa     1260
tgcgcgatat attacagtgg ctcggggggc gggaagtgag cagggaagcc atttcgtacg     1320
cactggaccg taaacagtca gtattgttgg ttccaggcgg acaacaagag atgatggagt     1380
cccaatctca gatgggcgag attcggatca ttacgaagca cgtcggcttc attagattag     1440
cactccagac aggcgcgccg ctcgtgcctg tgctctcatt tggcgaagtt gaagtgatgg     1500
attttgtccg gtaccgcgt ctacagcgtt tctttatctc gcgcatcggt attccggttc     1560
ccttcttccc atatggattg tttggatttc ccatcccaag gcccgtgccc gtgacggtcg     1620
tgtttggccg tccgattgca gtggagaaag tggagcaacc gacgcaggaa gaggtgcgta     1680
aattgtcgaa aaagtacttt gaaagtatcc aggaggtgtt tgataaaaat aaggcgaagg     1740
ccctggggca tggaaatcat aaattggtcc tgttgtgagg gaggaagaga agcaaaaggg     1800
tgggagacag ggagatggat ggggagaagg aggtttgtgg gggtaggctt tcggagagag     1860
aacaaacgga ctgatacaag acaaaagtgt aagatagaac ttcaggaaag cgaaataatg     1920
attgaacgac atagaaaaaa gaaagggcag cgaggaaggg agggagggag gaagggagga     1980
cagtactgaa atgccaccaa tggcggtccc agcatcggag aatgcacaat aaagcaacaa     2040
agctagtcgg taatgaaaaa aaaaaaaaaa aaaa                                 2074
```

<210> SEQ ID NO 40
<211> LENGTH: 1029
<212> TYPE: DNA
<213> ORGANISM: Nannochloropsis oculata

<400> SEQUENCE: 40

```
atgttgatgg cgccgtcgcg gcggccagca tcgtccttgg tggaccctt gccattgacg        60 gggaagctgc ctatcggggc aatcaggctc ttcacgtccc ggcctgcttc atggcgtacc      120
actcccatgg tcgtgggcgg ctccttgctg gtggtgggat ccttcgtctg ggtgccctt      180 gttatctggc tggttggaa gaaatgtagg acacggaatc gacgcattgt ctacgtcctt      240
gttttgtgtg tcatcttgac cctacctaca cggcgttggg acgcggtggt cttgaacggc      300
ctatggagcc gttttgtgga atattttca gtccaggtgg taggggacga cccttgccc        360 aaggaccgct ccgccgtcta cgccgtcatt cctcacggca ccttccctt tggtctcggc      420 gtggtctccc tcggtcctt gaacaagatc ttcaataagg tccggccgt ggtggcctcg       480
```

```
gcagtcttgc gctttccggg ctttggtcaa ctaataggct tcgccggtgg ggtcgacgca    540
gggcccaaag aagtaagcaa ggccatcaag aagggctgtt cagtgagtat ctgtcctggg    600
ggcatcgcag agatgttctg gggatttcca aaggagggct gcttaccgcg ggaggaatat    660
gcgttcttac agtcgaggaa agggtttatc cgcatggcca tgaaacacaa tgtgcctgtg    720
gtccctgtgt actgttttgg taacacccac gcgatgcata aggcgaagac gccttgggtc    780
ttggaggcgc tatcaaggct tctcaagacc tctcttatct taacctgggg ccggtggggg    840
ctgccgatcc cctaccgtgt gcctctcctc tacgccgtcg gtaagcccct ccgcctcctg    900
cacgcagaaa atccaacccc tgctcagatt gaggcggcgc acgccgagtt ctgcagggcc    960
ctttcggatt tgtttgatcg gtacaagttt tattatggat gggggcacaa gacgcttcgc   1020
atcgtctga                                                           1029
```

<210> SEQ ID NO 41
<211> LENGTH: 342
<212> TYPE: PRT
<213> ORGANISM: Nannochloropsis oculata

<400> SEQUENCE: 41

```
Met Leu Met Ala Pro Ser Arg Arg Pro Ala Ser Ser Leu Val Asp Pro
1               5                   10                  15

Leu Pro Leu Thr Gly Lys Leu Pro Ile Gly Ala Ile Arg Leu Phe Thr
            20                  25                  30

Ser Arg Pro Ala Ser Trp Arg Thr Thr Pro Met Val Val Gly Gly Ser
        35                  40                  45

Leu Leu Val Val Gly Ser Phe Val Trp Val Pro Leu Val Ile Trp Leu
50                  55                  60

Gly Trp Lys Lys Cys Arg Thr Arg Asn Arg Arg Ile Val Tyr Val Leu
65                  70                  75                  80

Val Leu Cys Val Ile Leu Thr Leu Pro Thr Arg Arg Trp Asp Ala Val
                85                  90                  95

Val Leu Asn Gly Leu Trp Ser Arg Phe Val Glu Tyr Phe Ser Val Gln
            100                 105                 110

Val Val Gly Asp Asp Pro Leu Pro Lys Asp Arg Ser Ala Val Tyr Ala
        115                 120                 125

Val Ile Pro His Gly Thr Phe Pro Phe Gly Leu Gly Val Val Ser Leu
    130                 135                 140

Gly Pro Leu Asn Lys Ile Phe Asn Lys Val Arg Pro Val Val Ala Ser
145                 150                 155                 160

Ala Val Leu Arg Phe Pro Gly Phe Gly Gln Leu Ile Gly Phe Ala Gly
                165                 170                 175

Gly Val Asp Ala Gly Pro Lys Glu Val Ser Lys Ala Ile Lys Lys Gly
            180                 185                 190

Cys Ser Val Ser Ile Cys Pro Gly Gly Ile Ala Glu Met Phe Trp Gly
        195                 200                 205

Phe Pro Lys Glu Gly Cys Leu Pro Arg Glu Glu Tyr Ala Phe Leu Gln
    210                 215                 220

Ser Arg Lys Gly Phe Ile Arg Met Ala Met Lys His Asn Val Pro Val
225                 230                 235                 240

Val Pro Val Tyr Cys Phe Gly Asn Thr His Ala Met His Lys Ala Lys
                245                 250                 255

Thr Pro Trp Val Leu Glu Ala Leu Ser Arg Leu Leu Lys Thr Ser Leu
            260                 265                 270
```

```
Ile Leu Thr Trp Gly Arg Trp Gly Leu Pro Ile Pro Tyr Arg Val Pro
        275                 280                 285

Leu Leu Tyr Ala Val Gly Lys Pro Leu Arg Leu Leu His Ala Glu Asn
        290                 295                 300

Pro Thr Pro Ala Gln Ile Glu Ala Ala His Ala Glu Phe Cys Arg Ala
305                 310                 315                 320

Leu Ser Asp Leu Phe Asp Arg Tyr Lys Phe Tyr Tyr Gly Trp Gly His
                325                 330                 335

Lys Thr Leu Arg Ile Val
        340
```

<210> SEQ ID NO 42
<211> LENGTH: 1585
<212> TYPE: DNA
<213> ORGANISM: Nannochloropsis oculata

<400> SEQUENCE: 42

```
attttcagca aagtaatcaa gataataaca aaaacaatcc tctaaaagga aaaacaacag      60
ctttaccctc agggacgtca tgttgatggc gccgtcgcgg cggccagcat cgtccttggt     120
ggaccctttg ccattgacgg ggaagctgcc tatcggggca atcaggctct tcacgtcccg     180
gcctgcttca tggcgtacca ctcccatggt cgtgggcggc tccttgctgg tggtgggatc     240
cttcgtctgg gtgccccttg ttatctggct ggggttggaag aaatgtagga cacggaatcg    300
acgcattgtc tacgtccttg ttttgtgtgt catcttgacc ctacctacac ggcgttggga    360
cgcggtggtc ttgaacggcc tatggagccg ttttgtggaa tattttttcag tccaggtggt    420
aggggacgac cccttgccca aggaccgctc cgccgtctac gccgtcattc ctcacggcac    480
cttcccctt ggtctcggcg tggtctccct cggtcccttg aacaagatct tcaataaggt     540
ccggcccgtg gtggcctcgg cagtcttgcg cttccgggc tttggtcaac taataggctt     600
cgccggtggg gtcgacgcag ggcccaaaga agtaagcaag gccatcaaga agggctgttc    660
agtgagtatc tgtcctgggg gcatcgcaga gatgttctgg ggatttccaa aggagggctg    720
cttaccgcgg gaggaatatg cgttcttaca gtcgaggaaa gggtttatcc gcatggccat    780
gaaacacaat gtgcctgtgg tccctgtgta ctgttttggt aacacccacg cgatgcataa    840
ggcgaagacg ccttgggtct tggaggcgct atcaaggtca gtcacggggg aatagtgggg    900
ttgagtggga cggcgggga gaaaatatat cttgatttt attgtaccgc atctgcgagg     960
ctgtctctaa tcgctttcta cgcgagacca ttcaaaattt tcgctatttc tttgcgtcgt   1020
ctttccgtac gcattaggct tctcaagacc tctcttatct taacctgggg ccggtggggg   1080
ctgccgatcc cctaccgtgt gcctctcctc tacgccgtcg gtaagcccct ccgcctcctg    1140
cacgcagaaa atccaacccc tgctcagatt gaggcggcgc acgccgagtt ctgcagggcc    1200
ctttcggatt tgtttgatcg gtacaagttt tattatggat gggggcacaa gacgcttcgc    1260
atcgtctgag aacgggggga ggggggagg ggtcgttagg ttatgctgga aggaaagaga    1320
atgggagaga gggagagaga aagagtgggg aagatattga tggtatagtc ctcgtctggg   1380
aggcaattgc tgcttgggga ggctcccgag ggagaatgag ggagcgaaga gtagggaaac    1440
caaattatta aatctttttc cttcgttaag acttaggaat aaatgtaaag tacaaagaag    1500
aagagcccgt ctcttgcatc aaattgaaag aaataaagat aaccaatgaa ctaaaaaaaa   1560
aaaaaaaaaa aaaaaaaaaa aaaaa                                         1585
```

-continued

<210> SEQ ID NO 43
<211> LENGTH: 1251
<212> TYPE: DNA
<213> ORGANISM: Nannochloropsis oculata

<400> SEQUENCE: 43

| | | | | |
|---|---|---|---|---|
| atgggcgcta | ccactgcgac | ccagactaaa | aagacgttgg | tcatgcggac agtcgcagtg | 60 |
| cgtaacgagg | atatagtgcc | ggaagcagcg | acgggagacg | agcagcagg cgatgcaact | 120 |
| gctggtggcc | tttctcgctc | aacaccaaca | gcggctccgg | aggcctccac ttcgctttca | 180 |
| tcgcgactgg | taccatcccc | agcacaagtt | tcatccatgc | cccagcaca agcttcagcc | 240 |
| acgcctattg | tggtgcggcc | cgaggcacgc | ccgcaggtc | cacaaggccg tctacaagca | 300 |
| ttaggtgcgg | tgctattttt | ggggctcatg | gggtcgtcgc | tgtacctagt gatcgcgtca | 360 |
| gcgctttaca | tcgtgattgg | tttcggtgtg | ttgggccacc | gcatttgccc ttcgatctta | 420 |
| ctcggggttt | gggtaggaca | agccctaatt | tccgtcaagg | tgctgcacca agacccggaa | 480 |
| ggtatcaagc | ggtcgtggct | tttccgagaa | atggtgaact | tttttgatgt gacactggtg | 540 |
| atggagcaga | aattggacac | ttccaagaag | tacctatttg | cacaacaccc gcacggtatc | 600 |
| cttcccctcg | ccccgtgtt | gtccgcttac | tttgtctcgg | acgtggtgcc cggcggaggc | 660 |
| aagatctttt | gtttgataca | tagcggcatc | tttcacctgc | ccatcgtccg ttttttcatg | 720 |
| ggtgaatggg | gtgcactctc | cgcaaacaag | gagtctgtcg | ccgaagcaaa gcaacaagga | 780 |
| cagcattgct | ccatcgtcgt | cggcggggtc | gcggagattt | tcctccaaaa cggagagacc | 840 |
| gagcaactgc | aactcagaaa | gggcttcatt | cgtgaggcac | ttcgtaatgg atatgacctt | 900 |
| gtgcccatgt | tcactttgg | ggccacgcgc | atgtatcatt | ttgttggccc tgtttcattt | 960 |
| tggcggtcct | tgtccaatta | cctgccgttt | cccttttcc | tcattggggg atggggaaaa | 1020 |
| gggttgacct | tgctccccaa | acctgtgcgt | attgtaattg | ctgtcggttc gcccataggc | 1080 |
| cttgcggctt | tgtatggggt | gccggaagga | cagtcggtgc | ctgatccaga cctggcgaaa | 1140 |
| gtggatttga | tatatgagga | gtggaagaag | cacttggcgg | gcctgtatta tcggcagcgg | 1200 |
| cctgagtggg | aaacgcggga | gttggagatt | ttggactgtc | cgaagtcgtg a | 1251 |

<210> SEQ ID NO 44
<211> LENGTH: 416
<212> TYPE: PRT
<213> ORGANISM: Nannochloropsis oculata

<400> SEQUENCE: 44

Met Gly Ala Thr Thr Ala Thr Gln Thr Lys Lys Thr Leu Val Met Arg
1               5                   10                  15

Thr Val Ala Val Arg Asn Glu Asp Ile Val Pro Glu Ala Ala Thr Gly
            20                  25                  30

Asp Gly Ala Ala Gly Asp Ala Thr Ala Gly Gly Leu Ser Arg Ser Thr
        35                  40                  45

Pro Thr Ala Ala Pro Glu Ala Ser Thr Ser Leu Ser Ser Arg Leu Val
    50                  55                  60

Pro Ser Pro Ala Gln Val Ser Ser Met Pro Pro Ala Gln Ala Ser Ala
65                  70                  75                  80

Thr Pro Ile Val Val Arg Pro Glu Ala Arg Pro Ala Gly Pro Gln Gly
                85                  90                  95

Arg Leu Gln Ala Leu Gly Ala Val Leu Phe Leu Gly Leu Met Gly Ser
            100                 105                 110

Ser Leu Tyr Leu Val Ile Ala Ser Ala Leu Tyr Ile Val Ile Gly Phe

```
            115                 120                 125
Gly Val Leu Gly His Arg Ile Cys Pro Ser Ile Leu Leu Gly Val Trp
            130                 135                 140
Val Gly Gln Ala Leu Ile Ser Val Lys Val Leu His Gln Asp Pro Glu
145                 150                 155                 160
Gly Ile Lys Arg Ser Trp Leu Phe Arg Glu Met Val Asn Phe Phe Asp
                165                 170                 175
Val Thr Leu Val Met Glu Gln Lys Leu Asp Thr Ser Lys Lys Tyr Leu
            180                 185                 190
Phe Ala Gln His Pro His Gly Ile Leu Pro Leu Ala Pro Val Leu Ser
        195                 200                 205
Ala Tyr Phe Val Ser Asp Val Val Pro Gly Gly Lys Ile Phe Cys
    210                 215                 220
Leu Ile His Ser Gly Ile Phe His Leu Pro Ile Val Arg Phe Met
225                 230                 235                 240
Gly Glu Trp Gly Ala Leu Ser Ala Asn Lys Glu Ser Val Ala Glu Ala
                245                 250                 255
Lys Gln Gln Gly Gln His Cys Ser Ile Val Val Gly Val Ala Glu
            260                 265                 270
Ile Phe Leu Gln Asn Gly Glu Thr Glu Gln Leu Gln Leu Arg Lys Gly
        275                 280                 285
Phe Ile Arg Glu Ala Leu Arg Asn Gly Tyr Asp Leu Val Pro Met Phe
    290                 295                 300
His Phe Gly Ala Thr Arg Met Tyr His Phe Val Gly Pro Val Ser Phe
305                 310                 315                 320
Trp Arg Ser Leu Ser Asn Tyr Leu Pro Phe Pro Phe Phe Leu Ile Gly
                325                 330                 335
Gly Trp Gly Lys Gly Leu Thr Leu Leu Pro Lys Pro Val Arg Ile Val
            340                 345                 350
Ile Ala Val Gly Ser Pro Ile Gly Leu Ala Ala Leu Tyr Gly Val Pro
        355                 360                 365
Glu Gly Gln Ser Val Pro Asp Pro Asp Leu Ala Lys Val Asp Leu Ile
    370                 375                 380
Tyr Glu Glu Trp Lys Lys His Leu Ala Gly Leu Tyr Tyr Arg Gln Arg
385                 390                 395                 400
Pro Glu Trp Glu Thr Arg Glu Leu Glu Ile Leu Asp Cys Pro Lys Ser
                405                 410                 415

<210> SEQ ID NO 45
<211> LENGTH: 1923
<212> TYPE: DNA
<213> ORGANISM: Nannochloropsis oculata

<400> SEQUENCE: 45
attttcagca aagtaatcaa gataataaac aaaaacaatc ctataaagga aaaacaacag        60
gaaagccacg ctgccacgct tgcataagaa caaagggggg catcaccacg cgacgctggg       120
gacggagaag gacatcaaac aaggacacaa gcatgggcgc taccactgcg acccagacta       180
aaaagacgtt ggtcatgcgg acagtcgcag tgcgtaacga ggatatagtg ccggaagcag       240
cgacgggaga cggagcagca ggcgatgcaa ctgctggtgg cctttctcgc tcaacaccaa       300
cagcggctcc ggaggcctcc acttcgcttt catcgcgact ggtaccatcc ccagcacaag       360
tttcatccat gccccagca caagcttcag ccacgcctat tgtggtgcgg cccgaggcac       420
gccccgcagg tccacaaggc cgtctacaag cattaggtgc ggtgctattt ttggggctca       480
```

| | |
|---|---:|
| tggggtcgtc gctgtaccta gtgatcgcgt cagcgcttta catcgtgatt ggtttcggtg | 540 |
| tgttgggcca ccgcatttgc ccttcgatct tactcggggt ttgggtagga caagccctaa | 600 |
| tttccgtcaa ggtgctgcac caagacccgg aaggtatcaa gcggtcgtgg cttttccgag | 660 |
| aaatggtgaa cttttttgat gtgacactgg tgatggagca gaaattggac acttccaaga | 720 |
| agtaccctatt tgcacaacac ccgcacggta tccttcccct cgccccgtg ttgtccgctt | 780 |
| actttgtctc ggacgtggtg cccggcgag gcaagatctt tgtttgata catagcggca | 840 |
| tctttcacct gcccatcgtc cgttttttca tgggtgaatg gggtgcactc tccgcaaaca | 900 |
| aggagtctgt cgccgaagca aagcaacaag gacagcattg ctccatcgtc gtcggcgggg | 960 |
| tcgcggagat tttcctccaa aacggagaga ccgagcaact gcaactcaga aagggcttca | 1020 |
| ttcgtgaggc acttcgtaat ggatatgacc ttgtgcccat gtttcacttt ggggccacgc | 1080 |
| gcatgtatca ttttgttggc cctgtttcat tttggcggtc cttgtccaat tacctgccgt | 1140 |
| ttcccttttt cctcattggg ggatggggaa aagggttgac cttgctcccc aaacctgtgc | 1200 |
| gtattgtaat tgctgtcggt tcgcccatag gccttgcggc tttgtatggg gtgccggaag | 1260 |
| gacagtcggt gcctgatcca gacctggcga aagtggattt gatatatgag gagtggaaga | 1320 |
| agcacttggc gggcctgtat tatcggcagc ggcctgagtg ggaaacgcgg gagttggaga | 1380 |
| ttttggactg tccgaagtcg tgagtgatta aaaagagatc gcatctgtgc gacgaagtgc | 1440 |
| tttgtacagc agccggatag ggggaaggt aatatttgga aaaggtcaaa aggtggagtg | 1500 |
| cagagtagga ggatttgaca aagattaaga cgtggacgac atgacgacat gggagaaaga | 1560 |
| ctggtcgaat ttaaccaaaa aaagagctac cgcagcaagc gtaacgcaga ggagcattta | 1620 |
| agtatgcatg ttgccaaggc aaggcaaggc aaaaggccat ccgagtagca ggcacacgca | 1680 |
| tgtaaagtgg cgacgcttac acttttggat attaacgaat aaaagacaca aggatgtcgc | 1740 |
| ttacagtgca gcagcagcaa ttacatgttt gtgcgaagtc tctaggggat acctccagca | 1800 |
| ctgtcatcaa cataagtaag atacgaagga cacagaagga taagtgggag gatggggtgt | 1860 |
| agtaggaggg tggggaggtt ggatggaaaa ggggggttcg gcgagtggag ttggacaggg | 1920 |
| ccc | 1923 |

<210> SEQ ID NO 46
<211> LENGTH: 930
<212> TYPE: DNA
<213> ORGANISM: Thraustochytrium aureum

<400> SEQUENCE: 46

| | |
|---|---:|
| atgtcgttcg ttgagcacag cgcggtggtg ctcgtgcttg cctttgtgat gggcggcgca | 60 |
| ctgtactggt cctgggccgg gctcgcgtg ctcatctggg ggtcgtggtc gcaggtggct | 120 |
| acttatgtgg tgctgacggc tgtgctggcc ctgcacccga tcccggacat ctcggatgcc | 180 |
| gtgtacagct cgtggatcgt gcagcaattg tacaagtact ttacctaccg ctttgtgtac | 240 |
| tcggggaacg cgcgcgtact agcgcagacg caggcgccgt tcatcggcgc aggcgtcccg | 300 |
| cacggcgcga tgccgttctc caacctgctc tcagtccctg ctgtcaactc gttttctccg | 360 |
| agccagaccg ggggcgaatt tgtcggggcg ccggcgagca ttgtgttccg cacgcctttc | 420 |
| ctgcgctact ttaccatgtt caagtcggtc acggtgtcac gcgagagcct caccaaacag | 480 |
| ctggagctcg ggaacacggt tggcctggtt ggcgatggca tcgctgggat cttccaatgc | 540 |
| gaccacaacg acgaggtcgt tgcgctccgg acgcgcaagg ggctcgcaaa actggcgctg | 600 |

```
cgaacggggc ggcccgtttt gccctgctac agcttgggaa acacggaagc gtttagcgtt    660
tggtttgacc gctggggcgt catggagcgc ctctcgcgca agctgcaggc gagcgtgttt    720
ttctactggg gcaggtacgg cctccctgtt ccgtaccgtg tcaatatcac gatgatcctc    780
ggcgacatgg tcctcgtcga ccaggtcgag aacccgacgc cggcacaggt cgatgcagtg    840
cacgagcgca ttcttgcgtc catcgagaac gccttcaatc ggcacaaggc cgcccttggt    900
tggggccaca agacgatgcg atttgtgtag                                     930
```

<210> SEQ ID NO 47  
<211> LENGTH: 309  
<212> TYPE: PRT  
<213> ORGANISM: Thraustochytrium aureum
<400> SEQUENCE: 47

```
Met Ser Phe Val Glu His Ser Ala Val Val Leu Val Leu Ala Phe Val
 1               5                  10                  15

Met Gly Gly Ala Leu Tyr Trp Ser Trp Ala Gly Leu Ala Val Leu Ile
            20                  25                  30

Trp Gly Ser Trp Ser Gln Val Ala Thr Tyr Val Leu Thr Ala Val
        35                  40                  45

Leu Ala Leu His Pro Ile Pro Asp Ile Ser Asp Ala Val Tyr Ser Ser
 50                  55                  60

Trp Ile Val Gln Gln Leu Tyr Lys Tyr Phe Thr Tyr Arg Phe Val Tyr
 65                  70                  75                  80

Ser Gly Asn Ala Arg Val Leu Ala Gln Thr Gln Ala Pro Phe Ile Gly
                85                  90                  95

Ala Gly Val Pro His Gly Ala Met Pro Phe Ser Asn Leu Leu Ser Val
            100                 105                 110

Pro Ala Val Asn Ser Phe Ser Pro Ser Gln Thr Gly Gly Glu Phe Val
            115                 120                 125

Gly Ala Pro Ala Ser Ile Val Phe Arg Thr Pro Phe Leu Arg Tyr Phe
        130                 135                 140

Thr Met Phe Lys Ser Val Thr Val Ser Arg Glu Ser Leu Thr Lys Gln
145                 150                 155                 160

Leu Glu Leu Gly Asn Thr Val Gly Leu Val Gly Asp Gly Ile Ala Gly
                165                 170                 175

Ile Phe Gln Cys Asp His Asn Asp Glu Val Val Ala Leu Arg Thr Arg
            180                 185                 190

Lys Gly Leu Ala Lys Leu Ala Leu Arg Thr Gly Arg Pro Val Leu Pro
            195                 200                 205

Cys Tyr Ser Leu Gly Asn Thr Glu Ala Phe Ser Val Trp Phe Asp Arg
210                 215                 220

Trp Gly Val Met Glu Arg Leu Ser Arg Lys Leu Gln Ala Ser Val Phe
225                 230                 235                 240

Phe Tyr Trp Gly Arg Tyr Gly Leu Pro Val Pro Tyr Arg Val Asn Ile
                245                 250                 255

Thr Met Ile Leu Gly Asp Met Val Leu Val Asp Gln Val Glu Asn Pro
            260                 265                 270

Thr Pro Ala Gln Val Asp Ala Val His Glu Arg Ile Leu Ala Ser Ile
            275                 280                 285

Glu Asn Ala Phe Asn Arg His Lys Ala Ala Leu Gly Trp Gly His Lys
        290                 295                 300

Thr Met Arg Phe Val
305
```

<210> SEQ ID NO 48
<211> LENGTH: 1134
<212> TYPE: DNA
<213> ORGANISM: Thraustochytrium aureum

<400> SEQUENCE: 48

| | | | | | | |
|---|---|---|---|---|---|---|
| aagcgtttag | cgtttggttt | gaccgagcag | gcgccaatgt | cgttcgttga | gcacagcgcg | 60 |
| gtggtgctcg | tgcttgcctt | tgtgatgggc | ggcgcactgt | actggtcctg | gccgggctc | 120 |
| gcggtgctca | tctggggggtc | gtggtcgcag | gtggctactt | atgtggtgct | gacggctgtg | 180 |
| ctggccctgc | acccgatccc | ggacatctcg | gatgccgtgt | acagctcgtg | gatcgtgcag | 240 |
| caattgtaca | agtactttac | ctaccgcttt | gtgtactcgg | ggaacgcgcg | cgtactagcg | 300 |
| cagacgcagg | cgccgttcat | cggcgcaggc | gtcccgcacg | gcgcgatgcc | gttctccaac | 360 |
| ctgctctcag | tccctgctgt | caactcgttt | tctccgagcc | agaccggggg | cgaatttgtc | 420 |
| ggggcgccgg | cgagcattgt | gttccgcacg | cctttcctgc | gctactttac | catgttcaag | 480 |
| tcggtcacgg | tgtcacgcga | gagcctcacc | aaacagctgg | agctcgggaa | cacggttggc | 540 |
| ctggttggcg | atggcatcgc | tgggatcttc | caatgcgacc | acaacgacga | ggtcgttgcg | 600 |
| ctccggacgc | gcaaggggct | cgcaaaactg | gcgctgcgaa | cggggcggcc | cgttttgccc | 660 |
| tgctacagct | tgggaaacac | ggaagcgttt | agcgtttggt | ttgaccgctg | gggcgtcatg | 720 |
| gagcgcctct | cgcgcaagct | gcaggcgagc | gtgttttttct | actggggcag | gtacggcctc | 780 |
| cctgttccgt | accgtgtcaa | tatcacgatg | atcctcggcg | acatggtcct | cgtcgaccag | 840 |
| gtcgagaacc | cgacgccggc | acaggtcgat | gcagtgcacg | agcgcattct | tgcgtccatc | 900 |
| gagaacgcct | tcaatcggca | aaggccgcc | cttggttggg | gccacaagac | gatgcgattt | 960 |
| gtgtaggagg | tgctgtttgc | caacaccaca | cttggcctgg | cctgggatgc | ggctgggcca | 1020 |
| atcgtttcgg | tcgatcgcgc | tcgagctcga | gctactcgag | agtcaccgcc | gagcgaggca | 1080 |
| gccataaaga | gtcgaacgaa | aatagcaaaa | tgtgcaattc | accaaaaaaa | aaaa | 1134 |

<210> SEQ ID NO 49
<211> LENGTH: 1179
<212> TYPE: DNA
<213> ORGANISM: Thraustochytrium aureum

<400> SEQUENCE: 49

| | | | | | | |
|---|---|---|---|---|---|---|
| atggtcttcc | tctgccttcc | ctacatgctc | cccgaagcgc | tgctcccttt | cttggacacg | 60 |
| gcgacgctag | gcctcatccc | ggccctgccc | ggagacaagg | agaactttgt | ccacacgttt | 120 |
| gccgtgtggt | ggacgctctt | gtgggcgatt | gcgttttgga | cgatcttttta | cgccgcgctc | 180 |
| aagaattggg | gcgtgcgagg | gtggcggctc | agcctggcgc | tcgctgtctt | cgcggtctgc | 240 |
| tcgttcggcg | gcactctgcg | gtaccactcg | gagagcccac | actacccgat | ggcggttctc | 300 |
| atctgctcgc | tcaactttgt | ctacatctcc | actacgttca | ccaagaagcc | agagtccaac | 360 |
| gcgtgccggg | agtggcccga | gctgcgcgag | ctgcgcatct | tgcccgacat | gtttgagcgc | 420 |
| ttcttcggcc | tgcaggtcct | gctcaccgac | ggtgccaagc | gcgtcgcgca | catgctgggc | 480 |
| gacgagtcga | gcgcagaccc | gcggatgcgc | caggtaatgc | tcctcttcca | cccgcacagc | 540 |
| atcttcccag | tctcgcacgc | ggcgctgggt | ctcacttcgc | tctggcgctc | gcactttccc | 600 |
| cacctctcgg | tcaacccct | aacagcgagc | attatccact | ttgtgccggt | catgcgcgac | 660 |
| gttttgcagt | ggctcggcat | ctgcgacgtc | tccaaagcga | gcgtggtcaa | cctcatcggc | 720 |

-continued

```
atggggcgca acgtccagat cgtgtgcggc gggcagaccg agatgttcga gtcccgctcc      780
tgggacaagg agatttctgt ggtgcgggcg cgccgccttg gcgttttcaa gatcgccatc      840
cagcagggcc tcggtatcgt gccgatttac agcttcggag agccgctcac ctttgacaac      900
atatacatgc cccgcttgca aacttttgc aagcgcgtgc tcggcttccc ctgcccgttc       960
gtgatgctcg gtcagtacgg ccttcccatt ccgcgccgcg tcccaatttc ggtggctgtt     1020
ggcgagcccg tctttcctgc tcggcagacc gccgatcctt cgctcgagga ggtcaaagag     1080
tttcacagac gttactttga ggccctgcag gccctgtttg accagttcaa ggaccaggcc     1140
gggcacggcc agtgtagcat caagtggctg gactcgtag                            1179
```

<210> SEQ ID NO 50
<211> LENGTH: 392
<212> TYPE: PRT
<213> ORGANISM: Thraustochytrium aureum

<400> SEQUENCE: 50

```
Met Val Phe Leu Cys Leu Pro Tyr Met Leu Pro Glu Ala Leu Leu Pro
  1               5                  10                  15

Phe Leu Asp Thr Ala Thr Leu Gly Leu Ile Pro Ala Leu Pro Gly Asp
             20                  25                  30

Lys Glu Asn Phe Val His Thr Phe Ala Val Trp Trp Thr Leu Leu Trp
         35                  40                  45

Ala Ile Ala Phe Trp Thr Ile Phe Tyr Ala Ala Leu Lys Asn Trp Gly
     50                  55                  60

Val Arg Gly Trp Arg Leu Ser Leu Ala Leu Ala Val Phe Ala Val Cys
 65                  70                  75                  80

Ser Phe Gly Gly Thr Leu Arg Tyr His Ser Glu Ser Pro His Tyr Pro
                 85                  90                  95

Met Ala Val Leu Ile Cys Ser Leu Asn Phe Val Tyr Ile Ser Thr Thr
            100                 105                 110

Phe Thr Lys Lys Pro Glu Ser Asn Ala Cys Arg Glu Trp Pro Glu Leu
        115                 120                 125

Arg Glu Leu Arg Ile Leu Pro Asp Met Phe Glu Arg Phe Phe Gly Leu
    130                 135                 140

Gln Val Leu Leu Thr Asp Gly Ala Lys Arg Val Ala His Met Leu Gly
145                 150                 155                 160

Asp Glu Ser Ser Ala Asp Pro Arg Met Arg Gln Val Met Leu Leu Phe
                165                 170                 175

His Pro His Ser Ile Phe Pro Val Ser His Ala Ala Leu Gly Leu Thr
            180                 185                 190

Ser Leu Trp Arg Ser His Phe Pro His Leu Ser Val Asn Pro Leu Thr
        195                 200                 205

Ala Ser Ile Ile His Phe Val Pro Val Met Arg Asp Val Leu Gln Trp
    210                 215                 220

Leu Gly Ile Cys Asp Val Ser Lys Ala Ser Val Val Asn Leu Ile Gly
225                 230                 235                 240

Met Gly Arg Asn Val Gln Ile Val Cys Gly Gly Gln Thr Glu Met Phe
                245                 250                 255

Glu Ser Arg Ser Trp Asp Lys Glu Ile Ser Val Val Arg Ala Arg Arg
            260                 265                 270

Leu Gly Val Phe Lys Ile Ala Ile Gln Gln Gly Leu Gly Ile Val Pro
        275                 280                 285

Ile Tyr Ser Phe Gly Glu Pro Leu Thr Phe Asp Asn Ile Tyr Met Pro
```

```
                    290                 295                 300
Arg Leu Gln Asn Phe Cys Lys Arg Val Leu Gly Phe Pro Cys Pro Phe
305                 310                 315                 320

Val Met Leu Gly Gln Tyr Gly Leu Pro Ile Pro Arg Arg Val Pro Ile
                325                 330                 335

Ser Val Ala Val Gly Glu Pro Val Phe Pro Ala Arg Gln Thr Ala Asp
                340                 345                 350

Pro Ser Leu Glu Glu Val Lys Glu Phe His Arg Arg Tyr Phe Glu Ala
            355                 360                 365

Leu Gln Ala Leu Phe Asp Gln Phe Lys Asp Gln Ala Gly His Gly Gln
        370                 375                 380

Cys Ser Ile Lys Trp Leu Asp Ser
385                 390

<210> SEQ ID NO 51
<211> LENGTH: 1303
<212> TYPE: DNA
<213> ORGANISM: Thraustochytrium aureum

<400> SEQUENCE: 51
agctttacct gctacatggt cttcctctgc cttccctaca tgctccccga agcgctgctc      60
cctttcttgg acacggcgac gctaggcctc atcccggccc tgcccggaga caaggagaac     120
tttgtccaca cgtttgccgt gtggtggacg ctcttgtggg cgattgcgtt ttggacgatc     180
ttttacgccg cgctcaagaa ttggggcgtg cgagggtggc ggctcagcct ggcgctcgct     240
gtcttcgcgt tctgctcgtt cggcggcact ctgcggtacc actcggagag cccacactac     300
ccgatggcgg ttctcatctg ctcgctcaac tttgtctaca tctccactac gttcaccaag     360
aagccagagt ccaacgcgtg ccgggagtgg cccgagctgc gcgagctgcg catcttgccc     420
gacatgtttg agcgcttctt cggcctgcag gtcctgctca ccgacggtgc caagcgcgtc     480
gcgcacatgc tgggcgacga gtcgagcgca gacccgcgga tgcgccaggt aatgctcctc     540
ttccacccgc acagcatctt cccagtctcg cacgcggcgc tgggtctcac ttcgctctgg     600
cgctcgcact tccccacct ctcggtcaac cccctaacag cgagcattat ccactttgtg     660
ccggtcatgc gcgacgtttt gcagtggctc ggcatctgcg acgtctccaa gcgagcgtg     720 gtcaacctca tcggcatggg cgcaacgtc cagatcgtgt gcggcgggca gaccgagatg     780
ttcgagtccc gctcctggga caaggagatt tctgtggtgc gggcgcgccg ccttggcgtt     840
ttcaagatcg ccatccagca gggcctcggt atcgtgccga tttacagctt cggagagccg     900
ctcacctttg acaacatata catgccccgc ttgcaaaaact tttgcaagcg cgtgctcggc     960
ttcccctgcc cgttcgtgat gctcggtcag tacggccttc ccattccgcg ccgcgtccca    1020
atttcggtgg ctgttggcga gcccgtcttt cctgctcggc agaccgccga tccttcgctc    1080
gaggaggtca agagtttca cagacgttac tttgaggccc tgcaggccct gtttgaccag    1140
ttcaaggacc aggccgggca cggccagtgt agcatcaagt ggctggactc gtagaggcag    1200
aaagccccgc gcactgcttt tgcgcctgtg ccgttcccgt tgtagaaac aaccttccaa    1260 cattcgttag ctttctctta aaaaaaaaa aaaaaaaaa aaa                        1303

<210> SEQ ID NO 52
<211> LENGTH: 1389
<212> TYPE: DNA
<213> ORGANISM: Thraustochytrium aureum

<400> SEQUENCE: 52
```

```
atgtttcttc gcatcgaacg ggaatggcga gaggaggacg agtgggccaa gcaggagccc      60
ggcgttgtct ccacgatgat ctggaccccg atcctgatcg ggctccgctg cttcaacatc     120
tggctctccg tggttacctg gccgctctcg tttctggctc gcgtcgtttt cggcatggag     180
atgaagaagg cgagcttctg ggacgtccct ctggagcggc gcaagcagac ggtggcagtt     240
gcgggcttcg tgatgctgct ccccctgcgtg ctgcttgcgt acgtctggtc gcttgtgctg    300
ctcgttttcc cgctgacgac gctgccaatg ctcgggtact acatctggat cttcaagatc     360
gacaagagcc ccgagaacgg gcagcgcacg ccgttcctgc gttactggtc ggcgtggcgc     420
cacttcgcct cctacttccc gctgcgcctc atcaagacgc acaacctcga cccgagccgc     480
aagtacgtct cgcgtacca cccgcacggc atcatcagca ttggcgcgtt cggcaacttt     540
gccaccaacg cgacggggtt tagccgcaag tttcccggaa tcgacctccg cctcctcacc     600
ttggaaatga acttttggtg ccctggatc cgcgagttcc tgctgagcat gggcgtctgc    660
tcagccgcca gcggtcctg caacaagatt ctcagcaagg ggcccggaag cgccatcatg     720
ctggtcgttg gcggcgccgc cgagtcgctc gacacggagc ccggcaccta caggctcacg     780
ttgggccgca agggctttat ccgcgtcgcg ctcgacaacg gggccgacct cgtgcctgtg     840
ctcgccttcg gggagaacga catctttgac accatctact acgagtccgg caccgtgatg     900
cgcaagatcc aggaggtcgt gcgcaagcgc ctcggctttg ccacccctgt ttttccggc     960
cgcggcttct tcaactacag ctttggcttc ctcccgcacc ggcgcccggt cattgtcgtc    1020
tgcgggcgcc ctatcaaggt cccaaaactc ccggaacacc tgcgcggctc ggcgctctcg    1080
accaccctg aaggcgtcgc gcttgtcgac cagtaccacc aaaagtacgt cgccgagctg    1140
cgccgcgtgt gggacctcta caagtccaag tgggccgtct cgcgggcaga gtcgctcatg    1200
atcaagggtg tgcaaaaccc ggcgctcccg cgctccccgt cgcgccgcat cccgccggcg    1260
cagcgcgttc ccgcgagtgc cgcctcgctt tcgtttcgcg aggtcgacga ggccgaattt   1320
gaggccaagg aggacggcgc gacctcttcg ccgcagtcca tgtctgcggc gctgtacacc    1380
gagggttag                                                            1389
```

<210> SEQ ID NO 53
<211> LENGTH: 462
<212> TYPE: PRT
<213> ORGANISM: Thraustochytrium aureum

<400> SEQUENCE: 53

Met Phe Leu Arg Ile Glu Arg Glu Trp Arg Glu Asp Glu Trp Ala
1               5                   10                  15

Lys Gln Glu Pro Gly Val Val Ser Thr Met Ile Trp Thr Pro Ile Leu
            20                  25                  30

Ile Gly Leu Arg Cys Phe Asn Ile Trp Leu Ser Val Val Thr Trp Pro
        35                  40                  45

Leu Ser Phe Leu Ala Arg Val Val Phe Gly Met Glu Met Lys Lys Ala
    50                  55                  60

Ser Phe Trp Asp Val Pro Leu Glu Arg Arg Lys Gln Thr Val Ala Val
65                  70                  75                  80

Ala Gly Phe Val Met Leu Leu Pro Cys Val Leu Ala Tyr Val Trp
            85                  90                  95

Ser Leu Val Leu Leu Val Phe Pro Leu Thr Thr Leu Pro Met Leu Gly
            100                 105                 110

Tyr Tyr Ile Trp Ile Phe Lys Ile Asp Lys Ser Pro Glu Asn Gly Gln

```
                115                 120                 125
Arg Thr Pro Phe Leu Arg Tyr Trp Ser Ala Trp Arg His Phe Ala Ser
            130                 135                 140

Tyr Phe Pro Leu Arg Leu Ile Lys Thr His Asn Leu Asp Pro Ser Arg
145                 150                 155                 160

Lys Tyr Val Phe Ala Tyr His Pro His Gly Ile Ile Ser Ile Gly Ala
                165                 170                 175

Phe Gly Asn Phe Ala Thr Asn Ala Thr Gly Phe Ser Arg Lys Phe Pro
            180                 185                 190

Gly Ile Asp Leu Arg Leu Leu Thr Leu Glu Met Asn Phe Trp Cys Pro
            195                 200                 205

Trp Ile Arg Glu Phe Leu Leu Ser Met Gly Val Cys Ser Ala Ala Lys
        210                 215                 220

Arg Ser Cys Asn Lys Ile Leu Ser Lys Gly Pro Gly Ser Ala Ile Met
225                 230                 235                 240

Leu Val Val Gly Gly Ala Ala Glu Ser Leu Asp Thr Glu Pro Gly Thr
                245                 250                 255

Tyr Arg Leu Thr Leu Gly Arg Lys Gly Phe Ile Arg Val Ala Leu Asp
            260                 265                 270

Asn Gly Ala Asp Leu Val Pro Val Leu Ala Phe Gly Glu Asn Asp Ile
        275                 280                 285

Phe Asp Thr Ile Tyr Tyr Glu Ser Gly Thr Val Met Arg Lys Ile Gln
290                 295                 300

Glu Val Val Arg Lys Arg Leu Gly Phe Ala Thr Pro Val Phe Ser Gly
305                 310                 315                 320

Arg Gly Phe Phe Asn Tyr Ser Phe Gly Phe Leu Pro His Arg Pro
                325                 330                 335

Val Ile Val Val Cys Gly Arg Pro Ile Lys Val Pro Lys Leu Pro Glu
            340                 345                 350

His Leu Arg Gly Ser Ala Leu Ser Thr Thr Pro Glu Gly Val Ala Leu
        355                 360                 365

Val Asp Gln Tyr His Gln Lys Tyr Val Ala Glu Leu Arg Arg Val Trp
370                 375                 380

Asp Leu Tyr Lys Ser Lys Trp Ala Val Ser Arg Ala Glu Ser Leu Met
385                 390                 395                 400

Ile Lys Gly Val Gln Asn Pro Ala Leu Pro Arg Ser Pro Ser Arg Arg
                405                 410                 415

Ile Pro Pro Ala Gln Arg Val Pro Ala Ser Ala Ser Leu Ser Phe
            420                 425                 430

Arg Glu Val Asp Glu Ala Glu Phe Glu Ala Lys Glu Asp Gly Ala Thr
        435                 440                 445

Ser Ser Pro Gln Ser Met Ser Ala Ala Leu Tyr Thr Glu Gly
450                 455                 460

<210> SEQ ID NO 54
<211> LENGTH: 1547
<212> TYPE: DNA
<213> ORGANISM: Thraustochytrium aureum

<400> SEQUENCE: 54
aggctgaccc gcgaagagcg cgagatgttt cttcgcatcg aacgggaatg gcgagaggag      60
gacgagtggg ccaagcagga gcccggcgtt gtctccacga tgatctggac ccgatcctg     120 atcgggctcc gctgcttcaa catctggctc tccgtggtta cctggccgct ctcgtttctg    180
```

```
gctcgcgtcg tttttcggcat ggagatgaag aaggcgagct tctgggacgt ccctctggag    240
cggcgcaagc agacggtggc agttgcgggc ttcgtgatgc tgctcccctg cgtgctgctt    300
gcgtacgtct ggtcgcttgt gctgctcgtt ttcccgctga cgacgctgcc aatgctcggg    360
tactacatct ggatcttcaa gatcgacaag agccccgaga acgggcagcg cacgccgttc    420
ctgcgttact ggtcggcgtg gcgccacttc gcctcctact tcccgctgcg cctcatcaag    480
acgcacaacc tcgacccgag ccgcaagtac gtcttcgcgt accacccgca cggcatcatc    540
agcattggcg cgttcggcaa ctttgccacc aacgcgacgg ggtttagccg caagtttccc    600
ggaatcgacc tccgcctcct caccttggaa atgaactttt ggtgcccctg gatccgcgag    660
ttcctgctga gcatgggcgt ctgctcagcc gccaagcggt cctgcaacaa gattctcagc    720
aaggggcccg gaagcgccat catgctggtc gttggcggcg ccgccgagtc gctcgacacg    780
gagcccggca cctacaggct cacgttgggc cgcaagggct ttatccgcgt cgcgctcgac    840
aacggggccg acctcgtgcc tgtgctcgcc ttcggggaga cgacatcttt tgacaccatc    900
tactacgagt ccggcaccgt gatgcgcaag atccaggagg tcgtgcgcaa gcgcctcggc    960
tttgccaccc ctgttttttc cggccgcggc ttcttcaact acagctttgg cttcctcccg   1020
caccggcgcc cggtcattgt cgtctgcggg cgccctatca aggtcccaaa actcccggaa   1080
cacctgcgcg gctcggcgct ctcgaccacc cctgaaggcg tcgcgcttgt cgaccagtac   1140
caccaaaagt acgtcgccga gctgcgccgc gtgtgggacc tctacaagtc caagtgggcc   1200
gtctcgcggg cagagtcgct catgatcaag ggtgtgcaaa acccggcgct ccgcgctcc    1260 ccgtcgcgcc gcatcccgcc ggcgcagcgc gttcccgcga gtgccgcctc gctttcgttt   1320
cgcgaggtcg acgaggccga atttgaggcc aaggaggacg gcgcgacctc ttcgccgcag   1380
tccatgtctg cggcgctgta caccgagggt tagtcctcat cagcttgccg atctcgccat   1440
cccgcccctg cctcgcgtcc cgccgagccg agttttgtca tgcaccagcg ccttcctgtt   1500
gttgaagtaa caaacgtaaa cgttttttct ttctttcaaa aaaaaaa                 1547
```

<210> SEQ ID NO 55
<211> LENGTH: 1977
<212> TYPE: DNA
<213> ORGANISM: Nannochloropsis oculata

<400> SEQUENCE: 55

```
atgccatccc gcagcaccat tgaggtcatt aaggccgata agaaccagaa taatctggcg     60
tatggcctga ttgttgtcat cctcctggcc attgaccccca accccgtcaa agtcatcgcc    120
gcctctctcg gcatcccctc tcgatggttc gcctacccct gcctggtcat gcttggccac    180
ctattcctca cccactccca ggaatttctc tacgacggcg tccgggtctt cttccgctcc    240
atcctttcga tcttcttccg tcaagtcgac attgtgggca tcgacaacat cccgaaacac    300
ggccctgtca tcttctccgg gaaccactcg aaccaatttg tcgacgggat catggtcctc    360
accaccgccc aacaccgcgt cggcttcctt atcgccgaaa agtcctacaa ccaccctgtt    420
gtcggcacat ttgcaaaact cgcgggcgcc gtgcccgtca cccgccctca agacagcgct    480
aagctcatgc aaggtaccat tatcatgtcc ggccgctctg tcaagggaca aggaaccgcc    540
tttagtcacg agctcgtccc cggcgacaag ctacgtctaa aggtggtgc tgatcaattc    600 aaagtcgagt ccatcacctc cgataccgag ctgatgctct ccgagaacgg cccccttcct    660
cccccctcct ctacctccgc ctcgcccttt gaaaaactag ggaaggtgga ccagacccgt    720
gtctacaatg ccgtgttcga gcaccttaag cacgggaaat gcatcggtat cttccccgaa    780
```

```
ggcggctcgc acgatcggac agacctccta cccctcaagg tagggattgc actcatcgcc    840
tgcggcatgg tcgataaata caatatcaca gtgcccatcg tccccgtggg tttgaactac    900
ttccgaggcc accggtttcg tggacgggtg gtagtagaat tcgggccagc aattcgcgtg    960
ccggaagagt tggcggagtt gtacaagacc aatcgacgcg aggcgtatca ccagtttctg   1020
accaacgtgg aggaagggat gcgggcgacg cttgtgacgg cgcctgatta ccacgcgttg   1080
catttggtgt acacggcacg gaggttattt cagaaggata attggattcc gagcccacgg   1140
gagaagatgg atttgaaccg gcggtttgcc gaggggtata aaattttgat gaataagtat   1200
ggggagcaga ggccggcggc gttggtggag ttggagagga ggttgaatga ttaccaaaaa   1260
actctgcata cgttgggttt gagggattac caagtgccga cgttggagga ggatgataac   1320
ttaaagttgt gttacacgat agcgcatttg ttttggtgt tgacgctggc gatgatgccg    1380
agcttggtgt tgaacgcgcc ggtggggttg attgcccgga ttgtttcgag tcgggagcag   1440
aaaaaggcct tggcggcgtc ccgggtaaag atcgaggcga gggatgtggt tatgagcaaa   1500
aaaatcacgt tgtcgattgt cttggttccg accctatgga tcgtgtacgc catcctcctc   1560
cttcggtaca cctccctcca gccctccacc gtcgccgtgc tcttcttctc ctgtcccctc   1620
ttttcctatc ttggggtcat ggccacagaa gctggcatgg ttgacgccaa ggatctcaaa   1680
cccgtcgtta tgcgtctttt acccggagct cgtaagaaaa tggcgaccct ccctgcggag   1740
cgcgcgcagc tacaaagaga aatccgcgcc tacatacacc agatcggccc tgaacttggg   1800
agtctctaca ccgacaaaac cgtcaagtgg gaagaatacg tccgcaagtc ctcatcggcg   1860
gctgacttgc aatcgttgtt gaacgaagcg acccaaccca agatgcaagg aagtcagacg   1920
gaaggaggga atggtggaga aaaggggga aggaagggg aagaggagct tgtctga       1977
```

<210> SEQ ID NO 56
<211> LENGTH: 658
<212> TYPE: PRT
<213> ORGANISM: Nannochloropsis oculata

<400> SEQUENCE: 56

```
Met Pro Ser Arg Ser Thr Ile Glu Val Ile Lys Ala Asp Lys Asn Gln
1               5                   10                  15

Asn Asn Leu Ala Tyr Gly Leu Ile Val Val Ile Leu Ala Ile Asp
            20                  25                  30

Pro Asn Pro Val Lys Val Ile Ala Ala Ser Leu Gly Ile Pro Ser Arg
        35                  40                  45

Trp Phe Ala Tyr Pro Cys Leu Val Met Leu Gly His Leu Phe Leu Thr
    50                  55                  60

His Ser Gln Glu Phe Leu Tyr Asp Gly Val Arg Val Phe Phe Arg Ser
65                  70                  75                  80

Ile Leu Ser Ile Phe Phe Arg Gln Val Asp Ile Val Gly Ile Asp Asn
                85                  90                  95

Ile Pro Lys His Gly Pro Val Ile Phe Ser Gly Asn His Ser Asn Gln
            100                 105                 110

Phe Val Asp Gly Ile Met Val Leu Thr Thr Ala Gln His Arg Val Gly
        115                 120                 125

Phe Leu Ile Ala Glu Lys Ser Tyr Asn His Pro Val Val Gly Thr Phe
    130                 135                 140

Ala Lys Leu Ala Gly Ala Val Pro Val Thr Arg Pro Gln Asp Ser Ala
145                 150                 155                 160
```

```
Lys Leu Met Gln Gly Thr Ile Ile Met Ser Gly Arg Ser Val Lys Gly
                165                 170                 175
Gln Gly Thr Ala Phe Ser His Glu Leu Val Pro Gly Asp Lys Leu Arg
            180                 185                 190
Leu Lys Gly Gly Ala Asp Gln Phe Lys Val Glu Ser Ile Thr Ser Asp
        195                 200                 205
Thr Glu Leu Met Leu Ser Glu Asn Gly Pro Leu Pro Pro Ser Ser
    210                 215                 220
Thr Ser Ala Ser Pro Phe Glu Lys Leu Gly Lys Val Asp Gln Thr Arg
225                 230                 235                 240
Val Tyr Asn Ala Val Phe Glu His Leu Lys His Gly Lys Cys Ile Gly
                245                 250                 255
Ile Phe Pro Glu Gly Gly Ser His Asp Arg Thr Asp Leu Leu Pro Leu
            260                 265                 270
Lys Val Gly Ile Ala Leu Ile Ala Cys Gly Met Val Asp Lys Tyr Asn
        275                 280                 285
Ile Thr Val Pro Ile Val Pro Val Gly Leu Asn Tyr Phe Arg Gly His
    290                 295                 300
Arg Phe Arg Gly Arg Val Val Val Glu Phe Gly Pro Ala Ile Arg Val
305                 310                 315                 320
Pro Glu Glu Leu Ala Glu Leu Tyr Lys Thr Asn Arg Arg Glu Ala Tyr
                325                 330                 335
His Gln Phe Leu Thr Asn Val Glu Glu Gly Met Arg Ala Thr Leu Val
            340                 345                 350
Thr Ala Pro Asp Tyr His Ala Leu His Leu Val Tyr Thr Ala Arg Arg
        355                 360                 365
Leu Phe Gln Lys Asp Asn Trp Ile Pro Ser Pro Arg Glu Lys Met Asp
    370                 375                 380
Leu Asn Arg Arg Phe Ala Glu Gly Tyr Lys Ile Leu Met Asn Lys Tyr
385                 390                 395                 400
Gly Glu Gln Arg Pro Ala Ala Leu Val Glu Leu Glu Arg Arg Leu Asn
                405                 410                 415
Asp Tyr Gln Lys Thr Leu His Thr Leu Gly Leu Arg Asp Tyr Gln Val
            420                 425                 430
Pro Thr Leu Glu Glu Asp Asp Asn Leu Lys Leu Cys Tyr Thr Ile Ala
        435                 440                 445
His Leu Phe Leu Val Leu Thr Leu Ala Met Met Pro Ser Leu Val Leu
    450                 455                 460
Asn Ala Pro Val Gly Leu Ile Ala Arg Ile Val Ser Ser Arg Glu Gln
465                 470                 475                 480
Lys Lys Ala Leu Ala Ala Ser Arg Val Lys Ile Glu Ala Arg Asp Val
                485                 490                 495
Val Met Ser Lys Lys Ile Thr Leu Ser Ile Val Leu Val Pro Thr Leu
            500                 505                 510
Trp Ile Val Tyr Ala Ile Leu Leu Leu Arg Tyr Thr Ser Leu Gln Pro
        515                 520                 525
Ser Thr Val Ala Val Leu Phe Phe Ser Cys Pro Leu Phe Ser Tyr Leu
    530                 535                 540
Gly Val Met Ala Thr Glu Ala Gly Met Val Asp Ala Lys Asp Leu Lys
545                 550                 555                 560
Pro Val Val Met Arg Leu Leu Pro Gly Ala Arg Lys Lys Met Ala Thr
                565                 570                 575
Leu Pro Ala Glu Arg Ala Gln Leu Gln Arg Glu Ile Arg Ala Tyr Ile
```

```
              580             585             590
His Gln Ile Gly Pro Glu Leu Gly Ser Leu Tyr Thr Asp Lys Thr Val
        595                 600                 605

Lys Trp Glu Glu Tyr Val Arg Lys Ser Ser Ala Ala Asp Leu Gln
        610                 615                 620

Ser Leu Leu Asn Glu Ala Thr Gln Pro Lys Met Gln Gly Ser Gln Thr
625                 630                 635                 640

Glu Gly Gly Asn Gly Gly Glu Lys Gly Gly Arg Lys Gly Glu Glu Glu
                645                 650                 655

Leu Val
```

<210> SEQ ID NO 57
<211> LENGTH: 2460
<212> TYPE: DNA
<213> ORGANISM: Nannochloropsis oculata

<400> SEQUENCE: 57

```
attttcagca aagtaatcaa gataataaac aaaaacaatc ctataaagga aaaacaacag     60
gcacgcgtcc tgaggtgccg gtgcctgtaa ttttcctcct tgggactgtc ggccatcgtc    120
aggaacaagc gcggccacca gggctcattt cgaatcaagc acatccgttc cacacccggg    180
caacaaaacc atgccatccc gcagcaccat tgaggtcatt aaggccgata agaaccagaa    240
taatctggcg tatggcctga ttgttgtcat cctcctggcc attgacccca accccgtcaa    300
agtcatcgcc gcctctctcg catcccctc tcgatggttc gcctacccct gctggtcat     360
gcttggccac ctattcctca cccactccca ggaatttctc tacgacggcg tccgggtctt    420
cttccgctcc atcctttcga tcttcttccg tcaagtcgac attgtgggca tcgacaacat    480
cccgaaacac ggccctgtca tcttctccgg gaaccactcg aaccaatttg tcgacgggat    540
catggtcctc accaccgccc aacaccgcgt cggcttcctt atcgccgaaa agtcctacaa    600
ccaccctgtt gtcggcacat ttgcaaaact cgcgggcgcc gtgcccgtca cccgccctca    660
agacagcgct aagctcatgc aaggtaccat tatcatgtcc ggccgctctg tcaagggaca    720
aggaaccgcc tttagtcacg agctcgtccc cggcgacaag ctacgtctaa aggtggtgc     780
tgatcaattc aaagtcgagt ccatcacctc cgataccgag ctgatgctct ccgagaacgg    840
ccccccttcct cccccctcct ctacctccgc ctcgcccttt gaaaaactag ggaaggtgga    900
ccagacccgt gtctacaatg ccgtgttcga gcaccttaag cacgggaaat gcatcggtat    960
cttccccgaa ggcggctcgc acgatcggac agacctccta ccccctcaagg tagggattgc   1020
actcatcgcc tgcggcatgg tcgataaata caatatcaca gtgccccatcg tccccgtggg   1080
tttgaactac ttccgaggcc accggtttcg tggacgggtg gtagtagaat tcgggccagc   1140
aattcgcgtg ccggaagagt tggcggagtt gtacaagacc aatcgacgcg aggcgtatca   1200
ccagtttctg accaacgtgg aggaagggat gcgggcgacg cttgtgacgg cgcctgatta   1260
ccacgcgttg catttggtgt acacggcacg gaggttattt cagaaggata attggattcc   1320
gagcccacgg gagaagatgg atttgaaccg gcggtttgcc gaggggtata aaattttgat   1380
gaataagtat ggggagcaga ggccggcggc gttggtggag ttggagagga ggttgaatga   1440
ttaccaaaaa actctgcata cgttgggttt gagggattac caagtgccga cgttggagga   1500
ggatgataac ttaaagttgt gttacacgat agcgcatttg ttttggtgt tgacgctggc    1560
gatgatgccg agcttggtgt tgaacgcgcc ggtggggttg attgcccgga ttgtttcgag   1620
tcgggagcag aaaaaggcct tggcggcgtc ccgggtaaag atcgaggcga gggatgtggt   1680
```

```
tatgagcaaa aaaatcacgt tgtcgattgt cttggttccg accctatgga tcgtgtacgc   1740
catcctcctc cttcggtaca cctccctcca gccctccacc gtcgccgtgc tcttcttctc   1800
ctgtcccctc ttttcctatc ttggggtcat ggccacagaa gctggcatgg ttgacgccaa   1860
ggatctcaaa cccgtcgtta tgcgtctttt acccggagct cgtaagaaaa tggcgaccct   1920
ccctgcggag cgcgcgcagc tacaaagaga aatccgcgcc tacatacacc agatcggccc   1980
tgaacttggg agtctctaca ccgacaaaac cgtcaagtgg gaagaatacg tccgcaagtc   2040
ctcatcggcg gctgacttgc aatcgttgtt gaacgaagcg acccaaccca agatgcaagg   2100
aagtcagacg gaaggaggga atggtggaga aaaaggggga aggaaggggg aagaggagct   2160
tgtctgatac gtcaccgaaa ttgtcgcatg cgatgaatgg aagagagacg ccgccaccag   2220
ttaagatgac tcaaaacccg ctggtgacgg ggaagaagga tgcataggag ggattatgag   2280
ggagggaggg cagggtggat gagttagaat tcgatgcaca tagagaagga tgttcctggc   2340
tgggactgta aattggttag ggttaatatt gtgtgtgctg catcgtcttt gtcacgtacg   2400
tgaaaggaaa cggaaaggaa aaaagtggaa atacaagaca aaaaaaaaaa aaaaaaaaa    2460

<210> SEQ ID NO 58
<211> LENGTH: 104
<212> TYPE: DNA
<213> ORGANISM: Artificial
<220> FEATURE:
<223> OTHER INFORMATION: Primer

<400> SEQUENCE: 58
ataaaagtat caacaaaaaa ttgttaatat acctctatac tttaacgtca aggagaaaaa   60
accccggatc ggcgcgccac catggacaag gcactggcac cgtt                    104

<210> SEQ ID NO 59
<211> LENGTH: 101
<212> TYPE: DNA
<213> ORGANISM: Artificial
<220> FEATURE:
<223> OTHER INFORMATION: Primer

<400> SEQUENCE: 59
aactataaaa aaataaatag ggacctagac ttcaggttgt ctaactcctt cctttcggt    60 tagagcggat ttaattaact aaactttctt ccttccctct a                       101

<210> SEQ ID NO 60
<211> LENGTH: 104
<212> TYPE: DNA
<213> ORGANISM: Artificial
<220> FEATURE:
<223> OTHER INFORMATION: Primer

<400> SEQUENCE: 60
ataaaagtat caacaaaaaa ttgttaatat acctctatac tttaacgtca aggagaaaaa   60
accccggatc ggcgcgccac catgaccacg actgtcatct ctag                    104

<210> SEQ ID NO 61
<211> LENGTH: 101
<212> TYPE: DNA
<213> ORGANISM: Artificial
<220> FEATURE:
<223> OTHER INFORMATION: Primer

<400> SEQUENCE: 61
```

```
aactataaaa aaataaatag ggacctagac ttcaggttgt ctaactcctt cctttcggt    60 tagagcggat ttaattaatc aaagcctccc gcacaacgag c                       101

<210> SEQ ID NO 62
<211> LENGTH: 104
<212> TYPE: DNA
<213> ORGANISM: Artificial
<220> FEATURE:
<223> OTHER INFORMATION: Primer

<400> SEQUENCE: 62
ataaaagtat caacaaaaaa ttgttaatat acctctatac tttaacgtca aggagaaaaa    60
accccggatc ggcgcgccac catggagggc atcgagtcga tagt                    104

<210> SEQ ID NO 63
<211> LENGTH: 101
<212> TYPE: DNA
<213> ORGANISM: Artificial
<220> FEATURE:
<223> OTHER INFORMATION: Primer

<400> SEQUENCE: 63
aactataaaa aaataaatag ggacctagac ttcaggttgt ctaactcctt cctttcggt    60 tagagcggat ttaattaact ataaggcttc tcccggcgcg g                      101

<210> SEQ ID NO 64
<211> LENGTH: 104
<212> TYPE: DNA
<213> ORGANISM: Artificial
<220> FEATURE:
<223> OTHER INFORMATION: Primer

<400> SEQUENCE: 64
ataaaagtat caacaaaaaa ttgttaatat acctctatac tttaacgtca aggagaaaaa    60
accccggatc ggcgcgccac catgaagacg cccacgagcc tggc                   104

<210> SEQ ID NO 65
<211> LENGTH: 101
<212> TYPE: DNA
<213> ORGANISM: Artificial
<220> FEATURE:
<223> OTHER INFORMATION: Primer

<400> SEQUENCE: 65
aactataaaa aaataaatag ggacctagac ttcaggttgt ctaactcctt cctttcggt    60 tagagcggat ttaattaatt aagctctcga atcgtccttc t                      101

<210> SEQ ID NO 66
<211> LENGTH: 104
<212> TYPE: DNA
<213> ORGANISM: Artificial
<220> FEATURE:
<223> OTHER INFORMATION: Primer

<400> SEQUENCE: 66
ataaaagtat caacaaaaaa ttgttaatat acctctatac tttaacgtca aggagaaaaa    60
accccggatc ggcgcgccac catggtcagg aggaagatgg acgt                   104

<210> SEQ ID NO 67
<211> LENGTH: 101
<212> TYPE: DNA
<213> ORGANISM: Artificial
```

```
<220> FEATURE:
<223> OTHER INFORMATION: Primer

<400> SEQUENCE: 67
aactataaaa aaataaatag ggacctagac ttcaggttgt ctaactcctt cctttttcggt    60 tagagcggat ttaattaatc acgacgccgg cgccttgcag t                        101

<210> SEQ ID NO 68
<211> LENGTH: 104
<212> TYPE: DNA
<213> ORGANISM: Artificial
<220> FEATURE:
<223> OTHER INFORMATION: Primer

<400> SEQUENCE: 68
ataaaagtat caacaaaaaa ttgttaatat acctctatac tttaacgtca aggagaaaaa    60
accccggatc ggcgcgccac catggcaccc tccccaccgg cccc                    104

<210> SEQ ID NO 69
<211> LENGTH: 101
<212> TYPE: DNA
<213> ORGANISM: Artificial
<220> FEATURE:
<223> OTHER INFORMATION: Primer

<400> SEQUENCE: 69
aactataaaa aaataaatag ggacctagac ttcaggttgt ctaactcctt cctttttcggt    60 tagagcggat ttaattaatc atttgaccac taaggtggcc t                       101

<210> SEQ ID NO 70
<211> LENGTH: 104
<212> TYPE: DNA
<213> ORGANISM: Artificial
<220> FEATURE:
<223> OTHER INFORMATION: Primer

<400> SEQUENCE: 70
ataaaagtat caacaaaaaa ttgttaatat acctctatac tttaacgtca aggagaaaaa    60
accccggatc ggcgcgccac catgggtcta tttggcagcg ggat                    104

<210> SEQ ID NO 71
<211> LENGTH: 101
<212> TYPE: DNA
<213> ORGANISM: Artificial
<220> FEATURE:
<223> OTHER INFORMATION: Primer

<400> SEQUENCE: 71
aactataaaa aaataaatag ggacctagac ttcaggttgt ctaactcctt cctttttcggt    60 tagagcggat ttaattaact aaaagaaatt caacgtccga t                       101

<210> SEQ ID NO 72
<211> LENGTH: 104
<212> TYPE: DNA
<213> ORGANISM: Artificial
<220> FEATURE:
<223> OTHER INFORMATION: Primer

<400> SEQUENCE: 72
ataaaagtat caacaaaaaa ttgttaatat acctctatac tttaacgtca aggagaaaaa    60
accccggatc ggcgcgccac catgttgagt atccccgagt cgtc                    104
```

<210> SEQ ID NO 73
<211> LENGTH: 101
<212> TYPE: DNA
<213> ORGANISM: Artificial
<220> FEATURE:
<223> OTHER INFORMATION: Primer

<400> SEQUENCE: 73
aactataaaa aaataaatag ggacctagac ttcaggttgt ctaactcctt cctttttcggt    60 tagagcggat ttaattaact aaaagaaatc cagctccctg t                        101

<210> SEQ ID NO 74
<211> LENGTH: 104
<212> TYPE: DNA
<213> ORGANISM: Artificial
<220> FEATURE:
<223> OTHER INFORMATION: Primer

<400> SEQUENCE: 74
ataaaagtat caacaaaaaa ttgttaatat acctctatac tttaacgtca aggagaaaaa    60
accccggatc ggcgcgccac catgacgccg caagccgata tcac                     104

<210> SEQ ID NO 75
<211> LENGTH: 101
<212> TYPE: DNA
<213> ORGANISM: Artificial
<220> FEATURE:
<223> OTHER INFORMATION: Primer

<400> SEQUENCE: 75
aactataaaa aaataaatag ggacctagac ttcaggttgt ctaactcctt cctttttcggt    60 tagagcggat ttaattaatt actcaatgga caacgggcgc g                        101

<210> SEQ ID NO 76
<211> LENGTH: 104
<212> TYPE: DNA
<213> ORGANISM: Artificial
<220> FEATURE:
<223> OTHER INFORMATION: Primer

<400> SEQUENCE: 76
ataaaagtat caacaaaaaa ttgttaatat acctctatac tttaacgtca aggagaaaaa    60
accccggatc ggcgcgccac catggcttac ctcttccgtc gtcg                     104

<210> SEQ ID NO 77
<211> LENGTH: 101
<212> TYPE: DNA
<213> ORGANISM: Artificial
<220> FEATURE:
<223> OTHER INFORMATION: Primer

<400> SEQUENCE: 77
aactataaaa aaataaatag ggacctagac ttcaggttgt ctaactcctt cctttttcggt    60 tagagcggat ttaattaatt aggcgatcgc aatgaactcc t                        101

<210> SEQ ID NO 78
<211> LENGTH: 104
<212> TYPE: DNA
<213> ORGANISM: Artificial
<220> FEATURE:
<223> OTHER INFORMATION: Primer

<400> SEQUENCE: 78

```
ataaaagtat caacaaaaaa ttgttaatat acctctatac tttaacgtca aggagaaaaa    60 acccggatc ggcgcgccac catgccttt ggacgggctg catc                      104
```

<210> SEQ ID NO 79
<211> LENGTH: 101
<212> TYPE: DNA
<213> ORGANISM: Artificial
<220> FEATURE:
<223> OTHER INFORMATION: Primer

<400> SEQUENCE: 79

```
aactataaaa aaataaatag ggacctagac ttcaggttgt ctaactcctt ccttttcggt    60
tagagcggat ttaattaatc acccgaaaat atcctccttc t                       101
```

<210> SEQ ID NO 80
<211> LENGTH: 104
<212> TYPE: DNA
<213> ORGANISM: Artificial
<220> FEATURE:
<223> OTHER INFORMATION: Primer

<400> SEQUENCE: 80

```
ataaaagtat caacaaaaaa ttgttaatat acctctatac tttaacgtca aggagaaaaa    60 acccggatc ggcgcgccac catggccaag gctaacttcc cgcc                     104
```

<210> SEQ ID NO 81
<211> LENGTH: 101
<212> TYPE: DNA
<213> ORGANISM: Artificial
<220> FEATURE:
<223> OTHER INFORMATION: Primer

<400> SEQUENCE: 81

```
aactataaaa aaataaatag ggacctagac ttcaggttgt ctaactcctt ccttttcggt    60
tagagcggat ttaattaatc actttataag cagcttcttg t                       101
```

<210> SEQ ID NO 82
<211> LENGTH: 104
<212> TYPE: DNA
<213> ORGANISM: Artificial
<220> FEATURE:
<223> OTHER INFORMATION: Primer

<400> SEQUENCE: 82

```
ataaaagtat caacaaaaaa ttgttaatat acctctatac tttaacgtca aggagaaaaa    60 acccggatc ggcgcgccac catgttgttg cagggattaa gctg                     104
```

<210> SEQ ID NO 83
<211> LENGTH: 101
<212> TYPE: DNA
<213> ORGANISM: Artificial
<220> FEATURE:
<223> OTHER INFORMATION: Primer

<400> SEQUENCE: 83

```
aactataaaa aaataaatag ggacctagac ttcaggttgt ctaactcctt ccttttcggt    60
tagagcggat ttaattaatc acaacaggac caatttatga t                       101
```

<210> SEQ ID NO 84
<211> LENGTH: 104
<212> TYPE: DNA

```
<213> ORGANISM: Artificial
<220> FEATURE:
<223> OTHER INFORMATION: Primer

<400> SEQUENCE: 84
ataaaagtat caacaaaaaa ttgttaatat acctctatac tttaacgtca aggagaaaaa    60
accccggatc ggcgcgccac catgttgatg gcgccgtcgc ggcg                    104

<210> SEQ ID NO 85
<211> LENGTH: 101
<212> TYPE: DNA
<213> ORGANISM: Artificial
<220> FEATURE:
<223> OTHER INFORMATION: Primer

<400> SEQUENCE: 85
aactataaaa aaataaatag ggacctagac ttcaggttgt ctaactcctt cctttcggt    60 tagagcggat ttaattaatc agacgatgcg aagcgtcttg t                       101

<210> SEQ ID NO 86
<211> LENGTH: 104
<212> TYPE: DNA
<213> ORGANISM: Artificial
<220> FEATURE:
<223> OTHER INFORMATION: Primer

<400> SEQUENCE: 86
ataaaagtat caacaaaaaa ttgttaatat acctctatac tttaacgtca aggagaaaaa    60
accccggatc ggcgcgccac catgggcgct accactgcga ccca                    104

<210> SEQ ID NO 87
<211> LENGTH: 101
<212> TYPE: DNA
<213> ORGANISM: Artificial
<220> FEATURE:
<223> OTHER INFORMATION: Primer

<400> SEQUENCE: 87
aactataaaa aaataaatag ggacctagac ttcaggttgt ctaactcctt cctttcggt    60 tagagcggat ttaattaatc acgacttcgg acagtccaaa a                       101

<210> SEQ ID NO 88
<211> LENGTH: 104
<212> TYPE: DNA
<213> ORGANISM: Artificial
<220> FEATURE:
<223> OTHER INFORMATION: Primer

<400> SEQUENCE: 88
ataaaagtat caacaaaaaa ttgttaatat acctctatac tttaacgtca aggagaaaaa    60
accccggatc ggcgcgccac catgtcgttc gttgagcaca gcgc                    104

<210> SEQ ID NO 89
<211> LENGTH: 101
<212> TYPE: DNA
<213> ORGANISM: Artificial
<220> FEATURE:
<223> OTHER INFORMATION: Primer

<400> SEQUENCE: 89
aactataaaa aaataaatag ggacctagac ttcaggttgt ctaactcctt cctttcggt    60 tagagcggat ttaattaact acacaaatcg catcgtcttg t                       101
```

<210> SEQ ID NO 90
<211> LENGTH: 104
<212> TYPE: DNA
<213> ORGANISM: Artificial
<220> FEATURE:
<223> OTHER INFORMATION: Primer

<400> SEQUENCE: 90
ataaaagtat caacaaaaaa ttgttaatat acctctatac tttaacgtca aggagaaaaa    60
accccggatc ggcgcgccac catggtcttc ctctgccttc ccta                    104

<210> SEQ ID NO 91
<211> LENGTH: 101
<212> TYPE: DNA
<213> ORGANISM: Artificial
<220> FEATURE:
<223> OTHER INFORMATION: Primer

<400> SEQUENCE: 91
aactataaaa aaataaatag ggacctagac ttcaggttgt ctaactcctt cctttcgt     60 tagagcggat ttaattaact acgagtccag ccacttgatg c                       101

<210> SEQ ID NO 92
<211> LENGTH: 104
<212> TYPE: DNA
<213> ORGANISM: Artificial
<220> FEATURE:
<223> OTHER INFORMATION: Primer

<400> SEQUENCE: 92
ataaaagtat caacaaaaaa ttgttaatat acctctatac tttaacgtca aggagaaaaa    60
accccggatc ggcgcgccac catgtttctt cgcatcgaac ggga                    104

<210> SEQ ID NO 93
<211> LENGTH: 101
<212> TYPE: DNA
<213> ORGANISM: Artificial
<220> FEATURE:
<223> OTHER INFORMATION: Primer

<400> SEQUENCE: 93
aactataaaa aaataaatag ggacctagac ttcaggttgt ctaactcctt cctttcgt     60 tagagcggat ttaattaact aaccctcggt gtacagcgcc g                       101

<210> SEQ ID NO 94
<211> LENGTH: 104
<212> TYPE: DNA
<213> ORGANISM: Artificial
<220> FEATURE:
<223> OTHER INFORMATION: Primer

<400> SEQUENCE: 94
ataaaagtat caacaaaaaa ttgttaatat acctctatac tttaacgtca aggagaaaaa    60
accccggatc ggcgcgccac catgccatcc cgcagcacca ttga                    104

<210> SEQ ID NO 95
<211> LENGTH: 101
<212> TYPE: DNA
<213> ORGANISM: Artificial
<220> FEATURE:
<223> OTHER INFORMATION: Primer

<400> SEQUENCE: 95

```
aactataaaa aaataaatag ggacctagac ttcaggttgt ctaactcctt ccttttcggt    60
tagagcggat ttaattaatc agacaagctc ctcttccccc t                      101
```

<210> SEQ ID NO 96
<211> LENGTH: 1197
<212> TYPE: DNA
<213> ORGANISM: Phytophtora sojae

<400> SEQUENCE: 96

```
atggcaattc tgaatccgga agcagatagc gcagcaaatc tggcaaccga ttcagaagca    60
aaacagcgtc agctggccga agcaggttat acccatgttg aaggtgcacc ggcaccgctg   120
ccgctggaac tgccgcattt ttcactgcgt gatctgcgtg cagcaattcc gaaacattgt   180
tttgaacgta gctttgttac cagcacctat tatatgatta aaaacgtgct gacctgcgca   240
gcactgtttt atgcagcaac ctttattgat cgtgctggtg cagcagccta tgttctgtgg   300
cctgtttatt ggttttttca gggttcatat ctgaccggtg tttgggttat tgcacatgaa   360
tgtggtcatc aggcctattg tagctcagaa gttgtgaata atctgattgg tctggttctg   420
cattcagcac tgctggttcc gtatcattct ggcgtatta  gccatcgtaa acatcattca   480
aataccggta gctgcgaaaa tgatgaagtt tttgttccgg ttacccgtag cgttctggca   540
agcagctgga atgaaaccct ggaagatagt ccgctgtatc agctgtatcg tattgtttat   600
atgctggttg ttggttggat gccgggttac ctgttttta  atgcaaccgg tccgaccaaa   660
tattggggta aatcacgtag ccatttttaat ccgtatagcg caatttatgc cgatcgtgaa   720
cgttggatga ttgttctgtc agatattttt ctggttgcaa tgctggcagt tctggcagca   780
ctggttcata cctttagctt taatacgatg gtgaagtttt atgtggtgcc gtattttatt   840
gtgaatgcct atctggtgct gattacctat ctgcagcaca ccgatacccta tattccgcac   900
tttcgtgaag gtgaatggaa ttggctgcgt ggtgcactgt gtaccgttga tcgtagcttt   960
ggtccgtttc tggattcagt tgttcatcgt attgttgata cccatgtgtg ccatcatatt  1020
tttagcaaaa tgccgtttta tcattgcgaa gaagccacca acgcaattaa accgctgctg  1080
ggtaaatttt atctgaaaga taccacaccg gttccggttg cactgtggcg ttcatatacc  1140
cattgtaaat tgtggaaga  tgatggcaaa gtggtgtttt acaaaaacaa actgtaa     1197
```

<210> SEQ ID NO 97
<211> LENGTH: 1371
<212> TYPE: DNA
<213> ORGANISM: Ostreococcus tauri

<400> SEQUENCE: 97

```
atgtgtgttg agaccgagaa caacgatgga atccctactg tggagatcgc tttcgatgga    60
gagagagaaa gagctgaggc taacgtgaag ttgtctgctg agaagatgga acctgctgct   120
ttggctaaga ccttcgctag aagatacgtg gttatcgagg agttgagtca cgatgtgacc   180
gatttcaaac accctggagg aaccgtgatt ttctacgctc tctctaacac tggagctgat   240
gctactgagg ctttcaagga gttccaccac agatctagaa aggctaggaa ggctttggct   300
gctttgcctt ctagacctgc taagaccgct aaagtggatg atgctgagat gctccaggat   360
ttcgctaagt ggagaaagga gttggagagg acggattct  tcaagccttc tcctgctcac   420
gttgcttaca gattcgctga gttggctgct atgtacgctt gggaaccta  cttgatgtac   480
gctagatacg ttgtgtcctc tgtgttggtt tacgcttgct tcttcggagc tagatgtgga   540
```

| | |
|---|---|
| tgggttcaac acgagggagg acactcttct ttgaccggaa acatctggtg ggataagaga | 600 |
| atccaagctt tcactgctgg attcggattg gctggatctg gagatatgtg gaactccatg | 660 |
| cacaacaagc accacgctac tcctcaaaaa gtgaggcacg atatggattt ggataccact | 720 |
| cctgctgttg ctttcttcaa caccgctgtg gaggataata gacctagggg attctctaag | 780 |
| tactggctca gattgcaagc ttggaccttc attcctgtga cttctggatt ggtgttgctc | 840 |
| ttctggatgt tcttcctcca cccttctaag gctttgaagg aggaaagta cgaggagctt | 900 |
| gtgtggatgt tggctgctca cgtgattaga acctggacca ttaaggctgt tactggattc | 960 |
| accgctatgc aatcctacgg actcttcttg gctacttctt gggtttccgg atgctacttg | 1020 |
| ttcgctcact tctctacttc tcacacccac ttggatgttg ttcctgctga tgagcacttg | 1080 |
| tcttgggtta ggtacgctgt ggatcacacc attgatatcg atccttctca gggatgggtt | 1140 |
| aactggttga tgggatactt gaactgccaa gtgattcacc acctcttccc ttctatgcct | 1200 |
| caattcagac aacctgaggt gtccagaaga ttcgttgctt tcgctaagaa gtggaacctc | 1260 |
| aactacaagg tgatgactta tgctggagct tggaaggcta ctttgggaaa cctcgataat | 1320 |
| gtgggaaagc actactacgt gcacggacaa cactctggaa agaccgcttg a | 1371 |

<210> SEQ ID NO 98
<211> LENGTH: 1320
<212> TYPE: DNA
<213> ORGANISM: Thraustochytrium sp.

<400> SEQUENCE: 98

| | |
|---|---|
| atgggaaaag gatctgaggg aagatctgct gctagagaga tgactgctga ggctaacgga | 60 |
| gataagagaa agaccatcct cattgaggga gtgttgtacg atgctaccaa cttcaaacac | 120 |
| ccaggaggtt ccattattaa cttcctcacc gagggagaag ctggagttga tgctacccaa | 180 |
| gcttacagag agttccatca gagatccgga aaggctgata agtacctcaa gtccctccca | 240 |
| aagttggatg cttctaaggt ggagtctagg ttctctgcta aggagcaggc tagaagggac | 300 |
| gctatgacca gggattacgc tgcttttcaga gaggagttgg ttgctgaggg atacttcgat | 360 |
| ccatctatcc cacacatgat ctacagagtg gtggagattg tggctttgtt cgctttgtct | 420 |
| ttctggttga tgtctaaggc ttctccaacc tctttggttt tgggagtggt gatgaacgga | 480 |
| atcgctcaag gaagatgcgg atgggttatg cacgagatgg gacacggatc tttcactgga | 540 |
| gttatctggc tcgatgatag gatgtgcgag ttcttctacg gagttggatg tggaatgtct | 600 |
| ggacactact ggaagaacca gcactctaag caccacgctc tccaaacag attggagcac | 660 |
| gatgtggatt tgaacaccct gccactcgtt gctttcaacg agagagttgt gaggaaggtt | 720 |
| aagccaggat ctttgttggc tttgtggctc agagttcagg cttatttgtt cgctccagtg | 780 |
| tcttgcttgt tgatcggatt gggatggacc ttgtacttgc acccaagata tatgctcagg | 840 |
| accaagagac acatggagtt tgtgtggatc ttcgctagat atatcggatg ttctccttg | 900 |
| atgggagctt tgggatattc tcctggaact tctgtgggaa tgtacctctg ctcttttcgga | 960 |
| cttggatgca tctacatctt cctccaattc gctgtgtctc acacccactt gccagttacc | 1020 |
| aacccagagg atcaattgca ctggcttgag tacgctgctg atcacaccgt gaacatctct | 1080 |
| accaagtctt ggttggttac ctggtggatg tctaacctca acttccaaat cgagcaccac | 1140 |
| ttgttcccaa ccgctccaca attcaggttc aaggagatct ctccaagagt tgaggctctc | 1200 |
| ttcaagagac acaacctccc ttactacgat ttgccataca cctctgctgt ttctactacc | 1260 |

```
ttcgctaacc tctactctgt tggacactct gttggagctg ataccaagaa gcaggattga    1320
```

<210> SEQ ID NO 99
<211> LENGTH: 873
<212> TYPE: DNA
<213> ORGANISM: Physcomitrella patens
<400> SEQUENCE: 99

```
atggaagttg ttgagaggtt ctacggagag ttggatggaa aggtttccca aggagtgaac      60
gctttgttgg gatctttcgg agttgagttg actgataccc aactactaa gggattgcca     120
ctcgttgatt ctccaactcc aattgtgttg ggagtgtctg tttacttgac catcgtgatc    180
ggaggattgc tttggatcaa ggctagagat ctcaagccaa gagcttctga gccattcttg    240
ttgcaagctt tggtgttggt gcacaacttg ttctgcttcg ctttgtctct ttacatgtgt    300
gtgggaatcg cttaccaagc tatcacctgg agatattcct tgtggggaaa cgcttataac    360
ccaaagcaca aggagatggc tatcctcgtt tacctcttct acatgtccaa gtacgtggag    420
ttcatggata ccgtgatcat gatcctcaag agatctacca gacagatttc tttcctccac    480
gtgtaccacc actcttctat ctcccttatc tggtgggcta ttgctcacca cgctccagga    540
ggagaggctt attggagcgc tgctctcaac tctggagtgc acgtgttgat gtacgcttac    600
tacttcttgg ctgcttgctt gagatcttcc ccaaagctca gaacaagta cctcttctgg    660
ggaagatacc tcacccaatt ccagatgttc cagtttatgc tcaacttggt gcaagcttac    720
tacgatatga gaccaacgc tccatatcca cagtggctca tcaagatcct cttctactac    780
atgatctccc tcttgttcct cttcggaaac ttctacgtgc aaaagtacat caagccatca    840
gatggaaagc aaaagggagc taagaccgag tga                                 873
```

<210> SEQ ID NO 100
<211> LENGTH: 1086
<212> TYPE: DNA
<213> ORGANISM: Phytophthora infestans
<400> SEQUENCE: 100

```
atggcgacga aggaggcgta tgtgttcccc actctgacgg agatcaagcg gtcgctacct      60
aaagactgtt tcgaggcttc ggtgcctctg tcgctctact acaccgtgcg ttgtctggtg    120
atcgcggtgg ctctaacctt cggtctcaac tacgctcgcg ctctgcccga ggtcgagagc    180
ttctgggctc tggacgccgc actctgcacg ggctacatct gctgcaggg catcgtgttc    240
tggggcttct tcacggtggg ccacgatgcc ggccacggcg ccttctcgcg ctaccacctg    300
cttaacttcg tggtgggcac tttcatgcac tcgctcatcc tcacgccctt cgagtcgtgg    360
aagctcacgc accgtcacca ccacaagaac acgggcaaca ttgaccgtga cgaggtcttc    420
tacccgcaac gcaaggccga cgaccacccg ctgtctcgca acctgattct ggcgctcggg    480
gcagcgtggc tcgcctattt ggtcgagggc ttccctcctc gtaaggtcaa ccacttcaac    540
ccgttcgagc ctctgttcgt gcgtcaggtg tcagctgtgg taatctctct tctcgcccac    600
ttcttcgtgg ccggactctc catctatctg agcctccagc tgggccttaa gacgatggca    660
atctactact atggacctgt ttttgtgttc ggcagcatgc tggtcattac caccttccta    720
caccacaatg atgaggagac cccatggtac gccgactcgg agtggacgta cgtcaagggc    780
aacctctcgt ccgtggaccg atcgtacggc gcgctcattg acaacctgag ccacaacatc    840
ggcacgcacc agatccacca ccttttccct atcattccgc actacaaact caagaaagcc    900
actgcggcct tccaccaggc tttccctgag ctcgtgcgca agagcgacga gccaattatc    960
```

-continued

```
aaggctttct tccggggttgg acgtctctac gcaaactacg gcgttgtgga ccaggaggcg   1020
aagctcttca cgctaaagga agccaaggcg gcgaccgagg cggcggccaa gaccaagtcc   1080
acgtaa                                                                1086
```

<210> SEQ ID NO 101
<211> LENGTH: 23777
<212> TYPE: DNA
<213> ORGANISM: Artificial
<220> FEATURE:
<223> OTHER INFORMATION: Plasmid

<400> SEQUENCE: 101

```
ctatacaaag ttgatagctt ggcgtaatcg atgtaccgat atcaatttaa attggccggc     60
cgagctccct gcaggggggcc cggcgcgcct ctagattaat taaaggcctt agttactaat   120
cagtgatcag attgtcgttt cccgccttca gtttaaacta tcagtgtttg acaggatata   180
ttggcgggta aacctaagag aaaagagcgt ttattagaat aatcggatat ttaaagggc    240 gtgaaaaggt ttatccgttc gtccatttgt atgtcaatat ccatgataag tcgcgctgta   300
tgtgtttgtt tgaatattca tggaacgcag tggcggtttt catggcttgt tatgactgtt   360
tttttggggt acagtctatg cctcgggcat ccaagcagca agcgcgttac gccgtgggtc   420
gatgtttgat gttatggagc agcaacgatg ttacgcagca gggcagtcgc cctaaaacaa   480
agttaaacat catgggtgaa gcggtcatcg ccgaggtgtc cacccagctg tcggaagtcg   540
tgggtgtcat cgagcgccac ctcgaaccga ccctcctcgc cgtgcatctg tatggtagcg   600
ccgttgacgg cggccttaag ccccattcgg acatcgacct gcttgtcacc gttaccgtcc   660
gtctcgacga gcacgcgc cgcgcgctta tcaacgacct tctggaaacg tccgcctccc    720
ccggcgagag cgaaatcctg cgcgcggttg aggtgacgat tgtggtgcac gatgacatca   780 tccctggcg ctatccggcc aaacgcgaac tccagttcgg cgaatggcag cgtaatgata   840
ttctggcggg tatctttgaa ccggccacca tcgacattga tctggcgatc ctgctcacca   900
aggcccggga gcatagcgtg gccctcgtcg gcccgcggc cgaggaactt ttcgacccgg   960
tgccggaaca ggatctgttc gaagcactga acgagacgcgt gaccctgtgg aactccccgc   1020
cggattgggc gggcgatgag cgcaatgtgg tccttacgct gagccggatt tggtactcgg   1080
cggttaccgg caagatcgcg ccgaaggatg tcgccgccga ctgggcgatg gagcgccttc   1140
cggcgcaata ccagcccgtg atcctcgaag cgcgccaagc ctatctgggc caagaagaag   1200
accgtctcgc gtcccgggcc gaccagctcg aagaatttgt ccactatgtc aagggcgaga   1260
tcacgaaggt cgttggcaaa taatgtctag ctagaaattc gttcaagccg acgccgcttc   1320
gcggcgcggc ttaactcaag cgttagatgc actaagcaca taattgctca cagccaaact   1380
atcgatgagt tgaaggaccc cgtagaaaag atcaaaggat cttcttgaga tcctttttt    1440 ctgcgcgtaa tctgctgctt gcaaacaaaa aaaccaccgc taccagcggt ggtttgtttg   1500
ccggatcaag agctaccaac tcttttttccg aaggtaactg gcttcagcag agcgcagata   1560
ccaaatactg tccttctagt gtagccgtag ttaggccacc acttcaagaa ctctgtagca   1620
ccgcctacat acctcgctct gctaatcctg ttaccagtgg ctgctgccag tggcgataag   1680
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
```

| | |
|---|---|
| tatccggtaa gcggcagggt cggaacagga gagcgcacga gggagcttcc aggggggaaac | 1920 |
| gcctggtatc tttatagtcc tgtcgggttt cgccacctct gacttgagcg tcgattttttg | 1980 |
| tgatgctcgt cagggggggcg gagcctatgg aaaaacgcca gcaacgcggc cttttttacgg | 2040 |
| ttcctggcct tttgctggcc ttttgctcac atgttctttc ctgcgttatc ccctgattct | 2100 |
| gtggataacc gtattaccgc cttttgagtga gctgataccg ctcgccgcag ccgaacgacc | 2160 |
| gagcgcagcg agtcagtgag cgaggaagcg gaagagcgcc tgatgcggta ttttctcctt | 2220 |
| acgcatctgt gcggtatttc acaccgcata ggccgcgata ggccgacgcg aagcggcggg | 2280 |
| gcgtagggag cgcagcgacc gaagggtagg cgcttttttgc agctcttcgg ctgtgcgctg | 2340 |
| gccagacagt tatgcacagg ccaggcgggt tttaagagtt ttaataagtt ttaaagagtt | 2400 |
| ttaggcggaa aaatcgcctt ttttctcttt tatatcagtc acttacatgt gtgaccggtt | 2460 |
| cccaatgtac ggctttgggt tcccaatgta cgggttccgg ttcccaatgt acggctttgg | 2520 |
| gttcccaatg tacgtgctat ccacaggaaa gagaccttttt cgaccttttt cccctgctag | 2580 |
| ggcaatttgc cctagcatct gctccgtaca ttaggaaccg gcggatgctt cgccctcgat | 2640 |
| caggttgcgg tagcgcatga ctaggatcgg gccagcctgc cccgcctcct ccttcaaatc | 2700 |
| gtactccggc aggtcatttg acccgatcag cttgcgcacg tgaaacaga acttcttgaa | 2760 |
| ctctccggcg ctgccactgc gttcgtagat cgtcttgaac aaccatctgg cttctgcctt | 2820 |
| gcctgcggcg cggcgtgcca ggcggtagag aaaacggccg atgccggggt cgatcaaaaa | 2880 |
| gtaatcgggg tgaaccgtca gcacgtccgg gttcttgcct tctgtgatct cgcggtacat | 2940 |
| ccaatcagca agctcgatct cgatgtactc cggccgcccg gtttcgctct ttacgatctt | 3000 |
| gtagcggcta atcaaggctt caccctcgga taccgtcacc aggcggccgt tcttggcctt | 3060 |
| cttggtacgc tgcatggcaa cgtgcgtggt gtttaaccga atgcaggttt ctaccaggtc | 3120 |
| gtctttctgc tttccgccat cggctcgccg gcagaacttg agtacgtccg caacgtgtgg | 3180 |
| acggaacacg cggccgggct tgtctcccttt cccttcccgg tatcggttca tggattcggt | 3240 |
| tagatgggaa accgccatca gtaccaggtc gtaatcccac acactggcca tgccggcggg | 3300 |
| gcctgcggaa acctctacgt gcccgtctgg aagctcgtag cggatcacct cgccagctcg | 3360 |
| tcggtcacgc ttcgacagac ggaaaacggc cacgtccatg atgctgcgac tatcgcgggt | 3420 |
| gcccacgtca tagagcatcg gaacgaaaaa atctggttgc tcgtcgccct tgggcggctt | 3480 |
| cctaatcgac ggcgcaccgg ctgccggcgg ttgccgggat tctttgcgga ttcgatcagc | 3540 |
| ggccccttgc cacgattcac cggggcgtgc ttctgcctcg atgcgttgcc gctgggcggc | 3600 |
| ctgcgcggcc ttcaacttct ccaccaggtc atcacccagc gccgcgccga tttgtaccgg | 3660 |
| gccgatggt ttgcgaccgc tcacgccgat tcctcgggct tgggggttcc agtgccattg | 3720 |
| cagggccggc agacaaccca gccgcttacg cctggccaac cgcccgttcc tccacacatg | 3780 |
| gggcattcca cggcgtcggt gcctggttgt tcttgatttt ccatgccgcc tcctttagcc | 3840 |
| gctaaaattc atctactcat ttattcattt gctcatttac tctggtagct gcgcgatgta | 3900 |
| ttcagatagc agctcggtaa tggtcttgcc ttggcgtacc gcgtacatct tcagcttggt | 3960 |
| gtgatcctcc gccggcaact gaaagttgac ccgcttcatg gctggcgtgt ctgccaggct | 4020 |
| ggccaacgtt gcagccttgc tgctgcgtgc gctcggacgg ccggcactta gcgtgtttgt | 4080 |
| gcttttgctc attttctctt tacctcatta actcaaatga gttttgattt aatttcagcg | 4140 |
| gccagcgcct ggacctcgcg ggcagcgtcg ccctcgggtt ctgattcaag aacggttgtg | 4200 |
| ccggcggcgg cagtgcctgg gtagctcacg cgctgcgtga tacgggactc aagaatgggc | 4260 |

```
agctcgtacc cggccagcgc ctcggcaacc tcaccgccga tgcgcgtgcc tttgatcgcc    4320
cgcgacacga caaaggccgc ttgtagcctt ccatccgtga cctcaatgcg ctgcttaacc    4380
agctccacca ggtcggcggt ggcccaaatg tcgtaagggc ttggctgcac cggaatcagc    4440
acgaagtcgg ctgccttgat cgcggacaca gccaagtccg ccgcctgggg cgctccgtcg    4500
atcactacga agtcgcgccg gccgatggcc ttcacgtcgc ggtcaatcgt cgggcggtcg    4560
atgccgacaa cggttagcgg ttgatcttcc cgcacggccg cccaatcgcg ggcactgccc    4620
tggggatcgg aatcgactaa cagaacatcg gccccggcga gttgcagggc gcgggctaga    4680
tgggttgcga tggtcgtctt gcctgacccg cctttctggt taagtacagc gataaccttc    4740
atgcgttccc cttgcgtatt tgtttattta ctcatcgcat catatacgca gcgaccgcat    4800
gacgcaagct gttttactca aatacacatc acctttttag atgatcagtg attttgtgcc    4860
gagctgccgg tcggggagct gttggctggc tggtggcagg atatattgtg gtgtaaacaa    4920
attgacgctt agacaactta ataacacatt gcggacgtct ttaatgtact gaatttagtt    4980
actgatcact gattaagtac tgcgatcgcc tcgacatatt gttttttgttt cacataaatg    5040
tcgttttgga ttattcatgt aatattttaa actaaagtac aattttttgac tactttagtt    5100
tactagttaa gcttttattt ttttgactaa ccattgaatg atgaagagat caacgcatca    5160
tatttacaac ttacatagtc ttttggaagt gtaaattgct aatactacct aaaatatatc    5220
tataattaac taatattttt tcgtcaatta taatagatca attaaaaggc tatcaaaagg    5280
aaaaaaatga aatccacatc ctgccatcat aacctcatgc tggaaaaaga aatgaaaaaa    5340
tataaaaaat ttcttttgtt tattaaattt acaactttaa tactagtttc ttttctattt    5400
tttaaaagct tttgtcactt acttaaaaaa aaaaactttt tgaaatatt cctacttcca     5460
atgtctgatt agtgcttctg gatttccttt ttggatcatg tgaatcctaa atcagaaaaa    5520
ttcatataat acccaattca gtatattttc atacttcaat ttacaagagt tctctatgtt    5580
tttagcttct ttcttttaag ccaaatgttt taagcatctt ttatacatta aaataatttta   5640
gtgttgagtt gagattttttt ttttttttttt ttggatttac ttgttcaaaa tctgaaaaaa   5700
tgtttacaga aggttaaaat gaaccaaaag gcatatcaag ctagattttg aattacccta    5760
tttcatcgta tacacaaaac tgataatgtg gacacagttg attttacttc tcgatgacat    5820
cgtagtttta tttaatttgg aaaccacggc ccatatgagc acatttcaat taaaaaccaa    5880
tggtaagagc attttccatg caagattcga gagatattaa cccagtgact gttaaaacag    5940
cttagaaccc taataacgaa tttcaattac tcaatttacc attcgcattt cgcaataacc    6000
aaactgagcc agtcacaagg agtaaaccga accggattat ttatttataa aatgaaagaa    6060
aggaaaccaa acaacaacag cagtagtagt ctgacgtaaa ccaaaaagca ggcagatcaa    6120
caactaaaag aaactcaaat taccaaaaca acaggaaat tgcaaactaa gttttttttac     6180
catatgcata caaagaccat aaaaggttct gataatcacc ggtttcatct cgtcgagatt    6240
accctgttat ccctatcagt atttaatccg gccatctcct tccgttatga catcgttgaa    6300
agtgccacca ttcgggatca tcggcaacac atgttcttgg tgcggacaaa tcacatccaa    6360
caggtaaggt cctggtgtat ccagcattgt ctgaatagct tctcggagat ctgctttctt    6420
tgtcaccctc gccgctggaa tcccgcaagc tgctgcaaac agcaacatgt tcgggaatat    6480
ctcgtcctcc tgagccggat ccccgagaaa tgtgtgagct cggttagctt tgtagaaccg    6540
atcttcccat tgcataacca tgccaagatg ctggttgttt aataaaagta ccttcactgg    6600
```

```
aagattctct acacgaatag tggctagctc ttgcacattc attataaagc ttccatctcc    6660
gtcaatatcc acaactatcg catcagggtt agcaacagac gctccaatcg cagcaggaag    6720
tccaaatccc atagctccaa ggcctcctga tgatagccac tgccttggtt tcttgtaatt    6780
gtagaactgc gccgcccaca tttgatgttg cccgacacca gtacttatta tggcttttcc    6840
atcagtcaac tcatcaagga ccttaatcgc atactgtgga ggaatagctt ccccaaacgt    6900
cttaaagctc aacggaaact tctgtttctg tacgttcaac tcattcctcc aaactccaaa    6960
atcaagctta agctcctccg ctcggttctc aagaaccttg ttcatccctt gcaaagccag    7020
cttaacatca ccacacacag acacatgagg agtcttattc ttcccaatct cagccgagtc    7080
aatatcaata tgaacaatct tagccctact agcaaaagcc tcaagcttac ccgtgacacg    7140
atcatcaaac cttaccccaa acgccaacaa caaatcacta tgctccacag cgtaatttgc    7200
atacacagtc ccatgcattc caagcatatg taacgacaac tcatcatcac aaggataaga    7260
tcccagcccc atcaacgtac tcgcaacagg gatcccgta agctcaacaa acctacccaa    7320
ttcatcgcta gaattcaaac aaccaccacc aacatacaac acaggcttct tagactcaga    7380
aatcaaccta acaatctgct ccaaatgaga atcttccgga ggtttaggca tcctagacat    7440
ataaccaggt aatctcatag cctgttccca attaggaatc gcaagctgtt gttgaatatc    7500
tttaggaaca tcaaccaaaa caggtccagg tctaccagaa gtagctaaaa agaaagcttc    7560
ctcaataatc ctaggatat cttcaacatc catcacaaga tagttatgct tcgtaatcga    7620
acgcgttacc tcaacaatcg gagtctcttg aaacgcatct gtaccaatca tacgacgagg    7680
gacttgtcct gtgattgcta caagaggaac actatctaac aacgcatcgg ctaatccgct    7740
aacgagattt gtagctccgg gacctgaagt ggctatacag atacctggtt tacctgagga    7800
tcgagcgtat ccttctgctg cgaatacacc tccttgttcg tgacgaggaa ggacgttacg    7860
gattgaggaa gagcgggtta aggcttggtg aatctccatt gatgtacctc cagggtaagc    7920
gaatacggtt tctacgcctt gacgttctaa agcttgacg aggatatcag cgcctttgcg    7980
gggttgatct ggagcgaatc gggagatgaa tgtttcgggt ttggtaggtt tggttggaga    8040
gggagtggtt gtgacattgg tggttgtgtt gagcacggcg gagatggagg agggagagct    8100
ggatttgata ccgcggcggc gggaggagga ggatgatttg ttggggttta gggagaatgg    8160
gagggagaat ctgagattg gtaatggtga tttggaggag gaaggagatg gtttggtgga    8220
gaaggagatc gaagaagatg ttgttgttgt tgttgttgcc gccgccatgg ttcagctgca    8280
catacataac atatcaagat cagaacacac atatacacac acaaatacaa tcaagtcaac    8340
aactccaaaa agtccagatc tacatatata catacgtaaa taacaaaatc atgtaaataa    8400
tcacaatcat gtaatccaga tctatgcaca tatatatata cacaattaat aaaaaaaatg    8460
atataacaga tctatatcta tgtatgtaac aacacaatca gatgagagaa gtgatgtttt    8520
cagatctgta tacatacaaa cacaaacaga tgaacaattg atacgtagat ccatatgtat    8580
acgtacaatt agctacacga ttaaatgaaa aaaatcaacg atttcggatt ggtacacaca    8640
aacgcaacaa tatgaagaaa ttcatatctg attagatata aacataacca cgtgtagata    8700
cacagtcaaa tcaacaaatt tatagcttct aaacggatga gatgaacaag ataaagatat    8760
tcacataagg catacataag ataagcagat taacaaacta gcaataatac ataccctaatt   8820 aaaacaagga ataacagaga gagagagaga gagagagatt taccttgaaa atgaagagga    8880
gaagagagga tttcttaaaa ttgggggtag agaaagaaag atgatgaatt gtgagaaagg    8940
agagatagaa gggggggttg tatatatagg ctgtagaaga ttattttgt gtttgaggcg    9000
```

```
gtgaaggaag aggggatctg actatgacac gtttgcggtt acgtatttcg ataggagtct   9060
ttcaacgctt aacgccgtta ctctatatga ccgtttgggc cgtaacgggg ccgtttgtta   9120
acgctgatgt tgattctttt ctttctttct ttcttccttt tttaaagaag caattgtaca   9180
atcgttgcta gctgtcaaac ggataattcg gatacggata tgcctatatt catatccgta   9240 attttttggat tcgaattttc ccctctaggg ataacagggt aatggatcta tattgttttt   9300
gtttcacata aatgtcgttt tggattattc atgtaatatt ttaaactaaa gtacaatttt   9360
tgactacttt agtttactag ttaagctttt attttttga ctaaccattg aatgatgaag   9420
agatcaacgc atcatattta caacttacat agtcttttgg aagtgtaaat tgctaatact   9480
acctaaaata tatctataat taactaatat ttttcgtca attataatag atcaattaaa   9540
aggctatcaa aaggaaaaaa atgaaatcca catcctgcca tcataacctc atgctggaaa   9600
aagaaatgaa aaatataaa aaatttcttt tgtttattaa atttacaact ttaatactag   9660
tttcttttct atttttaaa agcttttgtc acttacttaa aaaaaaaaaa cttttttgaaa   9720 tattcctact tccaatgtct gattagtgct tctggatttc cttttggat catgtgaatc   9780 ctaaatcaga aaaattcata taatacccaa ttcagtatat tttcatactt caatttacaa   9840
gagttctcta tgttttagc ttctttcttt taagccaaat gttttaagca tcttttatac   9900
attaaaataa tttagtgttg agttgagatt tttttttttt tttttggat ttacttgttc   9960 aaaatctgaa aaatgttta cagaaggtta aaatgaacca aaaggcatat caagctagat  10020
tttgaattac cctatttcat cgtatacaca aaactgataa tgtggacaca gttgattta  10080 cttctcgatg acatcgtagt tttatttaat ttggaaacca cggcccatat gagcacattt  10140
caattaaaaa ccaatggtaa gagcattttc catgcaagat tcgagagata ttaacccagt  10200
gactgttaaa acagcttaga accctaataa cgaatttcaa ttactcaatt taccattcgc  10260
atttcgcaat aaccaaactg agccagtcac aaggagtaaa ccgaaccgga ttatttattt  10320
ataaaatgaa agaaaggaaa ccaaacaaca acagcagtag tagtctgacg taaaccaaaa  10380
agcaggcaga tcaacaacta aaagaaactc aaattaccaa aacaaacagg aaattgcaaa  10440
ctaagttttt ttaccatatg catacaaaga ccataaaagg ttctgataat caccggtttc  10500
atctcagatc cgcgatcgcc aattgacgcg tactagtgta caagcttgcg gccgcgaatt  10560
cggtacatcc ggccagtgaa ttatcaacta tgtataataa agttgggtac cggcctatta  10620
ggccacggtc cgtacagtgt ttaaacgatt gacctgcagg atacaagtgc gcacagacta  10680
gcggccgcta atcccgggaa ttaccggtag taggcgccta ctttggccgg cctagtgat  10740 ttaaattggc cttagtggcc aagcttggcg taatcatggc cactttgtac aagaaagctg  10800
ggtggtaccg gcctattagg ccacggtccg tacagtgttt gccattgatg catgttgtca  10860
atcaattggc aagtcataaa atgcattaaa aaatattttc atactcaact acaaatccat  10920
gagtataact ataattataa agcaatgatt agaatctgac aaggattctg gaaaattaca  10980
taaaggaaag ttcataaatg tctaaaacac aagaggacat acttgtattc agtaacattt  11040
gcagcttttc taggtctgaa aatatatttg ttgcctagtg aataagcata atggtacaac  11100
tacaagtgtt ttactcctca tattaacttc ggtcattaga ggccacgatt tgacacattt  11160
ttactcaaaa caaaatgttt gcatatctct tataatttca aattcaacac acaacaaata  11220
agagaaaaaa caaataatat taatttgaga atgaacaaaa ggaccatatc attcattaac  11280
tcttctccat ccatttccat ttcacagttc gatagcgaaa accgaataaa aaacacagta  11340
```

```
aattacaagc acaacaaatg gtacaagaaa aacagttttc ccaatgccat aatactcgaa   11400
ccaatcaatt attaattaac tagagcttgt tcttgtagaa caccacctttt ccatcatcct   11460 caacgaactt gcaatgggtg taagatctcc agagagcaac aggaacagga gtggtatcct   11520
tcaagtagaa cttccgagg agaggcttaa tagcgttggt agcctcctcg caatgataga   11580
aaggcatctt ggagaagatg tggtggcaaa catgggtatc cacgattcta tgcaccacag   11640
aatcgaggaa tggaccaaat gatctatcca cagtgcacaa agctcctctc aaccaattcc   11700 actctcccctc tctgaaatga gggatgtagg tatcggtgtg ttggaggtag gtaatcaaca   11760
ccaagtaagc gttcacaatg aagtaaggca ccacgtagaa cttcaccatg gtgttgaagg   11820
agaaagtgtg caccaaagca gccaaaacag ccaacatagc caccaagaaa atatcggaga   11880
gcacgatcat ccatctctcc ctatcagcat agatagcgga gtaagggttg aagtgagacc   11940
tagactttcc ccagtactta gtaggtccag tagcgttgaa gaagaggtat ccaggcatcc   12000
atccaacaac caacatgtac acgatacggt agagttggta gagaggagaa tcctccaagg   12060
tctcgttcca agaagaagcc aacacagatc tggtcacagg aacgaaaacc tcatcgttct   12120
cgcaagatcc agtgttggaa tggtgctttc tgtgagagat tctccaagag tggtaaggca   12180
ccaacaaagc agaatgcaac acgagtccaa tcaagttgtt caccacctca gaagagcaat   12240
aagcctgatg tccacactca tgagcgataa cccacactcc agtcaagtaa gatccctgga   12300
agaaccagta cacaggccac aaaacataag cagcagctcc agctctatca atgaaggtag   12360
cagcgtagaa caaagcagcg caagtcaaca cgttcttgat catgtagtag gtggaggtca   12420
cgaaagatct ctcgaagcag tgcttaggaa tagcagctct gagatctctg agagagaaat   12480
gaggcaactc caaaggcaaa ggagcaggag caccctcaac atgagtgtat ccagcctcag   12540
ccaattgtct ttgcttagcc tcagaatcag tagcgaggtt agcagcagaa tcagcctcag   12600
ggttcaaaat agccatggcg gatccggcgc ggtgttttta atcttgtttg tattgatgag   12660
ttttggtttg agtaaagagt gaagccgatg agttaattta taggctataa aggagatttg   12720
catggcgatc acgtgtaata atgcatgcac gcatgtgatt gtatgtgtgt gctgtgagag   12780
agaagctctt aggtgtttga agggagtgac aagtggcgaa gaaaaacaat tctccgcggc   12840
tgcatgctat gtgtaacgtg tagctaatgt tctggcatgg catcttatga acgattcttt   12900
ttaaaaacaa ggtaaaaact taacttcata aaattaaaaa aaaaacgttt actaagttgg   12960
tttaaaaggg gatgagagtc tataaatttt ggaggtagtg ccgttgggaa tataaattgg   13020
gagcttaatc agaattatag aagttaaagt tgatttagtc acggtcaata taaattggga   13080
atttgagtca aaatcttcca aattcggaat ccgtcttgtt acacccggtg gataggagcc   13140
gaacggtttg aaaatacttg aaatgtggat gcaggtgcag gctggtttaa ttttatgttg   13200
aatggataca tgtcaatcga atttgagtta taggtacaca ttttactctg atactaaaat   13260
gtaacatttg tctcaagaat gggtaggtca tccttatggc cggcctaacc tgcaggatac   13320
aagtgcgcac agactagcgg ccgctaatcc cgggaattac cggtagtagg cgccattgat   13380
gcatgttgtc aatcaattgg caagtcataa aatgcattaa aaaatatttt catactcaac   13440
tacaaatcca tgagtataac tataattata agcaatgat tagaatctga caaggattct   13500
ggaaaattac ataaaggaaa gttcataaat gtctaaaaca caagaggaca tacttgtatt   13560
cagtaacatt tgcagctttt ctaggtctga aaatatattt gttgcctagt gaataagcat   13620
aatggtacaa ctacaagtgt tttactcctc atattaactt cggtcattag aggccacgat   13680
ttgacacatt tttactcaaa acaaaatgtt tgcatatctc ttataatttc aaattcaaca   13740
```

```
cacaacaaat aagagaaaaa acaaataata ttaatttgag aatgaacaaa aggaccatat   13800
cattcattaa ctcttctcca tccatttcca tttcacagtt cgatagcgaa aaccgaataa   13860
aaaacacagt aaattacaag cacaacaaat ggtacaagaa aaacagtttt cccaatgcca   13920
taatactcga actcaggtag acttggtctt agcagcagct tcagtagcag ccttagcctc   13980
cttcaaagtg aagagcttag cctcttgatc aaccactccg tagttagcat acaaccttcc   14040
cactctgaag aaagccttga tgattggctc atcggacttt ctcacaagct ctgggaaagc   14100
ttggtggaaa gcagcagtag ccttcttgag cttgtagtgt gggataattg ggaagaggtg   14160
gtggatctgg tgagttccga tgttgtggga gaggttatcg atgagagcac cgtaagatct   14220
atccacagag gacaagtttc ccttcacgta agtccactca gaatcagcat accatggagt   14280
ctcctcatcg ttgtggtgca agaaggtggt aatcaccaac atagatccga acacgaaaac   14340
tggtccgtag tagtagatag ccatggtctt aagtcccaac tggagagaca agtagataga   14400
gagtccagca acgaagaagt gagcgagcaa agagataacc acagcggaca cttgtctcac   14460
aaaaagtggc tcgaatgggt tgaagtggtt cacctttctt ggtgggaatc cctccaccaa   14520
ataagcaagc caagcagctc ccaaagccaa gatcaagttc ctggacaatg ggtgatcatc   14580
agcctttctc tgtgggtaga acacctcatc tctatcgatg tttccggtgt tcttgtggtg   14640
gtgtctgtgg gtcaacttcc aagactcgaa tggggtcaag atgagagagt gcatgaaggt   14700
tcccacaacg aagttcaaga ggtggtatct agagaaagct ccgtgtccag catcgtgtcc   14760
aacagtgaag aatcccccaga acacaattcc ctggaggagg atatatccag tgcacaaagc   14820
agcatccaaa gcccagaaag actcaacctc tggcaaagct ctagcgtagt tcaatccgaa   14880
ggtcaaagcc acagcaataa ccaagcatct cacagtgtag tagagagaca aaggcacaga   14940
agcctcgaag caatcctttg ggagagatct cttgatctcg gtgagagttg ggaaaacgta   15000
agcctccttt gtagccatgg ttgttttttaa tcttgtttgt attgatgagt tttggtttga   15060
gtaaagagtg aagccgatga gttaatttat aggctataaa ggagatttgc atggcgatca   15120
cgtgtaataa tgcatgcacg catgtgattg tatgtgtgtg ctgtgagaga gaagctctta   15180
ggtgtttgaa gggagtgaca agtggcgaag aaaaacaatt ctccgcggct gcatgctatg   15240
tgtaacgtgt agctaatgtt ctggcatggc atcttatgaa cgattctttt taaaaacaag   15300
gtaaaaactt aacttcataa aattaaaaaa aaacgtttta ctaagttggt ttaaaagggg   15360
atgagagtct ataaattttg gaggtagtgc cgttgggaat ataaattggg agcttaatca   15420
gaattataga agttaaagtt gatttagtca cggtcaatat aaattgggaa tttgagtcaa   15480
aatcttccaa attcggaatc cgtcttgtta cacccggtgg ataggagccg aacggtttga   15540
aaatacttga aatgtggatg caggtgcagg ctggtttaat tttatgttga atggatacat   15600
gtcaatcgaa tttgagttat aggtacacat tttactctga tactaaaatg taacatttgt   15660
ctcaagaatg ggtaggtcat ccttatggcc ggcctagtag atttaaattg gccttagtgg   15720
ccaagcttgg cgtaatcatg gagcctgctt ttttgtacaa acttgggtac cggcctatta   15780
ggccacggtc cgtacagtgt ttgcccccca ctccgcccta cactcgtata tatatgccta   15840
aacctgcccc gttcctcata tgtgatatta ttatttcatt attaggtata agatagtaaa   15900
cgataaggaa agacaattta ttgagaaagc catgctaaaa tatagataga tataccttag   15960
caggtgttta tttacaaaca taacataaca tagtagctag ccagcaggca ggctaaaaca   16020
tagtatagtc tatctgcagg gggtacggtc gaggcggcct taattaatca agcggtcttt   16080
```

```
ccagagtgtt gtccgtgcac gtagtagtgc tttcccacat tatcgaggtt tcccaaagta   16140
gccttccaag ctccagcata agtcatcacc ttgtagttga ggttccactt cttagcgaaa   16200
gcaacgaatc ttctggacac ctcaggttgt ctgaattgag gcatagaagg gaagaggtgg   16260
tgaatcactt ggcagttcaa gtatcccatc aaccagttaa cccatccctg agaaggatcg   16320
atatcaatgg tgtgatccac agcgtaccta acccaagaca agtgctcatc agcaggaaca   16380
acatccaagt gggtgtgaga agtagagaag tgagcgaaca agtagcatcc ggaaacccaa   16440
gaagtagcca agaagagtcc gtaggattgc atagcggtga atccagtaac agccttaatg   16500
gtccaggttc taatcacgtg agcagccaac atccacacaa gctcctcgta ctttcctccc   16560
ttcaaagcct tagaagggtg gaggaagaac atccagaaga gcaacaccaa tccagaagtc   16620
acaggaatga aggtccaagc ttgcaatctg agccagtact tagagaatcc cctaggtcta   16680
ttatcctcca cagcggtgtt gaagaaagca acagcaggag tggtatccaa atccatatcg   16740
tgcctcactt tttgaggagt agcgtggtgc ttgttgtgca tggagttcca catatctcca   16800
gatccagcca atccgaatcc agcagtgaaa gcttggattc tcttatccca ccagatgttt   16860
ccggtcaaag aagagtgtcc tccctcgtgt tgaacccatc cacatctagc tccgaagaag   16920
caagcgtaaa ccaacacaga ggacacaacg tatctagcgt acatcaagta ggttcccaaa   16980
gcgtacatag cagccaactc agcgaatctg taagcaacat gagcaggaga aggcttgaag   17040
aatccgtccc tctccaactc ctttctccac ttagcgaaat cctggagcat ctcagcatca   17100
tccactttag cggtcttagc aggtctagaa ggcaaagcag ccaaagcctt cctagccttt   17160
ctagatctgt ggtggaactc cttgaaagcc tcagtagcat cagctccagt gttagagaga   17220
gcgtagaaaa tcacggttcc tccaggatgt ttgaaatcgg tcacatcgta ctcaactccc   17280
tcgataacca cgtatcttct agcgaaggtc ttagccaaag cagcaggttc catcttctca   17340
gcagacaact tcacgttagc ctcagctctt tctctctctc catcgaaagc gatctccaca   17400
gtagggattc catcgttgtt ctcggtctca acacacatgg tagggttcag cttgatcgct   17460
ctattaatta gttcattgtt ttatacgtga agaaaaagaa agagacggaa tatatggcaa   17520
aaaacatgca aggggacgtg tgttaacata cgtgtcttat gactaattat tcgtagtggc   17580
agtttctacc atctggaaat ggaattgata tacacaggcc agcaagacac tctagcttac   17640
catagagcat tttcatgcac actttttttaa aagacaaagg aagtatatta atagatggtc   17700
ataattctga atgttttatt acctttaaca ttccaacaag gttaaaacca atgtttcaag   17760
atgtcaatgt gtccttcaca aactcatata ttgaattact agtttgacca agatataagg   17820
gttaactcta aaacataaga aaatatgaca caaatataaa ataaatatca gatatattga   17880
gagatctcaa aattattaag aataaaatat ctaagtatta atattgttgg tggtattcta   17940
aaggtgacag gtgataaatt atattattgt aaaatttaaa ataagagaat attttatat   18000 tgttgtaaaa tttaaaataa gagaatattt ttgagttacg ttttgtacta aatttctatt   18060
gatggatttt ggactttgaa ataccataat ttctattcaa ttcattacac attttttttcc   18120 agcatacaat ttagcattac aaagttttta tataggcttg aagaaaagta acatagaaaa   18180
caataattca aaaatcaaga cgaggactat ttggttttct caatcttaat gatacaactt   18240
tatcataatt ttaaataagg acaataatta taatgtgatg attacaattt tcttataata   18300
cttactaaag gtagtggtgg ttacaacaca ttaattttaa cactccccct taatgtgttg   18360
ctctttaact cccattactt ctctaagttg ttaaaatctt cctctttgta gtattttagt   18420
aaaagtgtct gtaagttgct cttatgaact gcagaaaggt aactgcacat ttccttcttc   18480
```

```
aatcactctt cgaatgaagt ggtgttttat gttaatgtgt ctagtccgac tatgaaaaac   18540
aggattcttt gtgttgtact acaaaatttt tcctctcagt cttcaagaat tttctcataa   18600
gatcttccat gacatcaagt ttgcagcact gatacatcaa tttaggtttg gaattggcac   18660
aagagcaaaa tggtcaattg cacactgaaa agtcaaactt tgacttttgc atcaacatca   18720
aatttcaaga atcacatttc atcaagacat gttagaatat gaagtttgtt ttattaagaa   18780
agtcaaaagt caagtttgct ttggaaaagt caaaattcta aacacttaga aattttctca   18840
actgttaaga aatatgacaa gttcagaact tctggccaga ttttcaccat gatgcaagtt   18900
gattctggaa gaacttctga cacaagagtt gtagatttca atgagatcta agacattgcg   18960
gaacagaact tctcttaaaa atgatgggat ttcaagttat aaatctttga agacacgtcc   19020
atgaaactga agtactcaat aaattttggg ccttcccaag acggaatttg gttagaactt   19080
ctggagcagt tttcacgtag gttcaatcag agtttgcaag agtaattcaa agaaagtcta   19140
caaagcatgt tacaagcttt ctgaaaagtc ttagaactcc ttcagaacat gttggaacag   19200
agagattcaa agatcagaag ttggatacag tccgggccgt cgatggccgg cctaacctgc   19260
aggatacaag tgcgcacaga ctagcggccg caatcggacc gataccggta ggcgccacaa   19320
tcagtaaatt gaacggagaa tattattcat aaaaatacga tagtaacggg tgatatattc   19380
attagaatga accgaaaccg gcggtaagga tctgagctac acatgctcag gttttttaca   19440
acgtgcacaa cagaattgaa agcaaatatc atgcgatcat aggcgtctcg catatctcat   19500
taaagcagca atcaattatt aattaatcaa tcctgcttct tggtatcagc tccaacagaa   19560
tgtccaacag agtagaggtt agcgaaggta gtagaaacag cagaggtgta tggcaaatcg   19620
tagtaaggga ggttatgtct cttgaagaga gcctcaactc ttggagagat ctccttgaac   19680
ctgaattgtg gagcggttgg gaacaaatga tgctcgattt ggaagttgag gttagacatc   19740
caccaggtaa ccaaccaaga cttggtagag atgttcacgg tatgatcagc agcgtactca   19800
agccaatgca attgatcctc tgggttggta actggcaaat gggtatgaga cacagcgaat   19860
tggaggaaga tgtagatgca tccaagtccg aaagagcaga ggtacattcc cacagaagtt   19920
ccaggagaat atcccaaagc tcccatcaag agaaccatcc cgatatatct agcgaagatc   19980
cacacaaact ccatatgtct cttggtcctg agcatatatc ttgggtgcaa gtacaaggtc   20040
catcccaatc cgatcaacaa gcaagacact ggagcgaaca aataagcctg aactctgagc   20100
cacaaagcca acaaagatcc tggcttaacc ttcctcacaa ctctctcgtt gaaagcaacg   20160
agtggcaagg tgttcaaatc cacatcgtgc tccaatctgt ttggagcagc atggtgctta   20220
gaatgctggt tcttccagta gtgtccagac attccacatc caactccgta gaagaactcg   20280
cacatcctat catcgagcca gataactcca gtgaaagatc cgtgtcccat ctcatgcata   20340
acccatccgc atcttccttg agcgattccg ttcatcacca ctcccaaaac caaagaggtt   20400
ggagaagcct tagacatcaa ccagaaagac aaagcgaaca aagccacaat ctccaccact   20460
ctgtagatca tgtgtgggat agatggatcg aagtatccct cagcaaccaa ctcctctctg   20520
aaagcagcgt aatccctggt catagcgtcc cttctagcct gctccttagc agagaaccta   20580
gactccacct tagaagcatc caactttggg agggacttga ggtacttatc agcctttccg   20640
gatctctgat ggaactctct gtaagcttgg gtagcatcaa ctccagcttc tccctcggtg   20700
aggaagttaa taatggaacc tcctgggtgt ttgaagttgg tagcatcgta caacactccc   20760
tcaatgagga tggtctttct cttatctccg ttagcctcag cagtcatctc tctagcagca   20820
```

```
gatcttccct cagatccttt tcccatggag gtgtgagagt gagttgtgag ttgtgtggtg   20880
ggtttggtga gattggggat ggtgggttta tatagtggag actgaggaat ggggtcgtga   20940
gtgttaactt tgcatgggct acacgtgggt tcttttgggc ttacacgtag tattattcat   21000
gcaaatgcag ccaatacata tacggtattt taataatgtg tgggaataca atatgccgag   21060
tattttacta attttggcaa tgacaagtgt acatttggat tatcttactt ggcctctctt   21120
gctttaattt ggattatttt tattctctta ccttggccgt tcatattcac atccctaaag   21180
gcaagacaga attgaatggt ggccaaaaat taaaacgatg gatatgacct acatagtgta   21240
ggatcaatta acgtcgaagg aaaatactga ttctattagg ggtgagagtt gatcggttaa   21300
ttatccaata catgccgttg gttaattagg attatataaa aaatcgatca tctattagaa   21360
tcgattacgg ttaaataggt ataaaaatgg agagaattga atcagttata aatttgtttt   21420
cagttaaaat atttctatga tcttcaatcg atttcggtat tttatactca acatggaaaa   21480
aatttcaaat gtatttcttc taaaagcaaa agaatctata aaaactatca ttttatccaa   21540
aacaccaaaa tagtctttta caatctttta cagccttcac ataaacgaaa acaaaagtga   21600
acaatttctt tttacagcct ttacaccaaa aagactacga tgaactatga taaaatttca   21660
taatctaaaa acattaatga ggtaaagact ctctcaaatg ggatattctt cgaaaatttt   21720
cataatcgaa cgatatactt gaatttgcaa ctcatgaccg aaattgtccc aatccataat   21780
actctttgac accctatcag atcccaacgt tgtccctggt ttcgaaacca ccatttcaaa   21840
catgaacata tcacaaaata aacatttaga caccaaatat ctgctaatgg ccggcctaac   21900
ctgcaggtat cccgggaatt accggtagta ggcgcctact ttggccggcc ctgaattaac   21960
gccgaattaa ttcggggggat ctggatttta gtactggatt ttggttttag gaattagaaa   22020
ttttattgat agaagtattt tacaaataca aatacatact aagggtttct tatatgctca   22080
acacatgagc gaaaccctat aggaacccta attcccttat ctgggaacta ctcacacatt   22140
attatggaga aactcgagct tgtcgatcac tcggtcttag ctcccttttg ctttccatcg   22200
gatggcttga tgtacttttg cacgtagaag tttccgaaga ggaacaagag ggagatcatg   22260
tagtagaaga ggatcttgat gagccattgt ggatatggag cgttggtttt catatcgtag   22320
taagcttgca ccaagttgag catgaactgg aacatctgga attgggtgag gtatcttccc   22380
cagaagaggt acttgttctt gagctttggg gaagatctca agcaagcagc caagaagtag   22440
taagcgtaca tcaacacgtg cactccagag ttgagagcag cactccaata agcctctcct   22500
cctggagcgt ggtgagcaat agcccaccag ataaggagaa tagaagagtg gtggtacacg   22560
tggaggaaag aaatctgtct ggtggatctc ttgaggatca tgatcacggt atccatgaac   22620
tccacgtact tggacatgta gaagaggtaa acgaggatag ccatctcctt gtgctttggg   22680
ttataagcgt tccccacaa ggaatatctc caggtgatag cttggtaagc gatacccacg   22740
cacatgtaaa gagacaaagc gaagcagaac aagttgtgca ccaacaccaa agcttgcaac   22800
aagaatggct cagaagctct tggcttgaga tctctagcct tgatccaaag caatcctccg   22860
atcacgatgg tcaagtaaac agacactccc aacacaattg gagttggaga atcaacgagt   22920
ggcaatccct tagtagttgg ggtatcagtc aactcaactc cgaaagatcc caacaaagcg   22980
ttcactcctt gggaaacctt tccatccaac tctccgtaga acctctcaac aacttccatg   23040
gtactggcta tgaagaaatt ataatcgtgt aaaacttagt gagtgtgtat gaatgaaagt   23100
attgcaaaat cctcattata tagactacat gcataactag ttgcatgtaa atttgtagtt   23160
ttcttcatta ttgcatcctc caagtggatg tcatggtttt acacatggct tccatgcaaa   23220
```

```
tcatttccaa aatatttta aactttccac agggcatcca tgcatgcacc tcaaaacttg    23280
tgtgtggtaa cattgttgtc ttgaaaaatt actaaacctt ttgtccacgt gacgttcatg    23340
cacctcaaat cttgtgtggt accattatta tcctcaagaa ttattgaatg tttggtgtat    23400
atgccatcca tgcagcattg caacaattaa atctccaaac cttgtggtac catattcact    23460
cactttaatt ctcctatagt agaaatatta gcaaatattt acatttccag ttgattagta    23520
tatgtattta gaagacaaaa ataatttaga atcaattaat caacttgcaa attgctaagt    23580
gttggcaaac gttagcataa aaggtgttat aaatttagta ccaaatataa aaatttatcg    23640
caaatcaaat acataacaca catagtaaaa caaaaacaaa ttacaagggt ttagacgttt    23700
agtggcaatg tgtaaatttg ctgcagggcg cgaaattggc cttagtggcc aagcttggcg    23760
taatcatggc aactttt                                                   23777
```

<210> SEQ ID NO 102
<211> LENGTH: 960
<212> TYPE: DNA
<213> ORGANISM: Nannochloropsis oculata

<400> SEQUENCE: 102

```
atggccgcca tctcaccgcg caaacatcct ccgcctgatc ttaaggagcg catgatcggg      60
ggtctgctcc tggcttcgct catctacgta tggctctttg gtgtcattgt tgtacccttg    120
gctacgtaca agatgctggc acagggcgac tatcgcctcg ccctcggcct cctcctttat    180
tacgcctacc gttgggtcta tccgaccaag gaatgggccc tcgtgcgcga catctaccga    240
gccggcaacc gatatttcta cccacaagag gtccttttg atggcttcaa ggagatcaaa     300
cccgaatcga ggtcattgat ttgcatgcac ccgcatggaa tcttgactat tggttgggcg    360
ttgaccagca cgagtcccac catgacgcac gccaatgtga agtggctggt gacggaggct    420
ttgttgcgct tgcctttat cagcgacttc ctgtcctgga acggcgtgc acacgctagc     480 aagagctaca tgcaaaaccg tatgacgaag ggtgcgaatc ttgccctgct ccccggaggg    540
tttgaagagg cttccctcta tcaacacagc tcttaccgtg tctacatccg aaagcgcaca    600
ggctttgttg tgtatgccct cagatatggt tataagattt atccttcgtt cgtctttggg    660
gaggagaagt gttatttctc tttgatgccc gactgggggt ggctaacggc ggcgaggcta    720
tggttgaatc agttccggtt cccggcagtt gcgtttgtcg gaaagttgtt tttggtgcct    780
gggtgggatt cgcatttgat cacggtgatc ggcgccccg tggtgttgcc gaggctagag     840
aagccaacgg aagaggaggt gaggaagtac cattcgttgt atgtgcgtgc attgatggaa    900
ttgtttgaga agcacaaaac ccaatattgt gagaaggggg cgaagttgga ggtgtggtag    960
```

<210> SEQ ID NO 103
<211> LENGTH: 319
<212> TYPE: PRT
<213> ORGANISM: Nannochloropsis oculata

<400> SEQUENCE: 103

```
Met Ala Ala Ile Ser Pro Arg Lys His Pro Pro Asp Leu Lys Glu
1               5                   10                  15

Arg Met Ile Gly Gly Leu Leu Leu Ala Ser Leu Ile Tyr Val Trp Leu
            20                  25                  30

Phe Gly Val Ile Val Val Pro Leu Ala Thr Tyr Lys Met Leu Ala Gln
        35                  40                  45

Gly Asp Tyr Arg Leu Ala Leu Gly Leu Leu Leu Tyr Tyr Ala Tyr Arg
```

```
                    50                  55                  60
Trp Val Tyr Pro Thr Lys Glu Trp Ala Leu Val Arg Asp Ile Tyr Arg
 65                  70                  75                  80

Ala Gly Asn Arg Tyr Phe Tyr Pro Gln Glu Val Leu Phe Asp Gly Phe
                 85                  90                  95

Lys Glu Ile Lys Pro Glu Ser Arg Ser Leu Ile Cys Met His Pro His
            100                 105                 110

Gly Ile Leu Thr Ile Gly Trp Ala Leu Thr Ser Thr Ser Pro Thr Met
        115                 120                 125

Thr His Ala Asn Val Lys Trp Leu Val Thr Glu Ala Leu Leu Arg Leu
    130                 135                 140

Pro Phe Ile Ser Asp Phe Leu Ser Trp Asn Gly Cys Ala His Ala Ser
145                 150                 155                 160

Lys Ser Tyr Met Gln Asn Arg Met Thr Lys Gly Ala Asn Leu Ala Leu
                165                 170                 175

Leu Pro Gly Gly Phe Glu Glu Ala Ser Leu Tyr Gln His Ser Ser Tyr
            180                 185                 190

Arg Val Tyr Ile Arg Lys Arg Thr Gly Phe Val Val Tyr Ala Leu Arg
        195                 200                 205

Tyr Gly Tyr Lys Ile Tyr Pro Ser Phe Val Phe Gly Glu Glu Lys Cys
    210                 215                 220

Tyr Phe Ser Leu Met Pro Asp Trp Gly Trp Leu Thr Ala Ala Arg Leu
225                 230                 235                 240

Trp Leu Asn Gln Phe Arg Phe Pro Ala Val Ala Phe Val Gly Lys Leu
                245                 250                 255

Phe Leu Val Pro Gly Trp Asp Ser His Leu Ile Thr Val Ile Gly Ala
            260                 265                 270

Pro Val Leu Pro Arg Leu Glu Lys Pro Thr Glu Glu Val Arg
        275                 280                 285

Lys Tyr His Ser Leu Tyr Val Arg Ala Leu Met Glu Leu Phe Glu Lys
    290                 295                 300

His Lys Thr Gln Tyr Cys Glu Lys Gly Ala Lys Leu Glu Val Trp
305                 310                 315
```

<210> SEQ ID NO 104
<211> LENGTH: 1265
<212> TYPE: DNA
<213> ORGANISM: Nannochloropsis oculata

<400> SEQUENCE: 104

```
attttcagca aagtaatcaa gataataaac aaaaacaatc ctataaagga aaacaacag     60 gcgcatcatc tacgacgata gccatggccg ccatctcacc gcgcaaacat cctccgcctg    120
atcttaagga gcgcatgatc gggggtctgc tcctggcttc gctcatctac gtatggctct    180
ttggtgtcat tgttgtaccc ttggctacgt acaagatgct ggcacagggc gactatcgcc    240
tcgccctcgg cctcctcctt tattacgcct accgttgggt ctatccgacc aaggaatggg    300
ccctcgtgcg cgacatctac cgagccggca accgatattt ctacccacaa gaggtccttt    360
ttgatggctt caaggagatc aaacccgaat cgaggtcatt gatttgcatg cacccgcatg    420
gaatcttgac tattggttgg cgttgaccag cacgagtcc accatgacg cacgccaatg    480 tgaagtggct ggtgacggag ctttgttgc gcttgccttt tatcagcgac ttcctgtcct    540
ggaacggctg tgcacacgct agcaagagct acatgcaaaa ccgtatgacg aagggtgcga    600
atcttgccct gctccccgga gggtttgaag aggcttccct ctatcaacac agctcttacc    660
```

```
gtgtctacat ccgaaagcgc acaggctttg ttgtgtatgc cctcagatat ggttataaga      720
tttatccttc gttcgtcttt ggggaggaga agtgttattt ctctttgatg cccgactggg      780
ggtggctaac ggcggcgagg ctatggttga atcagttccg gttcccggca gttgcgtttg      840
tcggaaagtt gttttggtg cctggtggg attcgcattt gatcacggtg atcggcgccc       900
ccgtggtgtt gccgaggcta gagaagccaa cggaagagga ggtgaggaag taccattcgt      960
tgtatgtgcg tgcattgatg gaattgtttg agaagcacaa acccaatat tgtgagaagg      1020 gggcgaagtt ggaggtgtgg taggataggg agagagggaa gggaaggtaa cacacatgta     1080
cagagctatg accaaagtaa tcgactgatg ggaggaggga gagggaaagt gaagggaga      1140 aagaaagaga gaggggagg ctgccacacc gcgacgctgc gtgagtgcgt ggtgtgtgtg       1200
tgtggagccc ttgatatttg aaataaaaat taaaaataaa aaaaaaaaaa aaaaaaaaa      1260 aaaaa                                                                  1265

<210> SEQ ID NO 105
<211> LENGTH: 1563
<212> TYPE: DNA
<213> ORGANISM: Arabidopsis thaliana

<400> SEQUENCE: 105
atggcgattt tggattctgc tggcgttact acggtgacgg agaacggtgg cggagagttc       60
gtcgatcttg ataggcttcg tcgacggaaa tcgagatcgg attcttctaa cggacttctt      120
ctctctggtt ccgataataa ttctccttcg gatgatgttg gagctcccgc cgacgttagg      180
gatcggattg attccgttgt taacgatgac gctcaggaa cagccaattt ggccggagat       240
aataacggtg gtgcgataa taacggtggt ggaagaggcg gcggagaagg aagaggaaac       300
gccgatgcta cgtttacgta tcgaccgtcg gttccagctc atcggagggc gagagagagt      360
ccacttagct ccgacgcaat cttcaaacag agccatgccg gattattcaa cctctgtgta      420
gtagttctta ttgctgtaaa cagtagactc atcatcgaaa atcttatgaa gtatggttgg      480
ttgatcagaa cggatttctg gtttagttca agatcgctgc gagattggcc gcttttcatg      540
tgttgtatat ccctttcgat cttccttttg gctgccttta cggttgagaa attggtactt      600
cagaaataca tatcagaacc tgttgtcatc tttcttcata ttattatcac catgacagag      660
gttttgtatc cagtttacgt caccctaagg tgtgattctg cttttttatc aggtgtcact      720
ttgatgctcc tcacttgcat tgtgtggcta aagttggttt cttatgctca tactagctat      780
gacataagat ccctagccaa tgcagctgat aaggccaatc ctgaagtctc ctactacgtt      840
agcttgaaga gcttggcata tttcatggtc gctcccacat tgtgttatca gccaagttat      900
ccacgttctg catgtatacg gaagggttgg gtggctcgtc aatttgcaaa actggtcata      960
ttcaccggat tcatgggatt tataatagaa caatatataa atcctattgt caggaactca     1020
aagcatcctt tgaaaggcga tcttctatat gctattgaaa gagtgttgaa gctttcagtt     1080
ccaaatttat atgtgtggct ctgcatgttc tactgcttct tccacctttg gttaaacata     1140
ttggcagagc ttctctgctt cgggatcgt gaattctaca agattggtg gaatgcaaaa      1200 agtgtgggag attactggag aatgtggaat atgcctgtta taaatggat ggttcgacat      1260 atatacttcc cgtgcttgcg cagcaagata ccaaagacac tcgccattat cattgctttc     1320
ctagtctctg cagtctttca tgagctatgc atcgcagttc cttgtcgtct cttcaagcta     1380
tgggcttttc ttgggattat gtttcaggtg cctttggtct tcatcacaaa ctatctacag     1440
```

```
gaaaggtttg gctcaacggt ggggaacatg atcttctggt tcatcttctg cattttcgga   1500
caaccgatgt gtgtgcttct ttattaccac gacctgatga accgaaaagg atcgatgtca   1560
tga                                                                 1563
```

<210> SEQ ID NO 106
<211> LENGTH: 520
<212> TYPE: PRT
<213> ORGANISM: Arabidopsis thaliana

<400> SEQUENCE: 106

```
Met Ala Ile Leu Asp Ser Ala Gly Val Thr Val Thr Glu Asn Gly
1               5                   10                  15

Gly Gly Glu Phe Val Asp Leu Asp Arg Leu Arg Arg Lys Ser Arg
                20                  25                  30

Ser Asp Ser Ser Asn Gly Leu Leu Leu Ser Gly Ser Asp Asn Asn Ser
                35                  40                  45

Pro Ser Asp Asp Val Gly Ala Pro Ala Asp Val Arg Asp Arg Ile Asp
50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Arg Gly Gly Glu
                85                  90                  95

Gly Arg Gly Asn Ala Asp Ala Thr Phe Thr Tyr Arg Pro Ser Val Pro
                100                 105                 110

Ala His Arg Arg Ala Arg Glu Ser Pro Leu Ser Ser Asp Ala Ile Phe
                115                 120                 125

Lys Gln Ser His Ala Gly Leu Phe Asn Leu Cys Val Val Leu Ile
            130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
                180                 185                 190

Phe Thr Val Glu Lys Leu Val Leu Gln Lys Tyr Ile Ser Glu Pro Val
            195                 200                 205

Val Ile Phe Leu His Ile Ile Thr Met Thr Glu Val Leu Tyr Pro
210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
                260                 265                 270

Asn Pro Glu Val Ser Tyr Tyr Val Ser Leu Lys Ser Leu Ala Tyr Phe
            275                 280                 285

Met Val Ala Pro Thr Leu Cys Tyr Gln Pro Ser Tyr Pro Arg Ser Ala
                290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
                340                 345                 350
```

```
Glu Arg Val Leu Lys Leu Ser Val Pro Asn Leu Tyr Val Trp Leu Cys
        355                 360                 365
Met Phe Tyr Cys Phe Phe His Leu Trp Leu Asn Ile Leu Ala Glu Leu
    370                 375                 380
Leu Cys Phe Gly Asp Arg Glu Phe Tyr Lys Asp Trp Trp Asn Ala Lys
385                 390                 395                 400
Ser Val Gly Asp Tyr Trp Arg Met Trp Asn Met Pro Val His Lys Trp
                405                 410                 415
Met Val Arg His Ile Tyr Phe Pro Cys Leu Arg Ser Lys Ile Pro Lys
            420                 425                 430
Thr Leu Ala Ile Ile Ile Ala Phe Leu Val Ser Ala Val Phe His Glu
        435                 440                 445
Leu Cys Ile Ala Val Pro Cys Arg Leu Phe Lys Leu Trp Ala Phe Leu
    450                 455                 460
Gly Ile Met Phe Gln Val Pro Leu Val Phe Ile Thr Asn Tyr Leu Gln
465                 470                 475                 480
Glu Arg Phe Gly Ser Thr Val Gly Asn Met Ile Phe Trp Phe Ile Phe
                485                 490                 495
Cys Ile Phe Gly Gln Pro Met Cys Val Leu Leu Tyr Tyr His Asp Leu
            500                 505                 510
Met Asn Arg Lys Gly Ser Met Ser
        515                 520

<210> SEQ ID NO 107
<211> LENGTH: 1506
<212> TYPE: DNA
<213> ORGANISM: Brassica napus

<400> SEQUENCE: 107
atggagattt tggattctgg aggcgtcact atgccgacgg agaacggtgg tgccgatctc      60
gatacgcttc gtcaccggaa accgagatcg gattcttcca atggacttct tcctgattcc     120
gtaactgttt ccgatgctga cgtgagggat cgggttgatt cagctgttga ggatactcaa     180
ggaaaagcca atttggccgg agaaaacgaa attagggaat ccgtggagag agcgggggga     240
aacgtggatg taaggtacac gtatcggccg tcggttccag ctcatcggag ggtgcgggag     300
agtccactca gctctgacgc catcttcaaa cagagccatg ctggactatt caacctgtgt     360
gtagtagttc ttgttgctgt aaacagtaga ctcatcatcg aaaatctcat gaagtacggt     420
tggttgatca gaactgattt ctggtttagt tcaacgtctc tgcgagattg ccccttttc      480
atgtgttgtc tctcccttc aatctttcct ttggctgcct ttaccgtcga gaattagta      540
cttcagaaat gcatatctga acctgttgtc atcattcttc atattattat caccatgacc     600
gaggtcttgt atccagtcta tgtcactcta aggtgtgatt ccgccttctt atcaggtgtc     660
acgttgatgc tcctcacttg cattgtgtgg ctgaagttgg tttcttacgc tcatactaac     720
tatgacataa gaaccctagc taattcatct gataaggcca atcctgaagt ctcctactat     780
gttagcttga gagcttggc gtatttcatg cttgctccca cattgtgtta tcagccgagc     840
tatccacgtt ctccatgtat ccggaagggt tgggtggctc gtcaatttgc aaagctgatc     900
atattcactg gattcatggg atttataata gagcaatata taaatcctat tgttaggaac     960
tcaaaacatc ctttgaaagg ggatctctta tacggtgttg aaagagtgtt gaagctttca    1020
gttccaaatt tatacgtgtg ctctgcatg ttctactgct tcttccacct ttggttaaac    1080
atattggcag agctcctctg cttcggggat cgtgaattct acaaagattg gtggaatgca    1140
```

```
aaaagcgtgg gagattattg gagaatgtgg aatatgcctg ttcataaatg gatggttcga    1200
catgtatact ttccgtgcct tcgcagaaat ataccgaaag tacccgctat tatccttgct    1260
ttcttagtct ctgcagtctt tcatgagtta tgcatcgcag ttccttgtcg tctcttcaaa    1320
ctatgggctt tcttggggat tatgtttcag gtgcctttgg tatttatcac aaactaccta    1380
caagaaaggt ttggctccat ggtgggaaac atgatattct ggtttacctt ctgcattttc    1440
ggacaaccga tgtgtgtgct tctttattat cacgacttga tgaaccgcaa aggaaagatg    1500
tcatag                                                               1506
```

<210> SEQ ID NO 108
<211> LENGTH: 501
<212> TYPE: PRT
<213> ORGANISM: Brassica napus

<400> SEQUENCE: 108

```
Met Glu Ile Leu Asp Ser Gly Gly Val Thr Met Pro Thr Glu Asn Gly
 1               5                  10                  15

Gly Ala Asp Leu Asp Thr Leu Arg His Arg Lys Pro Arg Ser Asp Ser
            20                  25                  30

Ser Asn Gly Leu Leu Pro Asp Ser Val Thr Val Ser Asp Ala Asp Val
        35                  40                  45

Arg Asp Arg Val Asp Ser Ala Val Glu Asp Thr Gln Gly Lys Ala Asn
    50                  55                  60

Leu Ala Gly Glu Asn Glu Ile Arg Glu Ser Gly Gly Glu Ala Gly Gly
65                  70                  75                  80

Asn Val Asp Val Arg Tyr Thr Tyr Arg Pro Ser Val Pro Ala His Arg
                85                  90                  95

Arg Val Arg Glu Ser Pro Leu Ser Asp Ala Ile Phe Lys Gln Ser
            100                 105                 110

His Ala Gly Leu Phe Asn Leu Cys Val Val Leu Val Ala Val Asn
        115                 120                 125

Ser Arg Leu Ile Ile Glu Asn Leu Met Lys Tyr Gly Trp Leu Ile Arg
    130                 135                 140

Thr Asp Phe Trp Phe Ser Ser Thr Ser Leu Arg Asp Trp Pro Leu Phe
145                 150                 155                 160

Met Cys Cys Leu Ser Leu Ser Ile Phe Pro Leu Ala Ala Phe Thr Val
                165                 170                 175

Glu Lys Leu Val Leu Gln Lys Cys Ile Ser Glu Pro Val Val Ile Ile
            180                 185                 190

Leu His Ile Ile Ile Thr Met Thr Glu Val Leu Tyr Pro Val Tyr Val
        195                 200                 205

Thr Leu Arg Cys Asp Ser Ala Phe Leu Ser Gly Val Thr Leu Met Leu
    210                 215                 220

Leu Thr Cys Ile Val Trp Leu Lys Leu Val Ser Tyr Ala His Thr Asn
225                 230                 235                 240

Tyr Asp Ile Arg Thr Leu Ala Asn Ser Ser Asp Lys Ala Asn Pro Glu
                245                 250                 255

Val Ser Tyr Tyr Val Ser Leu Lys Ser Leu Ala Tyr Phe Met Leu Ala
            260                 265                 270

Pro Thr Leu Cys Tyr Gln Pro Ser Tyr Pro Arg Ser Pro Cys Ile Arg
        275                 280                 285

Lys Gly Trp Val Ala Arg Gln Phe Ala Lys Leu Ile Ile Phe Thr Gly
    290                 295                 300
```

```
Phe Met Gly Phe Ile Ile Glu Gln Tyr Ile Asn Pro Ile Val Arg Asn
305                 310                 315                 320

Ser Lys His Pro Leu Lys Gly Asp Leu Leu Tyr Gly Val Glu Arg Val
            325                 330                 335

Leu Lys Leu Ser Val Pro Asn Leu Tyr Val Trp Leu Cys Met Phe Tyr
        340                 345                 350

Cys Phe Phe His Leu Trp Leu Asn Ile Leu Ala Glu Leu Leu Cys Phe
            355                 360                 365

Gly Asp Arg Glu Phe Tyr Lys Asp Trp Trp Asn Ala Lys Ser Val Gly
        370                 375                 380

Asp Tyr Trp Arg Met Trp Asn Met Pro Val His Lys Trp Met Val Arg
385                 390                 395                 400

His Val Tyr Phe Pro Cys Leu Arg Arg Asn Ile Pro Lys Val Pro Ala
                405                 410                 415

Ile Ile Leu Ala Phe Leu Val Ser Ala Val Phe His Glu Leu Cys Ile
            420                 425                 430

Ala Val Pro Cys Arg Leu Phe Lys Leu Trp Ala Phe Leu Gly Ile Met
            435                 440                 445

Phe Gln Val Pro Leu Val Phe Ile Thr Asn Tyr Leu Gln Glu Arg Phe
    450                 455                 460

Gly Ser Met Val Gly Asn Met Ile Phe Trp Phe Thr Phe Cys Ile Phe
465                 470                 475                 480

Gly Gln Pro Met Cys Val Leu Leu Tyr Tyr His Asp Leu Met Asn Arg
                485                 490                 495

Lys Gly Lys Met Ser
            500

<210> SEQ ID NO 109
<211> LENGTH: 104
<212> TYPE: DNA
<213> ORGANISM: Artificial Sequence
<220> FEATURE:
<223> OTHER INFORMATION: Primer

<400> SEQUENCE: 109
ataaaagtat caacaaaaaa ttgttaatat acctctatac tttaacgtca aggagaaaaa      60
accccggatc ggcgcgccac catggccgcc atctcaccgc gcaa                     104

<210> SEQ ID NO 110
<211> LENGTH: 101
<212> TYPE: DNA
<213> ORGANISM: Artificial Sequence
<220> FEATURE:
<223> OTHER INFORMATION: Primer

<400> SEQUENCE: 110
aactataaaa aaataaatag ggacctagac ttcaggttgt ctaactcctt cctttcggt      60 tagagcggat ttaattaact accacacctc caacttcgcc c                        101

<210> SEQ ID NO 111
<211> LENGTH: 104
<212> TYPE: DNA
<213> ORGANISM: Artificial Sequence
<220> FEATURE:
<223> OTHER INFORMATION: Primer

<400> SEQUENCE: 111
ataaaagtat caacaaaaaa ttgttaatat acctctatac tttaacgtca aggagaaaaa      60
```

```
acccggatc ggcgcgccac catggcgatt ttggattctg ctgg              104

<210> SEQ ID NO 112
<211> LENGTH: 101
<212> TYPE: DNA
<213> ORGANISM: Artificial Sequence
<220> FEATURE:
<223> OTHER INFORMATION: Primer

<400> SEQUENCE: 112
aactataaaa aaataaatag ggacctagac ttcaggttgt ctaactcctt cctttcggt    60 tagagcggat ttaattaatc atgacatcga tccttttcgg t                      101

<210> SEQ ID NO 113
<211> LENGTH: 104
<212> TYPE: DNA
<213> ORGANISM: Artificial Sequence
<220> FEATURE:
<223> OTHER INFORMATION: Primer

<400> SEQUENCE: 113
ataaaagtat caacaaaaaa ttgttaatat acctctatac tttaacgtca aggagaaaaa    60 acccggatc ggcgcgccac catggagatt ttggattctg gagg                    104

<210> SEQ ID NO 114
<211> LENGTH: 101
<212> TYPE: DNA
<213> ORGANISM: Artificial Sequence
<220> FEATURE:
<223> OTHER INFORMATION: Primer

<400> SEQUENCE: 114
aactataaaa aaataaatag ggacctagac ttcaggttgt ctaactcctt cctttcggt    60 tagagcggat ttaattaact atgacatctt cctttgcgg t                       101
```

ACYLTRANSFERASES AND USES THEREOF IN FATTY ACID PRODUCTION

RELATED APPLICATIONS

This application is a national stage application (under 35 U.S.C. §371) of PCT/EP2011/060315, filed Jun. 21, 2011 which claims benefit of European Application No. 10167342.4 filed Jun. 25, 2010, and U.S. Provisional Application No. 61/358,431, filed Jun. 25, 2010.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13987_00214_US. The size of the text file is 216 KB and the text file was created on Dec. 21, 2012.

The present invention relates to the recombinant manufacture of polyunsaturated fatty acids. Specifically, it relates to acyltransferase polypeptides, polynucleotides encoding said acyltransferase polypeptides as well to vectors, host cells, non-human transgenic organisms containing said polynucleotides. Moreover, the present invention contemplates methods for the manufacture of polyunsaturated fatty acids as well as oils obtained by such methods.

Fatty acids and triacylglycerides have a various applications in the food industry, in animal feed, supplement nutrition, and in the cosmetic and pharmacological and pharmaceutical field. The individual applications may either require free fatty acids or triacylglycerides. In both cases, however, polyunsaturated fatty acids either free or esterified are of pivotal interest for many of the aforementioned applications. In particular, polyunsaturated omega-3-fatty acids and omega-6-fatty acids are important constituents in animal and human food. These fatty acids are supposed to have beneficial effects on the overall health and, in particular, on the central nervous system, the cardivovascular system, the immune system, and the general metabolism. Within traditional food, the polyunsaturated omega-3-fatty acids are mainly found in fish and plant oils. However, in comparison with the needs of the industry and the need for a beneficial diet, this source is rather limited.

The various polyunsaturated fatty acids (PUFA) and PUFA-containing triglycerides are also mainly obtained from microorganisms such as *Mortierella* and *Schizochytrium* or from oil-producing plants such as soybean or oilseed rape, algae such as *Crypthecodinium* or *Phaeodactylum* and others, where they are usually obtained in the form of their triacylglycerides. The free PUFA are usually prepared from the triacylglycerides by hydrolysis. However, long chain polyunsaturated fatty acids (LCPUFA) having a C-18, C-20, C-22 or C-24 fatty acid body, such as docoahexaenoic acid (DHA), eicosapentaenoic acid (EPA), arachidonic acid (ARA), dihomo-gamma-linolenic acid or docosapentaenoic acid (DPA) can not be efficiently isolated from natural oil crop plants such as oilseed rape, soybean, sunflower or safflower. Conventional natural sources of these fatty acids are, thus, merely fish, such as herring, salmon, sardine, redfish, eel, carp, trout, halibut, mackerel, zander or tuna, or from algae.

Especially suitable microorganisms for the production of PUFA in industrial scale are microalgae such as *Phaeodactylum tricornutum*, *Porphoridium* species, *Thraustochytrium* species, *Nannochloropsis* species, *Schizochytrium* species or *Crypthecodinium* species, ciliates such as *Stylonychia* or *Colpidium*, fungi such as *Mortierella*, *Entomophthora* or *Mucor* and/or mosses such as *Physcomitrella*, *Ceratodon* and *Marchantia* (Vazhappilly 1998, Botanica Marina 41: 553-558; Totani 1987, Lipids 22: 1060-1062; Akimoto 1998, Appl. Biochemistry and Biotechnology 73: 269-278). Strain selection has resulted in the development of a number of mutant strains of the microorganisms in question which produce a series of desirable compounds including PUFA. However, the mutation and selection of strains with an improved production of a particular molecule such as the polyunsaturated fatty acids is a time-consuming and difficult process. This is why recombinant methods as described above are preferred whenever possible. However, only limited amounts of the desired PUFA or LCPUFA and, in particular, DHA or EPA, can be produced with the aid of the above mentioned microorganisms, and, depending on the microorganism used, these are generally obtained as fatty acid mixtures of, for example, EPA, DPA and DHA.

Many attempts in the past have been made to make available genes which are involved in the synthesis of fatty acids or triglycerides for the production of oils in various organisms. Various desaturases have been described in the art; see, e.g., documents WO 91/13972, WO 93/11245, WO 94/11516, EP-A-0 550 162, WO 94/18337, WO 97/30582, WO 97/21340, WO 95/18222, EP-A-0 794 250, Stukey 1990, J. Biol. Chem., 265: 20144-20149, Wada 1990, Nature 347: 200-203, Huang 1999, Lipids 34: 649-659, WO 93/06712, U.S. Pat. No. 5,614,393, WO 96/21022, WO 00/21557, WO 99/27111, WO 98/46763, WO 98/46764, WO 98/46765, WO 99/64616 or WO 98/46776. These enzymes can be used for the production of unsaturated fatty acids. Thus, due to modern molecular biology, it has become possible to increase at least to some extent the content of the desired polyunsaturated fatty acids and, in particular, the PUFA or LCPUFA in a given organism. Elongases for the production of fatty acids are disclosed in the document WO2009/016202.

The biosynthesis of LCPUFA and the incorporation of LCPUFA into membrane lipids or triacylglycerides proceeds via various metabolic pathways (Abbadi 2001, European Journal of Lipid Science & Technology 103:106-113). In bacteria such as *Vibrio*, and microalgae, such as *Schizochytrium*, malonyl-CoA is converted into LCPUFA via an LCPUFA-producing polyketide synthase (Metz 2001, Science 293: 290-293; WO 00/42195; WO 98/27203; WO 98/55625). In microalgae, such as *Phaeodactylum*, and mosses, such as *Physcomitrella*, unsaturated fatty acids such as linoleic acid or linolenic acid are converted in a plurality of desaturation and elongation steps to give LCPUFA (Zank 2000, Biochemical Society Transactions 28: 654-658). Desaturation takes place either on acyl groups bound to Coenzyme A (acyl-CoA) or on acyl groups of membrane lipids, whereas elongation is biochemicaly restricted to acyl chains bound to CoA. In mammals, the biosynthesis of DHA comprises a chain shortening via beta-oxidation, in addition to desaturation and elongation steps. In microorganisms and lower plants, LCPUFA are present either exclusively in the form of membrane lipids, as is the case in *Physcomitrella* and *Phaeodactylum*, or in membrane lipids and triacylglycerides, as is the case in *Schizochytrium* and *Mortierella*. Incorporation of LCPUFA into lipids and oils, as well as the transfer of the fatty acid moiety (acyl group) between lipids and other molecular species such as acyl-CoA, is catalyzed by various acyltransferases and transacylases. These enzymes are, known to carry out the incorporation or interexchange of saturated and unsaturated fatty acids (Slabas 2001, J. Plant Physiology 158: 505-513, Frentzen 1998, Fett/Lipid 100: 161-166, Cases 1998, Proc. Nat. Acad. Sci. USA 95: 13018-13023). One group of acyltransferases having three distinct enzymatic activities are enzymes of the "Kennedy pathway", which are located on the cytoplasmic side of the membrane system of the endoplasmic reticulum (ER). The ER-bound acyltransferases in the microsomal fraction use acyl-CoA as the activated form of fatty acids. Glycerol-3-phosphate acyltransferase (GPAT) catalyzes the incorporation of acyl groups at the sn-1 position of glycerol-3-phosphate. 1-Acylglycerol-3-phosphate acyltransferase, also known as lysophosphatidic acid acyltransferase (LPAAT), catalyze the incorporation of acyl groups at the sn-2 position of lysophosphatidic acid (LPA). After dephosphorylation of phosphatidic acid by phosphatidic acid phosphatase (PAP), diacylglycerol acyltransferase (DGAT) catalyzes the incorporation of acyl groups at the sn-3 position of diacylglycerols. Further enzymes directly involved in TAG biosynthesis—apart from the said Kennedy pathway enzymes—are the phospholipid diacylglycerol acyltransferase (PDAT), an enzyme that transfers acyl groups from the sn-2 position of membrane lipids to the sn-3 position of diacylglycerols, and diacylglyceroldiacylglycerol transacylase (DDAT), an enzyme that transfers acylgroups from the sn-2 position of one diacylglycerol-molecule to the sn-3 position of another diacylglycerol-molecule. Lysophospholipid acyltransferase (LPLAT) represents a class of acyltransferases that are capable of incorporating activated acyl groups from acyl-CoA to membrane lipids, and possibly catalyze also the reverse reaction. More specifically, LPLATs can have activity as lysophosphophatidylethanolamine acyltransferase (LPEAT) and lysophosphatidylcholine acyltransferase (LPCAT). Further enzymes, such as lecithin cholesterol acyltransferase (LCAT) can be involved in the transfer of acyl groups from membrane lipids into triacylglycerides, as well.

The documents WO 98/54302 and WO 98/54303 disclose a human LPAAT and its potential use for the therapy of diseases, as a diagnostic, and a method for identifying modulators of the human LPAAT. Moreover, a variety of acyltransferases with a wide range of enzymatic functions have been described in the documents WO 98/55632, WO 98/55631, WO 94/13814, WO 96/24674, WO 95/27791, WO 00/18889, WO 00/18889, WO 93/10241, Akermoun 2000, Biochemical Society Transactions 28: 713-715, Tumaney 1999, Biochimica et Biophysica Acta 1439: 47-56, Fraser 2000, Biochemical Society Transactions 28: 715-7718, Stymne 1984, Biochem. J. 223: 305-314, Yamashita 2001, Journal of Biological Chemistry 276: 26745-26752, and WO 00/18889.

Higher plants comprise PUFA, such as linoleic acid and linolenic acid. However, the LCPUFA ARA, EPA and DHA are not present in the seed oils of higher plants or only in traces (Ucciani: Nouveau Dictionnaire des Huiles Végétales. Technique & Documentation—Lavoisier, 1995. ISBN: 2-7430-0009-0). It is nevertheless highly desirable to produce LCPUFA in higher plants, preferably in oil seeds such as oilseed rape, linseed, sunflower and soybean, since large amounts of high-quality LCPUFA for the various aforementioned applications may be obtained thereby at low costs.

However, one drawback of using transgenic plants expressing various of the aforementioned desaturases and elongases involved in the synthesis of PUFA and LCPUFA is that the latter are not efficiently incorporated into triacylglycerides, but rather into membranes. Furthermore, efficient processing of a given acyl molecule-substrate, e.g. linoleic acid, by a plurality of desaturation and elongation steps towards the desired LCPUFA, e.g. ARA, EPA and/or DHA, is hindered by the requirement to transfer the acyl molecule and its derivatives generated by the elongation and desaturation reactions back and forth between membrane lipids and acyl-CoA. For this reason, intermediates towards desired LCPUFA are incorporated into oil before the synthesis of the desired LCPUFA is complete. These two problems are undesired for the following reasons: First, the main lipid fraction in oil seeds are triacylglycerides. This is why, for economical reasons, it is necessary to concentrate LCPUFA in triacylglycerides. Second, LCPUFA which are incorporated into membranes can modify the physical characteristics of the membranes and thus have harmful effects on the integrity and transport characteristics of the membranes and on the stress tolerance of plants. Third, for efficient LCPUFA synthesis, it is desirable to increase the flux of intermediate-LCPUFA between the two sites of biosynthesis—that are membrane lipids and acyl-CoA—and/or decrease the flux of intermediate-PUFA/-LCPUFA into oil. Transgenic plants which comprise and express genes coding for enzymes of LCPUFA biosynthesis and produce LCPUFA have been described, e.g., in DE 102 19 203 or WO2004/087902. However, these plants produce LCPUFA in amounts which require further optimization for processing the oils present in said plants. Moreover, it was proposed that delta 6 desaturated fatty acids may be shifted into the acyl-CoA pool for increasing efficiency of fatty acid elongation in plants (Singh 2005, *Curr. Opin. Plant Biol.*, 8: 197-203). Another publication demonstrated in *Arabidopsis*, that the additional expression of RcDGAT2 from *Ricinus communis* increase the storage of hydroxyfatty acids produced by a *Ricinus communis* fatty acid hydroxylase 12 (FAH12) from 17% to 30% in the seed oil.

Accordingly, means for increasing the content of PUFA or LCPUFA, such as EPA and DHA, in triglycerides in, e.g., plant seed oils, are still highly desirable.

Thus, the present invention relates to a polynucleotide comprising a nucleic acid sequence elected from the group consisting of:

a) a nucleic acid sequence having a nucleotide sequence as shown in any one of SEQ ID NOs: 52, 1, 4, 7, 10, 13, 16, 19, 22, 25, 28, 31, 34, 37, 40, 43, 46, 49, and 55;

b) a nucleic acid sequence encoding a polypeptide having an amino acid sequence as shown in any one of SEQ ID NOs: 53, 2, 5, 8, 11, 14, 17, 20, 23, 26, 29, 32, 35, 38, 41, 44, 47, 50, and 56;

c) a nucleic acid sequence being at least 40% identical to the nucleic acid sequence of a) or b), wherein said nucleic acid sequence encodes a polypeptide having acyltransferase activity;

d) a nucleic acid sequence encoding a polypeptide having acyltransferase activity and having an amino acid sequence which is at least 45% identical to the amino acid sequence of b); and e) a nucleic acid sequence which is capable of hybridizing under one of the following sets of conditions to any one of a) to d), wherein said nucleic acid sequence encodes a polypeptide having acyltransferase activity:

f) hybridization in 50 mM Tris, pH 7.6, 6×SSC, 5×Denhardt's, 1.0% sodium dodecyl sulfat (SDS) 100 µg denaturated calf thymus DNA at 34° C. overnight and wash twice with 2×SSC, 0.5% SDS at room temperature for 15 min each, repeat twice with 0.2×SSC, 0.5% SDS at room temperature for 15 min each and then repeat twice with 0.2 SSC, 0.5% SDS at 50° C. for 15 min;

g) hybridization in 6×SSPE (Sodium chloride Sodium Phosphate-EDTA), 5×Denhardt's solution, 0.5% SDS 100 µg denaturated calf thymus DNA at 34° C. overnight and wash twice with 2×SSC, 0.5% SDS at room temperature for 15 min each, repeat twice with 0.2×SSC, 0.5% SDS at room temperature for 15 min each and then repeat twice with 0.2 SSC, 0.5% SDS at 50° C. for 15 min;

h) hybridization in 20-30% formamide, 5×SSPE, 5×Denhardt's solution, 1% SDS 100 μg denatured salmon sperm DNA at 34° C. overnight and wash twice with 2×SSPE, 0.2% SDS at 42° C. for 15 min each, repeat twice with 2×SSPE, 0.2% SDS at 55° C. for 30 min each and repeat twice with 0.2 SSC, 0.5% SDS at 50° C. for 15 min;

i) hybridization in 7% SDS, 0.5 M NaPO4, 1 mM EDTA at 50° C. overnight and wash in 2×SSC, 0.1% SDS at 50° C. or 65° C.;

j) hybridization in 7% SDS, 0.5 M NaPO4, 1 mM EDTA at 50° C. overnight and wash in 1×SSC, 0.1% SDS at 50° C. or 65° C.; or k) hybridization in 7% SDS, 0.5 M NaPO4, 1 mM EDTA at 50° C. overnight and wash in 0.1×SSC, 0.1% SDS at 50° C. or 65° C.

The term "polynucleotide" as used in accordance with the present invention relates to a polynucleotide comprising a nucleic acid sequence which encodes a polypeptide having acyltransferase activity. Preferably, the polypeptide encoded by the polynucleotide of the present invention having acyltransferas activity upon expression in a plant shall be capable of increasing the amount of PUFA and, in particular, LCPUFA esterified to triglycerides in, e.g., seed oils or the entire plant or parts thereof. Such an increase is, preferably, statistically significant when compared to a LCPUFA producing transgenic control plant which expresses the minimal set of desaturases and elongases required for LCPUFA synthesis but does not express the polynucleotide of the present invention. Such a transgenic plant may, preferably, express desaturases and elongases comprised by the vector LJB765 listed in table 11 of example 5 in WO2009/016202 or a similar set of desaturases and elongases required for DHA synthesis. Whether an increase is significant can be determined by statistical tests well known in the art including, e.g., Student's t-test. More preferably, the increase is an increase of the amount of triglycerides containing LCPUFA of at least 5%, at least 10%, at least 15%, at least 20%, at least 25%, at least 30%, at least 35%, at least 40%, at least 45% or at least 50% compared to the said control. Preferably, the LCPUFA referred to before is a polyunsaturated fatty acid having a C-20, C-22 or C24 fatty acid body, more preferably, EPA or DHA, most preferably, DHA. Suitable assays for measuring the activities mentioned before are described in the accompanying Examples.

The term "acyltransferase activity" or "acyltransferase" as used herein encompasses all enymatic activities and enzymes which are capable of transferring or are involved in the transfer of PUFA and, in particular; LCPUFA from the acly-CoA pool or the membrane phospholipis to the triglycerides, from the acyl-CoA pool to membrane lipids and from membrane lipids to the acyl-CoA pool by a transesterification process. It will be understood that this acyltransferase activity will result in an increase of the LCPUFA esterified to triglycerides in, e.g., seed oils. In particular, it is envisaged that these acyltransferases are capable of producing triglycerides having esterified EPA or even DHA, or that these acyltransferases are capable of enhancing synthesis of desired PUFA by increasing the flux for specific intermediates of the desired PUFA between the acyl-CoA pool (the site of elongation) and membrane lipids (the predominant site of desaturation). Specifically, acyltransferase activity as used herein relates to lysophospholipid acyltransferase (LPLAT) activity, preferably, lysophosphatidylcholine acyltransferase (LPCAT) or Lysophosphophatidylethanolamine acyltransferase (LPEAT) activity, lysophosphatidic acid acyltransferase (LPAAT) activity, glycerol-3-phosphate acyltransferase (GPAT) activity or diacylglycerol acyltransferase (DGAT), and, more preferably, to LPLAT, LPAAT, DGAT or GPAT activity.

More preferably, polynucleotides having a nucleic acid sequence as shown in SEQ ID NOs: 1, 4, and 7, encoding polypeptides having amino acid sequences as shown in SEQ ID NOs: 2, 5, and 8 or variants thereof, preferably, exhibit LPLAT activity. Polynucleotides having a nucleic acid sequence as shown in SEQ ID NOs: 10, and 13, encoding polypeptides having amino acid sequences as shown in SEQ ID NOs: 11, and 14 or variants thereof, preferably, exhibit LPAAT activity. Polynucleotides having a nucleic acid sequence as shown in SEQ ID NOs: 16, 19, 22, 25, 28, 31, 34, 37, 40, 43, 46, 49, 52, and 55, encoding polypeptides having amino acid sequences as shown in SEQ ID NOs: 17, 20, 23, 26, 29, 32, 35, 38, 41, 44, 47, 50, 53, and 56 or variants thereof, preferably, exhibit DGAT activity. A polynucleotide having a nucleic acid sequence as shown in SEQ ID NO: 55, encoding a polypeptide having amino acid sequences as shown in SEQ ID NO: 56 or variants thereof, preferably, exhibit GPAT activity.

A polynucleotide encoding a polypeptide having a acyltransferase activity as specified above has been obtained in accordance with the present invention, preferably, from *Nannochloropsis oculata* and/or *Thraustochytrium aureum*. However, orthologs, paralogs or other homologs may be identified from other species.

Thus, the term "polynucleotide" as used in accordance with the present invention further encompasses variants of the aforementioned specific polynucleotides representing orthologs, paralogs or other homologs of the polynucleotide of the present invention. Moreover, variants of the polynucleotide of the present invention also include artificially generated muteins. Said muteins include, e.g., enzymes which are generated by mutagenesis techniques and which exhibit improved or altered substrate specificity, or codon optimized polynucleotides. The polynucleotide variants, preferably, comprise a nucleic acid sequence characterized in that the sequence can be derived from the aforementioned specific nucleic acid sequences shown in any one of SEQ ID NOs: 52, 1, 4, 7, 10, 13, 16, 19, 22, 25, 28, 31, 34, 37, 40, 43, 46, 49, and 55 or by a polynucleotide encoding a polypeptide having an amino acid sequence as shown in any one of SEQ ID NOs: 53, 2, 5, 8, 11, 14, 17, 20, 23, 26, 29, 32, 35, 38, 41, 44, 47, 50, and 56 by at least one nucleotide substitution, addition and/or deletion, whereby the variant nucleic acid sequence shall still encode a polypeptide having a acyltransferase activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled artisan and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled artisan knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 6×SSC (pH 7.2). If organic solvent is present in the abovementioned buffer, for example 50% formamide, the temperature under standard conditions is approximately 42° C. The hybridization conditions for DNA:DNA hybrids are, preferably, 0.1×SSC and 20° C. to 45° C., preferably between 30° C. and 45° C. and more preferably between 45° C. and 65° C. The hybridization conditions for DNA:RNA hybrids are, more preferably, 0.1× SSC and 30° C. to 55° C., most preferably between 45° C. and 65° C. The abovementioned hybridization temperatures are determined for example for a nucleic acid with approximately 100 bp (=base pairs) in length and a G+C content of 50% in the absence of formamide. The skilled artisan knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

In detail variants of polynucleotides still encode a polypeptide having a acyltransferase activity as specified above comprising a nucleic acid sequence which is capable of hybridizing preferably under conditions equivalent to hybridization in 50 mM Tris, pH 7.6, 6×SSC, 5×Denhardt's, 1.0% sodium dodecyl sulfat (SDS) 100 μg denaturated calf thymus DNA at 34° C. overnight, followed by washing twice with 2×SSC, 0.5% SDS at room temperature for 15 min each, then wash twice with 0.2×SSC, 0.5% SDS at room temperature for 15 min each and then wash twice with 0.2 SSC, 0.5% SDS at 50° C. for 15 min each to a nucleic acid described by any one of SEQ ID NOs: 52, 1, 4, 7, 10, 13, 16, 19, 22, 25, 28, 31, 34, 37, 40, 43, 46, 49, and 55 or the complement thereof.

More preferably, said variants of polynucleotides comprising a nucleic acid sequence which is capable of hybridizing under conditions equivalent to hybridization in 6×SSPE (Sodium chloride Sodium Phosphate-EDTA), 5×Denhardt's solution, 0.5% sodium dodecyl sulfat (SDS) 100 μg denaturated calf thymus DNA at 34° C. overnight, followed by washing twice with 2×SSC, 0.5% SDS at room temperature for 15 min each, then wash twice with 0.2×SSC, 0.5% SDS at room temperature for 15 min each and then wash twice with 0.2 SSC, 0.5% SDS at 50° C. for 15 min each to a nucleic acid described by any one of SEQ ID NOs: 52, 1, 4, 7, 10, 13, 16, 19, 22, 25, 28, 31, 34, 37, 40, 43, 46, 49, and 55 or the complement thereof.

Most preferably, said variants of polynucleotides comprising a nucleic acid sequence which is capable of hybridizing under conditions equivalent to hybridization in 20-30% formamide, 5×SSPE (Sodium chloride Sodium Phosphate-EDTA), 5×Denhardt's solution, 1% sodium dodecyl sulfat (SDS) 100 μg denaturated salmon sperm DNA at 34° C. overnight, followed by washing twice with 2×SSPE, 0.2% SDS at 42° C. for 15 min each, then wash twice with 2×SSPE, 0.2% SDS at 55° C. for 30 min each and then wash twice with 0.2 SSC, 0.5% SDS at 50° C. for 15 min each to a nucleic acid described by any one of SEQ ID NOs: 52, 1, 4, 7, 10, 13, 16, 19, 22, 25, 28, 31, 34, 37, 40, 43, 46, 49, and 55 or the complement thereof.

In another preferred embodiment aforementioned variants of polynucleotides still encode a polypeptide having a acyltransferase activity as specified above comprising a nucleic acid sequence which is capable of hybridizing under conditions equivalent to hybridization in 7% sodium dodecyl sulfate (SDS), 0.5 M NaPO4, 1 mM EDTA at 50° C. overnight with washing in 2×SSC, 0.1% SDS at 50° C. or 65° C., preferably 65° C. to a nucleic acid described by any one of SEQ ID NOs: 52, 1, 4, 7, 10, 13, 16, 19, 22, 25, 28, 31, 34, 37, 40, 43, 46, 49, and 55 or the complement thereof. In still another preferred embodiment, said variants of polynucleotides comprising a nucleic acid sequence which is capable of hybridizing under conditions equivalent to hybridization in 7% sodium dodecyl sulfate (SDS), 0.5 M NaPO4, 1 mM EDTA at 50° C. overnight with washing in 1×SSC, 0.1% SDS at 50° C. or 65° C., preferably 65° C. to a nucleotide sequence described by any one of SEQ ID NOs: 52, 1, 4, 7, 10, 13, 16, 19, 22, 25, 28, 31, 34, 37, 40, 43, 46, 49, and 55 or the complement thereof, most preferably, said variants of polynucleotides comprising a nucleic acid sequence which is capable of hybridizing under conditions equivalent to hybridization in 7% sodium dodecyl sulfate (SDS), 0.5 M NaPO4, 1 mM EDTA at 50° C. overnight with washing in 0.1×SSC, 0.1% SDS at 50° C. or 65° C., preferably 65° C. to a nucleic acid sequence described by any one of SEQ ID NOs: 52, 1, 4, 7, 10, 13, 16, 19, 22, 25, 28, 31, 34, 37, 40, 43, 46, 49, and 55 or the complement thereof.

The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

A "complement" of a nucleic acid sequence as used herein refers to a nucleotide sequence whose nucleic acid molecules show total complementarity to the nucleic acid molecules of the nucleic acid sequence.

The term "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands.

Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples. As a template, DNA or cDNA from bacteria, fungi, plants or animals may be used.

Further, variants include polynucleotides comprising nucleic acid sequences which are at least up to 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% identical to the nucleic acid sequences shown in any one of SEQ ID NOs: 52, 1, 4, 7, 10, 13, 16, 19, 22, 25, 28, 31, 34, 37, 40, 43, 46, 49, and 55, preferably, encoding polypeptides retaining a acyltransferase activity as specified above.

Moreover, also encompassed are polynucleotides (derivatives) which comprise nucleic acid sequences encoding a polypeptide having an amino acid sequences which are at least up to 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% identical to the amino acid sequences shown in any one of SEQ ID NOs: 53, 2, 5, 8, 11, 14, 17, 20, 23, 26, 29, 32, 35, 38, 41, 44, 47, 50, and 56, wherein the polypeptide, preferably, retains acyltransferase activity as specified above. The percent identity values are, preferably, calculated over the entire amino acid or nucleic acid sequence region. A series of programs based on a variety of algorithms is available to the skilled artisan for comparing different sequences. In a preferred embodiment, the percent identity between two amino acid sequences is determined using the Needleman and Wunsch algorithm (Needleman 1970, J. Mol. Biol. (48):444-453) which has been incorporated into the needle program in the EMBOSS software package (EMBOSS: The European Molecular Biology Open Software Suite, Rice, P., Longden, I., and Bleasby, A, Trends in Genetics 16(6), 276-277, 2000), using either a BLOSUM 45 or PAM250 scoring matrix for distantly related proteins, or either a BLOSUM 62 or PAM160 scoring matrix for closer related proteins, and a gap opening penalty of 16, 14, 12, 10, 8, 6, or 4 and a gap extension penalty of 0.5, 1, 2, 3, 4, 5, or 6. Guides for local installation of the EMBOSS package as well as links to WEB-Services can be found at http://emboss.sourceforge.net. A preferred, non-limiting example of parameters to be used for aligning two amino acid sequences using the needle program are the default parameters, including the EBLOSUM62 scoring matrix, a gap opening penalty of 10 and a gap extension penalty of 0.5. In yet another preferred embodiment, the percent identity between two nucleotide sequences is determined using the needle program in the EMBOSS software package (EMBOSS: The European Molecular Biology Open Software Suite, Rice, P., Longden, I., and Bleasby, A, Trends in Genetics 16(6), 276-277, 2000), using the EDNAFULL scoring matrix and a gap opening penalty of 16, 14, 12, 10, 8, 6, or 4 and a gap extension penalty of 0.5, 1, 2, 3, 4, 5, or 6. A preferred, non-limiting example of parameters to be used in conjunction for aligning two amino acid sequences using the needle program are the default parameters, including the EDNAFULL scoring matrix, a gap opening penalty of 10 and a gap extension penalty of 0.5. The nucleic acid and protein sequences of the present invention can further be used as a "query sequence" to perform a search against public databases to, for example, identify other family members or related sequences. Such searches can be performed using the BLAST series of programs (version 2.2) of Altschul et al. (Altschul 1990, J. Mol. Biol. 215:403-10). BLAST using acyltransferase nucleic acid sequences of the invention as query sequence can be performed with the BLASTn, BLASTx or the tBLASTx program using default parameters to obtain either nucleotide sequences (BLASTn, tBLASTx) or amino acid sequences (BLASTx) homologous to acyltransferase sequences of the invention. BLAST using acyltransferase protein sequences of the invention as query sequence can be performed with the BLASTp or the tBLASTn program using default parameters to obtain either amino acid sequences (BLASTp) or nucleic acid sequences (tBLASTn) homologous to acyltransferase sequences of the invention. To obtain gapped alignments for comparison purposes, Gapped BLAST using default parameters can be utilized as described in Altschul et al. (Altschul 1997, Nucleic Acids Res. 25(17):3389-3402).

TABLE 1

Relation of sequence types of querry and hit sequences for various BLASt programs

| Input query sequence | Converted Query | Algorithm | Converted Hit | Actual Database |
|---|---|---|---|---|
| DNA | | BLASTn | | DNA |
| PRT | | BLASTp | | PRT |
| DNA | PRT | BLASTx | | PRT |
| PRT | | tBLASTn | PRT | DNA |
| DNA | PRT | tBLASTx | PRT | DNA |

A polynucleotide comprising a fragment of any of the aforementioned nucleic acid sequences is also encompassed as a polynucleotide of the present invention. The fragment shall encode a polypeptide which still has acyltransferase activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The variant polynucleotides or fragments referred to above, preferably, encode polypeptides retaining acyltransferase activity to a significant extent, preferably, at least 10%, at least 20%, at least 30%, at least 40%, at least 50%, at least 60%, at least 70%, at least 80% or at least 90% of the acyltransferase activity exhibited by any of the polypeptide shown in any one of SEQ ID NOs: 2, 5, 8, 11, 14, 17, 20, 23, 26, 29, 32, 35, 38, 41, 44, 47, 50, 53, and 56 or derivative of any of these polypeptides. The activity may be tested as described in the accompanying examples.

The polynucleotides of the present invention either essentially consist of the aforementioned nucleic acid sequences or comprise the aforementioned nucleic acid sequences. Thus, they may contain further nucleic acid sequences as well. Preferably, the polynucleotide of the present invention may comprise in addition to an open reading frame further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the polynucleotides of the present invention may encode fusion proteins wherein one partner of the fusion protein is a polypeptide being encoded by a nucleic acid sequence recited above. Such fusion proteins may comprise as additional part other enzymes of the fatty acid or PUFA biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

The polynucleotide of the present invention shall be provided, preferably, either as an isolated polynucleotide (i.e. purified or at least isolated from its natural context such as its natural gene locus) or in genetically modified or exogenously (i.e. artificially) manipulated form. An isolated polynucleotide can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The polynucleotide, preferably, is provided in the form of double or single stranded molecule. It will be understood that the present invention by referring to any of the aforementioned polynucleotides of the invention also refers to complementary or reverse complementary strands of the specific sequences or variants thereof referred to before. The polynucleotide encompasses DNA, including cDNA and genomic DNA, or RNA polynucleotides.

However, the present invention also pertains to polynucleotide variants which are derived from the polynucleotides of the present invention and are capable of interfering with the transcription or translation of the polynucleotides of the present invention. Such variant polynucleotides include antisense nucleic acids, ribozymes, siRNA molecules, morpholino nucleic acids (phosphorodiamidate morpholino oligos), triple-helix forming oligonucleotides, inhibitory oligonucleotides, or micro RNA molecules all of which shall specifically recognize the polynucleotide of the invention due to the presence of complementary or substantially complementary sequences. These techniques are well known to the skilled artisan. Suitable variant polynucleotides of the aforementioned kind can be readily designed based on the structure of the polynucleotides of this invention.

Moreover, comprised are also chemically modified polynucleotides including naturally occurring modified polynucleotides such as glycosylated or methylated polynucleotides or artificial modified ones such as biotinylated polynucleotides.

Advantageously, it has been found in accordance with the present invention that the polynucleotides encoding the above mentioned polypeptides having acyltransferase activity and, in particular, LPLAT, LPAAT, DGAT and/or GPAT activity, can be used for the manufacture of PUFA and, in particular, LCPUFA when expressed in a transgenic host organism or cell. Specifically, the aforementioned acyltransferase activities will allow for an increase of LCPUFA esterified to triglycerides in seed oils by shifting the said LCPUFA from the acyl-CoA pool (by polypeptides having LPAAT, DGAT or GPAT activity as specified above) and/or from the acyl-CoA pool/pospholipid pool to the phospholipid pool/acyl-CoA pool (by polypeptides having LPLAT as specified above) via transesterification. Surprisingly, it was found that the acyltransferases encoded by the polynucleotides of the present invention are also capable of efficiently shifting rather long and highly unsaturated LCPUFA towards the triglyceride pool or between the phospholipid pool and the acyl-CoA pool, in particular, even the long chain intermediates. More surprisingly even, DHA which is known to be incorporated in triglycerides only in very low amounts, if at all, can be efficiently transesterified to triglycerides by the acyltransferases of the invention.

In particular the LPLAT of the present invention can efficiently catalyse the transesterfication of 18:2n-6 from the sn2 position of phosphatidylcholine (PC) to CoA and/or from CoA to lysophosphatidylcholine (LPC), the transesterfication of 18:2n-6 from the sn2 position of phosphatidylethanolamine (PE) to CoA and/or from CoA to lysophosphatidylethanolamine (LPE), the transesterfication of 18:2n-6 from the sn2 position of phosphatidylserine (PS) to CoA and/or from CoA to lysophosphatidylserine (LPS), the transesterfication of 18:3n-6 from the sn2 position of phosphatidylcholine (PC) to CoA and/or from CoA to lysophosphatidylcholine (LPC), the transesterfication of 18:3n-6 from the sn2 position of phosphatidylethanolamine (PE) to CoA and/or from CoA to lysophosphatidylethanolamine (LPE), the transesterfication of 18:3n-6 from the sn2 position of phosphatidylserine (PS) to CoA and/or from CoA to lysophosphatidylserine (LPS), the transesterfication of 18:3n-3 from the sn2 position of phosphatidylcholine (PC) to CoA and/or from CoA to lysophosphatidylcholine (LPC), the transesterfication of 18:3n-3 from the sn2 position of phosphatidylethanolamine (PE) to CoA and/or from CoA to lysophosphatidylethanolamine (LPE), the transesterfication of 18:3n-3 from the sn2 position of phosphatidylserine (PS) to CoA and/or from CoA to lysophosphatidylserine (LPS), transesterfication of 18:4n-3 from the sn2 position of phosphatidylcholine (PC) to CoA and/or from CoA to lysophosphatidylcholine (LPC), the transesterfication of 18:4n-3 from the sn2 position of phosphatidylethanolamine (PE) to CoA and/or from CoA to lysophosphatidylethanolamine (LPE), the transesterfication of 18:4n-3 from the sn2 position of phosphatidylserine (PS) to CoA and/or from CoA to lysophosphatidylserine (LPS), the transesterfication of 20:3n-6 from the sn2 position of phosphatidylcholine (PC) to CoA and/or from CoA to lysophosphatidylcholine (LPC), the transesterfication of 20:3n-6 from the sn2 position of phosphatidylethanolamine (PE) to CoA and/or from CoA to lysophosphatidylethanolamine (LPE), the transesterfication of 20:3n-6 from the sn2 position of phosphatidylserine (PS) to CoA and/or from CoA to lysophosphatidylserine (LPS), the transesterfication of 20:4n-3 from the sn2 position of phosphatidylcholine (PC) to CoA and/or from CoA to lysophosphatidylcholine (LPC), the transesterfication of 20:4n-3 from the sn2 position of phosphatidylethanolamine (PE) to CoA and/or from CoA to lysophosphatidylethanolamine (LPE), the transesterfication of 20:4n-3 from the sn2 position of phosphatidylserine (PS) to CoA and/or from CoA to lysophosphatidylserine (LPS), the transesterfication of 20:4n-6 from the sn2 position of phosphatidylcholine (PC) to CoA and/or from CoA to lysophosphatidylcholine (LPC), the transesterfication of 20:4n-6 from the sn2 position of phosphatidylethanolamine (PE) to CoA and/or from CoA to lysophosphatidylethanolamine (LPE), the transesterfication of 20:4n-6 from the sn2 position of phosphatidylserine (PS) to CoA and/or from CoA to lysophosphatidylserine (LPS), the transesterfication of 20:5n-3 from the sn2 position of phosphatidylcholine (PC) to CoA and/or from CoA to lysophosphatidylcholine (LPC), the transesterfication of 20:5n-3 from the sn2 position of phosphatidylethanolamine (PE) to CoA and/or from CoA to lysophosphatidylethanolamine (LPE), the transesterfication of 20:5n-3 from the sn2 position of phosphatidylserine (PS) to CoA and/or from CoA to lysophosphatidylserine (LPS), the transesterfication of 22:5n-3 from the sn2 position of phosphatidylcholine (PC) to CoA and/or from CoA to lysophosphatidylcholine (LPC), the transesterfication of 22:5n-3 from the sn2 position of phosphatidylethanolamine (PE) to CoA and/or from CoA to lysophosphatidylethanolamine (LPE), the transesterfication of 22:5n-3 from the sn2 position of phosphatidylserine (PS) to CoA and/or from CoA to lysophosphatidylserine (LPS), the transesterfication of 22:6n-3 from the sn2 position of phosphatidylcholine (PC) to CoA and/or from CoA to lysophosphatidylcholine (LPC), the transesterfication of 22:6n-3 from the sn2 position of phosphatidylethanolamine (PE) to CoA and/or from CoA to lysophosphatidylethanolamine (LPE) and/or the transesterfication of 22:6n-3 from the sn2 position of phosphatidylserine (PS) to CoA and/or from CoA to lysophosphatidylserine (LPS).

Preferably the LPAAT of the present invention can efficiently catalyse the transesterfication of 18:2n-6 from CoA to the sn2 position of lysophosphatidic acid (LPA), the transesterfication of 18:3n-6 from CoA to the sn2 position of lysophosphatidic acid (LPA), the transesterfication of 18:3n-3 from CoA to the sn2 position of lysophosphatidic acid (LPA) and/or the transesterfication of 18:4n-6 from CoA to the sn2 position of lysophosphatidic acid (LPA).

More preferably the LPAAT of the present invention can efficiently catalyse the transesterfication of 20:3n-6 from CoA to the sn2 position of lysophosphatidic acid (LPA), transesterfication of 20:4n-3 from CoA to the sn2 position of lysophosphatidic acid (LPA) and/or the transesterfication of 22:5n-3 from CoA to the sn2 position of lysophosphatidic acid (LPA).

Most preferably the LPAAT of the present invention can efficiently catalyse the transesterfication of 20:4n-6 from CoA to the sn2 position of lysophosphatidic acid (LPA), the transesterfication of 20:5n-3 from CoA to the sn2 position of lysophosphatidic acid (LPA) and/or the transesterfication of 22:6n-3 from CoA to the sn2 position of lysophosphatidic acid (LPA).

Preferably the GPAT of the present invention can efficiently catalyse the transesterfication of 18:2n-6 from CoA to the sn1 position of glycerole-3-phosphate (G3P), the transesterfication of 18:3n-6 from CoA to the sn1 position of glycerole-3-phosphate (G3P), the transesterfication of 18:3n-3 from CoA to the sn1 position of glycerole-3-phosphate (G3P) and/or the transesterfication of 18:4n-6 from CoA to the sn1 position of glycerole-3-phosphate (G3P).

More preferably the GPAT of the present invention can efficiently catalyse the transesterfication of 20:3n-6 from CoA to the sn1 position of glycerole-3-phosphate (G3P), the transesterfication of 20:4n-3 from CoA to the sn1 position of glycerole-3-phosphate (G3P) and/or the transesterfication of 22:5n-3 from CoA to the sn1 position of glycerole-3-phosphate (G3P).

Most preferably the GPAT of the present invention can efficiently catalyse the transesterfication of 20:4n-6 from CoA to the sn1 position of glycerole-3-phosphate (G3P), the transesterfication of 20:5n-3 from CoA to the sn1 position of glycerole-3-phosphate (G3P) and/or the transesterfication of 22:6n-3 from CoA to the sn1 position of glycerole-3-phosphate (G3P).

Preferably the DGAT of the present invention can efficiently catalyse the transesterfication of 18:2n-6 from CoA to the sn3 position of Diacylglycerol (DAG), transesterfication of 18:3n-6 from CoA to the sn3 position of Diacylglycerol (DAG), the transesterfication of 18:3n-3 from CoA to the sn3 position of Diacylglycerol (DAG) and/or the transesterfication of 18:4n-6 from CoA to the sn3 position of Diacylglycerol (DAG).

More preferably the DGAT of the present invention can efficiently catalyse the transesterfication of 20:3n-6 from CoA to the sn3 position of Diacylglycerol (DAG), the transesterfication of 20:4n-3 from CoA to the sn3 position of Diacylglycerol (DAG) and/or the transesterfication of 22:5n-3 from CoA to the sn3 position of Diacylglycerol (DAG).

Most preferably the DGAT of the present invention can efficiently catalyse the transesterfication of 20:4n-6 from CoA to the sn3 position of Diacylglycerol (DAG), the transesterfication of 20:5n-3 from CoA to the sn3 position of Diacylglycerol (DAG) and/or the transesterfication of 22:6n-3 from CoA to the sn3 position of Diacylglycerol (DAG).

The activity of the LPLAT, LPAAT, GPAT or DGAT of the present invention is useful for the specificity of a fatty acid. This fatty acid specificity is useful to generate an artificially ARA-specificity preferably. More preferably the activity of the LPLAT, LPAAT, GPAT or DGAT of the present invention is useful to generate an artificially EPA-specificity. Most preferably the activity of the LPLAT, LPAAT, GPAT or DGAT of the present invention is useful to generate an artificially DHA-specificity.

In a preferred embodiment of the polynucleotide of the present invention, said polynucleotide further comprises an expression control sequence operatively linked to the said nucleic acid sequence.

The term "expression control sequence" as used herein refers to a nucleic acid sequence which is capable of governing, i.e. initiating and controlling, transcription of a nucleic acid sequence of interest, in the present case the nucleic acid sequences recited above. Such a sequence usually comprises or consists of a promoter or a combination of a promoter and enhancer sequences. Expression of a polynucleotide comprises transcription of the nucleic acid molecule, preferably, into a translatable mRNA. Additional regulatory elements may include transcriptional as well as translational enhancers. The following promoters and expression control sequences may be, preferably, used in an expression vector according to the present invention. The cos, tac, trp, tet, trp-tet, lpp, lac, lpp-lac, laclq, T7, T5, T3, gal, trc, ara, SP6, λ-PR or λ-PL promoters are, preferably, used in Gram-negative bacteria. For Gram-positive bacteria, promoters amy and SPO2 may be used. From yeast or fungal promoters ADC1, AOX1r, GAL1, MFα, AC, P-60, CYC1, GAPDH, TEF, rp28, ADH are, preferably, used. For animal cell or organism expression, the promoters CMV-, SV40-, RSV-promoter (Rous sarcoma virus), CMV-enhancer, SV40-enhancer are preferably used. From plants the promoters CaMV/35S (Franck 1980, Cell 21: 285-294], PRP1 (Ward 1993, Plant. Mol. Biol. 22), SSU, OCS, lib4, usp, STLS1, B33, nos or the ubiquitin or phaseolin promoter. Also preferred in this context are inducible promoters, such as the promoters described in EP 0 388 186 A1 (i.e. a benzylsulfonamide-inducible promoter), Gatz 1992, Plant J. 2:397-404 (i.e. a tetracyclin-inducible promoter), EP 0 335 528 A1 (i.e. a abscisic-acid-inducible promoter) or WO 93/21334 (i.e. a ethanol- or cyclohexenol-inducible promoter). Further suitable plant promoters are the promoter of cytosolic FBPase or the ST-LSI promoter from potato (Stockhaus 1989, EMBO J. 8, 2445), the phosphoribosyl-pyrophosphate amidotransferase promoter from *Glycine max* (Genbank accession No. U87999) or the node-specific promoter described in EP 0 249 676 A1. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially preferred promoters are seed-specific promoters which can be used for monocotyledonous or dicotyledonous plants and which are described in U.S. Pat. No. 5,608,152 (napin promoter from oilseed rape), WO 98/45461 (oleosin promoter from *Arabidopsis*, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for monocots: Ipt-2 or Ipt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890. In a particular embodiment, seed-specific promoters are utilized to enhance the production of the desired PUFA or LCPUFA.

The term "operatively linked" as used herein means that the expression control sequence and the nucleic acid of interest are linked so that the expression of the said nucleic acid of interest can be governed by the said expression control sequence, i.e. the expression control sequence shall be functionally linked to the said nucleic acid sequence to be expressed. Accordingly, the expression control sequence and, the nucleic acid sequence to be expressed may be physically linked to each other, e.g., by inserting the expression control sequence at the 5' end of the nucleic acid sequence to be expressed. Alternatively, the expression control sequence and the nucleic acid to be expressed may be merely in physical proximity so that the expression control sequence is capable of governing the expression of at least one nucleic acid sequence of interest. The expression control sequence and the nucleic acid to be expressed are, preferably, separated by not more than 500 bp, 300 bp, 100 bp, 80 bp, 60 bp, 40 bp, 20 bp, 10 bp or 5 bp.

In a further preferred embodiment of the polynucleotide of the present invention, said polynucleotide further comprises a terminator sequence operatively linked to the nucleic acid sequence.

The term "terminator" as used herein refers to a nucleic acid sequence which is capable of terminating transcription. These sequences will cause dissociation of the transcription machinery from the nucleic acid sequence to be transcribed. Preferably, the terminator shall be active in plants and, in particular, in plant seeds. Suitable terminators are known in the art and, preferably, include polyadenylation signals such as the SV40-poly-A site or the tk-poly-A site or one of the plant specific signals indicated in Loke et al. 2005, Plant Physiol 138, pp. 1457-1468, downstream of the nucleic acid sequence to be expressed.

The present invention also relates to a vector comprising the polynucleotide of the present invention.

The term "vector", preferably, encompasses phage, plasmid, viral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homolgous or heterologous recombination as described in detail below. The vector encompassing the polynucleotide of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pBI101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus 1991, Annu. Rev. Plant Physiol. Plant Molec. Biol. 42, 205-225.

More preferably, the vector of the present invention is an expression vector. In such an expression vector, i.e. a vector which comprises the polynucleotide of the invention having the nucleic acid sequence operatively linked to an expression control sequence (also called "expression cassette") allowing expression in prokaryotic or eukaryotic cells or isolated fractions thereof. Suitable expression vectors are known in the art such as Okayama-Berg cDNA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith 1988, Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the recombinant target protein. Examples of suitable inducible nonfusion E. coli expression vectors are, inter alia, pTrc (Amann 1988, Gene 69:301-315) and pET 11d (Studier 1990, Methods in Enzymology 185, 60-89). The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the lacUV 5 promoter. The skilled artisan is familiar with other vectors which are suitable in prokaryotic organisms; these vectors are, for example, in E. coli, pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCl, in Streptomyces pIJ101, pIJ364, pIJ702 or pIJ361, in Bacillus pUB110, pC194 or pBD214, in Corynebacterium pSA77 or pAJ667. Examples of vectors for expression in the yeast S. cerevisiae comprise pYep Sec1 (Baldari 1987, Embo J. 6:229-234), pMFa (Kurjan 1982, Cell 30:933-943), pJRY88 (Schultz 1987, Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEM-BLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith 1983, Mol. Cell Biol. 3:2156-2165) and the pVL series (Lucklow 1989, Virology 170:31-39).

The polynucleotide of the present invention can be expressed in single-cell plant cells (such as algae), see Falciatore 1999, Marine Biotechnology 1 (3):239-251 and the references cited therein, and plant cells from higher plants (for example Spermatophytes, such as arable crops) by using plant expression vectors. Examples of plant expression vectors comprise those which are described in detail in: Becker 1992, Plant Mol. Biol. 20:1195-1197; Bevan 1984, Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from Agrobacterium tumefaciens T-DNA, such as the gene 3 of the Ti plasmid pTiACH5, which is known as octopine synthase (Gielen 1984, EMBO J. 3, 835) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie 1987, Nucl. Acids Research 15:8693-8711). As described above, plant gene expression must be functionally linked to a suitable promoter which performs the expression of the gene in a timely, cell-specific or tissue-specific manner. Promoters which can be used are constitutive promoters (Benfey 1989, EMBO J. 8:2195-2202) such as those which are derived from plant viruses such as 35S CAMV (Franck 1980, Cell 21:285-294), 19S CaMV (see U.S. Pat. No. 5,352,605 and WO 84/02913) or plant promoters such as the promoter of the Rubisco small subunit, which is described in U.S. Pat. No. 4,962,028. Other preferred sequences for the use in functional linkage in plant gene expression cassettes are targeting sequences which are required for targeting the gene product into its relevant cell compartment (for a review, see Kermode 1996, Crit. Rev. Plant Sci. 15, 4: 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (for a review, see Gatz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetracyclin-inducible promoter (Gatz 1992, Plant J. 2, 397-404) and an ethanol-inducible promoter. Promoters which respond to biotic or abiotic stress conditions are also suitable promoters, for example the pathogen-induced PRP1-gene promoter (Ward 1993, Plant Mol. Biol. 22:361-366), the heat-inducible hsp80 promoter from tomato (U.S. Pat. No. 5,187,267), the cold-inducible alpha-amylase promoter from potato (WO 96/12814) or the wound-inducible pinII promoter (EP 0 375 091 A). The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from Vicia faba (Baeumlein 1991, Mol. Gen. Genet. 225 (3):459-67), the oleosin promoter from Arabidopsis (WO 98/45461), the phaseolin promoter from Phaseolus vulgaris (U.S. Pat. No. 5,504,200), the Bce4 promoter from Brassica (WO 91/13980) or the legumin B4 promoter (LeB4; Baeumlein 1992, Plant Journal, 2 (2):233-9), and promoters which bring about the seed-specific expression in monocotyledonous plants such as maize, barley, wheat, rye, rice and the like. Suitable promoters to be taken into consideration are the Ipt2 or Ipt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the sorghum kasirin gene, the rye secalin gene). Likewise, especially suitable are promoters which bring about the plastid-specific expression since plastids are the compartment in which the precursors and some end products of lipid biosynthesis are synthesized. Suitable promoters such as the viral RNA-polymerase promoter are described in WO 95/16783 and WO 97/06250, and the clpP promoter from *Arabidopsis*, described in WO 99/46394.

The abovementioned vectors are only a small overview of vectors to be used in accordance with the present invention. Further vectors are known to the skilled artisan and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells see the chapters 16 and 17 of Sambrook, loc cit.

It follows from the above that, preferably, said vector is an expression vector. More preferably, the said polynucleotide of the present invention is under the control of a seed-specific promoter in the vector of the present invention. A preferred seed-specific promoter as meant herein is selected from the group consisting of Conlinin 1, Conlinin 2, napin, LuFad3, USP, LeB4, Arc, Fae, ACP, LuPXR, and SBP. For details, see, e.g., US 2003-0159174.

Moreover, the present invention relates to a host cell comprising the polynucleotide or the vector of the present invention.

Preferably, said host cell is a plant cell and, more preferably, a plant cell obtained from an oilseed crop. More preferably, said oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacao*), peanut (*Arachis* sp.), hemp, camelina, crambe, oil palm, coconuts, groundnuts, sesame seed, castor bean, lesquerella, tallow tree, sheanuts, tungnuts, kapok fruit, poppy seed, jojoba seeds and perilla.

Also preferably, said host cell is a microorganism. More preferably, said microorganism is a bacterium, a fungus or algae. More preferably, it is selected from the group consisting of *Candida, Cryptococcus, Lipomyces, Rhodosporidium, Yarrowia* and *Schizochytrium*.

Moreover, a host cell according to the present invention may also be an animal cell. Preferably, said animal host cell is a host cell of a fish or a cell line obtained therefrom. More preferably, the fish host cell is from herring, salmon, sardine, redfish, eel, carp, trout, halibut, mackerel, zander or tuna.

It will be understood that if the host cell of the invention shall be applied for LCPUFA production, it shall be capable of carrying out desaturation and elongation steps on fatty acids. To produce the LCPUFA according to the invention, the C16- or C18-fatty acids must first be desaturated by the enzymatic activity of a desaturase and subsequently be elongated by at least two carbon atoms via an elongase. After one elongation cycle, this enzyme activity gives C18- or C20- fatty acids and after two or three elongation cycles C22- or C24-fatty acids. The activity of the desaturases and elongases used in the process according to the invention preferably leads to C18-, C20-, C22- and/or C24-fatty acids, advantageously with at least two double bonds in the fatty acid molecule, preferably with three, four or five double bonds, especially preferably to give C20- and/or C22-fatty acids with at least two double bonds in the fatty acid molecule, preferably with three, four or five double bonds in the molecule. After a first desaturation and the elongation have taken place, further desaturation steps such as, for example, one in the delta-5 position may take place. Products of the process according to the invention which are especially preferred are DGLA, ARA, EPA DPA and/or DHA, most preferably EPA and/or DHA. Desaturases and elongases which are required for this process may not always be present naturally in the host cell. Accordingly, the present invention, preferably, envisages a host cell which in addition to the polynucleotide of the present invention comprises polynucleotides encoding such desaturases and/or elongases as required depending on the selected organism. Preferred desaturases and/or elongases which shall be present in the host cell are at least one enzyme selected from the group consisting of: Δ-4-desaturase, Δ-5-desaturase, Δ-5-elongase, Δ-6-desaturase, Δ12-desaturase, Δ15-desaturase, ω3-desaturase and Δ-6-elongase. Especially preferred are the bifunctional d12d15-Desaturases d12d15Des(Ac) from *Acanthamoeba castellanii* (WO2007042510), d12d15Des(Cp) from *Claviceps purpurea* (WO2008006202) and d12d15Des(Lg)1 from *Lottia gigantea* (WO2009016202), the d12-Desaturases d12Des (Co) from *Calendula officinalis* (WO200185968), d12Des (Lb) from *Laccaria bicolor* (WO2009016202), d12Des(Mb) from *Monosiga brevicollis* (WO2009016202), d12Des(Mg) from *Mycosphaerella graminicola* (WO2009016202), d12Des(Nh) from *Nectria haematococca* (WO2009016202), d12Des(Ol) from *Ostreococcus lucimarinus* (WO2008040787), d12Des(Pb) from *Phycomyces blakesleeanus* (WO2009016202), d12Des(Ps) from *Phytophthora sojae* (WO2006100241) and d12Des(Tp) from *Thalassiosira pseudonana* (WO2006069710), the d15-Desaturases d15Des(Hr) from *Helobdella robusta* (WO2009016202), d15Des(Mc) from *Microcoleus chthonoplastes* (WO2009016202), d15Des(Mf) from *Mycosphaerella fijiensis* (WO2009016202), d15Des(Mg) from *Mycosphaerella graminicola* (WO2009016202) and d15Des (Nh)2 from *Nectria haematococca* (WO2009016202), the d4-Desaturases d4Des(Eg) from *Euglena gracilis* (WO2004090123), d4Des(Tc) from *Thraustochytrium* sp. (WO2002026946) and d4Des(Tp) from *Thalassiosira pseudonana* (WO2006069710), the d5-Desaturases d5Des(Ol)2 from *Ostreococcus lucimarinus* (WO2008040787), d5Des (Pp) from *Physcomitrella patens* (WO2004057001), d5Des (Pt) from *Phaeodactylum tricornutum* (WO2002057465), d5Des(Tc) from *Thraustochytrium* sp. (WO2002026946), d5Des(Tp) from *Thalassiosira pseudonana* (WO2006069710) and the d6-Desaturases d6Des(Cp) from *Ceratodon purpureus* (WO2000075341), d6Des(Ol) from *Ostreococcus lucimarinus* (WO2008040787), d6Des(Ot) from *Ostreococcus tauri* (WO2006069710), d6Des(Pf) from *Primula farinosa* (WO2003072784), d6Des(Pir)_BO from *Pythium irregulare* (WO2002026946), d6Des(Pir) from *Pythium irregulare* (WO2002026946), d6Des(Plu) from *Primula luteola* (WO2003072784), d6Des(Pp) from *Physcomitrella patens* (WO200102591), d6Des(Pt) from *Phaeodactylum tricornutum* (WO2002057465), d6Des(Pv) from *Primula vialii* (WO2003072784) and d6Des(Tp) from *Thalassiosira pseudonana* (WO2006069710), the d8-Desaturases d8Des(Ac) from *Acanthamoeba castellanii* (EP1790731), d8Des(Eg) from *Euglena gracilis* (WO200034439) and d8Des(Pm) from *Perkinsus marinus* (WO2007093776), the o3-Desaturases o3Des(Pi) from *Phytophthora infestans* (WO2005083053), o3Des(Pir) from *Pythium irregulare* (WO2008022963), o3Des(Pir)2 from *Pythium irregulare* (WO2008022963) and o3Des(Ps) from

*Phytophthora sojae* (WO2006100241), the bifunctional d5d6-elongases d5d6Elo(Om)2 from *Oncorhynchus mykiss* (WO2005012316), d5d6Elo(Ta) from *Thraustochytrium aureum* (WO2005012316) and d5d6Elo(Tc) from *Thraustochytrium* sp. (WO2005012316), the d5-elongases d5Elo (At) from *Arabidopsis thaliana* (WO2005012316), d5Elo (At)2 from *Arabidopsis thaliana* (WO2005012316), d5Elo (Ci) from *Ciona intestinalis* (WO2005012316), d5Elo(Ol) from *Ostreococcus lucimarinus* (WO2008040787), d5Elo (Ot) from *Ostreococcus tauri* (WO2005012316), d5Elo(Tp) from *Thalassiosira pseudonana* (WO2005012316) and d5Elo(Xl) from *Xenopus laevis* (WO2005012316), the d6-elongases d6Elo(Ol) from *Ostreococcus lucimarinus* (WO2008040787), d6Elo(Ot) from *Ostreococcus tauri* (WO2005012316), d6Elo(Pi) from *Phytophthora infestans* (WO2003064638), d6Elo(Pir) from *Pythium irregulare* (WO2009016208), d6Elo(Pp) from *Physcomitrella patens* (WO2001059128), d6Elo(Ps) from *Phytophthora sojae* (WO2006100241), d6Elo(Ps)2 from *Phytophthora sojae* (WO2006100241), d6Elo(Ps)3 from *Phytophthora sojae* (WO2006100241), d6Elo(Pt) from *Phaeodactylum tricornutum* (WO2005012316), d6Elo(Tc) from *Thraustochytrium* sp. (WO2005012316) and d6Elo(Tp) from *Thalassiosira pseudonana* (WO2005012316), the d9-elongases d9Elo(Ig) from *Isochrysis galbana* (WO2002077213), d9Elo(Pm) from *Perkinsus marinus* (WO2007093776) and d9Elo(Ro) from *Rhizopus oryzae* (WO2009016208).

The present invention also relates to a cell, preferably a host cell as specified above or a cell of a non-human organism specified elsewhere herein, said cell comprising a polynucleotide which is obtained from the polynucleotide of the present invention by a point mutation, a truncation, an inversion, a deletion, an addition, a substitution and homologous recombination. How to carry out such modifications to a polynucleotide is well known to the skilled artisan and has been described elsewhere in this specification in detail.

The present invention furthermore relates to a method for the manufacture of a polypeptide encoded by a polynucleotide of any the present invention comprising a) cultivating the host cell of the invention under conditions which allow for the production of said polypeptide; and
b) obtaining the polypeptide from the host cell of step a).

Suitable conditions which allow for expression of the polynucleotide of the invention comprised by the host cell depend on the host cell as well as the expression control sequence used for governing expression of the said polynucleotide. These conditions and how to select them are very well known to those skilled in the art. The expressed polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. It is to be understood that depending on the host cell which is used for the aforementioned method, the polypeptides produced thereby may become posttranslationally modified or processed otherwise.

The present invention encompasses a polypeptide encoded by the polynucleotide of the present invention or which is obtainable by the aforementioned method.

The term "polypeptide" as used herein encompasses essentially purified polypeptides or polypeptide preparations comprising other proteins in addition. Further, the term also relates to the fusion proteins or polypeptide fragments being at least partially encoded by the polynucleotide of the present invention referred to above. Moreover, it includes chemically modified polypeptides. Such modifications may be artificial modifications or naturally occurring modifications such as phosphorylation, glycosylation, myristylation and the like (Review in Mann 2003, Nat. Biotechnol. 21, 255-261, review with focus on plants in Huber 2004, Curr. Opin. Plant Biol. 7, 318-322). Currently, more than 300 posttranslational modifications are known (see full ABFRC Delta mass list at http://www.abrf.org/index.cfm/dm.home). The polypeptide of the present invention shall exhibit the acyltransferase activities referred to above.

The present invention furthermore relates to an antibody or a fragment derived thereof as an antigen which specifically recognizes a polypeptide encoded by the nucleic acid sequences of the invention.

Antibodies against the polypeptides of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the antibody of the present invention is a monoclonal antibody, a polyclonal antibody, a single chain antibody, a chimerized antibody or a fragment of any of these antibodies, such as Fab, Fv or scFv fragments etc. Also comprised as antibodies by the present invention are bispecific antibodies, synthetic antibodies or chemically modified derivatives of any of the aforementioned antibodies. The antibody of the present invention shall specifically bind (i.e. does significantly not cross react with other polypeptides or peptides) to the polypeptide of the invention. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth. Enzymol. 73, 3, which comprise the fusion of mouse myeloma cells to spleen cells derived from immunized mammals. The antibodies can be used, for example, for the immunoprecipitation, immunolocalization or purification (e.g., by affinity chromatography) of the polypeptides of the invention as well as for the monitoring of the presence of said variant polypeptides, for example, in recombinant organisms, and for the identification of proteins or compounds interacting with the proteins according to the invention.

Moreover, the present invention contemplates a non-human transgenic organism comprising the polynucleotide or the vector of the present invention.

Preferably, the non-human transgenic organism is a microorganism, more preferably the non-human transgenic organism is a fungus and most preferably the non-human transgenic organism is a plant, plant part, or plant seed. Preferred plants to be used for introducing the polynucleotide or the vector of the invention are plants which are capable of synthesizing fatty acids, such as all dicotyledonous or monocotyledonous plants, algae or mosses. It is to be understood that host cells derived from a plant may also be used for producing a plant according to the present invention. Preferred plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*. Examples which may be mentioned are the following plants selected from the group consisting of: Adelotheciaceae such as the genera *Physcomitrella*, such as the genus and species *Physcomitrella patens*, Anacardiaceae such as the genera *Pistacia*, *Mangifera*, *Anacardium*, for example the genus and species *Pistacia vera* [pistachio], *Mangifer indica* [mango] or *Anacardium occidentale* [cashew], Asteraceae, such as the genera *Calendula*, *Carthamus*, *Centaurea*, *Cichorium*, *Cynara*, *Helianthus*, *Lactuca*, *Locusta*, *Tagetes*, *Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa*, *Lactuca crispa*, *Lactuca esculenta*, *Lactuca scariola* L. ssp. *sativa*, *Lactuca scariola* L. var. *integrate*, *Lactuca scariola* L. var. *integrifolia*, *Lactuca sativa* subsp. *romana*, *Locusta communis*, *Valeriana locusta* [salad vegetables], *Tagetes lucida*, *Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica*, *Melanosinapis*, *Sinapis*, *Arabadopsis*, for example the genera and species *Brassica napus*, *Brassica rapa* ssp. [oilseed rape], *Sinapis arvensis Brassica juncea*, *Brassica juncea* var. *juncea*, *Brassica juncea* var. *crispifolia*, *Brassica juncea* var. *foliosa*, *Brassica nigra*, *Brassica sinapioides*, *Melanosinapis communis* [mustard], *Brassica oleracea* [fodder beet] or *Arabidopsis thaliana*, Bromeliaceae, such as the genera *Anana*, *Bromelia* (pineapple), for example the genera and species *Anana comosus*, *Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea*, *Convolvulus*, for example the genera and species *Ipomoea batatus*, *Ipomoea pandurata*, *Convolvulus batatas*, *Convolvulus tiliaceus*, *Ipomoea fastigiata*, *Ipomoea tiliacea*, *Ipomoea triloba* or *Convolvulus panduratus* [sweet potato, batate], Chenopodiaceae, such as the genus *Beta*, such as the genera and species *Beta vulgaris*, *Beta vulgaris* var. *altissima*, *Beta vulgaris* var. *Vulgaris*, *Beta maritima*, *Beta vulgaris* var. *perennis*, *Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima*, *Cucurbita mixta*, *Cucurbita pepo* or *Cucurbita moschata* [pumpkin/squash], Cymbellaceae such as the genera *Amphora*, *Cymbella*, *Okedenia*, *Phaeodactylum*, *Reimeria*, for example the genus and species *Phaeodactylum tricornutum*, Ditrichaceae such as the genera *Ditrichaceae*, *Astomiopsis*, *Ceratodon*, *Chrysoblastella*, *Ditrichum*, *Distichium*, *Eccremidium*, *Lophidion*, *Philibertiella*, *Pleuridium*, *Saelania*, *Trichodon*, *Skottsbergia*, for example the genera and species *Ceratodon antarcticus*, *Ceratodon columbiae*, *Ceratodon heterophyllus*, *Ceratodon purpureus*, *Ceratodon purpureus*, *Ceratodon purpureus* ssp. *convolutus*, *Ceratodon*, *purpureus* spp. *stenocarpus*, *Ceratodon purpureus* var. *rotundifolius*, *Ceratodon ratodon*, *Ceratodon stenocarpus*, *Chrysoblastella chilensis*, *Ditrichum ambiguum*, *Ditrichum brevisetum*, *Ditrichum crispatissimum*, *Ditrichum difficile*, *Ditrichum falcifolium*, *Ditrichum flexicaule*, *Ditrichum giganteum*, *Ditrichum heteromallum*, *Ditrichum lineare*, *Ditrichum lineare*, *Ditrichum montanum*, *Ditrichum montanum*, *Ditrichum pallidum*, *Ditrichum punctulatum*, *Ditrichum pusillum*, *Ditrichum pusillum* var. *tortile*, *Ditrichum rhynchostegium*, *Ditrichum schimperi*, *Ditrichum tortile*, *Distichium capillaceum*, *Distichium hagenii*, *Distichium inclinatum*, *Distichium macounii*, *Eccremidium floridanum*, *Eccremidium whiteleggei*, *Lophidion strictus*, *Pleuridium acuminatum*, *Pleuridium alternifolium*, *Pleuridium holdridgei*, *Pleuridium mexicanum*, *Pleuridium ravenelii*, *Pleuridium subulatum*, *Saelania glaucescens*, *Trichodon borealis*, *Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia*, *Kalmia angustifolia*, *Kalmia microphylla*, *Kalmia polifolia*, *Kalmia occidentalis*, *Cistus chamaerhodendros* or *Kalmia lucida* [mountain laurel], Euphorbiaceae such as the genera *Manihot*, *Janipha*, *Jatropha*, *Ricinus*, for example the genera and species *Manihot utilissima*, *Janipha manihot*, *Jatropha manihot*, *Manihot aipil*, *Manihot dulcis*, *Manihot manihot*, *Manihot melanobasis*, *Manihot esculenta* [manihot] or *Ricinus communis* [castor-oil plant], Fabaceae such as the genera *Pisum*, *Albizia*, *Cathormion*, *Feuillea*, *Inga*, *Pithecolobium*, *Acacia*, *Mimosa*, *Medicajo*, *Glycine*, *Dolichos*, *Phaseolus*, *Soja*, for example the genera and species *Pisum sativum*, *Pisum arvense*, *Pisum humile* [pea], *Albizia berteriana*, *Albizia julibrissin*, *Albizia lebbeck*, *Acacia berteriana*, *Acacia littoralis*, *Albizia berteriana*, *Albizzia berteriana*, *Cathormion berteriana*, *Feuillea berteriana*, *Inga fragrans*, *Pithecellobium berterianum*, *Pithecellobium fragrans*, *Pithecolobium berterianum*, *Pseudalbizzia berteriana*, *Acacia julibrissin*, *Acacia nemu*, *Albizia nemu*, *Feuilleea julibrissin*, *Mimosa julibrissin*, *Mimosa speciosa*, *Sericanrda julibrissin*, *Acacia lebbeck*, *Acacia macrophylla*, *Albizia lebbek*, *Feuilleea lebbeck*, *Mimosa lebbeck*, *Mimosa speciosa* [silk tree], *Medicago sativa*, *Medicago falcata*, *Medicago varia* [alfalfa], *Glycine max Dolichos soja*, *Glycine gracilis*, *Glycine hispida*, *Phaseolus max*, *Soja hispida* or *Soja max* [soybean], Funariaceae such as the genera *Aphanorrhegma*, *Entosthodon*, *Funaria*, *Physcomitrella*, *Physcomitrium*, for example the genera and species *Aphanorrhegma serratum*, *Entosthodon attenuatus*, *Entosthodon bolanderi*, *Entosthodon bonplandii*, *Entosthodon californicus*, *Entosthodon drummondii*, *Entosthodon jamesonii*, *Entosthodon leibergii*, *Entosthodon neoscoticus*, *Entosthodon rubrisetus*, *Entosthodon spathulifolius*, *Entosthodon tucsoni*, *Funaria americana*, *Funaria bolanderi*, *Funaria calcarea*, *Funaria californica*, *Funaria calvescens*, *Funaria convoluta*, *Funaria flavicans*, *Funaria groutiana*, *Funaria hygrometrica*, *Funaria hygrometrica* var. *arctica*, *Funaria hygrometrica* var. *calvescens*, *Funaria hygrometrica* var. *convolute*, *Funaria hygrometrica* var. *muralis*, *Funaria hygrometrica* var. *utahensis*, *Funaria microstoma*, *Funaria microstoma* var. *obtusifolia*, *Funaria muhlenbergii*, *Funaria orcuttii*, *Funaria plano-convexa*, *Funaria polaris*, *Funaria ravenelii*, *Funaria rubriseta*, *Funaria serrata*, *Funaria sonorae*, *Funaria sublimbatus*, *Funaria tucsoni*, *Physcomitrella californica*, *Physcomitrella patens*, *Physcomitrella readeri*, *Physcomitrium australe*, *Physcomitrium californicum*, *Physcomitrium collenchymatum*, *Physcomitrium coloradense*, *Physcomitrium cupuliferum*, *Physcomitrium drummondii*, *Physcomitrium eurystomum*, *Physcomitrium flexifolium*, *Physcomitrium hookeri*, *Physcomitrium hookeri* var. *serratum*, *Physcomitrium immersum*, *Physcomitrium kellermanii*, *Physcomitrium megalocarpum*, *Physcomitrium pyriforme*, *Physcomitrium pyriforme* var. *serratum*, *Physcomitrium* rufipes, Physcomitrium sandbergii, Physcomitrium subsphaericum, Physcomitrium washingtoniense, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia* [macadamia], Prasinophyceae such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae such as the genus *Cofea*, for example the genera and species *Cofea* spp., *Coffea arabica, Coffea canephora* or *Coffea liberica* [coffee], Scrophulariaceae such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, macadamia, avocado, bay, pumpkin/squash, linseed, soybean, pistachios, borage, trees (oil palm, coconut, walnut) or crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred plants are plants such as sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon*. Preferred algae are *Isochrysis, Mantoniella, Ostreococcus* or *Crypthecodinium*, and algae/diatoms such as *Phaeodactylum* or *Thraustochytrium*. More preferably, said algae or mosses are selected from the group consisting of: *Shewanella, Physcomitrella, Thraustochytrium, Nannochloropsis, Fusarium, Phytophthora, Ceratodon, Isochrysis, Aleurita, Muscarioides, Mortierella, Phaeodactylum, Crypthecodinium*, specifically from the genera and species *Thallasiosira pseudonona, Euglena gracilis, Physcomitrella patens, Phytophtora infestans, Fusarium graminaeum, Cryptocodinium cohnii, Ceratodon purpureus, Isochrysis galbana, Aleurita farinosa, Thraustochytrium* sp., *Nannochloropsis oculata, Muscarioides viallii, Mortierella alpina, Phaeodactylum tricornutum* or *Caenorhabditis elegans* or especially advantageously *Phytophtora infestans* and *Cryptocodinium cohnii.*

Transgenic plants may be obtained by transformation techniques as elsewhere in this specification. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

Also encompassed are transgenic non-human animals comprising the vector or polynucleotide of the present invention. Preferred non-human transgenic animals envisaged by the present invention are fish, such as herring, salmon, sardine, redfish, eel, carp, trout, halibut, mackerel, zander or tuna.

It will be understood that in order to produce the LCPUFA according to the invention, the C16- or C18-fatty acids must first be desaturated by the enzymatic activity of a desaturase and subsequently be elongated by at least two carbon atoms via an elongase in the non-human transgenic organism. After one elongation cycle, this enzyme activity gives C18- or C20-fatty acids and after two or three elongation cycles C22- or C24-fatty acids. The activity of the desaturases and elongases used in the process according to the invention preferably leads to C18-, C20-, C22- and/or C24-fatty acids, advantageously with at least two double bonds in the fatty acid molecule, preferably with three, four or five double bonds, especially preferably to give C20- and/or C22-fatty acids with at least two double bonds in the fatty acid molecule, preferably with three, four or five double bonds in the molecule. After a first desaturation and the elongation have taken place, further desaturation steps such as, for example, one in the delta-5 position may take place. Products of the process according to the invention which are especially preferred are DGLA, ARA, EPA DPA and/or DHA, most preferably EPA and/or DHA. Desaturases and elongases which are required for this process may not always be present naturally in the organism. Accordingly, the present invention, preferably, envisages a transgenic non-human organism which in addition to the polynucleotide of the present invention comprises polynucleotides encoding such desaturases and/or elongases as required depending on the selected organism. Preferred desaturases and/or elongases which shall be present in the organism are at least one enzyme selected from the group consisting of: Δ-4-desaturase, Δ-5-desaturase, Δ-5-elongase, Δ-6-desaturase, Δ12-desaturase, Δ15-desaturase, ω3-desaturase and Δ-6-elongase. Especially preferred are the bifunctional d12d15-Desaturases d12d15Des(Ac) from *Acanthamoeba castellanii* (WO2007042510), d12d15Des(Cp) from *Claviceps purpurea* (WO2008006202) and d12d15Des(Lg)1 from *Lottia gigantea* (WO2009016202), the d12-Desaturases d12Des(Co) from *Calendula officinalis* (WO200185968), d12Des(Lb) from *Laccaria bicolor* (WO2009016202), d12Des(Mb) from *Monosiga brevicollis* (WO2009016202), d12Des(Mg) from *Mycosphaerella graminicola* (WO2009016202), d12Des(Nh) from *Nectria haematococca* (WO2009016202), d12Des(Ol) from *Ostreococcus lucimarinus* (WO2008040787), d12Des(Pb) from *Phycomyces blakesleeanus* (WO2009016202), d12Des(Ps) from *Phytophthora sojae* (WO2006100241) and d12Des(Tp) from *Thalassiosira pseudonana* (WO2006069710), the d15-Desaturases d15Des(Hr) from *Helobdella robusta* (WO2009016202), d15Des(Mc) from *Microcoleus chthonoplastes* (WO2009016202), d15Des(Mf) from *Mycosphaerella fijiensis* (WO2009016202), d15Des(Mg) from *Mycosphaerella graminicola* (WO2009016202) and d15Des(Nh)2 from *Nectria haematococca* (WO2009016202), the d4-Desaturases d4Des(Eg) from *Euglena gracilis* (WO2004090123), d4Des(Tc) from *Thraustochytrium* sp. (WO2002026946) and d4Des(Tp) from *Thalassiosira pseudonana* (WO2006069710), the d5-Desaturases d5Des(Ol)2 from *Ostreococcus lucimarinus* (WO2008040787), d5Des(Pp) from *Physcomitrella patens* (WO2004057001), d5Des(Pt) from *Phaeodactylum tricornutum* (WO2002057465), d5Des(Tc) from *Thraustochytrium* sp. (WO2002026946), d5Des(Tp) from *Thalassiosira pseudonana* (WO2006069710) and the d6-Desaturases d6Des(Cp) from *Ceratodon purpureus* (WO2000075341), d6Des(Ol) from *Ostreococcus lucimarinus* (WO2008040787), d6Des(Ot) from *Ostreococcus tauri* (WO2006069710), d6Des(Pf) from *Primula farinosa* (WO2003072784), d6Des(Pir)_BO from *Pythium irregulare* (WO2002026946), d6Des(Pir) from *Pythium irregulare* (WO2002026946), d6Des(Plu) from *Primula luteola* (WO2003072784), d6Des(Pp) from *Physcomitrella patens* (WO200102591), d6Des(Pt) from *Phaeodactylum tricornutum* (WO2002057465), d6Des(Pv) from *Primula vialii* (WO2003072784) and d6Des(Tp) from *Thalassiosira pseudonana* (WO2006069710), the d8-Desaturases d8Des(Ac) from *Acanthamoeba castellanii* (EP1790731), d8Des(Eg) from *Euglena gracilis* (WO200034439) and d8Des(Pm) from *Perkinsus marinus* (WO2007093776), the o3-Desaturases o3Des(Pi) from *Phytophthora infestans* (WO2005083053), o3Des(Pir) from *Pythium irregulare* (WO2008022963), o3Des(Pir)2 from *Pythium irregulare* (WO2008022963) and o3Des(Ps) from *Phytophthora sojae* (WO2006100241), the bifunctional d5d6-elongases d5d6Elo(Om)2 from *Oncorhynchus mykiss* (WO2005012316), d5d6Elo(Ta) from *Thraustochytrium aureum* (WO2005012316) and d5d6Elo(Tc) from *Thraustochytrium* sp. (WO2005012316), the d5-elongases d5Elo(At) from *Arabidopsis thaliana* (WO2005012316), d5Elo(At)2 from *Arabidopsis thaliana* (WO2005012316), d5Elo(Ci) from *Ciona intestinalis* (WO2005012316), d5Elo(Ol) from *Ostreococcus lucimarinus* (WO2008040787), d5Elo(Ot) from *Ostreococcus tauri* (WO2005012316), d5Elo(Tp) from *Thalassiosira pseudonana* (WO2005012316) and d5Elo(Xl) from *Xenopus laevis* (WO2005012316), the d6-elongases d6Elo(Ol) from *Ostreococcus lucimarinus* (WO2008040787), d6Elo(Ot) from *Ostreococcus tauri* (WO2005012316), d6Elo(Pi) from *Phytophthora infestans* (WO2003064638), d6Elo(Pir) from *Pythium irregulare* (WO2009016208), d6Elo(Pp) from *Physcomitrella patens* (WO2001059128), d6Elo(Ps) from *Phytophthora sojae* (WO2006100241), d6Elo(Ps)2 from *Phytophthora sojae* (WO2006100241), d6Elo(Ps)3 from *Phytophthora sojae* (WO2006100241), d6Elo(Pt) from *Phaeodactylum tricornutum* (WO2005012316), d6Elo(Tc) from *Thraustochytrium* sp. (WO2005012316) and d6Elo(Tp) from *Thalassiosira pseudonana* (WO2005012316), the d9-elongases d9Elo(Ig) from *Isochrysis galbana* (WO2002077213), d9Elo(Pm) from *Perkinsus marinus* (WO2007093776) and d9Elo(Ro) from *Rhizopus oryzae* (WO2009016208).

Furthermore, the present invention encompasses a method for the manufacture of polyunsaturated fatty acids comprising:

a) cultivating the host cell of the invention under conditions which allow for the production of polyunsaturated fatty acids in said host cell; and b) obtaining said polyunsaturated fatty acids from the said host cell.

The term "polyunsaturated fatty acids (PUFA)" as used herein refers to fatty acids comprising at least two, preferably, three, four, five or six, double bonds. Moreover, it is to be understood that such fatty acids comprise, preferably from 18 to 24 carbon atoms in the fatty acid chain. More preferably, the term polyunsaturated fatty acids relates to long chain PUFA (LCPUFA) having from 20 to 24 carbon atoms in the fatty acid chain. Preferred unsaturated fatty acids in the sense of the present invention are selected from the group consisting of arachidonic acid (ARA) 20:4 (5, 8, 11, 14), eicosapentaenoic acid (EPA) 20:5 (5, 8, 11, 14, 17), and docosahexaenoic acid (DHA) 22:6 (4, 7, 10, 13, 16, 19) and, more preferably, from EPA and DHA. Thus, it will be understood that most preferably, the methods provided by the present invention relating to the manufacture of EPA or DHA. Moreover, also encompassed are the intermediates of LCPUFA which occur during synthesis starting from oleic acid 18:1 (9), preferably, linoleic acid 18:2 (9,12), alpha-linolenic acid 18:3 (9, 12, 15), gamma-linolenic acid 18:3 (6, 9, 12), stearidonic acid 18:4 (6, 9, 12, 15), dihomo-gamma-linoleic acid 20:3 (8, 11, 14), eicosadienoic acid 20:2 (11,14), eicosatrienoic acid 20:3 (11, 14, 17), eicosatetraenoic acid 20:4 (8, 11, 14, 17) and docospentaenoic acid (DPA) 22:5 (4, 7, 10, 13, 16).

The term "cultivating" as used herein refers maintaining and growing the host cells under culture conditions which allow the cells to produce the said polyunsaturated fatty acid, i.e. the PUFA and/or LCPUFA referred to above, preferably, as triglyceride esters. This implies that the polynucleotide of the present invention is expressed in the host cell so that the acyltransferase activity is present. Suitable culture conditions for cultivating the host cell are described in more detail below.

The term "obtaining" as used herein encompasses the provision of the cell culture including the host cells and the culture medium as well as the provision of purified or partially purified preparations thereof comprising the polyunsaturated fatty acids, preferably, as triglyceride esters. More preferably, the PUFA and LCPUFA are to be obtained as triglyceride esters, e.g., in form of an oil. More details on purification techniques can be found elsewhere herein below.

The host cells to be used in the method of the invention are grown or cultured in the manner with which the skilled artisan is familiar, depending on the host organism. Usually, host cells are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C. under oxygen or anaerobic atmosphere dependent on the type of organism. The pH of the liquid medium can either be kept constant, that is to say regulated during the culturing period, or not. The cultures can be grown batchwise, semibatchwise or continuously. Nutrients can be provided at the beginning of the fermentation or administered semicontinuously or continuously: The produced PUFA or LCPUFA can be isolated from the host cells as described above by processes known to the skilled artisan, e.g., by extraction, distillation, crystallization, if appropriate precipitation with salt, and/or chromatography. It might be required to disrupt the host cells prior to purification. To this end, the host cells can be disrupted beforehand.

The culture medium to be used must suitably meet the requirements of the host cells in question. Descriptions of culture media for various microorganisms which can be used as host cells according to the present invention can be found in the textbook "Manual of Methods for General Bacteriology" of the American Society for Bacteriology (Washington D.C., USA, 1981). Culture media can also be obtained from various commercial suppliers. All media components are sterilized, either by heat or by filter sterilization. All media components may be present at the start of the cultivation or added continuously or batchwise, as desired. If the polynucleotide or vector of the invention which has been introduced in the host cell further comprises an expressible selection marker, such as an antibiotic resistance gene, it might be necessary to add a selection agent to the culture, such as an antibiotic in order to maintain the stability of the introduced polynucleotide. The culture is continued until formation of the desired product is at a maximum. This is normally achieved within 10 to 160 hours. The fermentation broths can be used directly or can be processed further. The biomass may, according to requirement, be removed completely or partially from the fermentation broth by separation methods such as, for example, centrifugation, filtration, decanting or a combination of these methods or be left completely in said broth. The fatty acid preparations obtained by the method of the invention, e.g., oils, comprising the desired PUFA or LCPUFA as triglyceride esters are also suitable as starting material for the chemical synthesis of further products of interest. For example, they can be used in combination with one another or alone for the preparation of pharmaceutical or cosmetic compositions, foodstuffs, or animal feeds. Chemically pure triglycerides comprising the desired PUFA or LCPUFA can also be manufactured by the methods described above. To this end, the fatty acid preparations are further purified by extraction, distillation, crystallization, chromatography or combinations of these methods. In order to release the fatty acid moieties from the triglycerides, hydrolysis may be also required. The said chemically pure triglycerides or free fatty acids are, in particular, suitable for applications in the food industry or for cosmetic and pharmacological compositions.

Moreover, the present invention relates to a method for the manufacture of polyunsaturated fatty acids comprising:

a) cultivating the non-human transgenic organism of the invention under conditions which allow for the production of polyunsaturated fatty acids in said host cell; and b) obtaining said polyunsaturated fatty acids from the said non-human transgenic organism.

Further, it follows from the above that a method for the manufacture of an oil, lipid or fatty acid composition is also envisaged by the present invention comprising the steps of any one of the aforementioned methods and the further step of formulating PUFA or LCPUFA as oil, lipid or fatty acid composition. Preferably, said oil, lipid or fatty acid composition is to be used for feed, foodstuffs, cosmetics or pharmaceuticals. Accordingly, the formulation of the PUFA or LCPUFA shall be carried out according to the GMP standards for the individual envisaged products. For example, oil may be obtained from plant seeds by an oil mill. However, for product safety reasons, sterilization may be required under the applicable GMP standard. Similar standards will apply for lipid or fatty acid compositions to be applied in cosmetic or pharmaceutical compositions. All these measures for formulating oil, lipid or fatty acid compositions as products are comprised by the aforementioned manufacture.

The present invention also relates to oil comprising a polyunsaturated fatty acid or a polyunsaturated fatty acid composition obtainable by the aforementioned methods.

The term "oil" refers to a fatty acid mixture comprising unsaturated and/or saturated fatty acids which are esterified to triglycerides. Preferably, the triglycerides in the oil of the invention comprise PUFA or LCPUFA as referred to above. The amount of esterified PUFA and/or LCPUFA is, preferably, approximately 30%, a content of 50% is more preferred, a content of 60%, 70%, 80% or more is even more preferred. The oil may further comprise free fatty acids, preferably, the PUFA and LCPUFA referred to above. For the analysis, the fatty acid content can be, e.g., determined by GC analysis after converting the fatty acids into the methyl esters by transesterification. The content of the various fatty acids in the oil or fat can vary, in particular depending on the source. The oil, however, shall have a non-naturally occurring composition with respect to the PUFA and/or LCPUFA composition and content. It will be understood that such a unique oil composition and the unique esterification pattern of PUFA and LCPUFA in the triglycerides of the oil shall only be obtainable by applying the methods of the present invention specified above. Moreover, the oil of the invention may comprise other molecular species as well. Specifically, it may comprise minor impurities of the polynucleotide or vector of the invention. Such impurities, however, can be detected only by highly sensitive techniques such as PCR.

The contents of all references cited throughout this application are herewith incorporated by reference in general and with respect to their specific disclosure content referred to above.

This invention is further illustrated by the following figures and examples which should not be construed as limiting the scope of the invention.

FIGURES

FIG. 1: Cloning strategy employed for stepwise buildup of plant expression plasmids of the invention.

Figure 2:
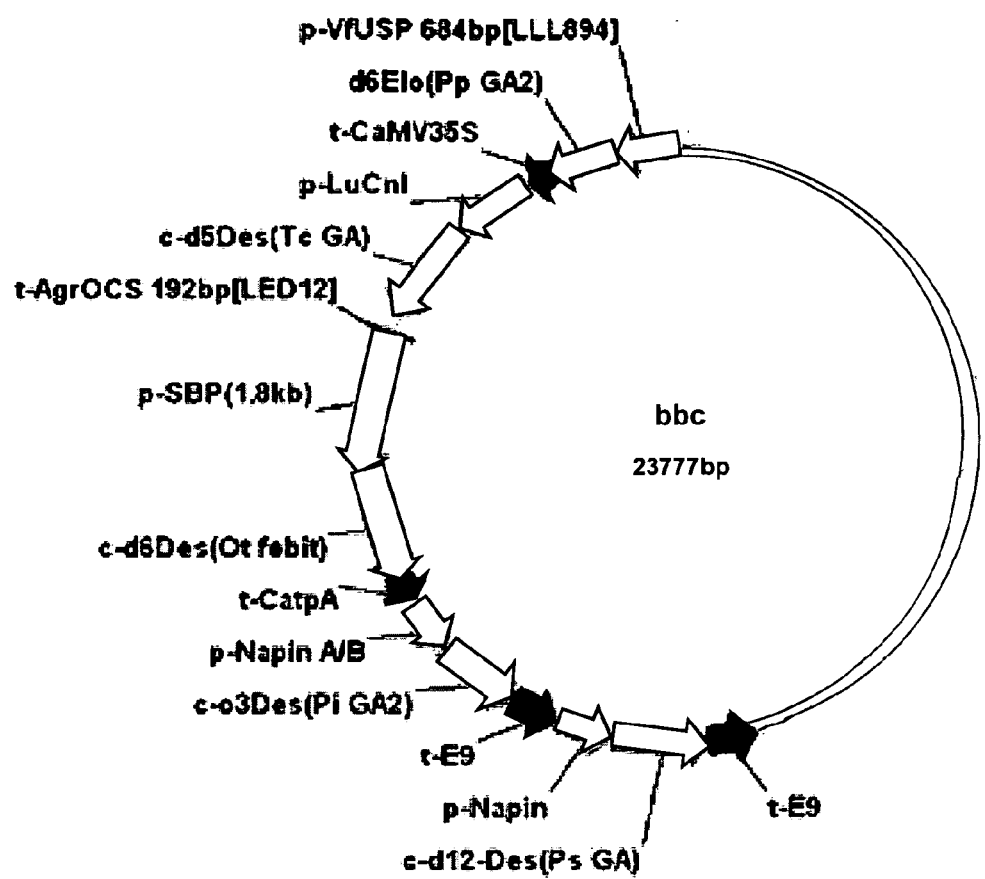

FIG. 2: Vector map of the bbc construct used for *Arabidopsis* transformation.

Figure 3:
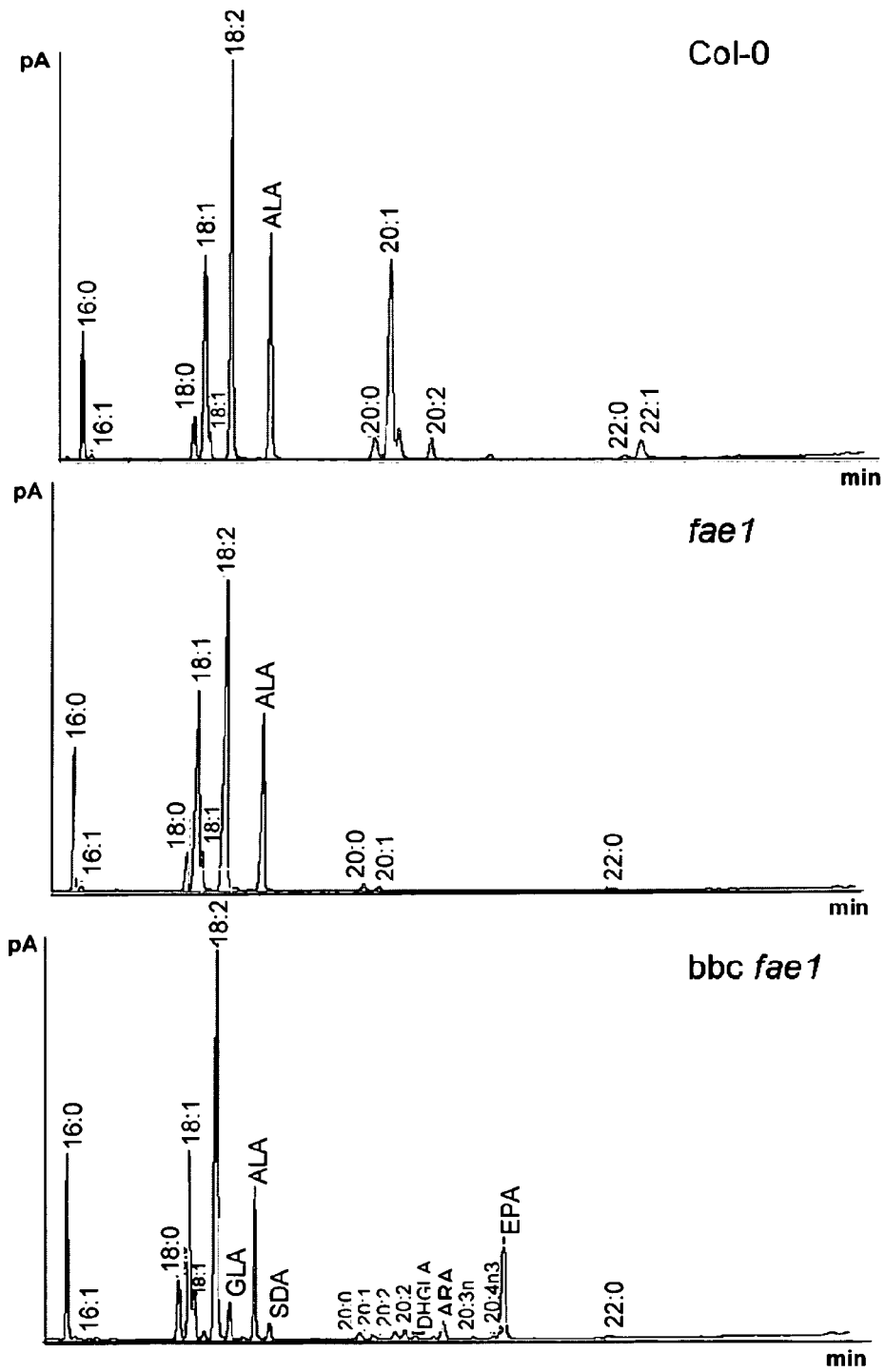

FIG. 3: GC chromatogram of fatty acids methyl esters of total fatty acids of Col-0, fae1 mutant and fee1 transformed with bbc. Total fatty acids were measured as described by Wu et al., 2005. The content of the different fatty is indicated in table 5.

Figure 4:
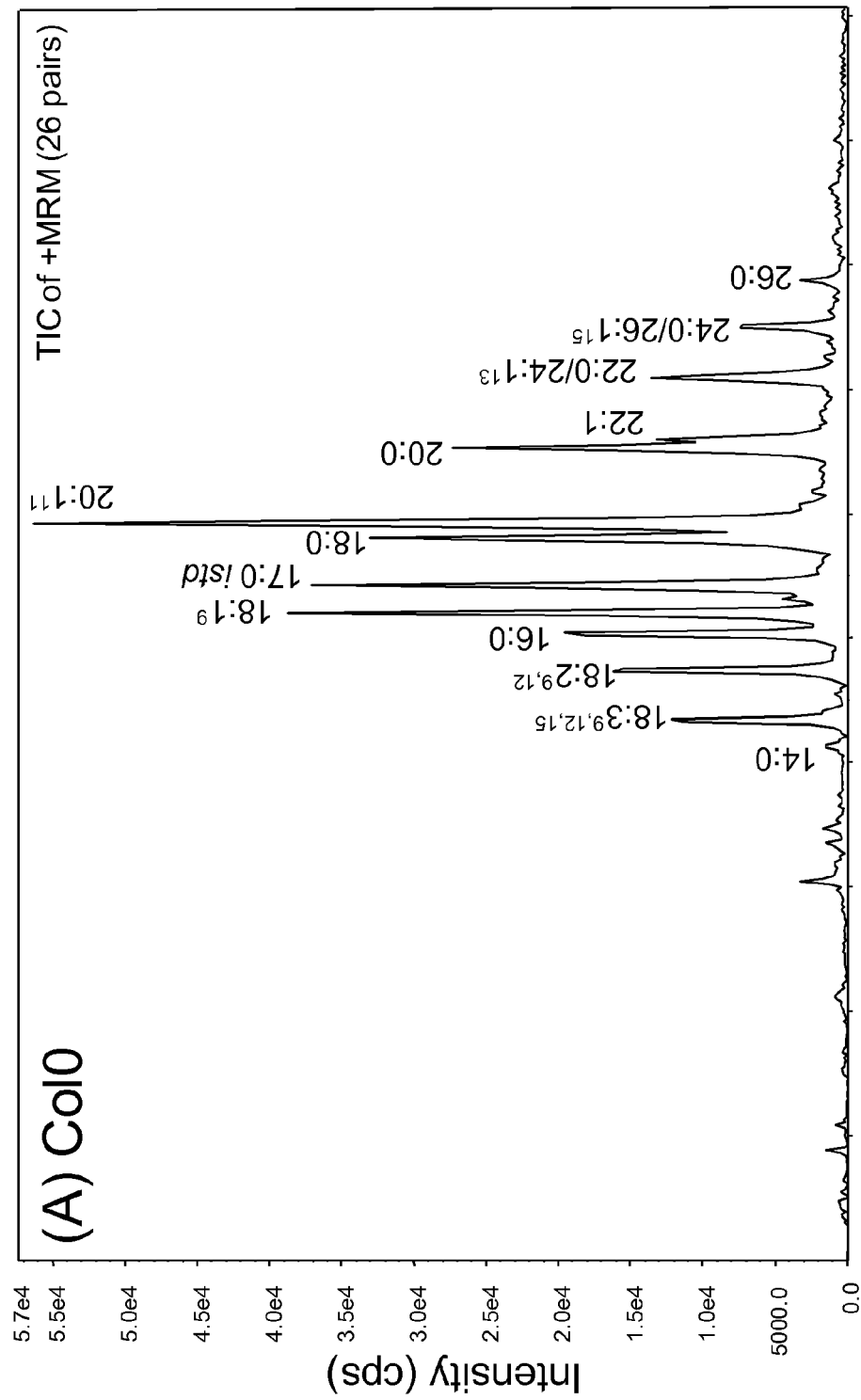
Figure 4:
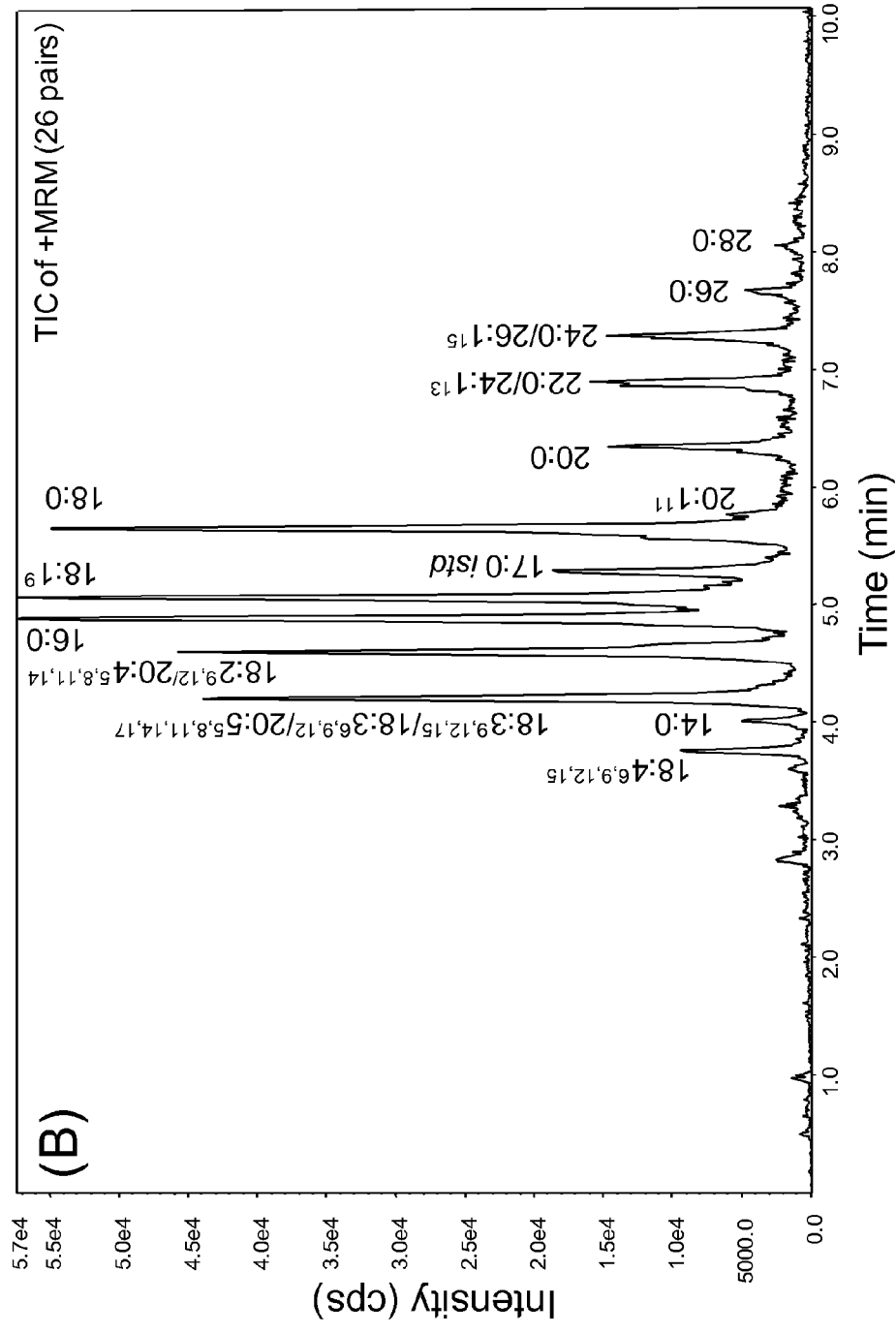

FIG. 4: Total ion count of 26 acyl CoA ESI-MS/MS MRM pairs for *Arabidopsis* (A) Col-0 and (B) fae1 harbouring EPA biosynthesis pathway. Maturing *Arabidopsis* seeds were harvested 18 days after flowering. Acyl-CoA was extracted according to Larson et al (2001) and LC conditions after Han et al. (2010).

Figure 5:
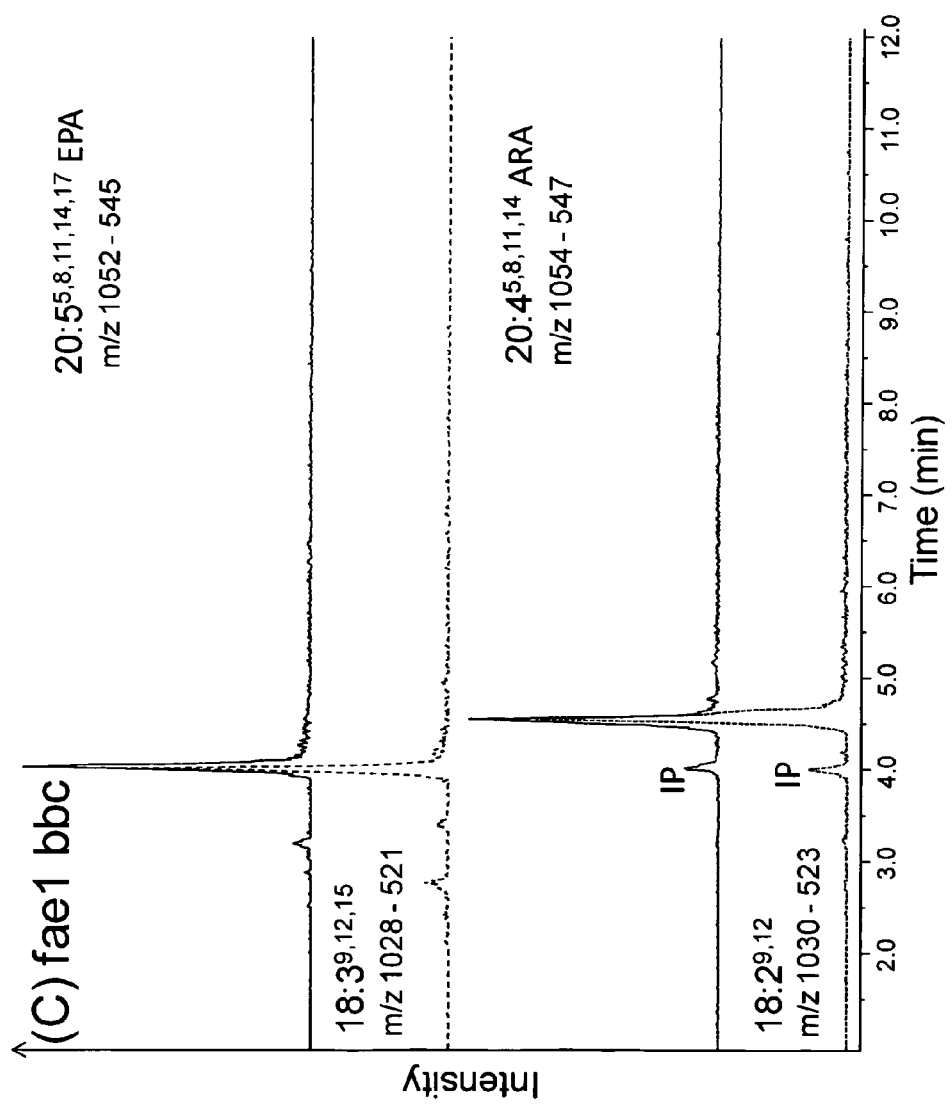

FIG. 5: Identification of Eicosapentaenoic and Arachidonic-CoA's in the acyl CoA pool of *Arabidopsis* Col-0 and EPA producing plants. MRM chromatograms of co-eluting acyl-CoA of interest in (A) wild type and (C) fee1 harbouring EPA biosynthetic pathway with recorded reactions shown for each transition, isotopic peaks (IP) of homologous long chain acyl CoA are shown. (B) Characteristic fragmentation of the protonated acyl-CoA by neutral loss of 507 to give the protonated acyl pantetheine group.

Figure 6:
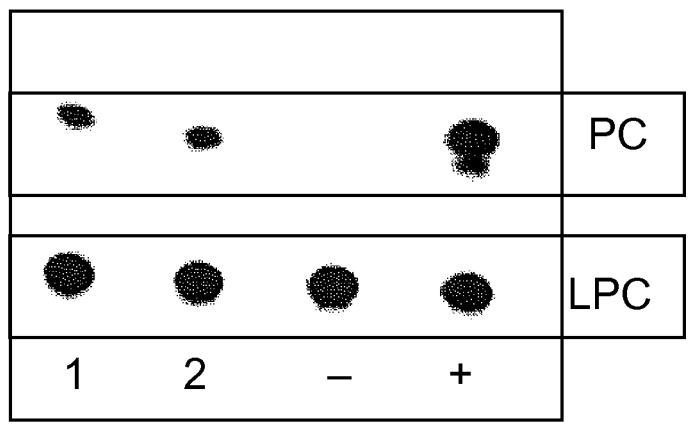

FIG. 6: LPCAT activity assay.

A yeast mutant lacking LPEAT and LPCAT activity (due to knockout of the gene YOR175c) was transformed with the empty vector pYES2.1 (lane marked "−") and with pYES2.1 harboring the cDNA of pLPAAT_c6316(No) (lane 1 and 2, SEQ-ID: 13). Microsomal isolations of these transformants and the wildtype yeast strain BY4742 (lane marked "+") containing 5 µg protein where incubated with alpha-linolenic acid-CoA and [$^{14}$C]-18:1-lysophosphatidylcholine (LPC). Thin layer chromatography was performed to separate lipid classes. Like for wildtype yeast (lane marked "+"), phosphatidylcholine (PC) is observed for both yeast clones shown in lane 1 and 2, indicating the gene pLPAAT_c6316(No) has LPCAT activity and complements the missing LPCAT activity of the knockout strain.

Figure 7:
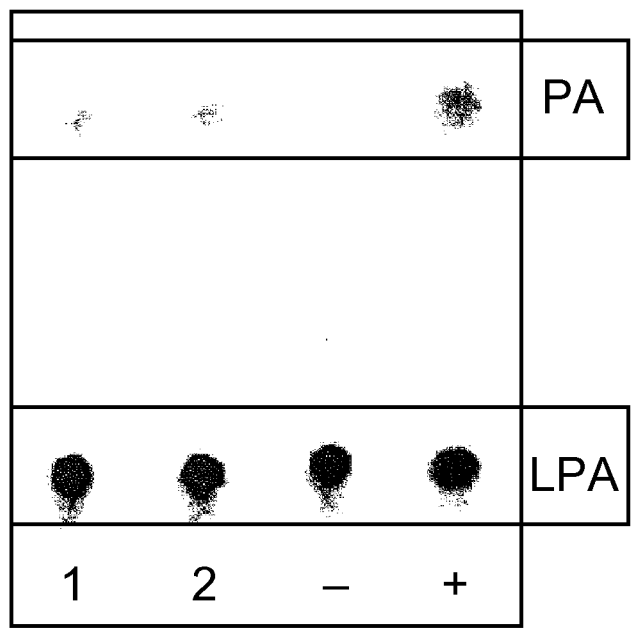

FIG. 7: LPAAT activity assay.

A yeast mutant lacking LPAAT activity (due to knockout of the gene YDL052c) was transformed with the empty vector pYES2.1 (lane marked "−") and with pYES2.1 harboring the cDNA of pLPAAT_c6316(No) (lane 1 and 2, SEQ-ID: 13). Microsomal isolations of these transformants and the wildtype yeast strain BY4742 (lane marked "+") containing 5 µg protein where incubated with alpha-linolenic acid-CoA and [$^{14}$C]-18:1-lysophosphatidic acid (LPA). Thin layer chromatography was performed to separate lipid classes. Like for wild-type yeast (lane marked "+"), phosphatidic acid (PA) is observed for both yeast clones shown in lane 1 and 2, indicating the gene pLPAAT_c6316(No) has LPAAT activity and complements the missing LPAAT activity of the knockout strain.

Figure 8:
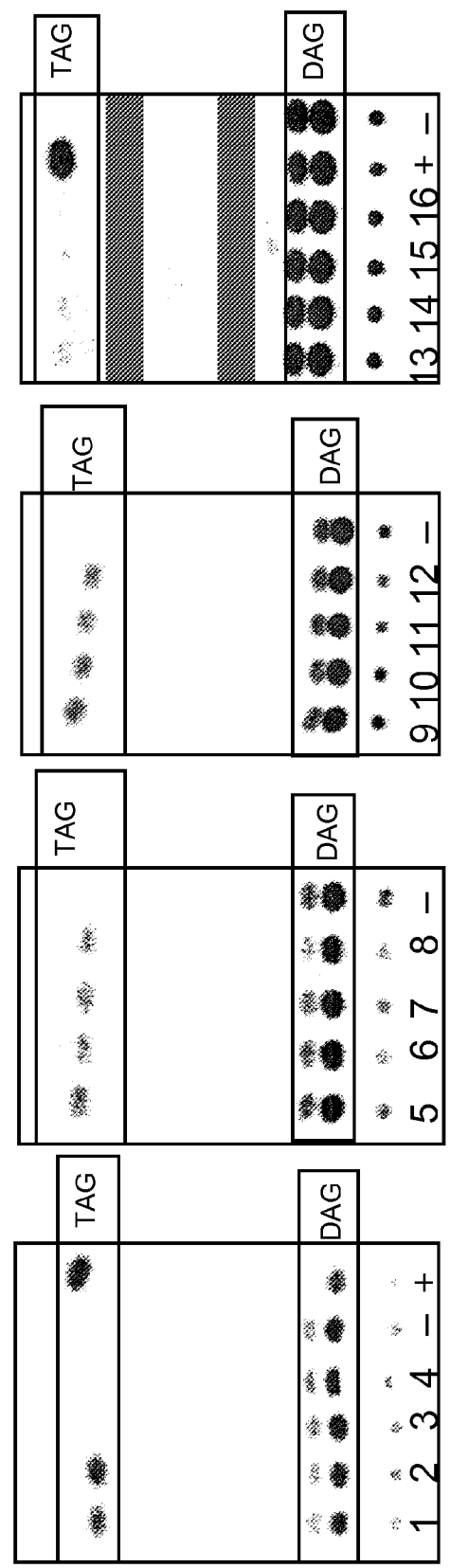

FIG. 8: DGAT activity assay.

A yeast mutant lacking the capability to synthesis TAG (due to knockout of the four genes YCR048W, YNR019W, YOR245C and YNR008W) was transformed with the empty vector pYES2.1 (lane marked "−") and with pYES2.1 harboring the cDNA of pDGAT2-c19425mod(Ta) (SEQ-ID 52, lane 1 and 2), pDGAT2_c4648(No) (SEQ-ID 34, lane 5 and 6), pDGAT2_c48271(No) (SEQ-ID 102, lane 7 and 8), BnDGAT1 (SEQ-ID 107, lane 9 and 10), AtDGAT1 (SEQ-ID 105, lane 11 and 12), pDGAT2_c699(No) (SEQ-ID 19, lane 13 and 14) and pDGAT2_c2959(No) (SEQ-ID 25, lane 15). Microsomal isolations of these transformants and the wildtype yeast strain G175 (lane marked "+") where incubated with $^{14}$C-labeled oleic acid and diacylglyerole (DAG). Thin layer chromatography was performed to separate lipid classes. Like for wildtype yeast (lane marked "+"), triacylglycerole (TAG) is observed in lane 1, 2, 5, 6, 7, 8, 9, 10, 11, 12, 13, 14 and 15, indicating pDGAT2-c19425mod(Ta), pDGAT2_c4648(No), pDGAT2_c48271(No), BnDGAT1, AtDGAT1, pDGAT2_c699(No) and pDGAT2_c2959(No) encode polypeptides having DGAT activity and complement the missing TAG-synthesis capability of the knockout.

Figure 9:
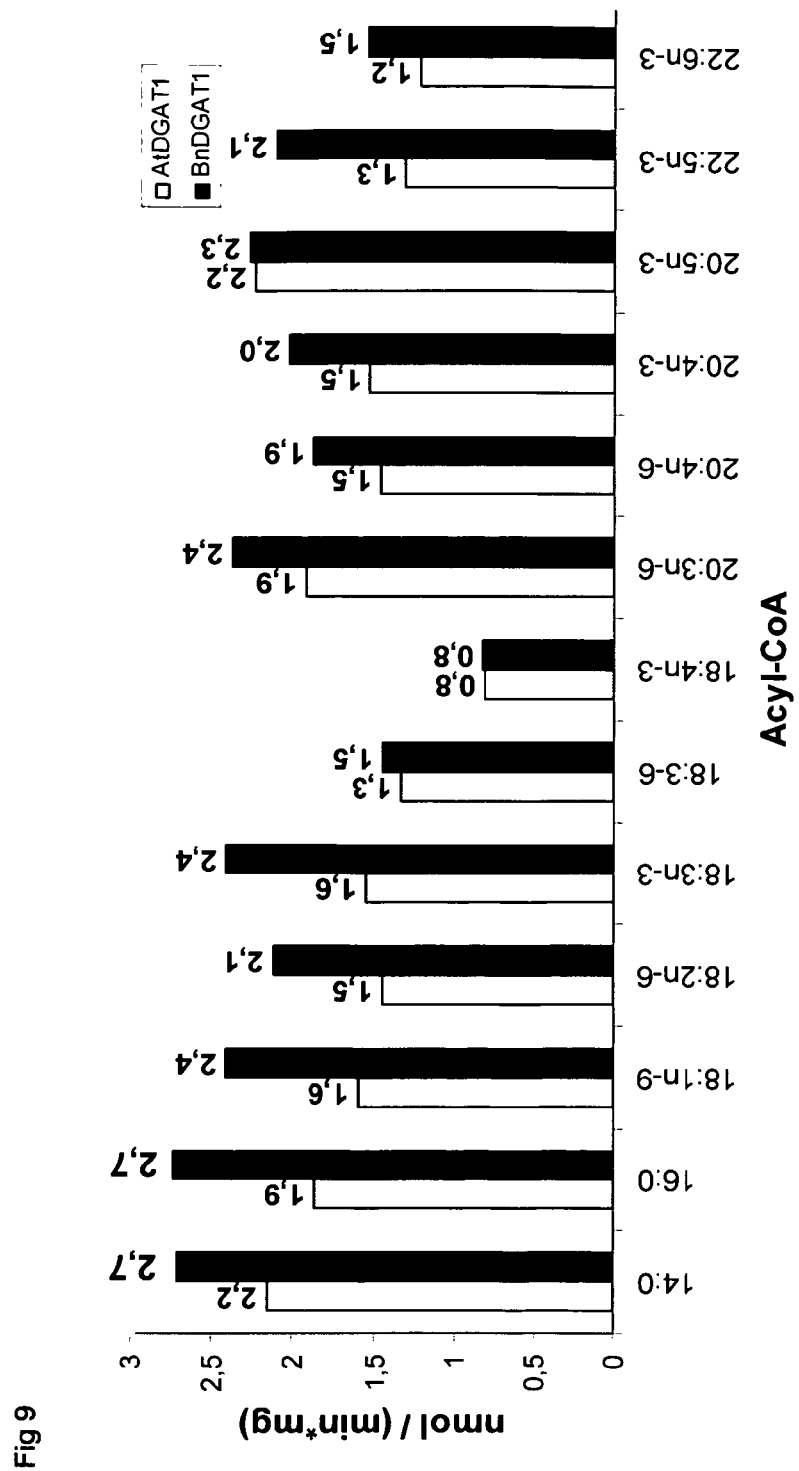

FIG. 9: Substrate specificity of AtDGAT1 and BnDGAT1. The specific activity of the enzymes AtDGAT1 and BnDGAT1 using the substrates indicated at the x-axis is given as the amount (in nmol) of substrate consumed in one minute per mg total protein and was determined as described in example 10.

Figure 10:
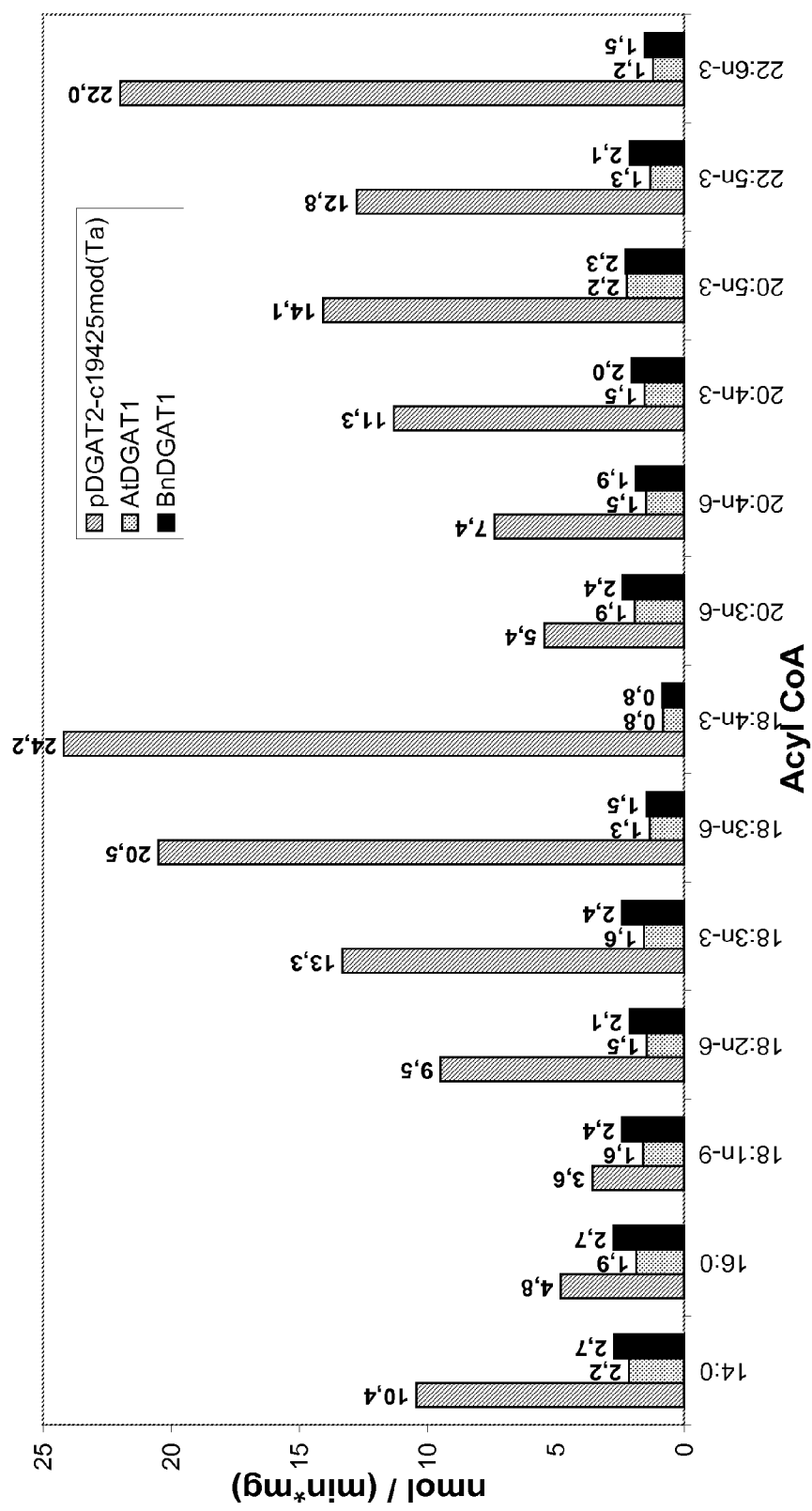

FIG. 10: Substrate specificity of pDGAT2-c19425(Ta) compared to AtDGAT1 and BnDGAT1. The specific activity of the enzymes pDGAT2-c19425(Ta), AtDGAT1 and BnDGAT1 using the substrates indicated at the x-axis is given as the amount (in nmol) of substrate consumed in one minute per mg total protein and was determined as described in example 10.

Figure 11:
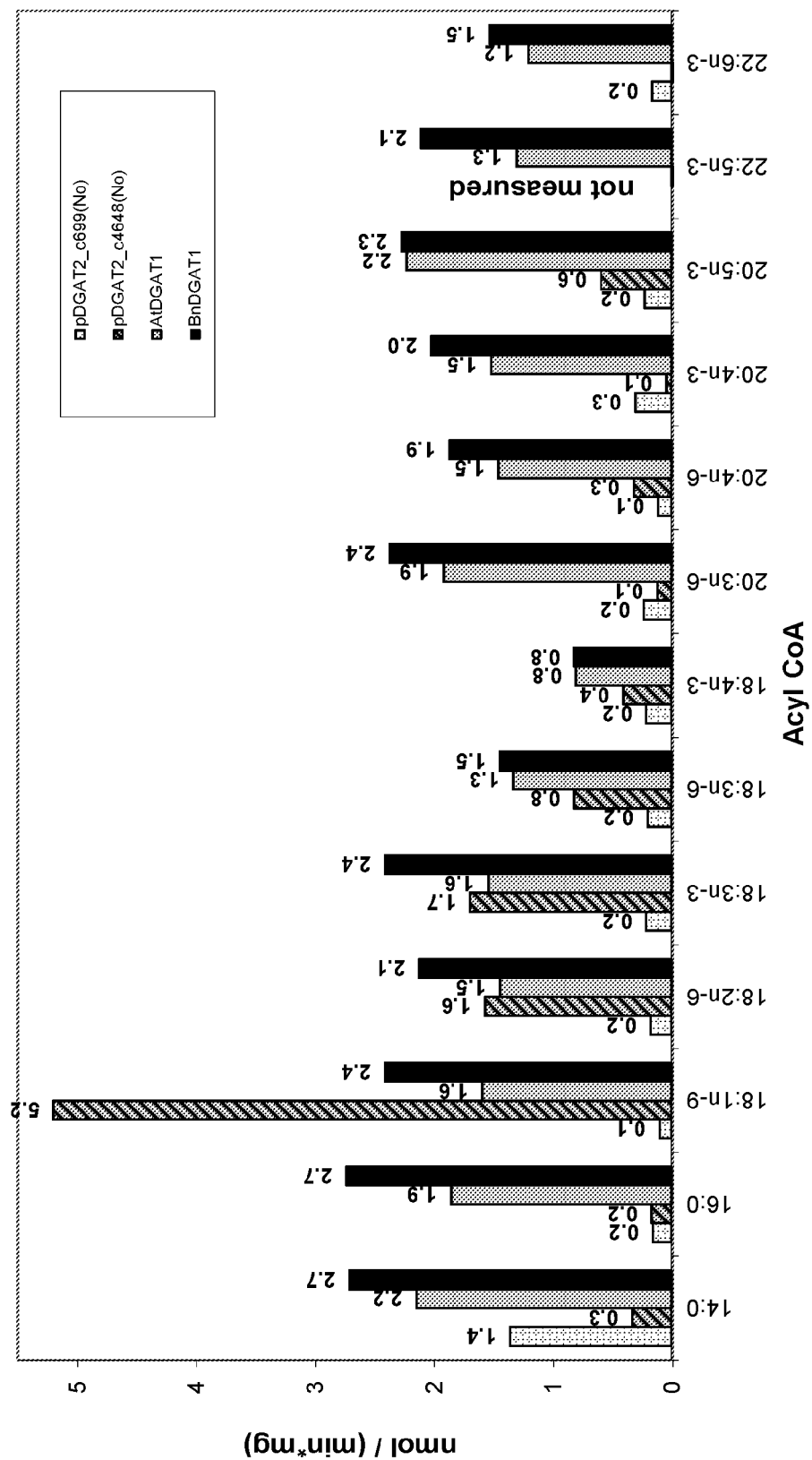

FIG. 11: Substrate specificity of pDGAT2_c699(No) and pDGAT2_c4648(No) compared to AtDGAT1 and BnDGAT1. The specific activity of the enzymes pDGAT2_c699(No) and pDGAT2_c4648(No), AtDGAT1 and BnDGAT1 using the substrates indicated at the x-axis is given as the amount (in nmol) of substrate consumed in one minute per mg total protein and was determined as described in example 10.

EXAMPLES

Example 1

General Cloning Methods

Cloning methods as e.g. use of restriction endonucleases to cut double stranded DNA at specific sites, agarose gel electrophoreses, purification of DNA fragments, transfer of nucleic acids onto nitrocellulose and nylon membranes, joining of DNA-fragments, transformation of *E. coli* cells and culture of bacteria where performed as described in Sambrook et al. (1989) (Cold Spring Harbor Laboratory Press: ISBN 0-87965-309-6).

Example 2

Sequence Analysis of Recombinant DNA

Sequencing of recombinant DNA-molecules was performed using a laser-fluorescence DNA sequencer (Applied Biosystems Inc, USA) employing the sanger method (Sanger et al. (1977) Proc. Natl. Acad. Sci. USA 74, 5463-5467). Expression constructs harboring fragments obtained by polymerase chain reactions were subjected to sequencing to confirm the correctness of expression cassettes consisting of promoter, nucleic acid molecule to be expressed and terminator to avoid mutations that might result from handling of the DNA during cloning, e.g. due to incorrect primers, mutations from exposure to UV-light or errors of polymerases.

Example 3

Cloning of Yeast Expression Construct Via Homologous Recombination

The open reading frame listed in SEQ ID NOs: 52, 1, 4, 7, 10, 13, 16, 19, 22, 25, 28, 31, 34, 37, 40, 43, 46, 49, 55, 102, 105 and 107 encoding polypeptides with the amino acid sequence SEQ ID NOs: 53, 2, 5, 8, 11, 14, 17, 20, 23, 26, 29, 32, 35, 38, 41, 44, 47, 50, 56, 103, 106 and 108 that have acyltransferase activity can amplified using the primer listed in table 2 in a polymerase chain reaction. By doing so, the open reading frame is 5' fused to about 60 nucleotides of the 3' end of the GAL1 promotor sequence with simultaneous introduction of and Asc I and/or Nco I restriction site between the fusion site and 3' fused to about 60 nucleotides of the 5' end of the CYC1 terminator sequence with simultaneous introduction of and Pac I restriction site. To integrate these fragments into pYES2.1 TOPO downstream of the galactose inducible GAL1 Promotor via homologous recombination, the vector pYES2.1 (Invitrogen) can be digested using the restriction endonucleases Pvu II and Xba I, and *Saccharomyces cerevisea* can be transformed with 5 to 20 ng of linearized pYES2.1 TOPO vector and 20 to 100 ng PCR product per 50 µl competent cells using the transformation method described by Schiestl et al. (Schiestl et al. (1989) Curr. Genet. 16(5-6), pp. 339-346), to obtain pYES-pLPLAT_c1216(No), pYES-pLPLAT_c3052(No), pYES-pLPEAT-c7109 (Ta), pYES-pLPAAT_c2283(No), pYES-pLPAAT_c6316(No), pYES-pDGAT2_Irc24907(No), pYES-pDGAT2_c699(No), pYES-pDGAT2_c1910(No), pYES-pDGAT2_c2959(No), pYES-pDGAT2_c4857(No), pYES-pDGAT1_c21701(No), pYES-pDGAT2_c4648(No), pYES-pDGAT2_c1660(No), pYES-pDGAT2_c29432(No), pYES-pDGAT2_c1052(No), pYES-pDGAT2-c18182(Ta), pYES-pDGAT2-c5568(Ta), pYES-pDGAT2-c19425(Ta), pYES-pDGAT2_c48271(No), AtDGAT1, BnDGAT1 and pYES-pGPAT_c813(No) in various wildtype yeasts and yeast mutants. Positive transformants can be selected based on the complementation of the URA auxotrophy of the chosen *S. cerevisia* strain. To validate the correctness of the expression construct harbored by a particular yeast clone, plasmids can be isolated as described in Current Protocols in Molecular Biology (Hoffmann, Curr. Protoc. Mol. Biol. 2001 May; Chapter 13:Unit13.11), transformed into *E. coli* for amplification and subjected to sequencing of the expression cassette as described in example 2. For later cloning into plant expression plasmids, the introduced restrictions site for Asc I and/or Nco I in combination with Pac I can be used.

TABLE 2

Primer sequences for cloning acyltransferase-polynucleotides of the invention for yeast expression

| Gene-Name | Primer | SEQ-ID |
|---|---|---|
| pLPLAT_c1216(No) | Forward:<br>ataaaagtatcaacaaaaaattgttaatatacctctatactttaacgt<br>caaggagaaaaaacccggatcggcgcgccaccatgga-<br>caaggcactggcaccgtt | 46 |
| | Reverse:<br>aactataaaaaaataaatagggacctagacttcaggttgtctaact<br>ccttccttttcggttagagcggatttaattaacta-<br>aactttcttccttccctcta | 47 |
| pLPLAT_c3052(No) | Forward:<br>ataaaagtatcaacaaaaaattgttaatatacctctatactttaacgt<br>caaggagaaaaaacccggatcggcgcgccaccatgaccac-<br>gactgtcatctctag | 48 |
| | Reverse:<br>aactataaaaaaataaatagggacctagacttcaggttgtctaact<br>ccttccttttcggttagagcggatttaattaatcaaagcctcccgca-<br>caacgagc | 49 |
| pLPEAT-c7109(Ta) | Forward:<br>ataaaagtatcaacaaaaaattgttaatatacctctatactttaacgt<br>caaggagaaaaaacccggatcggcgcgccaccatg-<br>gagggcatcgagtcgatagt | 50 |

TABLE 2-continued

Primer sequences for cloning acyltransferase-
polynucleotides of the invention for yeast expression

| Gene-Name | Primer | SEQ-ID |
|---|---|---|
| | Reverse: aactataaaaaaataaatagggacctagacttcaggttgtctaact ccttccttttcggttagagcggatttaattaacta-taaggcttctcccggcgcgg | 51 |
| pLPAAT_c2283(No) | Forward: ataaaagtatcaacaaaaaattgttaatatacctctatactttaacgt caaggagaaaaaaccccggatcggcgcgccaccatgaa-gacgcccacgagcctggc | 52 |
| | Reverse: aactataaaaaaataaatagggacctagacttcaggttgtctaact ccttccttttcggttagagcggatttaattaattaagctctc-gaatcgtccttct | 53 |
| pLPAAT_c6316(No) | Forward: ataaaagtatcaacaaaaaattgttaatatacctctatactttaacgt caaggagaaaaaaccccggatcggcgcgccaccatggtcag-gaggaagatggacgt | 54 |
| | Reverse: aactataaaaaaataaatagggacctagacttcaggttgtctaact ccttccttttcggttagagcggatttaattaatcac-gacgccggcgccttgcagt | 55 |
| pDGAT2_lrc24907(No) | Forward: ataaaagtatcaacaaaaaattgttaatatacctctatactttaacgt caaggagaaaaaaccccggatcggcgcgccaccatgg-caccctccccaccggcccc | 56 |
| | Reverse: aactataaaaaaataaatagggacctagacttcaggttgtctaact ccttccttttcggttagagcggatttaattaatcatttgaccac-taaggtggcct | 57 |
| pDGAT2_c699(No) | Forward: ataaaagtatcaacaaaaaattgttaatatacctctatactttaacgt caaggagaaaaaaccccggatcggcgcgccaccatgggtc-tatttggcagcgggat | 58 |
| | Reverse: aactataaaaaaataaatagggacctagacttcaggttgtctaact ccttccttttcggttagagcggatttaattaactaaaagaaatt-caacgtccgat | 59 |
| pDGAT2_c1910(No) | Forward: ataaaagtatcaacaaaaaattgttaatatacctctatactttaacgt caaggagaaaaaaccccggatcggcgcgccaccatgttgag-tatccccgagtcgtc | 60 |
| | Reverse: aactataaaaaaataaatagggacctagacttcaggttgtctaact ccttccttttcggttagagcggatttaattaactaaaagaaatc-cagctccctgt | 61 |
| pDGAT2_c2959(No) | Forward: ataaaagtatcaacaaaaaattgttaatatacctctatactttaacgt caaggagaaaaaaccccggatcggcgcgccaccat-gacgccgcaagccgatatcac | 62 |
| | Reverse: aactataaaaaaataaatagggacctagacttcaggttgtctaact ccttccttttcggttagagcggatttaattaattactcaatgga-caacgggcgcg | 63 |
| pDGAT2_c4857(No) | Forward: ataaaagtatcaacaaaaaattgttaatatacctctatactttaacgt caaggagaaaaaaccccggatcggcgcgccaccatggct-tacctcttccgtcgtcg | 64 |
| | Reverse: aactataaaaaaataaatagggacctagacttcaggttgtctaact ccttccttttcggttagagcggatttaattaattaggcgatcgcaat-gaactcct | 65 |
| pDGAT1_c21701(No) | Forward: ataaaagtatcaacaaaaaattgttaatatacctctatactttaacgt caaggagaaaaaaccccggatcggcgcgccac-catgcccttttggacgggctgcatc | 66 |

TABLE 2-continued

Primer sequences for cloning acyltransferase-
polynucleotides of the invention for yeast expression

| Gene-Name | Primer | SEQ-ID |
|---|---|---|
| | Reverse: aactataaaaaaataaatagggacctagacttcaggttgtctaact ccttccttttcggttagagcggatttaattaatcacccgaaaa-tatcctccttct | 67 |
| pDGAT2_c4648(No) | Forward: ataaaagtatcaacaaaaaattgttaatatacctctatactttaacgt caaggagaaaaaaccccggatcggcgcgccaccatggc-caaggctaacttcccgcc | 68 |
| | Reverse: aactataaaaaaataaatagggacctagacttcaggttgtctaact ccttccttttcggttagagcggatttaattaatcactttataag-cagcttcttgt | 69 |
| pDGAT2_c1660(No) | Forward: ataaaagtatcaacaaaaaattgttaatatacctctatactttaacgt caaggagaaaaaaccccggatcggcgcgccaccatgttgttg-cagggattaagctg | 70 |
| | Reverse: aactataaaaaaataaatagggacctagacttcaggttgtctaact ccttccttttcggttagagcggatttaattaatcacaacaggac-caatttatgat | 71 |
| pDGAT2_c29432(No) | Forward: ataaaagtatcaacaaaaaattgttaatatacctctatactttaacgt caaggagaaaaaaccccggatcggcgcgccaccatgtt-gatggcgccgtcgcggcg | 72 |
| | Reverse: aactataaaaaaataaatagggacctagacttcaggttgtctaact ccttccttttcggttagagcggatttaattaatcagacgatgc-gaagcgtcttgt | 73 |
| pDGAT2_c1052(No) | Forward: ataaaagtatcaacaaaaaattgttaatatacctctatactttaacgt caaggagaaaaaaccccggatcggcgcgccaccatgggcgc-taccactgcgaccca | 74 |
| | Reverse: aactataaaaaaataaatagggacctagacttcaggttgtctaact ccttccttttcggttagagcggatttaattaatcacgacttcgga-cagtccaaaa | 75 |
| pDGAT2-c18182(Ta) | Forward: ataaaagtatcaacaaaaaattgttaatatacctctatactttaacgt caaggagaaaaaaccccggatcggcgcgccac-catgtcgttcgttgagcacagcgc | 76 |
| | Reverse: aactataaaaaaataaatagggacctagacttcaggttgtctaact ccttccttttcggttagagcggatttaattaactacacaaatcg-catcgtcttgt | 77 |
| pDGAT2-c5568(Ta) | Forward: ataaaagtatcaacaaaaaattgttaatatacctctatactttaacgt caaggagaaaaaaccccggatcggcgcgccac-catggtcttcctctgccttccta | 78 |
| | Reverse: aactataaaaaaataaatagggacctagacttcaggttgtctaact ccttccttttcggttagagcggatttaattaactacgagtccagc-cacttgatgc | 79 |
| pDGAT2-c19425(Ta) | Forward: ataaaagtatcaacaaaaaattgttaatatacctctatactttaacgt caaggagaaaaaaccccggatcggcgcgccac-catgtttcttcgcatcgaacggga | 80 |
| | Reverse: aactataaaaaaataaatagggacctagacttcaggttgtctaact ccttccttttcggttagagcggatttaattaactaacccctcggtgta-cagcgccg | 81 |
| pGPAT_c813(No) | Forward: ataaaagtatcaacaaaaaattgttaatatacctctatactttaacgt caaggagaaaaaaccccggatcggcgcgccaccatgc-catcccgcagcaccattga | 82 |

TABLE 2-continued

Primer sequences for cloning acyltransferase-
polynucleotides of the invention for yeast expression

| Gene-Name | Primer | SEQ-ID |
|---|---|---|
| | Reverse:<br>aactataaaaaaataaatagggacctagacttcaggttgtctaact<br>ccttccttttcggttagagcggatttaattaatcaga-<br>caagctcctcttccccct | 83 |
| pDGAT2_c48271(No) | Forward:<br>ataaaagtatcaacaaaaaattgttaatatacctctatactttaacgt<br>caaggagaaaaaaccccggatcggcgcgccaccatggccgc-<br>catctcaccgcgcaa | 109 |
| | Reverse:<br>aactataaaaaaataaatagggacctagacttcaggttgtctaact<br>ccttccttttcggttagagcggatttaattaactaccacacctc-<br>caacttcgccc | 110 |
| AtDGAT1 | Forward:<br>ataaaagtatcaacaaaaaattgttaatatacctctatactttaacgt<br>caaggagaaaaaaccccggatcggcgcgccaccatggc-<br>gattttggattctgctgg | 111 |
| | Reverse:<br>aactataaaaaaataaatagggacctagacttcaggttgtctaact<br>ccttccttttcggttagagcggatttaattaatcatgacatc-<br>gatcctttcggt | 112 |
| BnDGAT1 | Forward:<br>ataaaagtatcaacaaaaaattgttaatatacctctatactttaacgt<br>caaggagaaaaaaccccggatcggcgcgccaccatgga-<br>gattttggattctggagg | 113 |
| | Reverse:<br>aactataaaaaaataaatagggacctagacttcaggttgtctaact<br>ccttccttttcggttagagcggatttaattaactatga-<br>catctttcctttgcggt | 114 |

TABLE 3

Coding polynucleotide sequences, amino acid sequences encoded thereby
and expressed sequences (mRNA) of the acyltransferases of the invention

| Gene name | Organism | ORF in bp | SEQ-ID No. | Amino acids | SEQ-ID No. | mRNA in bp | SEQ-ID No. |
|---|---|---|---|---|---|---|---|
| pLPLAT_c1216(No) | Nannochloropsis oculata | 1485 | 1 | 494 | 2 | 1908 | 3 |
| pLPLAT_c3052(No) | Nannochloropsis oculata | 1776 | 4 | 591 | 5 | 2247 | 6 |
| pLPEAT-c7109(Ta) | Thraustochytrium aureum | 1134 | 7 | 377 | 8 | 1288 | 9 |
| pLPAAT_c2283(No) | Nannochloropsis oculata | 1284 | 10 | 427 | 11 | 1826 | 12 |
| pLPAAT_c6316(No) | Nannochloropsis oculata | 1395 | 13 | 464 | 14 | 1771 | 15 |
| pD-GAT2_lrc24907(No) | Nannochloropsis oculata | 1026 | 16 | 341 | 17 | 1100 | 18 |
| pDGAT2_c699(No) | Nannochloropsis oculata | 1206 | 19 | 401 | 20 | 1772 | 21 |
| pDGAT2_c1910(No) | Nannochloropsis oculata | 1173 | 22 | 390 | 23 | 1239 | 24 |
| pDGAT2_c2959(No) | Nannochloropsis oculata | 1089 | 25 | 362 | 26 | 1609 | 27 |
| pDGAT2_c4857(No) | Nannochloropsis oculata | 1464 | 28 | 487 | 29 | 1682 | 30 |
| pD-GAT1_c21701(No) | Nannochloropsis oculata | 1539 | 31 | 512 | 32 | 1904 | 33 |
| pDGAT2_c4648(No) | Nannochloropsis oculata | 1083 | 34 | 360 | 35 | 1362 | 36 |
| pDGAT2_c1660(No) | Nannochloropsis oculata | 1695 | 37 | 564 | 38 | 2074 | 39 |
| pD-GAT2_c29432(No) | Nannochloropsis oculata | 1029 | 40 | 342 | 41 | 1585 | 42 |
| pDGAT2_c1052(No) | Nannochloropsis oculata | 1251 | 43 | 416 | 44 | 1923 | 45 |
| pDGAT2-c18182(Ta) | Thraustochytrium aureum | 930 | 46 | 309 | 47 | 1134 | 48 |
| pDGAT2-c5568(Ta) | Thraustochytrium aureum | 1179 | 49 | 392 | 50 | 1303 | 51 |
| pDGAT2-c19425(Ta) | Thraustochytrium aureum | 1389 | 52 | 462 | 53 | 1547 | 54 |
| pGPAT_c813(No) | Nannochloropsis oculata | 1977 | 55 | 658 | 56 | 2460 | 57 |
| pDGAT2_c48271(No) | Nannochloropsis oculata | 960 | 102 | 319 | 103 | 1265 | 104 |

Example 4

Assembly of Genes Required for PUFA Synthesis within a T-Plasmid

For synthesis of EPA in *Arabidopsis* seeds, the set of genes encoding the proteins of the metabolic EPA pathway (table 4) was combined with expression elements (promoter, terminators) and transferred into binary t-plasmids that were used for agrobacteria mediated transformation of plants as described in example 5. To this end, the general cloning strategy depicted in FIG. 1 was employed: Genes listed in table 4 were PCR-amplified using Phusion™ High-Fidelity DNA Polymerase (NEB, Frankfurt, Germany) according to the manufactures instructions from cDNA using primer introducing a Nco I and/or Asc I restriction site at the 5' terminus, and a Pac I restriction site at the 3' terminus (FIG. 1B). To obtain the final expression modules, PCR-amplified genes were cloned between promoter and terminator via Nco I and/or Pac I restriction sites (FIG. 1C). Up to three of those expression modules were combined as desired to expression cassettes harbored by either one of pENTR/A, pENTR/B or pENTR/C (FIG. 1D). Finally, the Multisite Gateway™ System (Invitrogen) was used to combine three expression cassette harbored by pENTR/A, pENTR/B and pENTR/C (FIG. 1E) to obtain the final binary T-plasmids bbc (SEQ-ID 101, FIG. 2).

by gas chromatography as described in Wu et al., (2005) Nature Biotechnology 23(8): 1013-1017.

In seeds of fae1 transformed with bbc the EPA accumulation was 12.2%, the seeds contained small amounts of intermediate or side products: ARA (3.2%), SDA (0.8%), GLA (2.6%) which were not present in wild-type or fae1 (FIG. 3, Table 5).

TABLE 5

Content of fatty acids in seeds of wild-type (Col-0), fae1 mutant and fae1 transformed with bbc construct

| Fatty acid | Common name of FA | Col-0 | fae1 | bbc fae1 |
|---|---|---|---|---|
| 16:0 | Palmitic acid | 6.2 | 8.8 | 6.8 |
| 18:0 | Stearic acid | 3.1 | 4.1 | 5.3 |
| 18:1 | Oleic acid | 16.3 | 27.5 | 18.9 |
| 18:2 | Linoleic acid | 28.2 | 39.0 | 30.8 |
| 18:3n6 | Gamma-Linolenic acid | 0.0 | 0.0 | 2.6 |
| 18:3n3 | Alpha-Linoleic acid | 15.6 | 18.4 | 11.9 |
| 18:4n3 | Stearidonic acid | 0.0 | 0.0 | 0.8 |
| 20:1 | Eicosenoic acid | 22.8 | 0.4 | 0.3 |
| 20:4n6 | Arachidonic acid | 0.0 | 0.0 | 3.2 |
| 20:5n3 | Eicosapentaenoic acid | 0.0 | 0.0 | 12.2 |
| Others | | 7.8 | 1.8 | 7.2 |

For PUFA biosynthesis the acyl-moiety has to be shuffled between different metabolic pools. For example, the elonga-

TABLE 4

Genes of the bbc construct for synthesis of EPA (20:5n − 3) in *Arabidopsis* seeds. The elements controlling the expression of the respective genes are as well indicated.

| Name | Source Organism | Activity | SEQ-ID | Promoter | Terminator |
|---|---|---|---|---|---|
| d12Des(Ps) | *Phytophtora sojae* | d-12 Desaturase | 96 | p-BnNapin | t-E9 |
| d6Des(Ot) | *Ostreococcus tauri* | d-6 Desaturase | 97 | p-SBP | t-CatpA |
| d5Des(Tc) | *Traustochytrium* ssp. | d-5 Desaturase | 98 | p-LuCnl | t-AgroOCS |
| d6Elo(Pp) | *Physcomitrella patens* | d-6 Elongase | 99 | p-VfUSP | t-CaMV35S |
| o-3Des(Pi) | *Phytophthora infestans* | o-3 Desaturase | 100 | p-Napin | t-E9 |

Example 5

Plant Transformation

The resulting binary vector bbc harboring the genes reconstituting EPA biosynthesis pathway were transformed into *Agrobacterium tumefaciens* (Hofgen and Willmitzer (1988) Nucl. Acids Res. 16: 9877). The transformation of *A. thaliana* was accomplished by means of the floral-dip method (Clough and Bent (1998) Plant Journal 16: 735-743), this method is known to the skilled person. Wild-type *Arabidopsis* seeds contain considerable amounts of eicosenoic acid (20:1) (Table 5). Biosynthesis of 20:1 competes for the substrates of the PUFA biosynthesis pathway. This competition was circumvented by transforming bbc into the *Arabidopsis* fae1 mutant (James et al., (1995) The Plant Cell 7:309-319).

Example 6

Quantification of Metabolic Fatty Acyl-CoAs in Wild-Type and EPA Producing *Arabidopsis* Seeds The selected transgenic *Arabidopsis* plants from example 3 were analyzed in respect to PUFA content in seeds. Seeds from wild-type, fae1 mutant and transgenics harboring the bbc construct were harvested 18 days after flowering. Total fatty acid, representing the fatty acids esterified to CoA, on lipids and as triacyl-glycerides were extracted and analyzed tion of the acyl chain by two carbon atoms occurs specifically on acyl-CoA (Zank et al., (2002) The Plant Journal 318(3): 255-268. The efficiency of the transfer of the acyl-residue between the metabolic pools may represent a bottleneck for PUFA production in plants. Therefore the accumulation of EPA or intermediates of EPA biosynthesis as CoA species was analyzed by LC/MS$^2$. As a control CoA pool of wild-type seeds were as well analyzed. The Acyl-CoA metabolites were extracted from the seed tissue according to Larson and Graham, 2001. LC/MS$^2$ was applied as described by Magnes et al., 2005. Briefly, CoA were separated with high resolution by reversed-phase high performance liquid chromatography (HPLC) with a ammonium hydroxide and acetonitrile gradient. The acyl-CoA species were identified and quantified by multireaction monitoring using triple quadrupole mass spectrometry. Only a few methods using mass spectrometry for characterization of long chain acyl-CoA have been published, the majority of which employ negative ionisation mode showing abundant ions. In contrast, positive ionisation has only one abundant ion [M-H]+, furthermore the predominant ion in MS$^2$ spectra is the fatty acyl-pantetheine fragment (m/z 507—FIG. 5B), characteristic of CoA-activated substances. In choosing the acyl-pantetheine of interest in multireaction monitoring mode (MRM) a very sensitive, selective and reproducible method was established. CoA-activated substances can be monitored by scanning for the neutral loss of phosphoadenosine diphosphate. Generally for reliable analysis, all interfering peaks must be chromatographically separated; in the case of EPA and ARA this is not possible (FIG. 4B). However through the use of MRM, incorporating very short dwell times (15 ms), it is possible to follow the individual chromatograms of acyl-CoA of interest and demonstrate the presence of EPA and ARA in the acyl CoA pool (FIG. 5C). According to internal standards the eicosapentaenoyl-CoA was in the range of . . . % of the total Co-A pool.

In conclusion these results show that PUFA accumulate in the metabolic CoA pool and are not transferred to DAG to be released as TAG into the seed oil. Such a bottleneck may be overcome by the co-expression of an acyltransferase from table 3, having the appropriate substrate specificity. The application of suitable acyltransferase may increase the flux of fatty acid between the metabolic pools and increase the PUFA biosynthesis rate.

Example 7

Activity Assays Using Yeast Extracts

To characterize the functions of the acyltransferase polypeptides of the invention, yeast mutants can be employed that are defective in certain acyltransferase activities. For example, the yeast mutant Y13749 (Genotype: BY4742; Mat alpha; his3Δ1; leu2Δ0; lys2Δ0; ura3Δ0; YDL052c::kanMX4) lacking LPAAT activity can be transformed with expression constructs harboring candidate polypeptides to check for restoration (complementation) of LPAAT activity, the yeast mutant Y12431 (genotype BY4742; Mat alpha; his3Δ1; leu2Δ0; lys2Δ0; ura3Δ0; YOR175c::kanMX4) lacking LPLAT activity can be transformed with expression constructs harboring candidate polypeptides to check for restoration (complementation) of LPLAT activity, the yeast mutant H1246 (genotype MATa leu2-3, 112 trp1-1 can1-100 ura3-1 ade2-1 his3-11, 15 YOR245::KanMX4 YNR008W:: TRP1 YCR048W::HIS3 YNR019W::LEU2) lacking the ability to synthesize triacylglycerole can be transformed with expression constructs harboring candidate polypeptides to check for restoration (complementation) of the ability to synthesis triacylglycerole. The yeast mutants can for example harbor the expression constructs listed in example 3 employing the transformation method described in example 3.

For LPAAT activity assay, clones of the yeast mutant Y13749 harboring pYES-pLPAAT_c6316(No) can be grown at 28° C. in 10 ml selective media (SC-URA) with 2% raffinose as carbon source over night. The next day, expression of the acyltransferase polypeptide can be induced by transferring the cells to fresh media containing 2% galactose, for example by inoculating 100 ml of fresh culture to an optical density (measure at 600 nm) of $OD_{600}=0.1$. Cells are harvested after 24 h incubation at 28° C. by centrifugation at 3000×g for 5 min and resuspended in 1 ml resuspension buffer (25 mM Tris/HCL pH 7.6) and disrupted using acid washed zirconium bead (200 µm average diameter) in a mill (Retsch, Germany) by three minutes agitation at 300 rpm. The supernatant is transferred to a fresh tube and centrifuged at 3000×g for 5 min. The obtained supernatant is the crude extract. Protein content is measured according to Bradford (Bradford, M. M. (1976), Anal. Biochem. Bd. 72, pp. 248-254) with bovine serum albumin as standard. Assay mixtures contain 1 to 50 µg of protein, 10 µl of 100 nM [$^{14}$C]-18:1-LPA (giving about 2000 dpm/nmol), 10 µl of 50 nM 18:1-CoA or 50 nM 18:3n-3-CoA in assay buffer (25 mM Tris/HCL pH 7.6, 0.5 mg/ml BSA) to give a total volume of 100 µl. Samples are incubated for 10 min at 30° C. The assays are terminated by extraction of the lipids into chloroform according to Blight and Dyer (Bligh, E. G. and Dyer, W. J. (1959), Can. J. Biochem. Physiol. 37, pp. 911-917). Lipids are separated on thin layer chromatography (TLC) silica 60 plates (Merck) using chloro-form/methanol/acetic acid/water (90:15:10:3), and autoradiographic pictures are taken using an instant imager (Packard). It can be seen by the formation of phosphatidic acid (PA) in FIG. 7, that pLPAAT_c6316(No) (SEQ-ID 13, lane 1 and 2) encodes a polypeptide having LPAAT activity.

For LPCAT and LPEAT activity assay, clones of the yeast mutant Y12431 harboring pYES-pLPAAT_c 6316(No) can be grown at 28° C. in 10 ml selective media (SC-URA) with 2% raffinose as carbon source over night. The next day, expression of the acyltransferase polypeptide can be induced by transferring the cells to fresh media containing 2% galactose, for example by inoculating 100 ml of fresh culture to an optical density (measure at 600 nm) of $OD_{600}=0.1$. Cells are harvested after 24 h incubation at 28° C. by centrifugation at 3000×g for 5 min and resuspended in 1 ml resuspension buffer (25 mM Tris/HCL pH 7.6) and disrupted using acid washed zirconium bead (200 µm average diameter) in a mill (Retsch, Germany) by three minutes agitation at 300 rpm. The supernatant is transferred to a fresh tube and centrifuged at 3000×g for 5 min. The obtained supernatant is the crude extract. Protein content is measured according to Bradford (Bradford, M. M. (1976), Anal. Biochem. Bd. 72, pp. 248-254) with bovine serum albumin as standard. Assay mixtures contain either 10 µl 100 nM [$^{14}$C]-LPC (LPCAT activity assay) or 10 µl 100 nM [$^{14}$C]-LPE (LPEAT activity assay), 1 to 50 µg of protein, 10 µl of 50 nM 18:1-CoA or 50 nM 18:3n-3-CoA in assay buffer (25 mM Tris/HCL pH 7.6, 0.5 mg/ml BSA) to give a total volume of 100 µl. Samples are incubated for 10 min at 30° C. The assays are terminated by extraction of the lipids into chloroform according to Blight and Dyer (Bligh, E. G. and Dyer, W. J. (1959), Can. J. Biochem. Physiol. 37, pp. 911-917). Lipids are separated on thin layer chromatography (TLC) silica 60 plates (Merck) using chloroform/methanol/acetic acid/water (90:15:10:3), and autoradiographic pictures are taken using an instant imager (Packard). It can be seen by the formation of phosphatidylethanolamine (PC) in FIG. 6, that pLPAAT_c6316(No) (SEQ-ID 13, lane 1 and 2) encodes a polypeptide having LPCAT activity.

For DGAT activity assay, clones of the yeast mutant H1246 harboring either one of pYES-pDGAT2_c699(No), pYES-pDGAT2_c2959(No), pYES-pDGAT2_c4648(No), pYES-pDGAT2_c48271(No), pYES-pDGAT2-c19425(Ta), pYES-AtDGAT1, or pYES-BnDGAT1 can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}=0.1$. Activity as indicated by the formation of TAG (as indicated, the mutant H1246 is unable to synthesize TAG) can be measured either by relying on yeast-endogenous substrate-DAG, or by providing substrate in an in vitro assay.

For the former type of assay, cells are harvested after reaching stationary phase during incubation at 28° C. by centrifugation at 3000×g for 5 min and resuspendet in 2 ml resuspension buffer (phosphate buffered saline (PBS) pH 7.4, see Sambrook et al., "Molecular Cloning", Cold Spring Harbor Laboratory, 1989). The equivalent of 200 mg cell pellet is taken, the volume adjusted to 210 µl using PBS and 790 µl of methanol:chloroform (2:1) are added. Cells are disrupted using acid washed zirconium bead (200 µm average diameter) in a mill (Retsch, Germany) by three minutes agitation at 300 rpm and lipids are extracted according to Blight and Dyer (Bligh, E. G. and Dyer, W. J. (1959), Can. J. Biochem. Physiol. 37, pp. 911-917).

The in vitro assay is the preferred way of testing for DGAT activity, when activity is known or expected to be week when relying on endogenous substrate. Instead, both the type and concentration of the DAG acceptor molecule, as well as the type and concentration of the fatty acid-CoA can be controlled. To do so, cells are harvested after 24 h incubation at 28° C. by centrifugation at 3000×g for 5 min and resuspended in 1 ml resuspension buffer (25 mM Tris/HCL pH 7.6) and disrupted using acid washed zirconium bead (200 μm average diameter) in a mill (Retsch, Germany) by three minutes agitation at 300 rpm. The supernatant is transferred to a fresh tube and centrifuged at 3000×g for 5 min. The obtained supernatant is the crude extract. Protein content is measured according to Bradford (Bradford, M. M. (1976), Anal. Biochem. Bd. 72, pp. 248-254) with bovine serum albumin as standard. Assay mixtures contain 10 μl 50 nM [$^{14}$C]-6:0-DAG (giving about 3000 dpm/nmol), 50 μg of microsomal protein (the amount can be adjusted to stay within linear conditions without substrate limitation), 10 μl of 50 nM 18:3n-3-CoA or 50 nM 22:6n-3-CoA in assay buffer (50 mM Hepes buffer pH 7.2, 1 mg/ml BSA) to give a total volume of 100 μl. Samples are incubated for 10 min at 30° C.

In either case—in vivo or in vitro assay—lipids are separated on thin layer chromatography (TLC) silica 60 plates (Merck) using hexane:diethylether:acetic acid (70:30:1), and stained in iodine vapor. It can be seen by the formation of triacylglycerole (TAG) using the in vitro assay-conditions in FIG. 8, that pDGAT2-c19425mod(Ta) (SEQ-ID 52, lane 1 and 2), pDGAT2_c4648(No) (SEQ-ID 34, lane 5 and 6), pDGAT2_c48271(No) (SEQ-ID 102, lane 7 and 8), BnDGAT1 (SEQ-ID 107, lane 9 and 10), AtDGAT1 (SEQ-ID 105, lane 11 and 12), pDGAT2_c699(No) (SEQ-ID 19, lane 13 and 14) and pDGAT2_c2959(No) (SEQ-ID 25, lane 15) encode polypeptides having DGAT activity.

Table 6 summarizes the results of the LPCAT, LPAAT and DGAT activity tests.

expression of the acyltransferase polypeptides can be induced by transferring the cells to fresh media containing 2% galactose, for example by inoculating 100 ml of fresh culture to an optical density (measure at 600 nm) of $OD_{600}$=0.1. Cells are harvested after 24 h incubation at 28° C. by centrifugation at 3000×g for 5 min and resuspended in 1 ml disruption buffer (20 mM Tris/HCL pH 7.6, 10 mM $MgCl_2$, 1 mM EDTA, 5% glycerol, 0.3 M $(NH_4)_2SO_4$) and disrupted using acid washed zirconium beads (200 μm average diameter) in a mill (Retsch, Germany) by three minutes agitation at 300 rpm. The supernatant and the beads are transferred to a fresh tube. Disruption buffer is added up to 20 ml and the tube is centrifuged at 8000×g for 5 min. The obtained supernatant is centrifuged for 2 hrs at 42000 rpm at 4° C. The pellet (microsomal fraction) is resuspended in a small volume of 0.1 M phosphate buffer pH 7.2. Protein content in the microsomal fraction is measured according to Bradford (Bradford, M. M. (1976), Anal. Biochem. Bd. 72, pp. 248-254) with bovine serum albumin as standard. Assay mixtures contain 1-5 μg of microsomal protein (the amount is adjusted to achieve linear conditions without substrate limitation), 10 μl of 1 mM [$^{14}$C]-18:1-LPA (5000 dpm/nmol), 10 μl of 1 mM acyl-CoA in assay buffer (0.1 M phosphate buffer pH 7.2, 10 mg/ml Bovine Serum Albumine (BSA)) to give a total volume of 100 μl. Like to amount of microsomal protein added to the assay, also the amount of BSA has influence on observed anzmye activities, where higher amounts of BSA result on lower activities and lower amounts of BSA result in higher activities. The enzyme specificity can be tested for different acyl-CoA:s, e.g. 14:0-CoA, 16:0-CoA, 18:1-CoA, 18:2-CoA, 18:3-CoA, γ18:3-CoA, 18:4-CoA, 20:3-CoA, 20:4-CoA, 20:4(n-3)-CoA, 20:5-CoA, 22:5-CoA, 22:6-CoA. Samples are incubated for 4 min at 30° C. The assays are terminated by extraction of the lipids into chloroform according to Bligh and Dyer (Bligh, E. G. and Dyer, W. J. (1959), Can. J. Biochem. Physiol. 37, pp. 911-917). Lipids are separated on thin layer chromatography (TLC) silica 60 plates (Merck) using chloroform/methanol/acetic acid/water (90:15:10:3), and autoradiographic pictures are taken using an instant imager (Packard). The amount of

TABLE 6

Measured with microsomal protein and [14C]-18:1-LPA, [14C]-18:1-LPC or [14C]-6:0-1,2-DAG. Ofr the in vitro DGAT assay, 1 mg/ml of BSA was added to reduce activity for staying in the linear range.

| Enzyme Class | Candidate | SEQ-IDs (ORF/protein/mRNA) | Activity in vitro using 18:3-CoA nmol/(mg*min) | Activity in vitro using 22:6-CoA nmol/(mg*min) | Activity in vivo |
|---|---|---|---|---|---|
| LPAAT | pLPAAT__c6316(No) | 13/14/15 | 81 | 64 | |
| LPCAT | pLPAAT__c6316(No) | 13/14/15 | 38 | 9 | |
| DGAT | pDGAT2__c699(No) | 19/20/21 | 0.22 | 0.17 | Yes |
| DGAT | pDGAT2__c2959(No) | 25/26/27 | 0.95 | 0.67 | Yes |
| DGAT | pDGAT2__c4648(No) | 34/35/36 | 1.4 | 0.17 | Yes |
| DGAT | pDGAT2_c48271(No) | 102/103/104 | 1.6 | 0 | Yes |
| DGAT | pDGAT2-c19425(Ta) | 52/53/54 | 4.0 | 5.6 | Yes |
| DGAT | AtDGAT1 | 105/106/— | 1.6 | 1.2 | Yes |
| DGAT | BnDGAT1 | 107/108/— | 2.4 | 1.5 | Yes |

Example 8

Determination of Substrate Specificity for LPAAT

For determination of substrate specificities of the LPAAT enzymes, clones of the yeast mutant Y13749 (described in example 7) harboring LPAAT genes in the pYES plasmid can be grown at 28° C. in 10 ml selective media (SC-URA) with 2% raffinose as carbon source over night. The next day, phosphatidic acid (PA) produced in the reaction (and hence the enzyme activity) can be determined from the picture.

Example 9

Determination of Substrate Specificity for LPLAT

For LPCAT and LPEAT activity assay, clones of the yeast mutant Y12431 harboring LPLAT genes in the pYES plasmid can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}$=0.1 Cells are harvested after 24 h incubation at 28° C. by centrifugation at 3000×g for 5 min and resuspended in 1 ml disruption buffer (20 mM Tris/HCL pH 7.6, 10 mM $MgCl_2$, 1 mM EDTA, 5% glycerol, 0.3 M $(NH_4)_2SO_4$) and disrupted using acid washed zirconium beads (200 μm average diameter) in a mill (Retsch, Germany) by three minutes agitation at 300 rpm. The supernatant and the beads are transferred to a fresh tube. Disruption buffer is added up to 20 ml and the tube is centrifuged at 8000×g for 5 min. The obtained supernatant is centrifuged for 2 hrs at 42000 rpm at 4° C. The pellet (microsomal fraction) is resuspended in a small volume of 0.1 M phosphate buffer pH 7.2. Protein content in the microsomal fraction is measured according to Bradford (Bradford, M. M. (1976), Anal. Biochem. Bd. 72, pp. 248-254) with bovine serum albumin as standard. Assay mixtures contain either 10 μl 1 mM [$^{14}$C]-18:1-Lysophosphatidlycholine (-LPC), 5000 dpm/nmol (LP-CAT assay) or 10 μl 1 mM [$^{14}$C]-18:1-Lysophosphatidyletha-nolamine (-LPE), 5000 dpm/nmol (LPEAT assay), 1-10 μg of microsomal protein (the amount is adjusted to achieve linear conditions without substrate limitation), 10 μl of 1 mM acyl-CoA in assay buffer (0.1 M phosphate buffer pH 7.2., 10 mg/ml BSA) to give a total volume of 100 μl. Like to amount of microsomal protein added to the assay, also the amount of BSA has influence on observed anzmye activities, where higher amounts of BSA result on lower activities and lower amounts of BSA result in higher activities. The enzyme specificity can be tested for different acyl-CoA:s, e.g. 14:0-CoA, 16:0-CoA, 18:1-CoA, 18:2-CoA, 18:3-CoA, γ18:3-CoA, 18:4-CoA, 20:3-CoA, 20:4-CoA, 20:4(n-3)-CoA, 20:5-CoA, 22:5-CoA, 22:6-CoA. Samples are incubated for 4 min at 30° C. The assays are terminated by extraction of the lipids into chloroform according to Bligh and Dyer (Bligh, E. G. and Dyer, W. J. (1959), Can. J. Biochem. Physiol. 37, pp. 911-917). Lipids are separated on thin layer chromatography (TLC) silica 60 plates (Merck) using chloroform/methanol/acetic acid/water (90:15:10:3), and autoradiographic pictures are taken using an instant imager (Packard). The amount of phosphatidyl choline (PC) or phosphatidyl ethanol amine (PE) produced in the reaction (and hence the enzyme activity) can be determined from the picture.

Example 10

Determination of Substrate Specificity for DGAT

For DGAT activity assay, clones of the yeast mutant H1246 harboring either one of pYES-pDGAT2_c699(No), pYES-pDGAT2_c2959(No), pYES-pDGAT2_c4648(No), pYES-pDGAT2_c48271(No), pYES-pDGAT2-c19425(Ta), pYES-AtDGAT1, or pYES-BnDGAT1 can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}$=0.1. Cells are harvested after 24 h incubation at 28° C. by centrifugation at 3000×g for 5 min and resuspended in 1 ml disruption buffer (20 mM Tris/HCL pH 7.6, 10 mM $MgCl_2$, 1 mM EDTA, 5% glycerol, 0.3 M $(NH_4)_2SO_4$) and disrupted using acid washed zirconium beads (200 μm average diameter) in a mill (Retsch, Germany) by three minutes agitation at 300 rpm. The supernatant and the beads are transferred to a fresh tube. Disruption buffer is added up to 20 ml and the tube is centrifuged at 8000×g for 5 min. The obtained supernatant is centrifuged for 2 hrs at 42000 rpm at 4° C. The pellet (microsomal fraction) is resuspended in a small volume of 0.1 M phosphate buffer pH 7.2. Protein content in the microsomal fraction is measured according to Bradford (Bradford, M. M. (1976), Anal. Biochem. Bd. 72, pp. 248-254) with bovine serum albumin as standard. Assay mixtures contain 5 μl 1 mM [$^{14}$C]-6:0-DAG, 3000 dpm/nmol, 1-100 μg of microsomal protein (the amount is adjusted to achieve linear conditions without substrate limitation), 5 μl of 1 mM acyl-CoA in assay buffer (50 mM Hepes buffer pH 7.2, 1 mg/ml BSA) to give a total volume of 100 μl. The enzyme specificity can be tested for different acyl-CoA:s, e.g. 14:0-CoA, 16:0-CoA, 18:1-CoA, 18:2-CoA, 18:3-CoA, γ18:3-CoA, 18:4-CoA, 20:3-CoA, 20:4-CoA, 20:4(n-3)-CoA, 20:5-CoA, 22:5-CoA, 22:6-CoA. Samples are incubated for 4 min at 30° C. The assays are terminated by extraction of the lipids into chloroform according to Bligh and Dyer (Bligh, E. G. and Dyer, W. J. (1959), Can. J. Biochem. Physiol. 37, pp. 911-917). Lipids are separated on thin layer chromatography (TLC) silica 60 plates (Merck) using hexane:diethylether:acetic acid (70:30:1), and autoradiographic pictures are taken using an instant imager (Packard). The amount of triacylglycerol (TAG) produced in the reaction (and hence the enzyme activity) can be determined from the picture. In *Brassica napus* and *Arabidopsis*, the DGAT involved in TAG-formation in seeds are of the DGAT1 type. The enzyme activity AtDGAT1 and BnDGAT1 for the different substrates can be seen in FIG. 9. The enzyme activity of pDGAT2-c19425 (Ta) for the different substrates, compared to AtDGAT1 and BnDGAT1 is shown in FIG. 10. The enzyme activity of pDGAT2_c699(No) and pDGAT2_c4648(No) for the different substrates, compared to AtDGAT1 and BnDGAT1 is shown in FIG. 11. The data in FIGS. 10 and 11 show clearly, that all DGAT2 enzymes shown in these figures vary strongly towards their activities for the various substrates, whereas the DGAT1 involved in TAG formation in *Arabidopsis* and *Brassica napus* exhibit less variability towards these different substrates.

Example 11

Determination of Substrate Selectivity for LPAAT

For determination of substrate selectivities of the LPAAT enzymes, clones of the yeast mutant Y13749 (described in example 7) harboring LPAAT genes can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}$=0.1. Cells are harvested after 24 h incubation at 28° C. by centrifugation at 3000×g for 5 min and resuspended in 1 ml disruption buffer (20 mM Tris/HCL pH 7.6, 10 mM $MgCl_2$, 1 mM EDTA, 5% glycerol, 0.3 M $(NH_4)_2SO_4$) and disrupted using acid washed zirconium beads (200 μm average diameter) in a mill (Retsch, Germany) by three minutes agitation at 300 rpm. The supernatant and the beads are transferred to a fresh tube. Disruption buffer is added up to 20 ml and the tube is centrifuged at 8000×g for 5 min. The obtained supernatant is centrifuged for 2 hrs at 42000 rpm at 4° C. The pellet (microsomal fraction) is resuspended in a small volume of 0.1 M phosphate buffer pH 7.2. Protein content in the microsomal fraction is measured according to Bradford (Bradford, M. M. (1976), Anal. Biochem. Bd. 72, pp. 248-254) with bovine serum albumin as standard. The substrate selectivity can be determined by mixing equimolar amounts of different acyl-CoA:s in the same reaction and measure the preference for using the different acyl groups as substrates. The assay is run as in the specificity studies (Example 5) but scaled up 18 times to get sufficient amount of PA for detection. Up to 4 different acyl-CoA:s can be used in the assay in equimolar amount instead of one single acyl-CoA. Samples are incubated for 4 min at 30° C. The assays are terminated by extraction of the lipids into chloroform according to Bligh and Dyer (Bligh, E. G. and Dyer, W. J. (1959), Can. J. Biochem. Physiol. 37, pp. 911-917). Lipids are separated on thin layer chromatography (TLC) silica 60 plates (Merck) using chloroform/methanol/acetic acid/water (90:15:10:3), and autoradiographic pictures are taken using an instant imager (Packard). The phosphatidic acid (PA) is recovered from the plate and the fatty acids methylated in situ on the gel with sulphuric acid (2%) in methanol. Fatty acid methyl esters are extracted with hexane and separated by gas-liquid chromatography (GLC) using a WCOT fused silica 50 m×0.32 mm ID capillary column coated with CP-Wax 58-CB DF=0.3 (Chrompack inc., The Netherlands) and quantified relative to methyl-heptadecanoate added as an internal standard. The selectivity can be determined by calculating the amount of each acyl group that has been acylated to LPA.

Example 12

Determination of Substrate Selectivity for LPLAT

For LPCAT and LPEAT activity assay, clones of the yeast mutant Y12431 harboring LPLAt genes can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}$=0.1 Cells are harvested after 24 h incubation at 28° C. by centrifugation at 3000×g for 5 min and resuspended in 1 ml disruption buffer (20 mM Tris/HCL pH 7.6, 10 mM $MgCl_2$, 1 mM EDTA, 5% glycerol, 0.3 M $(NH_4)_2SO_4$) and disrupted using acid washed zirconium beads (200 µm average diameter) in a mill (Retsch, Germany) by three minutes agitation at 300 rpm. The supernatant and the beads are transferred to a fresh tube. Disruption buffer is added up to 20 ml and the tube is centrifuged at 8000×g for 5 min. The obtained supernatant is centrifuged for 2 hrs at 42000 rpm at 4° C. The pellet (microsomal fraction) is resuspended in a small volume of 0.1 M phosphate buffer pH 7.2. Protein content in the microsomal fraction is measured according to Bradford (Bradford, M. M. (1976), Anal. Biochem. Bd. 72, pp. 248-254) with bovine serum albumin as standard. The substrate selectivity can be determined by mixing equimolar amounts of different acyl-CoA:s in the same reaction and measure the preference for using the different acyl groups as substrates. The assay is run as in the specificity studies (Example 6) but scaled up 18 times to get sufficient amount of PC or PE for detection. Up to 4 different acyl-CoA:s can be used in the assay in equimolar amount instead of one single acyl-CoA. Samples are incubated for 4 min at 30° C. The assays are terminated by extraction of the lipids into chloroform according to Bligh and Dyer (Bligh, E. G. and Dyer, W. J. (1959), Can. J. Biochem. Physiol. 37, pp. 911-917). Lipids are separated on thin layer chromatography (TLC) silica 60 plates (Merck) using chloroform/methanol/acetic acid/water (90:15:10:3), and autoradiographic pictures are taken using an instant imager (Packard). The PC or PE is recovered from the plate and the fatty acids methylated in situ on the gel with sulphuric acid (2%) in methanol. Fatty acid methyl esters are extracted with hexane and separated by gas-liquid chromatography (GLC) using a WCOT fused silica 50 m×0.32 mm ID capillary column coated with CP-Wax 58-CB DF=0.3 (Chrompack inc., The Netherlands) and quantified relative to methyl-heptadecanoate added as an internal standard. The selectivity can be determined by calculating the amount of each acyl group that has been acylated to LPC or LPE.

Example 13

Determination of Substrate Selectivity for DGAT

For DGAT activity assay, clones of the yeast mutant H1246 harboring DGAT genes can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}$=0.1. Cells are harvested after 24 h incubation at 28° C. by centrifugation at 3000×g for 5 min and resuspended in 1 ml disruption buffer (20 mM Tris/HCL pH 7.6, 10 mM $MgCl_2$, 1 mM EDTA, 5% glycerol, 0.3 M $(NH_4)_2SO_4$) and disrupted using acid washed zirconium beads (200 µm average diameter) in a mill (Retsch, Germany) by three minutes agitation at 300 rpm. The supernatant and the beads are transferred to a fresh tube. Disruption buffer is added up to 20 ml and the tube is centrifuged at 8000×g for 5 min. The obtained supernatant is centrifuged for 2 hrs at 42000 rpm at 4° C. The pellet (microsomal fraction) is resuspended in a small volume of 0.1 M phosphate buffer pH 7.2. Protein content in the microsomal fraction is measured according to Bradford (Bradford, M. M. (1976), Anal. Biochem. Bd. 72, pp. 248-254) with bovine serum albumin as standard. The substrate selectivity can be determined by mixing equimolar amounts of different acyl-CoA:s in the same reaction and measure the preference for using the different acyl groups as substrates. The assay is run as in the specificity studies (Example 7) but scaled up 18 times to get sufficient amount of TAG for detection. Up to 4 different acyl-CoA:s can be used in the assay in equimolar amount instead of one single acyl-CoA. Samples are incubated for 4 min at 30° C. The assays are terminated by extraction of the lipids into chloroform according to Bligh and Dyer (Bligh, E. G. and Dyer, W. J. (1959), Can. J. Biochem. Physiol. 37, pp. 911-917). Lipids are separated on thin layer chromatography (TLC) silica 60 plates (Merck) using chloroform/methanol/acetic acid/water (90:15:10:3), and autoradiographic pictures are taken using an instant imager (Packard). The TAG is recovered from the plate and the fatty acids methylated in situ on the gel with sulphuric acid (2%) in methanol. Fatty acid methyl esters are extracted with hexane and separated by gas-liquid chromatography (GLC) using a WCOT fused silica 50 m×0.32 mm ID capillary column coated with CP-Wax 58-CB DF=0.3 (Chrompack inc., The Netherlands) and quantified relative to methyl-heptadecanoate added as an internal standard. The selectivity can be determined by calculating the amount of each acyl group that has been acylated to TAG.

The invention claimed is:

1. A polynucleotide comprising an expression control sequence operatively linked to a heterologous nucleic acid sequence selected from the group consisting of:
   a) the nucleic acid sequence of SEQ ID NO: 10 or 13;
   b) a nucleic acid sequence encoding a polypeptide comprising the amino acid sequence of SEQ ID NO: 11 or 14;
   c) a nucleic acid sequence having at least 85% sequence identity to the nucleic acid sequence of a) or b), wherein said nucleic acid sequence encodes a polypeptide having lysophosphatidic acid acyltransferase activity; and
   d) a nucleic acid sequence encoding a polypeptide having lysophosphatidic acid acyltransferase activity and having an amino acid sequence which is at least 85% identical to the amino acid sequence of SEQ ID NO: 11 or 14.

2. The polynucleotide of claim 1, wherein said polynucleotide further comprises a terminator sequence operatively linked to the nucleic acid sequence.

3. A vector comprising the polynucleotide of claim 1.

4. A host cell comprising:
   a) the polynucleotide of claim 1; or
   b) a vector comprising said polynucleotide.

5. A method for the manufacture of a polypeptide, comprising:
   a) cultivating the host cell of claim 4 under conditions which allow for the production of said polypeptide; and
   b) obtaining the polypeptide from said host cell.

6. A non-human transgenic organism comprising:
   a) the polynucleotide of claim 1; or
   b) a vector comprising said polynucleotide
   wherein the non-human transgenic organism is a plant, or microorganism.

7. The non-human transgenic organism of claim 6, wherein the microorganism is a fungus, algae, moss, or yeast.

8. A method for the manufacture of polyunsaturated fatty acids, comprising:
   a) cultivating the host cell of claim 4 under conditions which allow for the production of polyunsaturated fatty acids in said host cell; and
   b) obtaining said polyunsaturated fatty acids from said host cell.

9. A method for the manufacture of polyunsaturated fatty acids, comprising:
   a) cultivating the non-human transgenic organism of claim 6 under conditions which allow for the production of polyunsaturated fatty acids in said host cell; and
   b) obtaining said polyunsaturated fatty acids from said non-human transgenic organism.

10. The method of claim 8, wherein said polyunsaturated fatty acid is arachidonic acid (ARA), eicosapentaenoic acid (EPA), and/or docosahexaenoic acid (DHA).

11. A method for the manufacture of an oil, lipid, or fatty acid composition, comprising:

a) cultivating the host cell of claim 4 under conditions which allow for the production of polyunsaturated fatty acids in said host cell;
b) obtaining said polyunsaturated fatty acids from said host cell; and
c) formulating the polyunsaturated fatty acid as an oil, lipid, or fatty acid composition.

12. The method of claim 11, wherein said oil, lipid, or fatty acid composition is to be used for feed, foodstuffs, cosmetics, or pharmaceuticals.

13. A method for the manufacture of polyunsaturated fatty acids, comprising:
a) cultivating a plant comprising the polynucleotide of claim 1 or a vector comprising said polynucleotide under conditions which allow for the production of polyunsaturated fatty acids in said plant or seeds thereof; and
b) obtaining said polyunsaturated fatty acids from said plant or seeds thereof.

14. The method of claim 13, wherein the polyunsaturated fatty acids are obtained from the seeds of said plant.

15. A method for the manufacture of an oil-, lipid- or fatty acid-composition, comprising:
a) providing a polyunsaturated fatty acid produced by the method of claim 13; and
b) formulating said polyunsaturated fatty acid as an oil-, lipid- or fatty acid-composition.

16. A method for the manufacture of an oil-, lipid- or fatty acid-composition, comprising:
a) cultivating a plant comprising the polynucleotide of claim 1 or a vector comprising said polynucleotide under conditions which allow for the production of polyunsaturated fatty acids in said plant or seeds thereof; and
b) obtaining an oil-, lipid- or fatty acid-composition from said plant or seeds thereof.

17. The method of claim 16, wherein the oil-, lipid- or fatty acid-composition is obtained from the seeds of said plant.

18. A method for the production of feed, foodstuffs, cosmetics or pharmaceuticals, comprising:
a) obtaining an oil-, lipid- or fatty acid-composition produced by the method of claim 16; and
b) processing said oil-, lipid- or fatty acid-composition to produce feed, foodstuffs, cosmetics or pharmaceuticals.

19. The polynucleotide of claim 1, wherein said heterologous nucleic acid sequence comprises the nucleic acid sequence of SEQ ID NO: 10 or 13, or encodes a polypeptide comprising the amino acid sequence of SEQ ID NO: 11 or 14.

20. The polynucleotide of claim 1, wherein said heterologous nucleic acid sequence encodes a polypeptide having lysophosphatidic acid acyltransferase activity and having at least 90% sequence identity to the amino acid sequence of SEQ ID NO: 11 or 14.

21. The polynucleotide of claim 1, wherein said heterologous nucleic acid sequence encodes a polypeptide having lysophosphatidic acid acyltransferase activity and having at least 95% sequence identity to the amino acid sequence of SEQ ID NO: 11 or 14.

22. The host cell of claim 4, wherein the host cell is a plant cell or a microorganism.

23. The host cell of claim 4, wherein the host cell is yeast, fungus, algae, moss, or an insect cell.

24. A method for the manufacture of polyunsaturated fatty acids, comprising:
a) obtaining an oil-, lipid- or fatty acid-composition produced by the method of claim 16; and
b) obtaining polyunsaturated fatty acids from said oil-, lipid- or fatty acid-composition.

* * * * *